US007223729B2

(12) United States Patent
Gorczynski

(10) Patent No.: US 7,223,729 B2
(45) Date of Patent: May 29, 2007

(54) METHODS OF TREATING ALLERGY BY ADMINISTERING A CD200 PROTEIN

(75) Inventor: Reginald M. Gorczynski, Willowdale (CA)

(73) Assignee: Trillium Therapeutics Inc., Toronto, Ontario (CA)

(*) Notice: Subject to any disclaimer, the term of this patent is extended or adjusted under 35 U.S.C. 154(b) by 0 days.

(21) Appl. No.: 10/850,562

(22) Filed: May 21, 2004

(65) Prior Publication Data
US 2005/0048069 A1    Mar. 3, 2005

Related U.S. Application Data

(60) Continuation-in-part of application No. 09/948,725, filed on Sep. 10, 2001, now Pat. No. 6,984,625, which is a continuation-in-part of application No. 09/917,278, filed on Jul. 30, 2001, now Pat. No. 6,955,811, which is a continuation-in-part of application No. 09/934,634, filed on Aug. 23, 2001, now Pat. No. 6,749,854, said application No. 09/948,725 is a continuation-in-part of application No. 09/570,367, filed on May 5, 2000, now Pat. No. 6,338,851, said application No. 09/917,278 is a continuation-in-part of application No. 09/570,367, filed on May 5, 2000, now Pat. No. 6,338,851, which is a division of application No. 09/934,634, which is a continuation-in-part of application No. 09/570,367, filed on May 5, 2000, now Pat. No. 6,338,851, which is a continuation of application No. PCT/CA98/01038, filed on Nov. 6, 1998.

(60) Provisional application No. 60/064,764, filed on Nov. 7, 1997, provisional application No. 60/222,725, filed on Aug. 3, 2000.

(51) Int. Cl.
A61K 38/17 (2006.01)
C07K 14/47 (2006.01)

(52) U.S. Cl. .............................. 514/2; 514/12; 514/21; 530/350

(58) Field of Classification Search ..................... None
See application file for complete search history.

(56) References Cited

U.S. PATENT DOCUMENTS

| 5,434,131 | A | 7/1995 | Linsley et al. |
| 5,916,560 | A | 6/1999 | Larsen et al. |
| 6,338,851 | B1* | 1/2002 | Gorczynski ............... 424/185.1 |
| 2002/0192215 | A1* | 12/2002 | Hoek et al. ............... 424/144.1 |
| 2004/0018972 | A1* | 1/2004 | Gorczynski et al. ........... 514/12 |
| 2004/0054145 | A1* | 3/2004 | Gorczynski ................. 530/350 |
| 2005/0107314 | A1* | 5/2005 | Gorczynski et al. ........... 514/44 |

FOREIGN PATENT DOCUMENTS

WO    WO 97/21450    *  6/1997
WO    WO 99/24565       5/1999

OTHER PUBLICATIONS

Heaney et al., Lancet, 2005, 365: 974-976.*
Romagnani, Clin. Immunol. Immunopathol. 1996; 80(3):225-235.*
Steinman, Neuron, 1999; 24:511-514.*
Gorczynski, Current Opinion in Investigational Drugs, 2005, 6: 483-488.*
Borriello et al., J. Immunol. 158:4548-4554, 1997.*
Gorczynski et al., 2004, Transplantation, 77: 1138-1144.*
Tetlow et al., 1995, Ann. Rheum. Dis., 54: 549-555.*
Ibrahim et al., 1996, J. Neuroimmunol., 70: 131-138.*
Williams et al., 2000, J. Allergy Clin. Immunol., 105: 847-859.*
Zhang et al., 2004, J. Immunol., 173: 6786-6793.*
Chervinski et al., 2005, J. Immunol., 174: 1348-1356.*
Shiratori et al., 2005, J. Immunol., 175: 4441-4449.*
Auchincloss, H., Jr. 1995 Transplantation Immunology, 211-218.
Bach, 1993, Immunol. Today, 14(6):322-326.
Barclay, 1981, Immunology, 44, pp. 727-736.
Barclay and Ward, 1982, European Journal Biochem, 129, pp. 447-458.
Bohen, S.P., 2003, PNAS, vol. 100, No. 4, 1926-193.
Boon, 1992, Adv. Cancer Res. 58:177-210.
Borriello, F. et al., 1998, Mammalian Genome, Feb., 9(2), pp. 114-118.
Borriello, F. et al., 1997, J. Immunol, 158, pp. 4548-4554.
Broderick, C., 2002, Am. J. of Pathology, vol. 161, No. 5 p. 1669-1677.
Clark, D.A., 1994, Am. J. or Reproductive Immunology, 32:290-293.
Clark, D.A. et al., 1999, Amer. Soc. For Reproductive Medicine, 55th Annual Meeting.
Clark, D.A. et al., 2000, Amer. Soc. Reprod. Immunol. 43:326.
Clark, D.A. et al., 2000, 6th Congress of the Adria-Alps Soc. of Immunol. of Reprod.
Clark, D.A. et al., 2001, Mol. Human Reprod. 7:185-194.
Chen, Z et al., Database Medline, 1997, Biochimica et Biophysica Acta, Nov. 28, 1362(1), pp. 6-10.
Cohen, P.L., 1999, "Systemic Autoimmunity" in Fundamental Immunology, Fourth edition, W.E. Paul, Editor, Lippincott-Raven Publishers, Philadelphia 1999, Ch. 33, p. 1067-1088.
Dick, A.D., 3003, J. of Leukocyte Bio. vol. 74, p. 161-166.
Gorczynski, R.M. et al., 1998, Transplantation, Apr. 27, 65(8), pp. 1106-1114.

(Continued)

Primary Examiner—Philip Gambel
Assistant Examiner—Ilia Ouspenski
(74) Attorney, Agent, or Firm—Bereskin & Parr; Micheline Gravelle

(57) ABSTRACT

Methods and compositions for inducing immune suppression are disclosed. The methods involve administering an effective amount of a CD200 protein or a nucleic acid encoding a CD200 protein. The methods are useful in preventing graft rejection, fetal loss, autoimmune disease, and allergies. Methods and compositions for preventing immune suppression are also disclosed. The methods involve administering an effective amount of an agent that inhibits CD200. Such methods are useful in treating cancer.

7 Claims, 41 Drawing Sheets

OTHER PUBLICATIONS

Gorczynski, R.M. et al., 1999, J. Immunol, 163:1654-1660.
Gorczynski, R.M. et al., 2001, Graft:4:338-345.
Hoek, R.M., 2000, Science, vol. 290, p. 1768-1771.
Huang, 2000, Pharmacol. Therapeutics, 86:201-215.
Jain, 1998, Nature Medicine, 4(6):655-657.
Keil, A. et al., 2001, Amer. J. Reprod. Immunol., 45:343.
Kim et al., 2001, Cancer Res. 61:2031-2037.
Kjaergaard, et al. 2000, Cancer Res. 60:5514-5521.
Ni, J. et al., 1999, FASEB Journal, vol. 13, No. 5, p. A983.
Pardoll, 2000, Clin. Immunol. 95(1):S44-S62.
Preston, S. et al., 1997, European Journal of Immunology, vol. 27, No. 8, pp. 1911-1918.
Ragheb, R. et al., 1999. Immunol. Letters, vol. 68, No. 2-3, 311-315.
Romagnani, 1996, Clin. Immunol. Immunopath, 80(3):225-235.
Rosenwald, A., 2001. J. of Exp. Med. vol. 194, No. 11, 1639-1647.
Steinman, Lawrence, 1999 Neuron, vol. 24, 511-514.
Tangri, S. and Raghupathy, R., 1993, Biology of Reproduction 49, 850-856.
Toder, V. et al., 1991, Am. J. of Reproductive Immunology, 26:42-46.

* cited by examiner

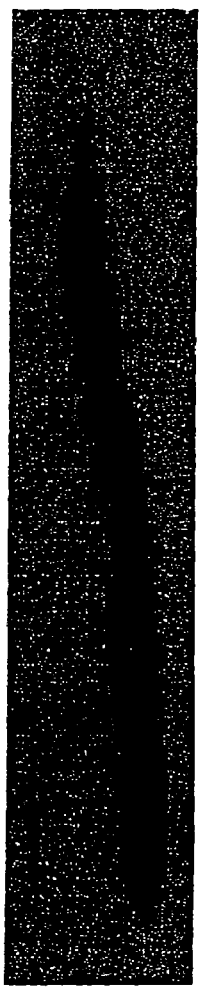
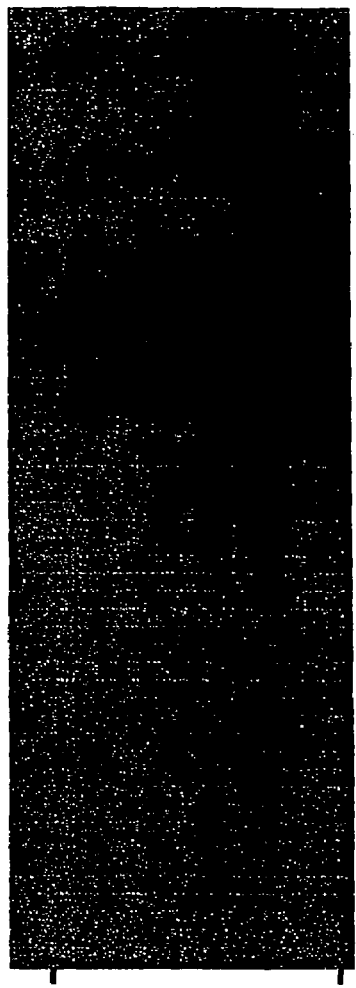
FIGURE 5A
FIGURE 5B

FIGURE 7

```
        Leader ----------
RAT     ATGGGCAGTCCGGTATTCAGGAGACCTTTCTGCCATCTGTCCACCTACAGCCTGCTCTGGGCCATAG    67
MOU     -----------T-------------------------C----------------A-T----G-----    67
HUM             --GA------TG--C----CT---------T-----------G-T----T---G-      55
                         |V-like domain -----------
RAT     CAGCAGTAGCGCTGAGCACAGCTCAAGTGGAAGTGGTGACCCAGGATGAAAGAAAGCTGCTGCACAC   134
MOU     ----------------------------------------------------------GC-------   134
HUM     --------G-T----T-------A------C------------------------A----T----   122

RAT     AACTGCATCCTTACGCTGTTCTCTAAAAACAACCCAGGAACCCTTGATTGTGACATGGCAGAAAAAG   201
MOU     ----------------A---------------T----------------------------------   201
HUM     ------T-------AAA-C-----GC----ATG---------G--C-C------------------   189

RAT     AAAGCCGTAGGCCCAGAAAACATGGTCACTTACAGCAAAGCCCATGGGGTTGTCATTCAGCCCACCT   268
MOU     ---------GA---------------C---------A--------------A--C-----TG---   268
HUM     -----T---A--------------------C-T----G-GAA---------G--G--C-----TG---   256

RAT     ACAAAGACAGGATAAACATCACTGAGCTGGGACTCTTGAACACAAGCATCACCTTCTGGAACACAAC   335
MOU     ----------------TG----A-------------G----T-----------------------CA   335
HUM     -T--G----A----------T--CC----------C-A---T---C----------------T-TC--   323

RAT     CCTGGATGATGAGGGTTGCTACATGTGTCTCTTCAACATGTTTGGATCTGGGAAGGTCTCTGGGACA   402
MOU     -A-T-GA----GA---C---------------------C------T---CA---------A--A---   402
HUM     ------G-----A--G--T--------------T-CC-----T-T------------A--A--G    390
                        |C-like domain ----------
RAT     GCTTGCCTTACTCTCTATGTACAGCCCATAGTACACCTTCACTACAACTATTTTGAAGACCACCTAA   469
MOU     --------------------------------------------------------C---------   469
HUM     --C-----C--CG--------------------TC------------A-TC-C--------------   457

RAT     ACATCACGTGCTCTGCAACTGCCCGCCCAGCCCCTGCCATCTCCTGGAAGGGCACTGGGTCAGGAAT   536
MOU     -------T---------G--------T----------------A-----------T------A-------   536
HUM     -T-----T---------C-----------------CATGG---T---------T-C-C----------   524

RAT     TGAGAATAGTACTGAGAGTCACTCCCATTCAAATGGGACTACATCTGTCACCAGCATCCTCCGGGTC   603
MOU     ------------C---------T-------------------------------------------   603
HUM     ---A---------A-T--C--TG--T--CC----------C--G-----T------------ATA--   591

RAT     AAAGACCCCAAAACTCAGGTTGGAAAGGAAGTGATCTGCCAGGTTTTATACTTGGGGAATGTGATTG   670
MOU     -----------------------------------------------------------------   670
HUM     --------T--G-A------G--G----------------------GC-GC--C------C-----CC-   658
                        |Transmembrane region ---------
RAT     ACTACAAGCAGAGTCTGGACAAAGGATTTTGGTTTTCAGTCCCACTGCTGCTGAGCATTGTTTCTCT   737
MOU     ------------------------------------------T------T----A----------   737
HUM     ---TT-----A-CCG-CA--------C-A------------T--G--AT----A-----------C--   725
                                                |Cytoplasmic region ---------
RAT     GGTAATTCTTCTGGTCTTGATCTCCATCTTATTATACTGGAAACGGCACCGAAATCAGGAGCGGGGT   804
MOU     ------------A---------------C---------T--------------------------   804
HUM     ------------C---C-A-----A-------C-G------------T-----G--------C--A---   792

RAT     GAGTCATCACAGGGGATGCAAAGAATGAAATAA                                    837
MOU     --A------------------------------                                    837
HUM     ----TG--------AG-T----A-----C----                                    825
```

FIGURE 8

```
        Leader sequence ———
        -30                                                              -1
RAT     M G S P V F R R P F C H L S T Y S L L W A I A A V A L S T A
MOU     - - - - - L - - - - - - - - - - - - - - - - - I - - - G - - - - - - - - - - - - - - -
HUM           - I — M - - - - S - - - - - - - - - - - - - - V - - - V M - - - - - - V - - C - - - -

|V-like domain (domain I) ———                   *
RAT     Q V E V V T Q D E R K L L H T T A S L R C S L K T T Q E P L
MOU     - - - - - - - - - - - - - - - - — A - - - - - - - - - - - - - - - - - - - - - - S - - - - - - - - -
HUM     - - - - Q - - - - - - - - - - - - - E - - - - Y - - - - - - - - - - — K - - - - - Q N A - - - - A - -

31                            **
RAT     I V T W Q K K K A V G P E N M V T Y S K A H G V V I Q P T Y
MOU     - - - - - - - - - - - - - - - - - - - S - - - - - - - - - - - - - - - T - - - - - - - - - - - - - - A - -
HUM     - - - - - - - - - - - - - - - - - - - - - - - - - - - - - - E N - - - - - - - - - - - - - - - - - -

61        **            **                **
RAT     K D R I N I T E L G L L N T S I T F W N T T L D D G G C Y M
MOU     - - - - - - - - - V - - - - - - - - - W - - S - - - - — - - - - - - H I G - - - - - - - - - - - -
HUM     - - - - K - - - - - - - Q - - - - - - Q - - - - T - - - - - - - - - - — I - - - - E - - - - - - - - - - - - -

91*    **                              | C-like domain ( domain II ) ———
RAT     C L F N M F G S G K V S G T A C L T L Y V Q P I V H L H Y N
MOU     - - - - - - - - - T - - - - - - - Q - - - - - - - - - - - - - - - - - - - - - - - - - - - - - - - - -
HUM     - - - - - - - - - - - - — F G - - - I - - - - - - - - - - V - - - - - - - - - - - - - - - - S - - - - - - K 121                            **    *
RAT     Y F E H H L N I T C S A T A R P A P A I S W K G T G S G I E
MOU     - - - - - - - - - - - - - - - - - - - - - - - - - - - - - - - - - - - - T - - - - - - - - - - - T - - - - -
HUM     F S - - - - - - - - - - - - - - - - - - - - - - - - - - - - M V F - - - - - V P R - - - - - - - —

151**
RAT     N S T E S H S H S N G T T S V T S I L R V K D P K T Q V G K
MOU     - - - - - - - - - - - F - - - - - - - - - - - - - - - - - - - - - - - - - - - - - - - - - - - - - - - -
HUM     - - - - - - V T L S - - P - - - - - - - - - - - - - - - - - H I - - - - - - - - - N - - - - - - - -

181              *                              |Transmembrane region ———
RAT     E V I C Q V L Y L G N V I D Y K Q S L D K G F W F S V P L L
MOU     - - - - - - - - - - - - - - - - - - - - - - - - - - - - - - - - - - - - - - - - - - - - - - - - - - - - -
HUM     - - - - - - - - - - - - H - - - - T - - T - - - F - - - - T V N - - - - Y - - - - - - - - - - - - - -

211                                          | Cytoplasmic region ———
RAT     L S I V S L V I L L V L I S I L L Y W K R H R N Q E R G E S
MOU     - - - - - - - - - - - - - - - - - I - - - - - - - - - - - - - - - - - - - - - - - - - - - - - - -
HUM     - - - - - - - - - - - - - - - - - - V - - - - - - - - - - - - - - - - - - - - - - - - - - D - - - - - - - L 241
RAT     S Q G M Q R M K
MOU     - - - - - - - - - - - - - - - - -
HUM     - - - - - - V - - K - - - T
```

* invariant cysteine residues:   ** invariant asparagine (N-linked oligosaccharides)

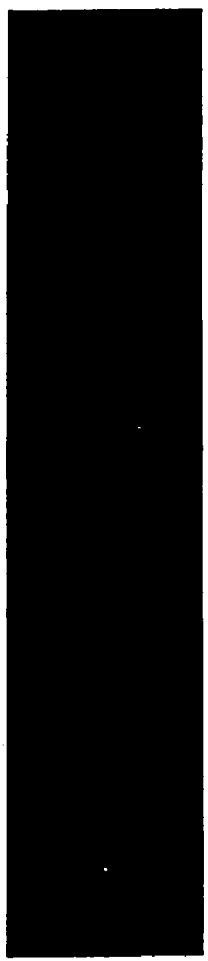
FIGURE 12

CD200Fc inhibits collagen induced arthritis in DBA/1 mice

FIGURE 34A and B

FIGURE 35A and B

FIGURE 36A and B

FIGURE 39
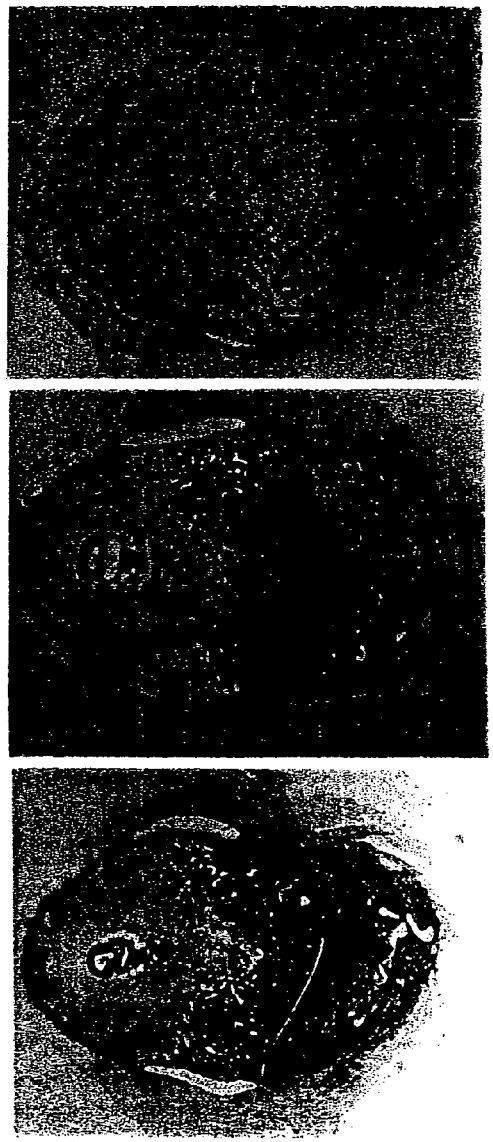
FGL 2
OX-2

FIGURE 40
EXPRESSION OF OX-2 ON CYTOKERATIN-POSITIVE CELLS (TROPHOBLAST)
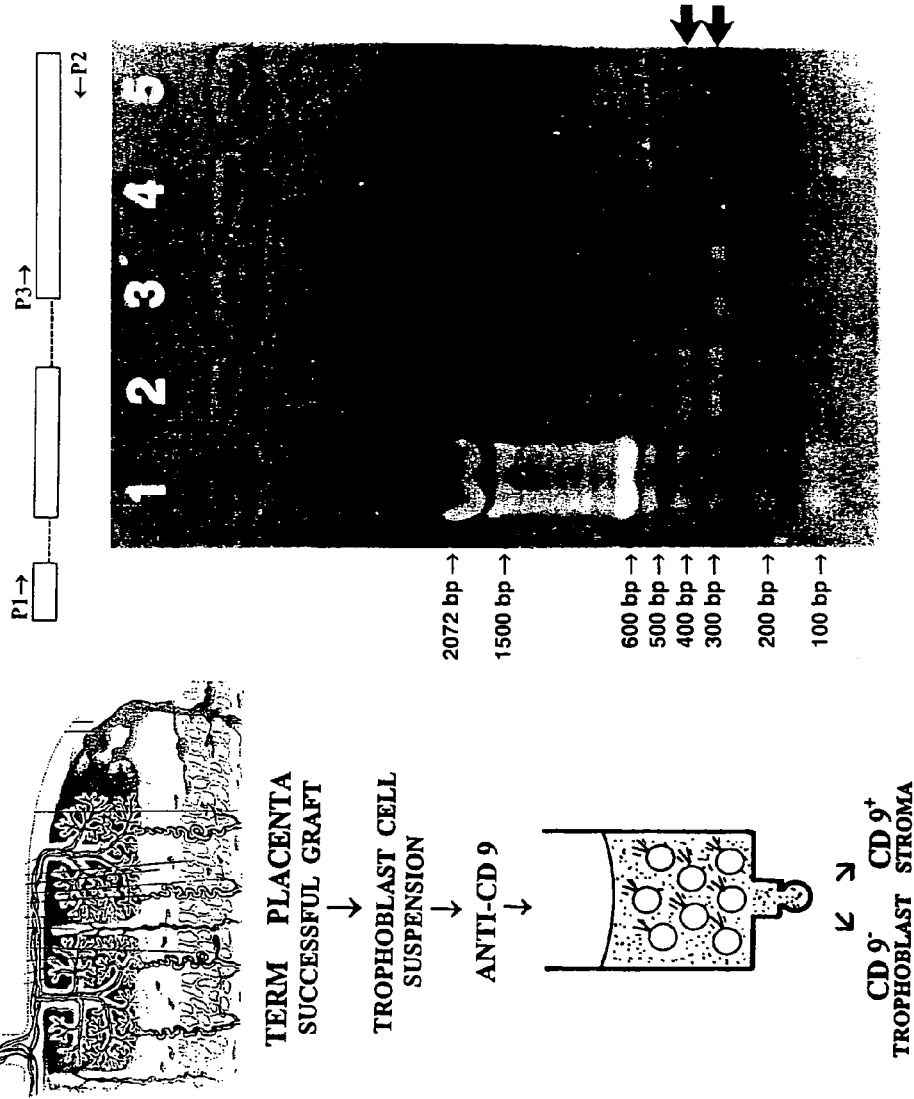
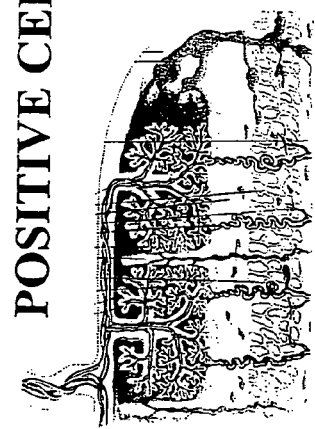

EXPRESSION OF OX-2 ON CYTOKERATIN-POSITIVE CELLS (TROPHOBLAST)

METHODS OF TREATING ALLERGY BY ADMINISTERING A CD200 PROTEIN

This application is a continuation-in-part of (1) U.S. patent application Ser. No. 09/948,725 filed Sep. 10, 2001 (now U.S. Pat. No. 6,984,625); (2) U.S. patent application Ser. No. 09/917,278 filed Jul. 30, 2001 (now U.S. Pat. No. 6,955,811); and (3) U.S. patent application Ser. No. 09/934,634 filed Aug. 23, 2001 (now U.S. Pat. No. 6,749,854), each of which are a continuation-in-part of U.S. application Ser. No. 09/570,367 filed May 5, 2000 (now U.S. Pat. No. 6,338,851) which is a continuation of PCT/CA98/01038 filed Nov. 6, 1998 (which designated the U.S.) which claims the benefit of U.S. provisional application Ser. No. 60/064,764 filed Nov. 7, 1997(now abandoned). U.S. patent application Ser. No. 09/917,278 also claimed the benefit of U.S. provisional Ser. No. 60/222,725 filed Aug. 3, 2000(now abandoned). All of the prior applications are incorporated herein by reference in their entirety.

FIELD OF THE INVENTION

The present invention relates to methods and compositions for modulating an immune response. The invention includes the use of the protein CD200 to suppress an immune response and the use of an agent that inhibits CD200 to prevent immune suppression.

BACKGROUND OF THE INVENTION

The immune system protects the body from infectious agents and disease and is critical to our survival. However, in certain instances, the immune system can be the cause of illness. One example is in autoimmune disease wherein the immune system attacks its own host tissues, in many instances causing debilitating illness and sometimes resulting in death. Examples of autoimmune diseases include multiple sclerosis, type 1 insulin-dependent diabetes mellitus, lupus erythematosus and arthritis. A second example where the immune system can cause illness is during tissue or organ transplantation. Except in the cases of genetically identical animals, such as monozygotic twins, tissue and organ transplants are rejected by the recipient's immune system as foreign. The immune reaction against transplants is even more pronounced in transplantation across species or xenotransplantation. A third example where the immune system harms the host is during an allergic reaction where the immune system is activated by a generally innocuous antigen causing inflammation and in some cases tissue damage.

In order to inhibit the detrimental immune reactions during transplantation, autoimmune disease and allergic reactions, immunosuppressive drugs (such as cyclosporin A, tacrolimus, and corticosteroids) or antibody therapies (such as anti-T cell antibodies) are generally administered. Unfortunately, these non-specific modes of immunosuppression generally have undesirable side effects. For example, cyclosporin may cause decreased renal function, hypertension, toxicity and it must be administered for the life of the patient. Corticosteroids may cause decreased resistance to infection, painful arthritis, osteoporosis and cataracts. The anti-T cell antibodies may cause fever, hypertension, diarrhea or sterile meningitis and are quite expensive.

In view of the problems associated with immunosuppression, there has been an interest in developing methods or therapies that induce unresponsiveness or tolerance in the host to a transplant, to "self" tissues in autoimmune disease and to harmless antigens associated with allergies. The inventor has been studying the mechanisms involved in transplant rejection and has developed methods for inducing a state of antigen-specific immunological tolerance in transplantation. In particular, in animal allograft models, the inventor has demonstrated that graft survival can been increased if the recipient animal is given a pre-transplant infusion via the portal vein of irradiated spleen cells from the donor animal. In contrast, a pre-transplant infusion via the tail vein does not prolong graft survival.

Understanding the molecular mechanisms involved in the induction of tolerance following portal-venous (pv) immunization may lead to the development of methods of inducing immune tolerance that may be useful in transplant, autoimmune disease and allergies.

SUMMARY OF THE INVENTION

The present inventors have shown that CD200, a molecule with previously unknown function belonging to the Ig superfamily, is an immune suppressant. The inventors have shown that administering antibodies to CD200 inhibited the graft survival generally seen following pre-transplant pv immunization. The inventors have also shown that there is a negative association between levels of CD200 and the risk of fetal loss. In particular, the inventors have shown administering CD200 reduced fetal loss rates while inhibiting CD200 reversed the effect. The inventors have also shown that administering CD200 inhibits the development of autoimmune diseases such as arthritis. The inventors have further shown that CD200 inhibits cytotoxic cells and IL-2 production and induces IL-4 production. The inventors have also shown that CD200 is responsible for promoting tumor metastases and inhibiting CD200 reduces tumor cell growth. All of these results demonstrate that CD200 is involved in immune suppression.

Consequently, in one aspect, the present invention provides a method of suppressing an immune response comprising administering an effective amount of a CD200 protein, or a fragment thereof, or a nucleic acid sequence encoding a CD200 protein, or a fragment thereof, to an animal in need of such treatment.

In one embodiment, the present invention provides a method of preventing or inhibiting an autoimmune disease comprising administering an effective amount of a CD200 protein or a nucleic acid sequence encoding a CD200 protein to an animal in need thereof.

In another embodiment, the present invention provides a method of preventing or inhibiting fetal loss comprising administering an effective amount of a CD200 protein or a nucleic acid sequence encoding a CD200 protein to an animal in need thereof.

In a further embodiment, the present invention provides a method of inducing tumor cell growth or metastases comprising administering an effective amount of a CD200 protein or a nucleic acid sequence encoding a CD200 protein to an animal in need thereof.

In another embodiment, the present invention provides a method of suppressing an immune response to a transplanted organ, tissue or cell comprising administering an effective amount of a CD200 protein or a nucleic acid sequence encoding a CD200 protein to an animal in need thereof.

In yet another embodiment, the present invention provides a method of preventing or inhibiting allergy comprising administering an effective amount of a CD200 protein or a nucleic acid sequence encoding a CD200 protein to an animal in need thereof.

The invention also includes pharmaceutical compositions containing CD200 proteins or nucleic acids encoding CD200 proteins for use in suppressing an immune response.

The inventors have shown that inhibiting CD200 is useful in preventing immune suppression and is useful in treating cancer and inducing fetal loss.

Therefore, in another aspect, the present invention provides a method of preventing immune suppression or inducing an immune response comprising administering an effective amount of an agent that inhibits CD200 to an animal in need thereof. In a preferred embodiment the CD200 inhibitor is an antibody that binds CD200 or an antisense oligonucleotide that inhibits the expression of CD200.

In one embodiment, the present invention provides a method of inhibiting the growth of a tumor cell comprising administering an effective amount of an agent that inhibits CD200 to a cell or animal in need thereof.

In another embodiment, the present invention provides a method of inducing fetal loss comprising administering an effective amount of an agent that inhibits CD200 to an animal in need thereof.

The invention also includes pharmaceutical compositions containing a CD200 inhibitor for use in inducing or augmenting an immune response.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIGS. 5A and B are Western Blots illustrating the increased expression of OX-2 antigen after pv immunization. FIG. 5A shows staining with a control mouse antibody, anti-mouse CD8a. FIG. 5B shows staining with anti-rat MRC OX-2.

FIG. 7 shows the cDNA sequence of rat (SEQ ID NO:20), mouse (SEQ ID NO:22) and human MRC OX-2 (SEQ ID NO:18).

FIG. 8 shows the deduced protein sequence of rat (SEQ ID NO:21), mouse (SEQ ID NO:2) and human MRC OX-2 (SEQ ID NO:19) protein.

FIG. 12 shows PCR analysis mRNA expression of B7-1, B7-2 and OX-2 in various hepatic NPMC cell fractions.

FIG. 39 shows the importance of CD200 (OX-2) in rescuing potentially doomed embryos which are low in OX-2 mRNA expression by the in situ hybridisation result.

FIG. 40 shows the molecule size ladder (lane 1), trophoblast with full length primers (lane 2) and exon 3 primers (lane 3). The full length and shorter mRNA OX-2 transcripts are seen. Lane 4 (corresponding to lane 2) and lane 5 (corresponding to lane 3) represent negative result obtained with $CD9^+$ stromal cells.

DETAILED DESCRIPTION OF THE INVENTION

Figure 1:
FIG. 1 illustrates PCR validation of suppressive subtractive hybridization using β-actin primers.

The present inventors have identified genes that show an increase in expression following portal venous immunization. These genes play a role in the development of immune suppression or tolerance and may be useful in developing therapies for the prevention and treatment of transplant rejection, fetal loss, autoimmune disease, allergies and cancer.

Using suppression subtractive hybridization (SSH), the inventor has isolated a clone that is preferentially expressed in mice receiving allogenic renal grafts along with pre-transplant donor-specific immunization and that encodes the protein CD200 (previously known as OX-2). The CD200 protein (also known as MRC CD200 in rat) was described as a 41 Kd-47 Kd glycoprotein which is expressed on the cell surface of thymocytes, follicular dendritic cells and endothelium, B cells and neuronal cells. Differences in apparent size of the molecule in different tissues is probably a function of differential glycosylation. The function of the molecule was previously unknown, but DNA and amino acid sequence analysis shows it has a high degree of homology to molecules of the immunoglobulin gene family, which includes molecules important in lymphocyte antigen recognition and cell-cell interaction (e.g. CD4, CD8, ICAMs, VCAMs), as well as adhesion receptor molecules (NCAMs) in the nervous system. Members of the immunoglobulin superfamily are distinct from other molecules of the integrin and selectin families, which, at least within the immune system, also seem to play critical role in cell recognition, migration and even development of the lymphocyte recognition repertoire (by regulating intra-thymic selection events). It has become increasingly evident that molecules of these different families play an important role in human disease.

The inventor has shown that administering antibodies to CD200 inhibited the graft survival generally seen following pre-transplant pv immunization. The inventors have also shown that administering CD200 inhibits autoimmune disease. The inventors have further shown that there is negative association between levels of CD200 and risk of fetal loss and that administering CD200 prevents fetal loss and inhibiting CD200 causes fetal loss. The inventors have further shown that CD200 inhibits cytotoxic cells and IL-2 production and induces IL-4 production. The inventors have further shown that CD200 promotes tumor cell growth and inhibiting CD200 inhibits tumor cell growth. The data supports the role of CD200 in immune suppression.

A. Therapeutic Methods

1. Inducing Immune Suppression

In one aspect, the present invention provides a method of suppressing an immune response comprising administering an effective amount of a CD200 protein or a nucleic acid sequence encoding a CD200 protein to an animal in need of such treatment. The invention includes a use of an effective amount of a CD200 protein or a nucleic acid sequence encoding a CD200 protein to suppress an immune response.

The term "CD200 protein" includes CD200 from any species or source and includes a full length CD200 protein as well as fragments or portions of the protein. The term "CD200" was previously referred to as "OX-2" although there has been a change in nomenclature. Both "CD200" and "OX-2" may be used interchangeably in the application. Preferred fragments or portions of the CD200 or OX-2 protein are those that are sufficient to suppress an immune response. Determining whether a particular CD200 protein or fragments thereof can suppress an immune response can be assessing using known in vitro immune assays including, but not limited to, inhibiting a mixed leucocyte reaction; inhibiting a cytotoxic T cell response; inhibiting interleukin-2 production; inhibiting IFNγ production; inhibiting a Th1 cytokine profile; inducing IL-4 production; inducing TGFβ production; inducing IL-10 production; inducing a Th2 cytokine profile; inhibiting immunoglobulin production; altering serum immunoglobulin isotype profiles (from those associated with Th1 type immunity-in the mouse, IgG1 and IgG2a, to those associated with Th2 type immunity-in the mouse, IgG2b, IgG3); and any other assay that would be known to one of skill in the art to be useful in detecting immune suppression.

The term "administering a CD200 protein" includes both the administration of the CD200 protein as well as the administration of a nucleic acid sequence encoding a CD200 protein. In the latter case, the CD200 protein is produced in vivo in the animal.

In a preferred embodiment, the CD200 protein is prepared and administered as a soluble fusion protein. The fusion protein may contain the extracellular domain of CD200 linked to an immunoglobulin (Ig) Fc Region. The CD200 fusion may be prepared using techniques known in the art. Generally, a DNA sequence encoding the extracellular domain of CD200 is linked to a DNA sequence encoding the Fc of the Ig and expressed in an appropriate expression system where the CD200—FcIg fusion protein is produced.

The CD200 protein may be obtained from known sources or prepared using recombinant DNA techniques. The protein may have any of the known published sequences for Cb200 or OX-2. The sequences can be obtained from GenBank. The human sequence has accession no. M17226 X0523; the rat sequence has accession no. X01785; and the mouse sequence has accession no. AF029214. The nucleic acid and protein sequences of CD200 (OX-2) from human, mouse and rat are also shown in FIGS. 7 and 8 and in SEQ ID Nos:18, 22 and 20 (nucleic acid) and SEQ ID Nos:19, 21 and 2 (protein).

The CD200 protein may also be modified to contain amino acid substitutions, insertions and/or deletions that do not alter the immunosuppressive properties of the protein. Conserved amino acid substitutions involve replacing one or more amino acids of the CD200 amino acid sequence with amino acids of similar charge, size, and/or hydrophobicity characteristics. When only conserved substitutions are made the resulting analog should be functionally equivalent to the CD200 protein. Non-conserved substitutions involve replacing one or more amino acids of the CD200 amino acid sequence with one or more amino acids which possess dissimilar charge, size, and/or hydrophobicity characteristics.

The CD200 protein may be modified to make it more therapeutically effective or suitable. For example, the CD200 protein may be cyclized as cyclization allows a peptide to assume a more favourable conformation. Cyclization of the CD200 peptides may be achieved using techniques known in the art. In particular, disulphide bonds may be formed between two appropriately spaced components having free sulfhydryl groups. The bonds may be formed between side chains of amino acids, non-amino acid components or a combination of the two. In addition, the CD200 protein or peptides of the present invention may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and tolunesulphonic acids.

Administration of an "effective amount" of the CD200 protein and nucleic acid of the present invention is defined as an amount effective, at dosages and for periods of time necessary to achieve the desired result. The effective amount of the CD200 protein or nucleic acid of the invention may vary according to factors such as the disease state, age, sex, and weight of the animal. Dosage regima may be adjusted to provide the optimum therapeutic response. For example, several divided doses may be administered daily or the dose may be proportionally reduced as indicated by the exigencies of the therapeutic situation.

The term "animal" as used herein includes all members of the animal kingdom including humans.

(i) Autoimmune Disease

As stated previously, the method of the present invention may be used to treat or prevent autoimmune disease. In an autoimmune disease, the immune system of the host fails to recognize a particular antigen as "self" and an immune reaction is mounted against the host's tissues expressing the antigen. Normally, the immune system is tolerant to its own host's tissues and autoimmunity can be thought of as a breakdown in the immune tolerance system.

Accordingly, in a further embodiment, the present invention provides a method of preventing or treating an autoimmune disease comprising administering an effective amount of a CD200 protein or fragment thereof, or a nucleic acid sequence encoding a CD200 protein or fragment thereof to an animal having, suspected of having, or susceptible to having an autoimmune disease. The invention includes a use of an effective amount of a CD200 protein on a nucleic acid molecule encoding a CD200 protein to prevent or inhibit an autoimmune disease.

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treating" can also mean prolonging survival as compared to expected survival if not receiving treatment.

Autoimmune diseases that may be treated or prevented according to the present invention include, but are not limited to, arthritis, type 1 insulin-dependent diabetes mellitus, adult respiratory distress syndrome, inflammatory bowel disease, dermatitis, meningitis, thrombotic thrombocytopenic purpura, Sjögren's syndrome, encephalitis, uveitis, leukocyte adhesion deficiency, rheumatoid arthritis, rheumatic fever, Reiter's syndrome, psoriatic arthritis, progressive systemic sclerosis, primary biliary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, autoimmune haemolytic anemia, Hashimoto's thyroiditis, Graves disease, habitual spontaneous abortions, Reynard's syndrome, glomerulonephritis, dermatomyositis, chronic active hepatitis, celiac disease, tissue specific autoimmunity, degenerative autoimmunity delayed hypersensitivities, autoimmune complications of AIDS, atrophic gastritis, ankylosing spondylitis and Addison's disease.

One of skill in the art can determine whether or not a particular CD200 or fragment thereof is useful in preventing autoimmune disease. As mentioned previously, one of skill in the art can readily test a CD200 or CD200 fragment for its ability to suppress an immune response using known in vitro assays. In addition the CD200 or CD200 fragment can also be tested for its ability to prevent autoimmune in an animal model. For example, one could use the model described in Example 8 wherein the ability of CD200 to prevent collagen induced arthritis is assessed. Further, many other autoimmune animal models are available, including, but not limited to, experimental allergic encephalomyelitis which is an animal model for multiple sclerosis, animal models of inflammatory bowel disease (induced by immunization, or developing in cytokine-knockout mice), and models of autoimmune myocarditis and inflammatory eye disease.

(ii) Fertility

The present inventors have shown that there is an association between levels of CD200 expression and fertility. In particular the inventor has shown that low levels (or no levels) of CD200 is related to fetal loss. Further, administering a CD200:Fc fusion protein prevented fetal loss.

Accordingly, the present invention provides a method of preventing, reducing or inhibiting fetal loss comprising administering an effective amount of a CD200 protein or a nucleic acid sequence encoding a CD200 protein to an animal in need thereof. The invention includes a use of an effective amount of a CD200 protein on a nucleic acid molecules encoding a CD200 protein to prevent or inhibit fetal loss. The CD200 protein may be from any species and may be the full length sequence or a fragment thereof that is capable of preventing or inhibiting fetal loss.

One of skill in the art can determine whether or not a particular CD200 or fragment thereof is useful in preventing fetal loss. As mentioned above, one of skill in the art can readily test a CD200 or CD200 fragment for its ability to suppress an immune response using known in vitro assays. In addition the CD200 or CD200 fragment can also be tested for its ability to prevent fetal loss in an animal model. For example, one could use the model described in Example 14 wherein the ability of CD200 to prevent cytokine induced abortion in abortion-prone CBA×DBA/2 mice is assessed. Further, mice pre-immunized with anti-phospholipid may also be used.

(iii) Graft Rejection

In another embodiment, the present invention provides a method of suppressing an immune response to a transplanted organ, cell or tissue in a recipient animal comprising administering an effective amount of a CD200 protein or a nucleic acid sequence encoding a CD200 protein to the recipient animal, preferably prior to the transplantation of the organ or tissue. The invention includes a use of an effective amount of a CD200 protein or a nucleic acid sequence encoding a CD200 protein to suppress an immune response to a transplanted organ, cell or tissue.

The recipient can be any member of the animal kingdom including rodents, pigs, cats, dogs, ruminants, non-human primates and preferably humans. The organ, cell or tissue to be transplanted can be from the same species as the recipient (allograft) or can be from another species (xenograft). The tissues, cells or organs can be any tissue or organ including heart, liver, kidney, lung, pancreas, pancreatic islets, brain tissue, cornea, bone, intestine, skin and haematopoietic cells and stem cells.

One of skill in the art can determine whether or not a particular CD200 or fragment thereof is useful in preventing graft rejection. As mentioned above, one of skill in the art can readily test a CD200 or CD200 fragment for its ability to suppress an immune response using known in vitro assays. In addition the CD200 or CD200 fragment can also be tested for its ability to prevent graft rejection in an animal model. For example, one could use the animal models described in Examples 3 to 6.

The method of the invention may be used to prevent graft versus host disease wherein the immune cells in the transplant mount an immune attack on the recipient's immune system. This can occur when the tissue to be transplanted contains immune cells such as when bone marrow or lymphoid tissue is transplanted when treating leukemias, aplastic anemias and. enzyme or immune deficiencies, for example.

Accordingly, in another embodiment, the present invention provides a method of preventing or inhibiting graft versus host disease in a recipient animal receiving an organ or tissue transplant comprising administering an effective amount of a CD200 protein or a nucleic acid sequence encoding a CD200 protein to the organ or tissue prior to the transplantation in the recipient animal. The invention includes a use of an effective amount of a CD200 protein or a nucleic acid molecule encoding a CD200 protein to prevent or inhibit graft versus host disease.

(iv) Allergy

As stated previously, the method of the present invention may also be used to treat or prevent an allergic reaction. In an allergic reaction, the immune system mounts an attack against a generally harmless, innocuous antigen or allergen. Allergies that may be prevented or treated using the methods of the invention include, but are not limited to, hay fever, asthma, atopic eczema as well as allergies to poison oak and ivy, house dust mites, bee pollen, nuts, shellfish, penicillin and numerous others.

Accordingly, in a further embodiment, the present invention provides a method of preventing or treating an allergy comprising administering an effective amount of a CD200 protein or a nucleic acid sequence encoding a CD200 protein to an animal having or suspected of having an allergy. The invention includes a use of an effective amount of a CD200 protein or a nucleic acid molecule encoding a CD200 protein to prevent or treat an allergy.

One of skill in the art can determine whether or not a particular CD200 or fragment thereof is useful in preventing allergy. As mentioned above, one of skill in the art can readily test a CD200 or CD200 fragment for its ability to suppress an immune response using known in vitro assays. In addition the CD200 or CD200 fragment can also be tested for its ability to prevent allergy in an animal model.

2. Preventing Immune Suppression

In another aspect, the present invention provides a method of preventing immune suppression or inducing or augmenting an immune response comprising administering an effective amount of an agent that inhibits CD200 to an animal in need thereof.

There are a large number of situations whereby it is desirable to prevent immune suppression including, but not limited to, the treatment of infections, cancer and Acquired Immune Deficiency Syndrome and the induction of fetal loss. One may also wish to induce an autoimmune reaction to develop an animal model for treating or studying autoimmune disease.

The agent that inhibits CD200 can be any agent that decreases the expression or activity of a CD200 protein such that the immune suppression caused by CD200 is reduced, inhibited and/or prevented. The agent that inhibits CD200 can be any agent that decreases the expression or activity of a CD200 protein such that the immune suppression caused by CD200 is reduced, inhibited and/or prevented. Such agents can be selected from agents that inhibit CD200 activity (such as antibodies, CD200 ligands, small molecules), agents that inhibit CD200 expression (such as antisense molecules) or agents that inhibit the interaction of CD200 with its receptor (such as soluble CD200 receptor and antibodies that bind the CD200 receptor). Specific agents that may be used are provided in Section B.

One of skill in the art can readily determine whether or not a particular agent is effective in inhibiting CD200. For example, the agent can be tested in in vitro assays to determine if the function or activity of CD200 is inhibited. The agent can also be tested for its ability to induce an immune response using in vitro immune assays including, but not limited to, enhancing a cytotoxic T cell response; inducing interleukin-2 (IL-2) production; inducing IFNγ production; inducing a Th1 cytokine profile; inhibiting IL-4 production; inhibiting TGFβ production; inhibiting IL-10 production; inhibiting a Th2 cytokine profile and any other assay that would be known to one of skill in the art to be useful in detecting immune activation.

(i) Fetal Loss

In one embodiment, the present invention provides a method of inducing fetal loss comprising administering an effective amount of an agent that inhibits CD200 to an animal in need thereof. The animal is preferably a pregnant female.

One of skill in the art can determine whether a particular agent is useful in inducing fetal loss. As mentioned above, one can test the agent for its ability to induce an immune response using known in vitro assays. In naddition, the agent can be tested in an animal model, for example as described in Example 11, wherein the agent is administered to a pregnant rodent.

(ii) Tumor Growth

The inventors have shown that inhibiting the immune suppression caused by CD200 can be used to treat tumors. The data provided in Example 9 demonstrates that increased expression of CD200 allows a tumor to evade the immune system which results in tumor growth and increased mortality. However, administering antibodies to CD200 to animals having a tumor and increased CD200 levels results in improved tumor immunity, reduced tumor cell growth and improved survival. This was demonstrated with two different types of tumor, an EL4 tumor which is a thymoma and a C1498 tumor which is a myeloid tumor. Therefore, inhibiting CD200 can be used to treat cancers that are treatable by inhibiting or preventing immune suppression caused by CD200.

In another embodiment, the present invention provides a method of inhibiting, preventing or reducing tumor cell growth comprising administering an effective amount of an agent that inhibits CD200 to a cell or an animal in need thereof. Preferably, the animal is an animal with cancer, more preferably human.

One of skill in the art can determine whether a particular agent is useful in inhibiting tumor cell growth, As mentioned above, one can test the agent for its ability to induce an immune response using known in vitro assays. In addition, the agent can be tested in an animal model, for example as described in Examples 9 and 10, wherein the agent is administered to an animal with cancer.

The term "inhibiting or reducing tumor cell growth" means that the agent that inhibits CD200 causes an inhibition or reduction in the growth or metastasis of a tumor as compared to the growth observed in the absence of the agent. The agent may also be used prophylactically to prevent the growth of tumor cells.

The tumor cell can be any type of cancer that is treatable by inhibiting CD200 including, but not limited to, hematopoietic cell cancers (including leukemias and lymphomas), colon cancer, lung cancer, kidney cancer, pancreas cancer, endometrial cancer, thyroid cancer, oral cancer, laryngeal cancer, hepatocellular cancer, bile duct cancer, squamous cell carcinoma, prostate cancer, breast cancer, cervical cancer, colorectal cancer, melanomas. and any other tumors which are antigenic or weakly antigenic. This could include, for example, EBV-induced neoplasms, and neoplasms occurring in immunosuppressed pateints, e.g. transplant patients, AIDS patients, etc.

Once a particular tumor has been identified for treatment, one of skill in the art could determine whether or not it can evade the immune system through the CD200 pathway. In particular, one can immunize an animal with the tumor and determine whether or not it increases CD200 expression as was done for the tumor cells used in Example 9. Further, one can also directly assess the tumor to see if it expresses CD200 using methods that are routine in the art.

B. CD200 Inhibitors

In the above therapeutic methods for preventing immune suppression (or augmenting an immune response), any agent that can inhibit CD200 may be used, some of which are discussed below.

(a) Antibodies

In a preferred embodiment, the agent that inhibits CD200 is a CD200 specific antibody. The present inventor has prepared antibodies to CD200 which are described in Examples 4 and 5. Antibodies to CD200 may also be prepared using techniques known in the art such as those described by Kohler and Milstein, Nature 256, 495 (1975) and in U.S. Pat. Nos. RE 32,011; 4,902,614; 4,543,439; and 4,411,993, which are incorporated herein by reference. (See also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference). Within the context of the present invention, antibodies are understood to include monoclonal antibodies, polyclonal antibodies, antibody fragments (e.g., Fab, and F(ab')$_2$) and recombinantly produced binding partners.

Conventional methods can be used to prepare the antibodies. For example, by using the CD200 protein, polyclonal antisera or monoclonal antibodies can be made using standard methods. A mammal, (e.g., a mouse, hamster, or rabbit) can be immunized with an immunogenic form of the CD200 protein which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)); the EBV-hybridoma technique to produce human monoclonal antibodies (Cole et al. Monoclonal Antibodies in Cancer Therapy (1985) Allen R. Bliss, Inc., pages 77-96); and screening of combinatorial antibody libraries (Huse et al., Science 246, 1275 (1989)). Hybridoma cells can be screened immunochemically for production of antibodies specifically reactive with the CD200 protein and the monoclonal antibodies can be isolated. Therefore, the invention also contemplates hybridoma cells secreting monoclonal antibodies with specificity for CD200.

The term "antibody" as used herein is intended to include fragments thereof which also specifically react with CD200 or a peptide thereof. Antibodies can be fragmented using conventional techniques and the fragments screened for utility in the same manner as described above. For example, F(ab')$_2$ fragments can be generated by treating antibody with pepsin. The resulting F(ab')2 fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes a CD200 protein (See, for example, Morrison et al., Proc. Natl Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with the CD200 as described herein can be further humanized by producing human constant region chimeras, in which parts of the variable regions, particularly the conserved framework regions of the antigen-binding domain, are of human origin and only the hypervariable regions are of non human origin. Such immunoglobulin molecules may be made by techniques known in the art (e.g., Teng et al., Proc. Natl . Acad. Sci. U.S.A., 80, 7308-7312 (1983); Kozbor et al., Immunology Today, 4, 7279 (1983); Olsson et al., Meth. Enzymol., 92, 3-16 (1982); and PCT Publication WO 92/06193 or EP 0239400). Humanized antibodies can also be commercially produced (Scotgen Limited, 2 Holly Road, Twickenham, Middlesex, Great Britain.)

Specific antibodies, or antibody fragments reactive against CD200 may also be generated by screening expression libraries encoding immunoglobulin genes, or portions thereof, expressed in bacteria with peptides produced from nucleic acid molecules of the present invention. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)).

Accordingly, the present invention provides a method of preventing immune suppression or inhibiting, preventing or reducing tumor cell growth comprising administering an effective amount of an antibody that inhibits CD200 to an animal in need thereof. The invention also includes the use of an antibody that inhibits CD200 to prepare a medicament to inhibit, prevent or reduce tumor cell growth.

The present invention further provides a method of inducing fetal loss comprising administering an effective amount of an antibody that inhibits CD200 to an animal in need thereof.

(b) Antisense Oligonucleotides

In another embodiment, the CD200 inhibitor is an antisense oligonucleotide that inhibits the expression of CD200. Antisense oligonucleotides that are complimentary to a nucleic acid sequence from a CD200 gene can be used in the methods of the present invention to inhibit CD200. The present inventor has prepared antisense oligonucleotides to CD200 which are described in Example 3.

Accordingly, the present invention provides a method of preventing immune suppression comprising administering an effective amount of an antisense oligonucleotide that is complimentary to a nucleic acid sequence from a CD200 gene to an animal in need thereof.

In another embodiment, the present invention provides a method of inducing fetal loss or inhibiting tumor cell growth comprising administering an effective amount of an antisense oligonucleotide that is complimentary to a nucleic acid sequence from a CD200 gene to an animal in need thereof.

The term antisense oligonucleotide as used herein means a nucleotide sequence that is complimentary to its target.

In one embodiment of the invention, the present invention provides an antisense oligonucleotide that is complimentary to a nucleic acid molecule having a sequence as shown in FIG. 7 (SEQ ID Nos:18,20,22), wherein T can also be U, or a fragment thereof.

The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucleotide.

The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates, and phosphorodithioates. In an embodiment of the invention there are phosphorothioate bonds links between the four to six 3'-terminus bases. In another embodiment phosphorothioate bonds link all the nucleotides.

The antisense oligonucleotides of the invention may also comprise nucleotide analogs that may be better suited as therapeutic or experimental reagents. An example of an oligonucleotide analogue is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogues have been shown to be resistant to degradation by enzymes and to have extended lives in vivo and in vitro. PNAs also bind stronger to a complimentary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, or a group for improving the pharmacodynamic properties of an antisense oligonucleotide. Antisense oligonucleotides may also have sugar mimetics.

The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

(c) Other CD200 Inhibitors

In addition to antibodies and antisense molecules, other agents that inhibit CD200 may also be used in the present invention.

Accordingly, the present invention also includes the isolation of other ligands or molecules that can bind to CD200 or the CD200 receptor. Biological samples and commercially available libraries may be tested for proteins that bind to CD200 or the CD200 receptor. In addition, antibodies prepared to the CD200 or the CD200 receptor may be used to isolate other peptides with CD200 or CD200 receptor binding affinity. For example, labelled antibodies may be used to probe phage displays libraries or biological samples.

Conditions which permit the formation of protein complexes may be selected having regard to factors such as the nature and amounts of the substance and the protein.

The substance-protein complex, free substance or non-complexed proteins may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, the antibodies, proteins, or substances may be labelled with a detectable substance.

Once potential binding partners have been isolated, screening methods may be designed in order to determine if the molecules that bind to the CD200 peptide or CD200 receptor and are useful in the methods of the present invention.

Therefore, the invention also provides methods for identifying substances which are capable of binding to the CD200. In particular, the methods may be used to identify substances which are capable of binding to and which suppress the effects of CD200. Accordingly the invention provides a method of identifying substances which bind with CD200, comprising the steps of:

(a) reacting CD200 and a substance, under conditions which allow for formation of a complex, and (b) assaying for complexes, for free substance, and for non complexed CD200.

Substances which can bind with the CD200 of the invention may be identified by reacting CD200 with a substance which potentially binds to the CD200, and assaying for complexes, for free substance, or for non-complexed CD200. Any assay system or testing method that detects protein-protein interactions may be used including co-immunoprecipitation, crosslinking and co-purification through gradients or chromatographic columns may be used. Additionally, x-ray crystallographic studies may be used as a means of evaluating interactions with substances and molecules. For example, purified recombinant molecules in a complex of the invention when crystallized in a suitable form are amenable to detection of intra-molecular interactions by x-ray crystallography. Spectroscopy may also be used to detect interactions and in particular, Q-TOF instrumentation may be used. Biological samples and commercially available libraries may be tested for CD200-binding peptides. In addition, antibodies prepared to the peptides of the invention may be used to isolate other peptides with CD200 binding affinity. For example, labelled antibodies may be used to probe phage display libraries or biological samples. In this respect peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. (see Christian et al. 1992, J. Mol. Biol. 227:711; Devlin et al., 1990 Science 249:404; Cwirla et al. 1990, Proc. Natl. Acad, Sci. USA, 87:6378). Libraries may also be constructed by concurrent synthesis of overlapping peptides (see U.S. Pat. No. 4,708,871).

It will be understood that the agonist and antagonist that can be assayed using the methods of the invention may act on one or more of the binding sites on the protein or substance including agonist binding sites, competitive antagonist binding sites, non-competitive antagonist binding sites or allosteric sites.

The invention also makes it possible to screen for antagonists that inhibit the effects of an agonist of the interaction of CD200 with a substance which is capable of binding to CD200. Thus, the invention may be used to assay for a substance that competes for the same binding site of CD200. As such it will also be appreciated that intracellular substances which are capable of binding to CD200 may be identified using the methods described herein.

The reagents suitable for applying the methods of the invention to evaluate substances and compounds that affect or modulate a CD200 may be packaged into convenient kits providing the necessary materials packaged into suitable containers. The kits may also include suitable supports useful in performing the methods of the invention.

C. Compositions

The invention also includes pharmaceutical compositions containing CD200 proteins or nucleic acids for use in immune suppression as well as pharmaceutical compositions containing a CD200 inhibitor for use in preventing immune suppression.

Such pharmaceutical compositions can be for intralesional, intravenous, topical, rectal, parenteral, local, inhalant or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions.

The pharmaceutical compositions of the invention can be intended for administration to humans or animals. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., U.S.A. 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as immunosuppressive drugs or antibodies to enhance immune tolerance or immunostimulatory agents to enhance the immune response.

In one embodiment, the pharmaceutical composition for use in immune suppression, treating autoimmunity, preventing graft rejection or preventing fetal loss comprises an effective amount of a CD200 protein in admixture with a pharmaceutically acceptable diluent or carrier. The CD200 protein is preferably prepared as an immunoadhesion molecule in soluble form which can be administered to the patient.

In another embodiment, the pharmaceutical composition for use in immune suppression, treating autoimmunity, preventing graft rejection or preventing fetal loss comprises an effective amount of a nucleic acid molecule encoding a CD200 protein in admixture with a pharmaceutically acceptable diluent or carrier.

The nucleic acid molecules of the invention encoding a CD200 protein may be used in gene therapy to induce immune tolerance. Recombinant molecules comprising a nucleic acid sequence encoding a CD200 protein, or fragment thereof, may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage. The nucleic acid molecules of the invention may also be applied extracellularly such as by direct injection into cells. The nucleic acid molecules encoding CD200 are preferably prepared as a fusion with a nucleic acid molecule encoding an immunoglobulin (Ig) Fc region. As such, the CD200 protein will be expressed in vivo as a soluble fusion protein.

In another aspect, the pharmaceutical composition for use in preventing immune suppression, inhibiting tumor growth or inducing fetal loss comprises an effective amount of a CD200 inhibitor in admixture with a pharmaceutically acceptable diluent or carrier. Such compositions may be administered as a vaccine either alone or in combination with other active agents.

In one embodiment, the pharmaceutical composition for use in preventing immune suppression, inhibiting tumor growth or inducing fetal loss comprises an effective amount of an antibody to CD200 in admixture with a pharmaceutically acceptable diluent or carrier. The antibodies may be delivered intravenously.

In another embodiment, the pharmaceutical composition for use in preventing immune suppression, inhibiting tumor growth or inducing fetal loss comprises an effective amount of an antisense oligonucleotide nucleic acid complimentary to a nucleic acid sequence from a CD200 gene in admixture with a pharmaceutically acceptable diluent or carrier. The oligonucleotide molecules may be administered as described above for the compositions containing CD200 nucleic acid sequences.

D. Murines CD200

The inventor has cloned and sequenced the murine CD200 gene. Accordingly, the invention also includes an isolated nucleic acid sequence encoding a murine CD200 gene and having the sequence shown in FIG. 7 and SEQ ID NO:22.

The term "isolated" refers to a nucleic acid substantially free of cellular material or culture medium when produced by recombinant DNA techniques, or chemical precursors, or other chemicals when chemically synthesized. The term "nucleic acid" is intended to include DNA and RNA and can be either double stranded or single stranded.

Preferably, the purified and isolated nucleic acid molecule of the invention comprises (a) a nucleic acid sequence as shown in SEQ ID NO:22, wherein T can also be U; (b) nucleic acid sequences complementary to (a); (c) a fragment of (a) or (b) that is at least 15 bases, preferably 20 to 30 bases, and which will hybridize to (a) or (b) under stringent hybridization conditions; or (a) a nucleic acid molecule differing from any of the nucleic acids of (a) or (b) in codon sequences due to the degeneracy of the genetic code.

It will be appreciated that the invention includes nucleic acid molecules encoding truncations of the murine CD200 proteins of the invention, and analogs and homologs of the proteins of the invention and truncations thereof, as described below. It will further be appreciated that variant forms of the nucleic acid molecules of the invention which arise by alternative splicing of an mRNA corresponding to a CDNA of the invention are encompassed by the invention.

An isolated nucleic acid molecule of the invention which is DNA can also be isolated by selectively amplifying a nucleic acid encoding a novel protein of the invention using the polymerase chain reaction (PCR) methods and cDNA or genomic DNA. It is possible to design synthetic oligonucleotide primers from the nucleic acid molecules as shown in FIG. 7 and SEQ ID NO:22 for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294-5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a novel protein of the invention into an appropriate vector which allows for transcription of the cDNA to produce an RNA molecule which encodes a CD200 protein of the invention. For example, a cDNA can be cloned downstream of a bacteriophage promoter, (e.g. a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

The sequence of a nucleic acid molecule of the invention may be inverted relative to its normal presentation for transcription to produce an antisense nucleic acid molecule. Preferably, an antisense sequence is constructed by inverting a region preceding the initiation codon or an unconserved region. In particular, the nucleic acid sequences contained in the nucleic acid molecules of the invention or a fragment thereof, preferably a nucleic acid sequence shown in FIG. 7. and SEQ ID NO:22 may be inverted relative to its normal presentation for transcription to produce antisense nucleic acid molecules.

The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The invention also provides nucleic acids encoding fusion proteins comprising a CD200 protein of the invention and a selected protein, or a selectable marker protein.

The invention further includes an isolated protein which has the amino acid sequence as shown in FIG. 8 and SEQ ID NO:2.

Within the context of the present invention, a protein of the invention may include various structural forms of the primary protein which retain biological activity. For example, a protein of the invention may be in the form of acidic or basic salts or in neutral form. In addition, individual amino acid residues may be modified by oxidation or reduction.

In addition to the full length amino acid sequence (FIG. 8), the protein of the present invention may also include truncations of the protein, and analogs, and homologs of the protein and truncations thereof as described herein. Truncated proteins may comprise peptides of at least fifteen amino acid residues.

Analogs of the protein having the amino acid sequence shown in FIG. 8, and/or truncations thereof as described herein, may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequences shown in FIG. 8. Amino acid insertions may consist of single amino acid residues or sequential amino acids ranging from 2 to 15 amino acids in length. For example, amino acid insertions may be used to render the protein is no longer active. This procedure may be used in vivo to inhibit the activity of a protein of the invention.

Deletions may consist of the removal of one or more amino acids, or discrete portions from the amino acid sequence shown in FIG. 8. The deleted amino acids may or may not be contiguous. The lower limit length of the resulting analog with a deletion mutation is about 10 amino acids, preferably 100 amino acids.

Analogs of a protein of the invention may be prepared by introducing mutations in the nucleotide sequence encoding the protein. Mutations in nucleotide sequences constructed for expression of analogs of a protein of the invention must preserve the reading frame of the coding sequences. Furthermore, the mutations will preferably not create complementary regions that could hybridize to produce secondary mRNA structures, such as loops or hairpins, which could adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The invention also contemplates isoforms of the proteins of the invention. An isoform contains the same number and kinds of amino acids as a protein of the invention, but the isoform has a different molecular structure. The isoforms contemplated by the present invention are those having the same properties as a protein of the invention as described herein.

The present invention also includes a protein of the invention conjugated with a selected protein, or a selectable marker protein to produce fusion proteins. Additionally, immunogenic portions of a protein of the invention are within the scope of the invention.

The proteins of the invention (including truncations, analogs, etc.) may be prepared using recombinant DNA methods. Accordingly, the nucleic acid molecules of the present invention having a sequence which encodes a protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Such expression vectors may be useful in the above-described therapies using a nucleic acid sequence encoding a CD200 protein. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleotide sequence comprising the nucleotides as shown in FIG. 7 and SEQ ID NO:22. Regulatory sequences operatively linked to the antisense nucleic acid can be chosen which direct the continuous expression of the antisense RNA molecule.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as b-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformant host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as E. coli, insect cells (using baculovirus), yeast cells or mammalian cells. Other suitable host cells can be found in Goeddel, Gene Expression Technology: Methods in Enzymology 185, Academic Press, San Diego., Calif. (1991).

The proteins of the invention may also be prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart).

The following non-limiting examples are illustrative of the present invention:

EXAMPLES

Example 1

This example demonstrates the increased expression of certain genes following pv immunization.

Mice:

C3H/HEJ and C57BL/6 mice were purchased from The Jackson Laboratory, Bar Harbor, Me. Mice were housed five/cage and allowed food and water ad libitum. All mice were used at 8-12 weeks of age.

Monoclonal Antibodies:

The following monoclonal antibodies (Mabs) from Pharmingen (San Diego, Calif.) were used: anti-IL-2 (JES6-1A12; biotinylated JES6-5H4); anti-IL-4 (11B11; biotinylated BVD6-24G2); anti-IFNγ (R4-6A2; biotinylated XMG1.2); anti-IL-10 (JES5-2A5; biotinylated SXC-1, Pharmingen, San Diego, Calif.); mouse IgG1 isotype control (clone 107.3, BALB/c anti-TNP). Strepavidin horse radish peroxidase and recombinant mouse GM-CSF was also purchased from Pharmingen (San Diego, Calif.).

NLDC-145 (anti-mouse dendritic cells), and F(ab')$_2$ rabbit anti-rat IgG FITC conjugate (non-cross reactive with mouse IgG), or F(ab')$_2$ rabbit anti-mouse IgG PE was obtained from Serotec, Canada.

Rabbit complement, L3T4, anti-thy1.2, anti-Ly2.2, anti-Ly2.1 (mouse IgG3), FITC-MAC-1 and mouse IgG1 anti-rat CD200 were obtained from Cedarlane Labs, Hornby, Ontario.

Anti-CD28 (PV-1) and anti-CTLA (UC10-4F10-11) were obtained from Drs. C. June and J. Bluestone respectively, while anti-B7-1, anti-B7-2 were obtained from Dr. G. Powers. High titres of all 4 of the latter antibodies were produced by in vitro culture in a CELLMAX system (CELLCO Inc., Germantown, Md., U.S.A.).

Preparation of Cells:

Spleen, Peyer's Patch (PP) and mesenteric lymph node (MLN) cell suspensions were prepared aseptically from individual mice of the different treated groups in each experiment.

Where dendritic cells were obtained by culture of bone marrow cells in vitro the following technique was used (Gorczynski et al., 1996a). Bone marrow plugs were aspirated from the femurs of donor male C57BL/6 (or BALB/c) mice, washed and resuspended in aF10. Cells were treated sequentially with a mixture of antibodies (L3T4, anti-thy1.2, anti-Ly2.2) and rabbit complement and dead cells removed by centrifugation over mouse lymphopaque (Cederlane Labs, Ontario). Cells were washed ×3 in aF10, and cultured in 10 ml aF10 in tissue culture flasks, at a concentration of 2×10$^6$/ml with 500 U/ml recombinant murine GM-CSF (Pharmingen, U.S.A.). Fresh GM-CSF was added at 36 hr intervals. Cells were separated over lymphopaque on days 3.5 and 7 of culture, again reculturing in aF10 with recombinant GM-CSF. At 10 days an aliquot of the sample was stained with NLDC-145 and FITC anti-rat IgG, anti-CD200 and PE anti-mouse IgG, FITC-anti-B7-1 or FITC anti-B7-2. Mean staining with these antibodies using cells harvested from such cultures has been 93%±7%, 14%±5%, 78%±9% and 27%±6% respectively. Remaining cells were washed, and injected into the portal vein as described.

Portal Vein Immunizations and Renal Transplantation:

The pv Immunizations and Renal Transplantation Were Performed as described earlier (Gorczynski et al., 1994). All C3H mice received pv/iv immunization with 15×10$^6$ C57BL/6 10-day cultured, bone marrow derived, dendritic cells, followed by C57BL/6 kidney transplantation. Animals received 1 intramoscular (im) injection with 10 mg/Kg cyclosporin A on the day of transplantation. Mice were sacrificed for tissue harvest and RNA preparation 5 days after transplantation. In other studies animals were sacrificed as described in the text.

Where monoclonal antibodies were injected into transplanted mice, animals received 100 mg intravenous (iv) at 2 day intervals (×4 injections) beginning within 2 hours of transplantation.

Cytokine Poroduction from Spleen Cells of Transplanted Mice:

In cultures used to assess induction of cytokine production spleen responder cells stimulated with irradiated (2000R) C57BL/6 spleen stimulator cells in triplicate in aF10 have been used. In multiple studies significant quantitative or qualitative differences in cytokine production from spleen, lymph node or Peyer's Patch of transplanted mice have not been seen. (Gorczynski et al., 1994b). Supernatants were pooled at 40 hr from replicate wells and assayed in triplicate in ELISA assays for lymphokine production. All capture antibodies, biotinylated detection antibodies, and recombinant cytokines were obtained from Pharmingen (San Diego, Calif.—see above).

For IFNγ the assay used flat-bottomed 96-well Nunc plates (Gibco, BRL) coated with 100 ng/ml R4-6A2. Varying volumes of supernatant were bound in triplicate at 4° C., washed ×3, and biotinylated anti-IFNγ (XMG1.2) added. After washing, plates were incubated with strepavidin-horse radish peroxidase (Cedarlane Labs), developed with appropriate substrate and OD$_{405}$ determined using an ELISA plate reader. IL-10 was assayed using a similar ELISA system with JES5-2A5 as the capture antibody, and biotinylated SXC-1 as developing antibody. Each assay reliably detected cytokine levels in the range 0.01 to 0.1 ng/ml. ELISA assays for IL-2 and IL-4 used JES6-1A12 and 11B11 as capture antibodies, with biotinylated JES6-5H4 or BVD6-24G2 as developing antibodies. Sensitivity of detection was 10 pg/ml for each cytokine.

Oligonucleotide Primers:

The primers used for PCR amplification for b-actin, and different cytokines, are described in previous publications (Gorczynski, R. M., 1995a; Gorczynski, R. M., 1995b; Gorczynski, R. M., 1996a). In addition, the following oligonucleotides were synthesized.

cDNA synthesis primer for driver ds cDNA (DP):

5'-TTTTGTACAAGCTT$_{30}$-3'
(SEQ ID NO:3)

Adapter 1 (Ad1):
5'-CTAATACGACTCACTATAGGGCTCGAGCGGCCGCCCGGGCAGGT-3'
(SEQ ID NO:4)

Adapter 2 (Ad2):
5'-TGTAGCGTGAAGACGACAGAAAGGGCGTGGTGCGGAGGGCGGT-3'
(SEQ ID NO:5)

PCR Primer1 (P1):
5'-CTAATACGACTCACTATAGGGC-3'
(SEQ ID NO:6)

-continued

Nested Primer 1 (NP1):
5'-TCGAGCGGCCGCCCGGGCAGGT-3'
(SEQ ID NO:7)

PCR Primer2 (P2):
5'-TGTAGCGTGAAGACGACAGAA-3'
(SEQ ID NO:8)

Nested Primer 2 (NP2):
5'-AGGGCGTGGTGCGGAGGGCGGT-3'
(SEQ ID NO:9)

Driver and Tester Preparation:

RNA was extracted from pooled mesenteric lymph node (MLN) and Peyer's Patches (PP) of 5/group renal transplant mice with iv or pv immunization. Poly(A)$^+$mRNA was prepared from the driver (iv) group, and 2 mg material used for ds cDNA synthesis with 1 ng DP primer and a cDNA Synthesis Kit (Clontech) with T4 DNA polymerase. The final cDNA preparation was digested with Rsal in a 50 ml reaction mixture with 15 units enzyme (GIBCO) for 3 hrs, and the cDNA phenol-extracted, ethanol precipitated, and resuspended in 7 ml of deionized water (concentration approximately 300 ng/ml).

Rsal digested ds tester CDNA (pv group) was prepared in a similar fashion. 50 ng of tester cDNA diluted in TE buffer was ligated with 2 ml of Ad1 and Ad2 (each at 10 mM) in separate ligation reactions at 16° C. for 18 hrs with 50 Units/ml T4 ligase. Thereafter 1 ml of 0.2M EDTA was added, the mixture heated at 70° C. for 5 min to inactivate the ligase, and the product stored at -70° C.

Subtractive Hybridization and PCR Amplification:

600 ng driver (iv) ds cDNA was added to each of two tubes containing 20 ng Ad1- and Ad2-ligated pv cDNA. The samples were mixed, precipitated with ethanol, resuspended in hybridization buffer, overlaid with mineral oil and denatured/annealed in standard fashion. The two independent samples were then combined, 200 ng fresh driver cDNA added to allow for further enrichment of differentially expressed mRNAs, and the mixture again denatured and annealed for 10 hrs at 68° C. The final sample was dilutes in Hepes buffer with EDTA and stores at -20° C.

After subtraction two PCR amplifications were performed on the subtracted cDNA. In the first 1 ml of subtracted cDNA was amplified using 1 ml each of P1 and P2. The conditions for amplification were as described by Diatchenko. The amplified products were diluted 10-fold in deionized water and 1 ml of product used for further amplification using the nested primers (NP1 and NP2) and a 10-cycle amplification reaction. Aliquots of the original driver/tester and subtracted cDNAs were used for PCR reactions with control oligonucleotide primers (β-actin) for known "housekeeping genes", and with primers for genes whose expression has been previously documented to be different in iv/pv immunized mice. These data are shown in FIGS. 1 and 2.

FIG. 1 shows PCR validation of suppressive subtractive hybridization. Samples from unsubtracted (lanes 1, 3, 5 and 7) or subtracted (lanes 2, 4, 6 and 8) mRNA were reverse transcribed and tested in PCR with b-actin primers for different PCR cycle times. Lanes 1 and 2: 15 cycles; lanes 3 and 4: 20 cycles; lanes 5 and 6: 25 cycles; lanes 7 and 8: 30 cycles.

Figure 2:
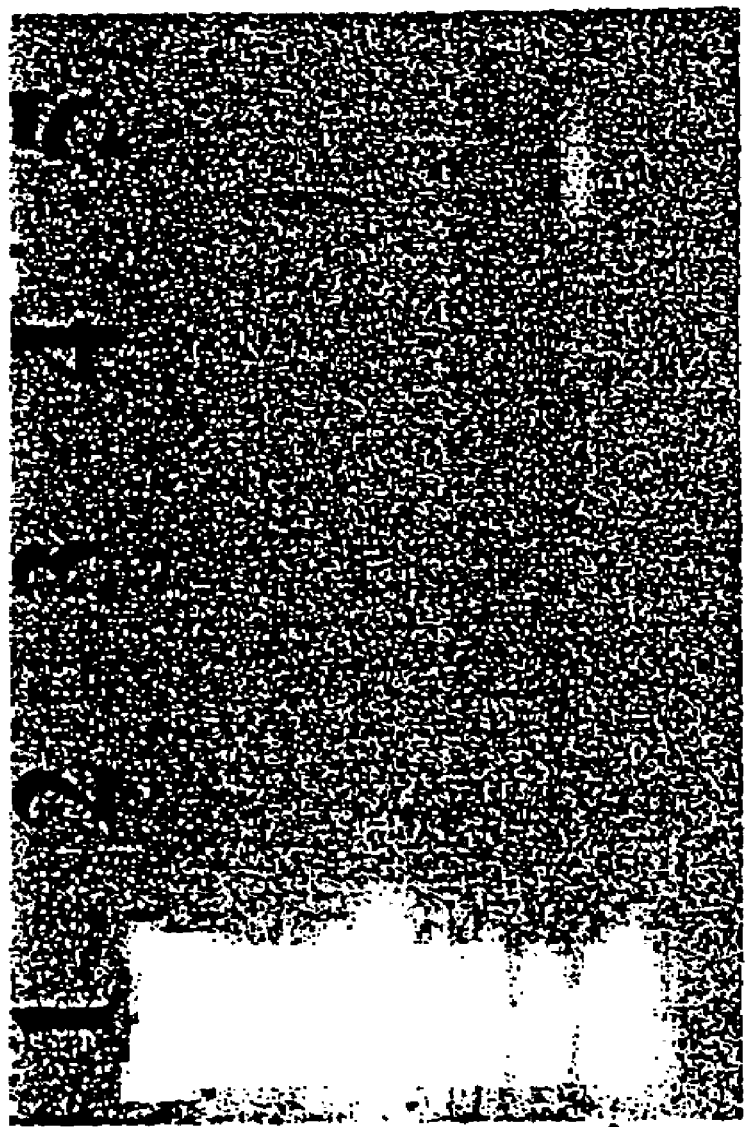
FIG. 2 illustrates PCR validation of suppressive subtractive hybridization using IL-10 primers.

FIG. 2 shows PCR validation of suppressive subtractive hybridization. Samples from unsubtracted (lanes 2 and 4) or subtracted (lanes 3 and 5) mRNA were tested as in FIG. 1, except primers used were for IL-10, and different cycle times are shown. Lanes 2 and 3: 20 cycles; lanes 4 and 5: 30 cycles, lane 1: mol. wt. standard.

In addition, cloning of the subtracted cDNA was performed as follows.

Cloning and Further Analysis of Subtracted cDNA:

The PCR amplified cDNA was cloned with a TA cloning kit (Invitrogen, Calif.) by directly ligating into the PCR II vector. Ligation was performed at an insert:vector ratio of 3:1 in 1× ligation buffer with T4 ligase (3 U/ml) overnight at 14° C. Ligation products were then inserted into INFaF' competent *Escherichia Coli* using a standard transformation protocol, and selected with ampicillin on plates containing X-gal (5-bromo4-chloro-3-indolyl-D-galactoside). Miniprep plasmid DNA was purified with a Plasmid extraction Spin kit (Qiagen, Germany) and cut with EcoR I restriction enzyme to determine whether the plasmids contained the expected insert. Plasmids with inserts were sequenced by the dideoxy sequencing method using a T7 sequencing kit (Pharmacia Biotech, Canada). Nucleic acid homology searches were performed using the BLAST program at the National Center for Biotechnology Information (NIH, Bethesda, U.S.A.).

Figure 3:
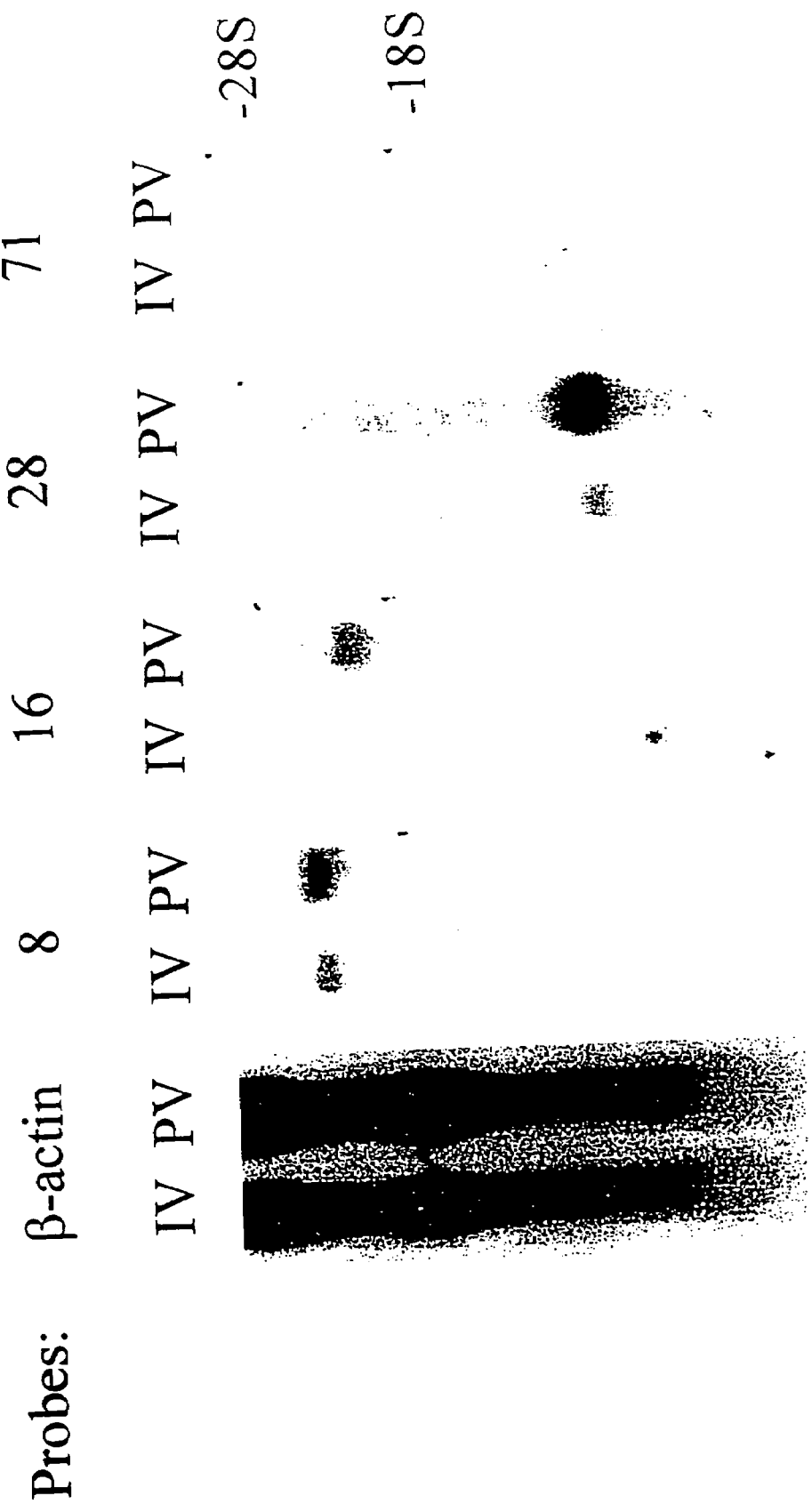
FIG. 3 is an autoradiograph using $^{32}$P-labeled probes from 4 clones obtained from the subtractive hybridization process.

Further analyses of cloned material, using Northern hybridization, was as follows. Inserts in pCRII were amplified for 12 cycles using nested PCR primers. The amplified material was purified using Qiaquick Spin PCR Purification Kits (Qiagen), $^{32}$P-labeled by random priming, and used as a probe for Northern hybridization with 20 mg samples of the original (and fresh) iv or pv total RNA. Hybridization was performed in 5 ml of ExpressHyb solution (Clontech) with a minimum of 5×10$^6$ cpm per 10 ng cDNA probe and 0.1 mg/ml sonicated heat-denatured salmon sperm DNA. Filters were washed 4 times, each at 15 min at 27° C. with 1×SSC and 0.1% SDS, followed by a high stringency wash at 42° C. for 30 min with 0.2×SSC and 0.1% SDS. Exposure times varied from 18 hrs to 6 days. FIG. 3 shows an autoradiograph using $^{32g}$P-labeled probes prepared from 4 clones obtained using the subtraction hybridization approach described above (with pv cDNA as tester material and iv cDNA as driver). A labeled control probe was prepared with a PCR amplicon for mouse β-actin. Total RNA was prepared from mice receiving iv or pv immunization and equivalent amounts loaded in replicate lanes as shown, with gels developed from 18 hours (clone #28) to 6 days (#71). Clone 8 is most homologous with mouse poly (A) binding protein. Clone 16 is most homologous with rat MRC OX-2. Clone 28 is most homologous with human zinc-finger protein. Clone 71 has no homologous sequence.

Western Blotting Protocol:

The technique used was essentially that described by Sandhu et al. (1991) as modified by Bronstein et al. (1992). Samples were obtained 14 days post renal transplantation, using groups described in FIG. 5. Fresh rat thymus cells were used as control. Samples were electrophoresed in 12% SDS-PAGE and transferred to PVDF membranes (Novex Co., San Diego, Calif.) prior to addition of primary antibody. A commercial anti-rat OX-2 was used as test reagent; control antibody was an antibody to mouse CD8a. The developing antibody used was a commercial horse-radish peroxidase labeled anti-mouse IgG. All reagents were obtained from Cedarlane Labs (Hornby, Ontario, Canada).

DNA Sequence Homology Comparison:

Comparison of mouse OX-2 with known cDNA sequences for B7-1, B7-2, CD28 and CTLA-4 was performed using a DNASIS program (version 2.0).

Results

Evaluation of Suppression Subtraction Hybridization(SSH) Technique

In order to evaluate the efficacy of the SSH technique used, the inventor used his previous evidence that, by PCR analysis, increased expression of mRNA for IL-10 genes was evident in lymphoid tissue from pv immunized mice. Accordingly, a dilution analysis of cDNA from the tester, driver and subtracted material, using PCR primers for β-actin and IL-10 was performed. As shown in FIG. 1, after SSH there was a detectable signal for b-actin in subtracted material only after 35 cycles of amplification. By contrast, a signal was present in the unsubtracted material after only 15 cycles. Using additional quantitative measures of template, it was found to correspond to some 1000-10,000 depletion of β-actin mRNA. In a separate study, analyzing IL-10 mRNA (FIG. 2), significant enrichment of IL-10 mRNA was found as determined by comparison of the amplification detected at 30 cycles in subtracted/unsubtracted material (see lanes 4 and 5, FIG. 2).

In a further test of the efficiency of subtraction the mixture of unsubtracted and subtracted tester (pv) cDNA was labeled and hybridized to Northern blots of iv (tester) and pv (driver) total RNA. The results (data not shown) indicated that the subtracted tester cDNA probe did indeed produce a significantly stronger signal with the tester RNA. Given the evidence that for any cDNA species to produce a signal in a Norther blot it must represent a concentration greater than 0.1-0.3% of the cDNA mixture, these data are again consistent with our having produced a high level of enrichment of pv-specific cDNA, with a concomitant reduction in abundant cDNAs common between tester (pv) and driver (iv) material.

Detection of Unique cDNA Fragments in Tissue from pv Immunized Mice

The efficiency and validity of SSH for detection of cDNAs unique to the tissue sample from the pv immunized mice was further confirmed after cloning and sequence analysis of selected tester-specific cDNAs. 10 randomly selected cDNA clones (of 66 sequenced) were used to probe multiple preparations of pv or iv whole RNA. All revealed unique mRNAs expressed preferentially in the pv samples. Autoradiograms from 4 of these Northern blots, along with a b-actin probe as control, are shown in FIG. 3. Exposure times from 18 hrs to 6 days were used which were interpreted as indicative of pv specific cDNAs of different abundance in the samples of interest.

The cDNA inserts of the 4 clones shown, along with the other 62 clones, were partially sequenced and analyzed for homology in the GenBank and EMBL data bases. A summary of these data are shown in Table 1. Note that some 30 cDNA fragments had at least 50% homology (BLAST score >250 over at least 50 nt) with other described sequences. A further 14 clones showed similar homology with known rat/human genes. Both sets may represent members of different gene families. An additional 22 clones demonstrated no significant matches with entries in the database, and thus may represent novel genes up-regulated after pv immunization. That the data shown are a minimal estimate of such differentially expressed genes is evident from the fact that homology with IL-4 or IL-10 gene sequences (mRNAs known to be over-expressed following pv immunization-see also FIG. 2) were NOT detected in any of the 66 clones analyzed.

The sequence homology for the clones shown in FIG. 3 (>80% homology over the compared sequence) led to the further characterization of these clones. Clone 8 was shown to be most homologous with mouse poly (A) binding protein; clone 16 was shown to be most homologous with rat MRC OX-2; and clone 28 was shown to be most homolgous with human zinc-finger protein. No homologous sequence was found for clone 71. In the data that follows, the analysis of one of these clones which showed homology to a rat cDNA (for OX-2, a molecule previously characterized as being preferentially expressed on rat thymocytes and dendritic cells) is described. The rationale for further investigation of this clone lies in data showing that infusion of dendritic cells via the portal vein is a potent method for prolonging allograft survival in our model systems. Note, however, that while the bone marrow derived dendritic cells that were infused via the portal vein themselves express OX-2 (see above), identical data has been obtained in Northern gels to those shown in FIG. 3 using tissue harvested from mice receiving, as the earliest studies(1-5) irradiated spleen cells (OX-2$^-$ by FACS analysis) via the portal vein. In addition, in both situations, OX-2 mRNA was not detected by this suppression subtraction hybridization approach when we used tissue harvested at 0.5-2.5 days post transplantation. These results are consistent with the idea that the OX-2 signal detected is a result of novel increased expression in cells following pv immunization.

Probing a cDNA Library from Tissue from pv Immunized Mice for Expression of the Murine Equivalent of Rat OX-2

A cDNA library was constructed from mRNA prepared from a pool of 5 C3H mice receiving pv immunization with $25 \times 10^6$ irradiated (2000 Rads) C57BL/6 bone marrow cells followed by renal transplantation as described in the Materials and Methods, using a kit purchased from ClonTech. Clones were plated in LB medium and probed with the $^{32}$P-labeled amplicon described in FIG. 3 as showing homology with rat OX-2. A 1.3 Kb clone was detected, amplified, and shown after $^{32}$P labeling to detect a differentially expressed product by Northern gel analysis. After sequencing using an automated DNA sequencer and fluorescent-labeled deoxynucleotides, this 1.3 Kb fragment was found to share >95% homology with the region encoding the 3'untranslated region of the rat OX-2 mRNA as determined from the GeneBank sequence for rat OX-2.

Using a primer construct program, a 5'PCR primer representing positions 1-19 of the rat GeneBank sequence (corresponding to a portion of the 5'untranslated region, and the leader sequence) and 3' primers from our characterized mouse sequence were synthesized, and long-distance amplification performed to produce an amplicon predicted to encode the open-reading-frame (ORF) of the murine equivalent of the rat OX-2 gene. This amplicon was determined (as expected) to be of some 1.4 Kb length. Automated sequencing produced a full-length sequence for the mouse homologue of the rat MRC OX-2 gene, including an ORF with >90% homology (predicted amino acid sequence) with the corresponding rat product, along with the 3'untranslated region. This sequence has been submitted to the Genebank (accession number AF004023).

Using a DNASIS program the predicted mouse protein sequence has some 51% homology with B7-1 and B7-2, 48% with CD28 and 54% with CTLA4 (unpublished).

Figure 4:
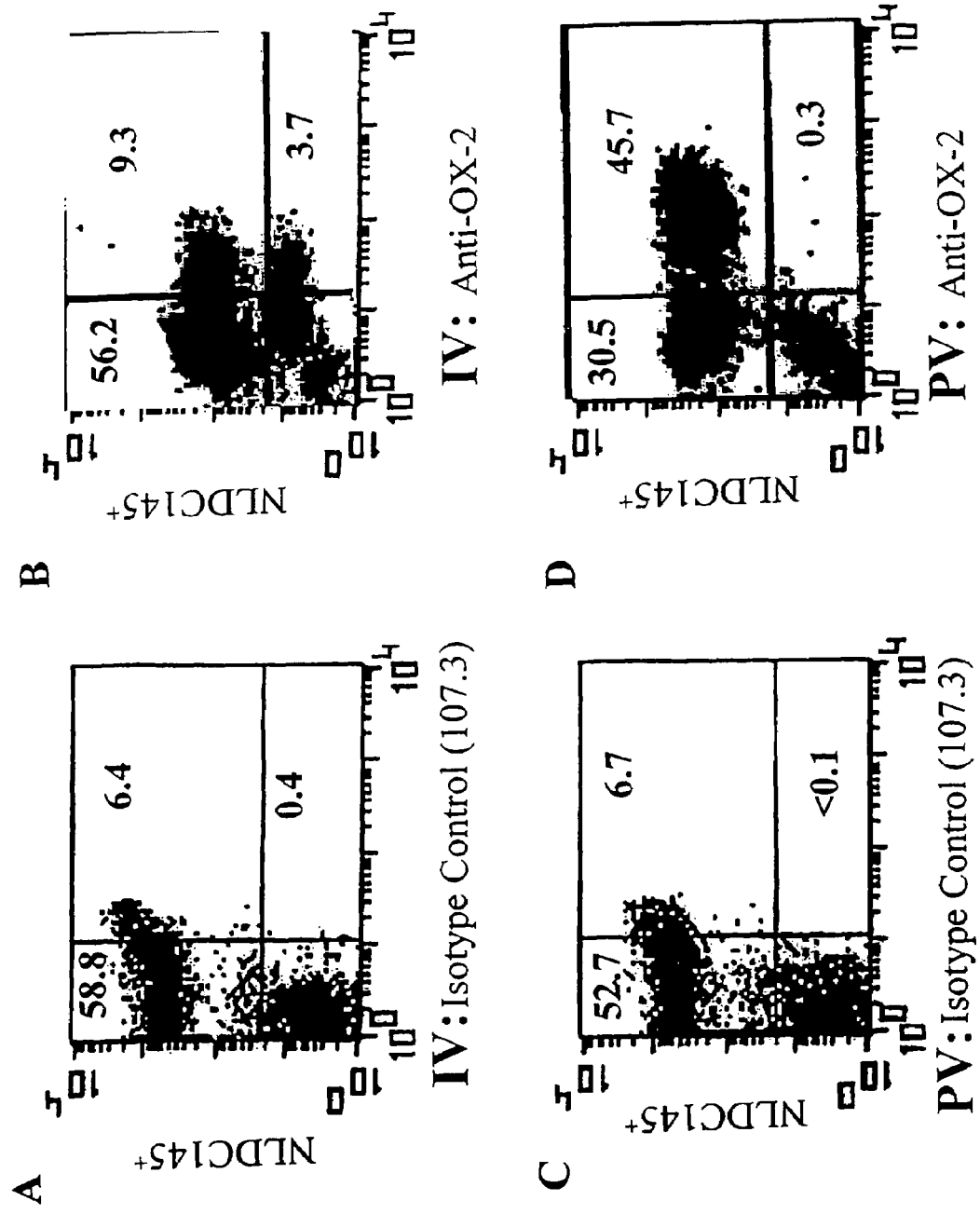
FIG. 4 is flow cytometry profile of spleen adherent cells.

Evidence for an Important Role for the Expressed OX-2 Homologue in Prolonged Graft Survival Following pv Immunization In an attempt to define the potential importance of the product encoded by the OX-2 gene we used a commercial antibody to rat OX-2 in a transplant model in mice receiving pv immunization and renal transplantation. In the first such study, it was asked whether there was evidence for specifically increased expression of the OX-2 molecule following pv immunization. By FACS analysis, using dual staining of hepatic mononuclear cells and spleen cells with OX-2 and NLDC145, similar numbers of NLDC145$^+$ cells in liver or spleen samples from iv and pv immunized mice were found, ($5 \times 10^5$ and $6.5 \times 10^6$ respectively), but a 4-fold increase in the numbers of OX-2$^+$ NLDC145$^+$ following pv immunization. FIG. 4 shows a flow cytometry profile of spleen adherent cells from iv immunized/grafted mice (panels A and B) or pv immunized/grafted mice (panels C and D). Cells were harvested 7 days after transplantation and stained with NLDC145 and F(ab')$_2$FITC-anti-rat IgG, as well as with control (clone 107.3) mouse IgG1 serum (left hand panels) or anti-OX-2 (right hand panels) and F(ab')$_2$PE-anti-mouse IgG. Data are representative of one of three different studies. Values shown represent the total cell population in each quadrant. The absolute numbers ($\times 10^5$) of double positive cells in the liver or spleen of pv immunized mice were 3.2±0.5 and 39±8 respectively (see FIG. 4 for FACS profiles of spleen adherent cells). This 4-fold increase was seen regardless of the cells used for pv immunization, either bone marrow derived dendritic cells (some 20% OX-2$^+$-see above) or irradiated whole spleen lymphoid cells (OX-2$^-$), suggesting that they were not merely detecting surviving OX-2$^+$ (donor) cells, but novel expression of OX-2 in vivo.

Western blot, FIG. 5, shows increased expression of OX-2 antigen after pv immunization. The technique used for Western blotting is previously described. Samples were obtained 14 days post renal transplantation, using the groups described in FIG. 6. Fresh rat thymus cells (lane 5) were used as control. Lanes 1 and 2 represent samples pooled from 3 donors/group (iv immunized; pv immunized+infusion of anti-OX-2 respectively). Samples in lanes 3 and 4 are from individual mice receiving pv immunization and renal transplantation only (no antibody treatment). Staining with anti-rat MRC OX-2 is shown in FIG. 5B; with a control antibody (to mouse Ly2.1), anti-mouse cD8a, shown in FIG. 5A. The developing antibody used was a commercial horseradish peroxidase labeled anti-mouse IgG. No signal was seen using the mouse IgG1 isotype control clone 107.3 (BALB/c anti-TNP)-data not shown. Data are representative of 1 of 3 equivalent studies.

Western blotting (see FIGS. 5A and 5B) of samples prepared from the spleen of iv vs pv immunized and grafted mice 14 days following renal transplantation revealed staining of a band migrating with estimated molecular weight 43 Kd, in agreement with data elsewhere reporting extensive glycosylation of this molecule in isolates from rat thymus. In mice receiving pv immunization along with in vivo treatment with anti-OX-2, no detectable signal was seen in Western blots (see lane 2, FIG. 5). No staining was seen with a murine IgG1 isotype control (BALB/c anti-TNP, clone 107.3: unpublished), making it unlikely that the band observed was Fc receptor.

Figure 6:
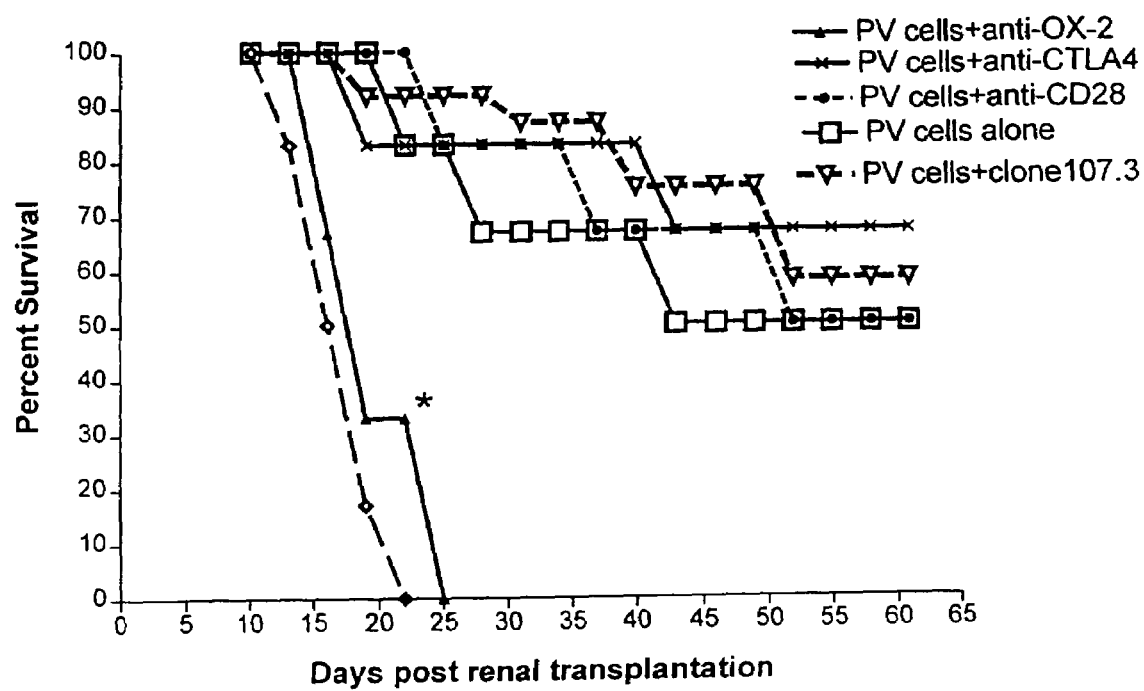
FIG. 6 is a graft showing percent survival versus days post renal transplantation.

FIG. 6 is a graph showing percent survival versus days post renal transplantation. Commercial anti-OX-2 monoclonal antibody, but not anti-mouse CD28 or anti-mouse CTLA4, reverses the graft prolongation following donor-specific pv immunization. Groups of 6 C3H mice received C57BL6 renal allografts with no other treatment (cyclosporin A only, or additional pv immunization with 15×10⁶ C57BL/6 bone marrow derived dendritic cells as described previously. Subsets of these latter mice received iv injection (every second day ×4 injections) with 100 mg/mouse of a commercial anti-rat OX-2 monoclonal antibody or the isotype control, or of antibodies to mouse CD28 or CTLA4. The animal survival for the different groups shown are pooled from 2 studies. Note that the mouse isotype control itself produced no modification of the increased renal graft survival following pv immunization. * $p<0.02$, Mann-Whitney U-test).

In two final studies mice received pv immunization and transplantation as before, but now also received iv injection with commercial anti-rat OX-2 (×4 injections; 100 mg/mouse at 2 day intervals). As shown in FIGS. 5A and B and 6 these infusions of anti-OX-2 significantly decreased the prolonged graft survival (FIG. 6) and increased expression of OX-2 antigen (Western blotting-FIGS. 5A and 5B) seen following pv immunization. No perturbation of graft survival following pv immunization was seen using additional treatments with anti-CD28/anti-CTLA4 (see FIG. 6), or, in studies not shown, using anti-B7-1 or anti-B7-2. Again infusion of the IgG1 isotype control Mab (clone 107.3) did not alter the increased graft survival seen following pv immunization (see FIG. 6).

In separate experiments cells were harvested from mice receiving pv immunization along with additional treatment with monoclonal antibodies as show (see Table 2). Following treatment with anti-OX-2 there was no longer the altered cytokine production (with polarization to production of IL-4 and IL-10) which the inventor has described in multiple model systems in which animals received pv donor-specific pre-transplant immunization. Treatment with any of the other 4 monoclonal antibodies tested did not produce this reversal in polarization of cytokine production seen following pv immunization-indeed, using these Mabs alone in the absence of pv immunization produced a trend to increased graft survival (not shown) and significant polarization in cytokine production to increased IL-4 and IL-10 production, akin to that produced by pv immunization itself (upper half of Table 2).

OX-2 is a molecule previously characterized by Barclay et al. (1981, 1982) as being preferentially expressed on rat thymocytes and dendritic cells. Dendritic cells are known to be important signalling cells for lymphocytes, which also potentially regulate cytokine production and graft rejection, and infusion of dendritic cells is a potent means of inducing pv tolerance. The inventor has determined that OX-2 expression increased following pv immunization, and further studied whether this had any functional consequences. As shown in FIGS. 4 and 5, there is indeed significantly increased expression of OX-2 in spleen cells isolated from pv immunized mice, along with the increased graft survival and polarization in cytokine production (FIG. 6 and Table 2). In contrast, in vivo infusion of anti-OX-2 abolishes increased expression of this molecule, simultaneously reversing the increased graft survival and altered cytokine profile seen. This data is consistent with the possible function of OX-2⁺ cells in promoting allograft survival.

In the studies described the donor dendritic cells infused via the portal vein were themselves OX-2⁺ (see description of materials and methods above). However, identical data in FACS analysis (FIG. 4) and Western Blots (FIG. 5), and from suppression subtraction hybridization (FIG. 3), have been obtained in studies in which we used irradiated whole spleen cells (OX-2⁻ by FACS) for pv infusion. This is consistent with the lack of evidence for increased mRNA expression of OX-2 early (1-2 days) post transplant, as noted above. Thus it seems most likely that an operationally important "OX-2 signal" detected in the spleen of the pv immunized mice can derive from new expression, rather than necessarily from infused OX-2⁺ cells. In the absence of a polymorphic marker for OX-2, however, it cannot be determined whether increased expression is from donor or host cells (or both). Indeed, it is perhaps somewhat surprising that the murine antibody to rat OX-2 cross-reacts in the fashion shown with murine OX-2. Definitive analysis of the in vivo role of OX-2 awaits similar studies to those above, using antibodies developed against the murine OX-2 homologue-these experiments are currently in progress. It is also important to point out that while pv immunization led to only a 4-fold alteration in the absolute number of detectable OX-2⁺ NLDC⁺ cells in the spleen/liver (see text and FIG. 4), nevertheless in the face of this 4-fold difference a clear difference in OX-2 signals in Northern gels using RNA from pv vs iv immunized mice (FIG. 3), along with evidence for a role for this quantitative difference in the outcome of graft survival (FIG. 6) were detected. Presumably these results reflect respectively the limitation to the sensitivity of the Northern assay used, and some function of the quantitation of "co-stimulation" occurring after OX-2:OX-2 ligand interaction.

While there was some 50% homology of the predicted protein sequence of murine OX-2 with murine B7-1, B7-2, CD28 and CTLA4 (Borriello et al., 1997), antibodies to the latter molecules did not reverse the prolonged graft survival and altered cytokine production following pv immunization (FIG. 6, Table 2—see also (Castle et al., 1993)). In fact these latter antibodies themselves, infused in the absence of pv immunization, produced some of the same changes in cytokine production induced by pv immunization (Table 2).

Example 2

Murine OX-2

This example describes the cloning and sequencing of murine MRC OX-2.

A cDNA library was constructed from MLN cells derived from adult C3H mice, preimmunized 5 days earlier with 10×106 allogeneic B10.BR bone marrow-derived dendritic cells allogeneic cells by the portal venous (pv) route, using a Cap Finder PCR cDNA library construction kit (Clontech). The inventor had previously isolated, using a PCR-Select cDNA subtraction hybridization kit (Clontech) and RNAs obtained from pooled MLN of mice immunized by the pv route or via the lateral tail vein (iv), a 350 bp amplicon which showed over 98% homology with the 3' untranslated region of rat MRC OX-2 cDNA. Northern blot analysis confirmed that this amplicon detected a differentially expressed product in RNAs prepared from iv vs pv immunized mice. This amplicon was used to screen 5×10⁵ clones of the amplified library. The sequences of cDNA clones were established with an Applied Biosystems 377 Automated Sequencer, utilizing the Dye Terminator Cycle Sequencing method (Applied Biosystems, Foster City, Calif.). The nucleotide sequence reported in this paper has been submitted to the GenBank/EMBL Data Bank with accession number AF004023.

The cDNA shown in FIG. 7 has an open reading frame of 837 base pairs, and a deduced amino acid sequence (FIG. 8) of 248 amino acids, of which 30 represent a cleaved leader sequence. The predicted molecular weight of this, and the equivalent molecules in rat and human, is approximately 25 kDa. The measured molecular weight in rat thymocytes, where the molecule is highly gylcosylated, is 47 kDa.

The murine MRC OX-2 shows some 92% and 77% homology overall at the amino acid level with equivalent molecules in rat or human respectively. As noted for the rat molecule, the sequence from a 203-229 seems likely to represent a membrane spanning domain (highly hydrophobic region), while the region from 229-248 is likely the intracytoplasmic region, with a stretch of highly basic residues immediately C-terminal to position 229. Homology in the combined transmembrane and C-terminal regions with rat and human shows some 98% and 85% similarity respectively. As predicted from membership in the Ig supergene family, there are a number of conserved Cys residues forming the disulphide bonds between b-strands of Ig-like domains, (21 and 91; 130 and 184 respectively); residue 91 was previously found to be the most highly conserved among members of the immunoglobulin superfamily. Homology between the N-terminal Ig-domain with rat and human, versus the next Ig-domain, is 88% and 82%, or 97% and 73% respectively. This relative concentration in variability between rat and mouse in the V-terminal Ig-domain may be more understandable when the ligand specificity for the molecules in these species is clarified. Note that the presumed extracellular portion of the molecule (1-202) contains a number of sites for N-glycosylation which are preserved across species (44, 65, 73, 80, 94, 127, 130 and 151). This was previously reported for the rat cDNA sequence, and inferred from the measured size of the expressed material in rat thymocytes.

The intracytoplasmic region of the molecules has no sequence identity with known signaling kinases, nor does it have the well-described consensus sequence for the immunoreceptor tyrosine activation motif (ITAM: DXXYXX-LXXXXXXXYDXL). In addition, it lacks typical SH2 or SH3 domains to serve as "docking sites" for adapter molecules which might in turn co-opt other protein kinases in an activation cascade. Accordingly the ligand-binding activity of the extracellular domains presumably represent the biologically important region of the molecule. Some possible functions attributable to ligand interaction with OX-2 can be inferred from other data in the literature. A homologous molecule, Ng-CAM, has been reported to bind a protein-tyrosine phosphatase via N-linked oligosaccharide residues, and protein tyrosine phosphatases are known to play a key regulatory role in immune responses. More recently ALCAM, another adhesion molecule member of the Ig superfamily, the gene for which is located close to that for OX-2 on chromosome 3 in humans, has been shown to bind CD6 (a member of the scavenger receptor cystein rich family, SRCR), and antibodies to CD6 may themselves play a role in regulating immune function.

Example 3

OX-2 Positive Cells Inhibit Type-1 Cytokine Production

The inventor has shown that hepatic mononuclear, non-parenchymal, cells (NPC) can inhibit the immune response seen when allogeneic C57BL/6 dendritic cells (DC) are incubated with C3H spleen responder cells. Cells derived from these cultures transfer increased survival of C57BL/6 renal allografts in C3H mice. The inventor also found that increased expression of OX-2 on dendritic cells was associated with inhibition of cytokine production and renal allograft rejection. The inventor further explored whether inhibition by hepatic NPC was a function of OX-2 expression by these cells.

Fresh C57BL/6 spleen derived DC were cultured with C3H spleen responder cells and other putative co-regulatory cells. The latter were derived from fresh C3H or C57BL/6 liver NPC, or from C3H or C57BL/6 mice treated for 10 days by intravenous infusion of human Flt3 ligand (Flt3L). Different populations of murine bone-marrow derived dendritic cells from cultures of bone marrow with (IL-4+GM-CSF) were also used as a source of putative regulator cells. Supernatants of all stimulated cultures were examined for functional expression of different cytokines (IL-2, IL-4, IFNγ, TGFβ). It was found that fresh C57BL/6 splenic DC induced IL-2 not IL-4 production. Cells from the sources indicated inhibited IL-2 and IFNγ production, and promoted IL-4 and TGFβ production. Inhibition was associated with increased expression of OX-2 on these cells, as defined by semi-quantitative PCR and FACS analysis. By size fractionation, cells expressing OX-2 were a subpopulation of NLDC145+cells. This data implies a role for cells expressing OX-2 in the regulation of induction of cytokine production by conventional allostimulatory DC.

Materials and Methods

Mice: Male and female C3H/HEJ and B10.BR (H-$2^{k/k}$), B10.D2 (H-$2^{d/d}$) and C57BL/6 (H-$2^{b/b}$) mice were purchased from the Jackson laboratories, Bar Harbour, Me. Mice were housed 5/cage and allowed food and water ad libitum. All mice were used at 8-12 weeks of age.

Monoclonal antibodies: The following monoclonal antibodies (Mabs), all obtained from Pharmingen (San Diego, Calif., U.S.A.) unless stated otherwise, were used: anti-IL-2 (JES6-1A12; biotinylated, JES6-5H4); anti-IL-4 (11B11, ATCC; biotinylated, BVD6-24G2); anti-IFNγ (R4-6A2, ATCC; biotinylated XMG1.2); anti-IL-10 (JES5-2A5; biotinylated SXC-1); PE anti-B7-1/B7-2 (Cedarlane Labs, Hornby, Ontario, Canada).

Rat anti-mouse OX-2 monoclonal antibodies were prepared by Immuno-Precise Antibodies Ltd. (Victoria, BC, Canada) following immunization of rats with a crude membrane extract of LPS stimulated murine DC, followed by fusion with a non-secreting rat myeloma parent cell line (YB2/3HI.P2.G11.16Ag.20). Hybridoma supernatants were screened in ELISA using plates pre-coated with a 40-45 Kd preparation of DC extracts run on Western gels (Barclay, A. N. 1981. *Immunology* 44:727; Barclay, A. N., and H. A. Ward. 1982. *Eur. J. Biochem.* 129:447). Positive clones were re-screened using FACS analysis of CHO cells transduced with a cDNA clone encoding full-length murine OX-2 (Chen, Z., H. Zeng, and R. M. Gorczynski. 1997. *BBA. Mol. Basis Dis.* 1362:6-10). FITC-conjugated F(ab')2 rabbit anti-rat IgG (non cross-reactive with mouse IgG) from Serotec, Canada was used as second antibody. The Mab selected for further analysis (M3B5) was grown in bulk in a CELLMAX system (Cellico Inc., Germantown, Md.). A crude preparation of rat immunoglobulin (30% saturated ammonium sulphate preparation) was used as a control Ig.

In tissue culture assays where anti-cytokine Mabs were used to confirm the specificity of the assay used 10 μg/ml of the relevant Mabs was found to neutralize up to 10 ng/ml of the cytokine tested.

NLDC145 (anti-mouse DC) was also obtained from Serotec. Recombinant mouse IL-4 was a kind gift from Dr. L. Yang (The Toronto Hospital); mouse rGM-CSF was purchased from Pharmingen. Recombinant human Flt3L (derived from CHO cells) was a kind gift from Dr. A. B. Troutt, Immunex Corp., Seattle, Wash., U.S.A.

Renal Transplantation

Renal transplantation was performed essentially as described elsewhere (Gorczynski, R. M. et al. 1994a. *Transplantation* 58:816-820). Animals were anesthetized with a combination of halothane and nitrous oxide inhalation, using novogesic for post-op analgesia. Orthotopic renal transplantation was performed using routine procedures. In brief, Donor animals received 200 Units of heparin, and kidneys were flushed with 2 ml of ice cold heparinized physiological saline solution, prior to removal and transplantation into recipient animals with left nephrectomy. The graft renal artery was anastomosed to the recipient's abdominal aorta, and the renal artery was anastomosed to the recipient's inferior vena cava. The ureter was sewn into the recipient bladder using a small donor bladder patch. All recipients received im injection with cefotetan (30 mg/Kg) on the day of transplantation and for 2 succeeding days. The remaining host kidney was removed 2 days after transplantation, unless otherwise indicated. Treatment of recipients with pv immunization, by monoclonal antibodies, or by oral immunization was as described in individual studies.

Portal Vein and Oral Immunization

Portal vein and oral immunization was performed as described earlier (Gorczynski, R. M. 1995a. *Cell. Immunol.* 160:224-231; Gorczynski, R. M. et al. *Transplantation* 62:1592-1600). All animals were anaesthetized with nembutal. A midline abdominal incision was made and the viscera exposed. Cells were injected in 0.1 ml through a superior mesenteric vein using a 30 gauge needle. After injection the needle was rapidly withdrawn and hemostasis secured without hematoma formation by gentle pressure using a 2 mm 3 gel-foam.

Bone-marrow derived dendritic cells (DC) for pv immunization were obtained by culture of T depleted bone marrow cells in vitro with rIL-4 and rGM-CSF (Gorczynski, R. M. et al. *Transplantation* 62:1592-1600). Staining with NLDC145 and FITC anti-rat IgG, or with FITC anti-CD3 confirmed >95% NLDC145+ and <5% CD3+ cells at day 10 of culture (Gorczynski, R. M. et al. *Transplantation* 62:1592-1600). These cells were washed and injected into mice or used for mixed leucocyte cultures.

Preparation of Cells:

Spleen and bone marrow (Gorczynski, R. M. et al. *Transplantation* 62:1592-1600) cell suspensions were prepared aseptically from individual mice in each experiment. Hepatic mononuclear nonparenchymal cells (NPC) were isolated essentially as described elsewhere (Gorczynski, R. M. 1994b. *Immunology* 81:27-35). Tissue was first digested at 37° C. for 45 min with a mixture of collagenase/dispase, prior to separation (15 min at 17,000 rpm at room temperature) over mouse lymphopaque (Cedarlane Labs). Mononuclear cells were resuspended in α-Minimal Essential Medium supplemented with 2-mercaptoethanol and 10% fetal calf serum (αF10). Where cells were obtained from Flt3L injected mice, animals were treated by iv injection of 10 mg/mouse Flt3L daily for 10 days. After enzyme digestion recovery of liver/spleen cells from these mice was markedly increased compared with saline-injected controls ($120 \times 10^6$, $390 \times 10^6$ vs $7 \times 10^6$ and $120 \times 10^6$ respectively).

Cytotoxicity and Cytokine Assays:

In cultures used to assess induction of cytotoxicity or cytokine production responder cells were stimulated with irradiated (2000R) stimulator cells in triplicate in αF10. Supernatants were pooled from replicate wells at 40 hrs for cytokine assays (below). No reproducible differences in cytokine levels have been detected from cultures assayed between 36 and 54 hrs of stimulation. In some experiments the cultures received 1 mCi/well (at 72 hrs) of $^3$HTdR and proliferation was assessed by harvesting cells 14 hrs later and counting in a well-type b-counter.

Where cytoxicity was measured cells were harvested and pooled from equivalent cultures at 5 days, counted, and recultured at different effector:target with $^{51}$Cr EL4 ($H2^{b/b}$) or P815 ($H2^{d/d}$) tumor target cells. Supernatants were sampled at 4 hrs for assessment of specific cytotoxicity.

IL-2 and IL-4 activity were assayed by bioassay using the IL-2/IL-4 dependent cell lines, CTLL-2 and CT4.S respectively. Recombinant cytokines for standardization of assays was purchased from Genzyme (Cambridge, Mass.). IL-2 assays were set up in the presence of 11B11 to block potential stimulation of CTLL-2 with IL-4; IL-4 assays were set up in the presence of S4B6 to block IL-2 mediated stimulation. Both the IL-2 and IL-4 assays reproducibly detected 50 pg of recombinant lymphokine added to cultures.

In addition, IL-2, IL-4, IFNγ and IL-10 were assayed using ELISA assays. For IFNγ the assay used flat-bottomed Nunc plates (Gibco, BRL) coated with 100 ng/ml R4-6A2. Varying dilutions of supernatant were bound in triplicate at 4° C., washed ×3, and biotinylated anti-IFNγ (XMG1.2) added. After washing, plates were incubated with streptavidin-horse radish peroxidase (Cedarlane Labs, Hornby, Ontario), developed with appropriate substrate, and $OD_{405}$ determined using an ELISA plate reader. Recombinant IFNγ for standardization was from Pharmingen. IL-10 was similarly assayed by ELISA, using JES5-2A5 as a capture antibody and biotinylated SXC-1 as developing antibody. rIL-10 for standardization was from Pepro Tech Inc. (Rocky Hill, N.J.). Each assay detected 0.1 ng/ml cytokine. ELISA assays for IL-2 and IL-4 used JES6-1A12 and 11B11 as capture antibodies, with JAS6-5H4 or BVD6-24G2 as developing antibodies. Sensitivity of detection was 20 pg/ml for each cytokine. Where checked the correlation between bioassay and ELISA for IL-2 or IL-4 was excellent (r>0.90). In all studies reported below, data are shown from ELISA assays only. Where cytokine data are pooled from several studies (e.g. FIGS. 14, 16, 17), absolute values of cytokine production were obtained as above using commercial recombinant cytokines to standardize the assays. In our hands, supernatants from C3Hanti-C57BL/6 cultures, under the conditions described, reproducibly contain 950±200 and 80±25 pg/ml IL-2 and IL-4 respectively.

Preparation of RNA:

Different sources of tissue from renal-grafted female mice receiving DC and kidney allografts from male mice were harvested for RNA extraction as described elsewhere (Gorczynski, R. M. 1995a. *Cell. Immunol.* 160:224-231). The OD280/260 of each sample was measured and reverse transcription performed using oligo (dT) primers (27-7858: Pharmacia, U.S.A.). The cDNA was diluted to a total volume of 100 ml with water and frozen at −70° C. until use in PCR reactions with primers for murine GAPDH, B7-1, B7-2 or OX-2. The sense (S) and antisense (AS) primers were synthesized by the Biotechnology Service Centre, Hospital for Sick Children, Toronto, using published sequences. 5' primers were $^{32}$P end-labeled for PCR and had comparable levels of specific activity after purification by ethanol precipitation. 5 ml cDNA was amplified for 35 cycles by PCR, and samples were analyzed in 12.5% polyacrylamide gels followed by overnight (18 hrs) exposure for autoradiography. In control studies, using H—Y primer sets, this technique reliably detects H—Y mRNA from extracts of female spleen cells to which male cells are added at a concentration of 1:10$^5$ (Gorczynski, R. M. 1995a. *Cell. Immunol.* 160:224-231; Gorczynski, R. M. et al. *Transplantation* 62:1592-1600). Quantitative comparison of expression of different PCR products used densitometric scanning of the autoradiograms.

```
GAPDH Sense:       5'TGATGACATCAAGAAGGTGGTGAAG3'   (SEQ ID NO:10)

GAPDH Antisense:   5'TCCTTGGAGGCCATGTAGGCCAT3'     (SEQ ID NO:11)

B7-1 Sense:        5'CCTTGCCGTTACAACTCTCC3'        (SEQ ID NO:12)

B7-1 Antisense:    5'CGGAAGCAAAGCAGGTAATC3'        (SEQ ID NO:13)

B7-2 Sense:        5'TCTCAGATGCTGTTTCCGTG3'        (SEQ ID NO:14)

B7-2 Antisense:    5'GGTTCACTGAAGTTGGCGAT3'        (SEQ ID NO:15)

OX-2 Sense:        5'GTGGAAGTGGTGACCCAGGA3'        (SEQ ID NO:16)

OX-2 Antisense:    5'ATAGAGAGTAAGGCAAGCTG3'        (SEQ ID NO:17)
```

Statistical Analysis:

In studies with multiple groups, ANOVA was performed to compare significance. In some cases (as defined in individual circumstances) pairwise comparison between groups was also subsequently performed.

Results

Antigen Stimulation, in the Presence of Hepatic NPC, Induces Development of a Cell Population Capable of Inhibiting Proliferation and IL-2 Production on Adoptive Transfer:

In a previous manuscript (Gorczynski, R. M. et al., *Transplantation.* 66: 339-349) it was reported that C3H spleen cells stimulated in the presence of syngeneic NPC and allogeneic (C57BL/6) DC produced a cell population able to inhibit generation of IL-2 from fresh spleen cells stimulated with C57BL/6 DC, and capable of inhibiting C57BL/6 renal allograft rejection in vivo. In order to ask whether this function of NPC was MHC restricted or not, the following study was performed.

C57BL/6 (H2$^{b/b}$) spleen cells were stimulated in vitro with B10.BR (H2$^{k/k}$) bone-marrow derived DC, in the presence/absence of the following NPC: C57BL/6; B10.BR; B10.D2 (H2$^{d/d}$). In addition, control cultures were incubated with the NPC only. Proliferation and IL-2/IL-4 production was measured in one aliquot of these primary cultures. In addition, at 5 days, cells were harvested from another set of the primary cultures, washed, and 2×10$^5$ cells added to cultures containing 5×10$^6$ fresh C57BL/6 spleen cells and B10.BR DC. Proliferation and cytokine production was measured in these latter cultures in standard fashion. Data pooled from three equivalent studies are shown in panels A) and B) of FIG. 9.

Figure 9:
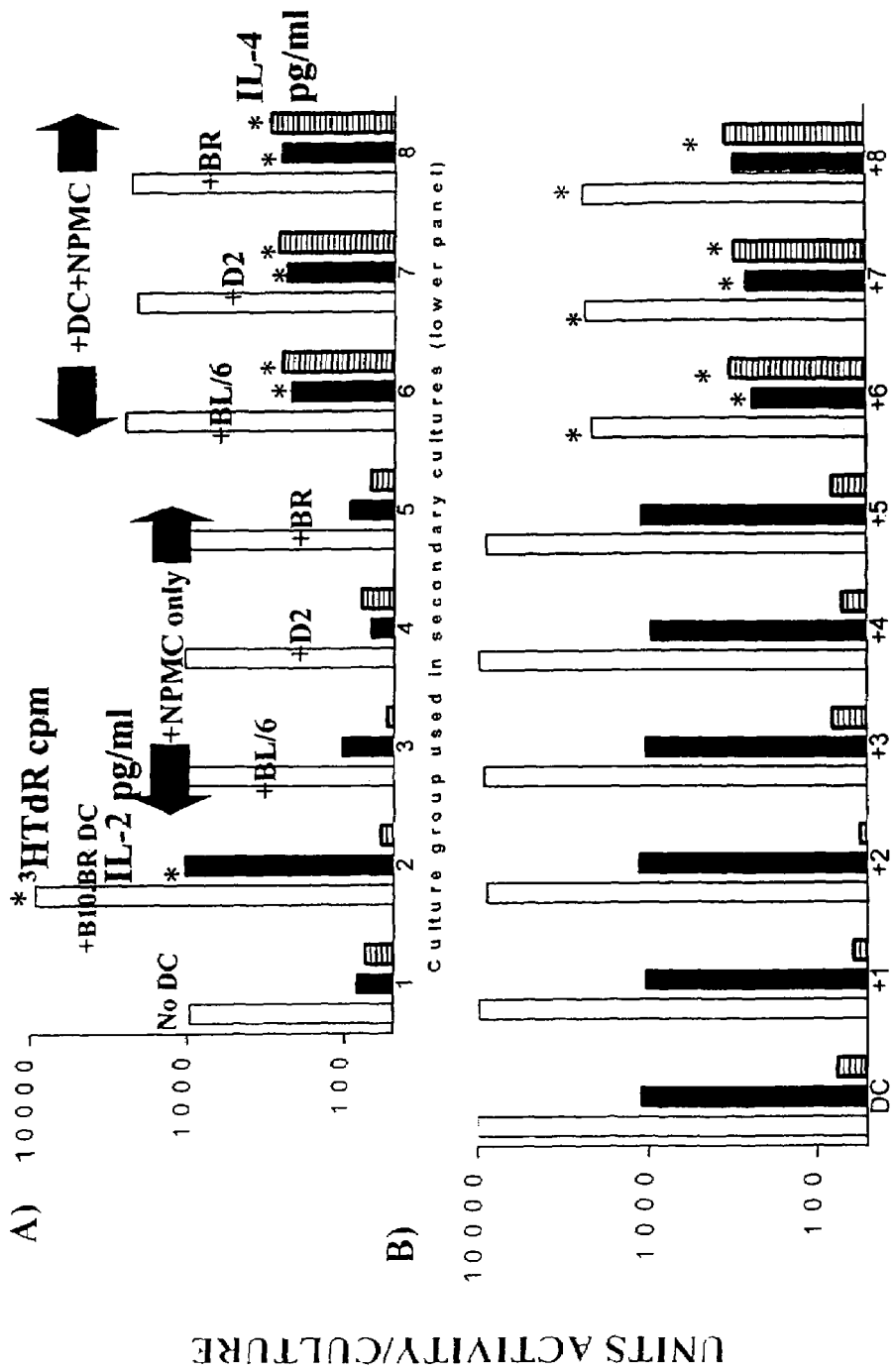
FIGS. 9A and 9B are bar graphs showing cytokine production and cell proliferation following stimulation by allogeneic DC using hepatic NPMC.

FIG. 9 is a bar graph showing regulation of proliferation and cytokine production following stimulation by allogeneic DC using hepatic NPC in accordance with the methods described herein. In panel A) cultures were initiated with 5×10$^6$ C57BL/6 responder spleen cells alone (group 1), or with 2×10$^5$ B10.BR DC (group 2). Further groups (3-5, and 6-8 respectively) contained C57BL/6 responder cells and 2×10$^5$ NPC from either C57BL/6, B10.D2 or B10.BR respectively (3-5) or these same NPC and B10.BR DC (6-8). Data show mean proliferation and cytokine production from triplicate cultures in three separate studies. In panel B) data show proliferation and cytokine production from cultures of 5×10$^6$ C57BL/6 responder spleen cells stimulated in triplicate with 2×10$^5$ B10.BR DC alone, or with the addition also of 2×10$^5$ cells harvested from the cultures shown in the upper panel. Again data represent arithmetic means of 3 separate experiments. * p<0.05 compared with control cultures (far left in each panel).

There are a number of points of interest. As previously documented, addition of NPC syngeneic with spleen responder cells (C57BL/6 in this case) to cells stimulated with allogeneic (B10.BR) DC led to decreased proliferation and IL-2 production from those responder cells compared with cells stimulated by DC alone (compare groups 6 and 2 of upper panel of FIG. 9, panel A). IL-4 production in contrast was enhanced. NPC alone, whether syngeneic or allogeneic to the responder cells, produced no obvious effect (groups 3-5, panel A) of FIG. 9). Furthermore, cells from primary cultures receiving the DC+NPC mixture were able to inhibit proliferation and IL-2 production (while promoting IL-4 production) from fresh spleen cells stimulated in secondary cultures with the same (B10.BR) DC (see panel B) of FIG. 9). However, data in this Figure make another important point. The same inhibition of proliferation/IL-2 production in primary cultures was seen using either B10.BR NPC (MHC matched with the DC stimulus-group 8, panel A) of FIG. 9) or with third-party B10.D2 NPC (MHC-mismatched with both spleen responder cells and allogeneic stimulator DC-group 7, panel A) of FIG. 9). Again no obvious effect was seen in cultures stimulated with B10.BR or B10.D2 NPC alone (groups 4 and 5). Finally, cells taken from primary cultures stimulated with DC and NPC from eiher B10.BR or B10.D2 could also inhibit proliferation/IL-2 production from secondary C57BL/6 spleen cell cultures stimulated with B10.BR DC-again cells taken from primary cultures with NPC alone produced no such inhibition (see panel B) of FIG. 9). Thus the inhibition of proliferation/IL-2 production and enhancement of IL-4 production seen in primary cultures, as well as the induction of suppression measured in secondary cultures, all induced by NPC, are not MHC-restricted.

Specificity of Inhibition/suppression Induced by Hepatic NPC:

One interpretation of the data shown in FIG. 9 and elsewhere is that NPC deliver a signal to DC-stimulated cells which is distinct from the antigen-signal provided by the DC themselves (and is MHC non-restricted). This signal modulates the antigen-specific signal provided by the DC. In order to assess the antigen-specificity of the immunoregulation described in FIG. 9, the following experiment was performed.

C57BL/6 spleen responder cells were stimulated with B10.D2 or B10.BR bone marrow-derived DC, in the presence/absence of NPC from B10.BR or B10.D2 mice. Proliferation and cytokine production was measured in aliquots of these cultures as before. In addition, further aliquots of cells harvested from these primary cultures were added to cultures of fresh C57BL/6 spleen cells stimulated with B10.BR (panel B)—FIG. 10) or B10.D2 (panel C)—FIG. 10) DC. Again proliferation and cytokine production was measured. Data pooled from three such studies are shown in FIG. 10.

Figure 10:
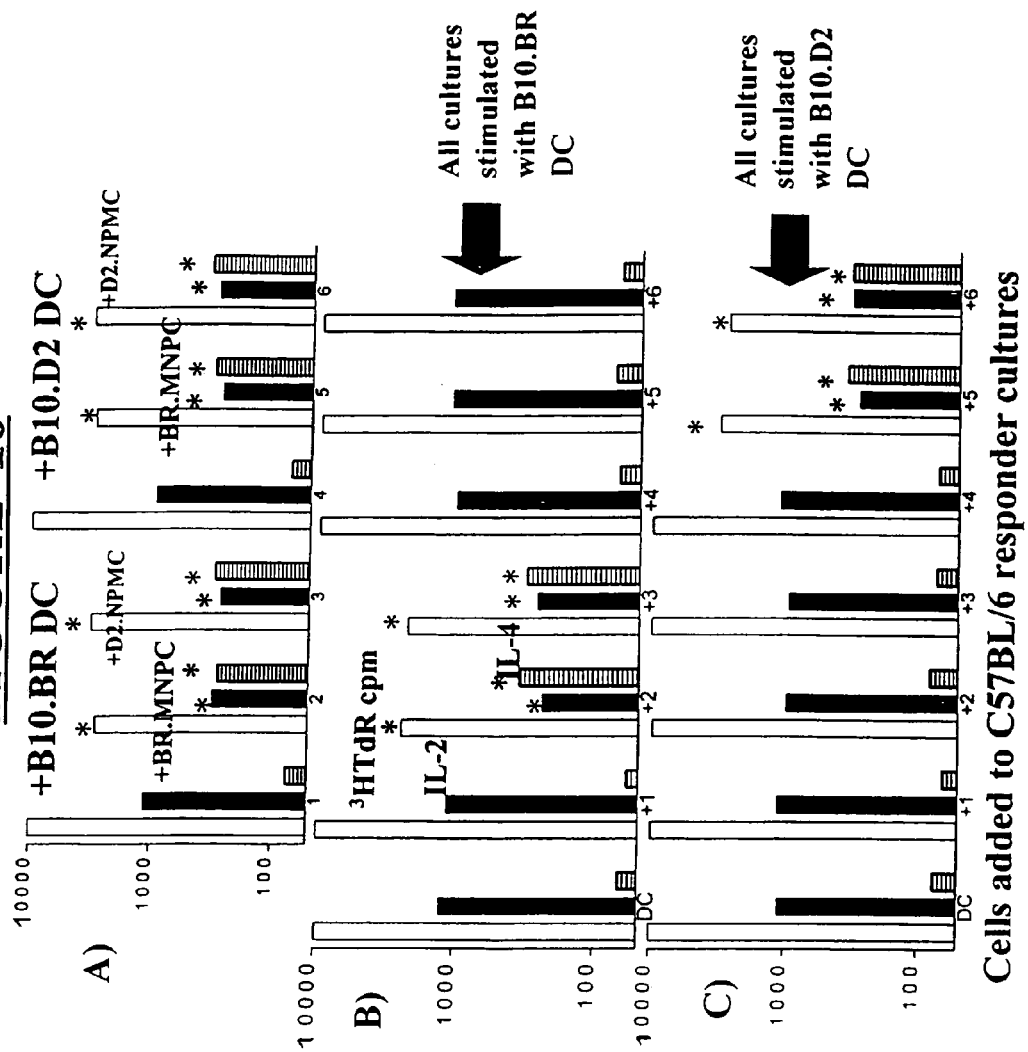
FIGS. 10A, 10B and 10C are bar graphs showing inhibition of cell proliferation and cytokine production by hepatic NPMC.

FIG. 10 shows specificity of inhibition of proliferation of cytokine production by hepatic NPC (see FIG. 9 and description of FIG. 9 for more details). In panel A), $5 \times 10^6$ C57BL/6 spleen cells were stimulated in triplicate for 3 days with $2 \times 10^5$ B10.BR or B10.D2 DC, with/without $2 \times 10^5$ NPC derived from B10.D2 or B10.BR mice. Data shown are arithmetic means of 3 repeat studies. In panels B) and C), fresh C57BL/6 responder spleen cells were cultured in triplicate with either B10.BR DC (panel B), or B10.D2 DC (Panel C), with/without $2 \times 10^5$ additional cells from the primary cultures (groups 1-6 in panel A). Again data represent arithmetic means of proliferation/cytokine production from 3 studies. * $p<0.05$ compared with control cultures (far left in each panel).

Data from the primary cultures (panel A)) recapitulates the observations made in FIG. 9, and show that NPC inhibit proliferation and IL-2 production from DC-stimulated responder cells in an antigen and MHC-unrestricted fashion. However, the data in panels B) and C) of this figure show clearly that adoptive transfer of inhibition using cells from these primary cultures occurs in an antigen-restricted fashion, dictated by the antigen-specificity of the DC used in the primary cultures, not of the NPC used for induction of suppression. These auxiliary cells in the NPC population thus have a functional property of being "facilitator cells for induction of suppression". Note that in other studies (data not shown) where the final assay system involved measuring cytotoxicity to allogeneic target cells, a similar inhibition of lysis (rather than cytokine production) was seen using cells harvested from primary cultures stimulated with DC and hepatic NPC (see Gorczynski, R. M., et al. 1998a. *Transplantation*. 66: 339-349).

Hepatic Cell Preparations from Flt3L Treated Mice are a Potent Source of DC and "Facilitator" Cells:

It has been reported at length that pv infusion of alloantigen, or iv infusion of liver-derived allogeneic mononuclear cells induces operational unresponsiveness in recipient animals (Gorczynski, R. M. 1995a. *Cell. Immunol.* 160:224-231; Gorczynski, R. M. et al. *Transplantation* 62:1592-1600; Gorczynski, R. M. et al. 1994a. *Transplantation* 58:816-820.; Gorczynski, R. M., and D. Wojcik. 1992. *Immunol. Lett.* 34:177-182; Gorczynski, R. M. et al. 1995b. *Transplantation*. 60:1337-1341). The total hepatic mononuclear cell yield from normal mice is of the order of $5 \times 10^6$ cells/mouse. In order to increase the yield, and explore the possibility that the liver itself might be a source both of allostimulatory DC and "facilitator" cells 2 C57BL/6 mice were exposed for 10 days to daily iv infusions of 10 mg/mouse human CHO-derived Flt3L, a known growth factor for DC (Steptoe, R. J. et al. 1997. *J Immunol.* 159:5483-5491). Liver tissue was harvested and pooled from these donors and mononuclear cells prepared as described in the Materials and Methods section above (mean $130 \times 10^6$ cells/donor). These cells were further subjected to sub-fractionation by size using unit gravity sedimentation techniques (Miller, R. G., and R. A. Phillips. 1969. *J. Cell. Comp. Physiol.* 73:191-198). A typical size profile for recovered cells is shown in FIG. 11 (one of 3 studies).

Figure 11:
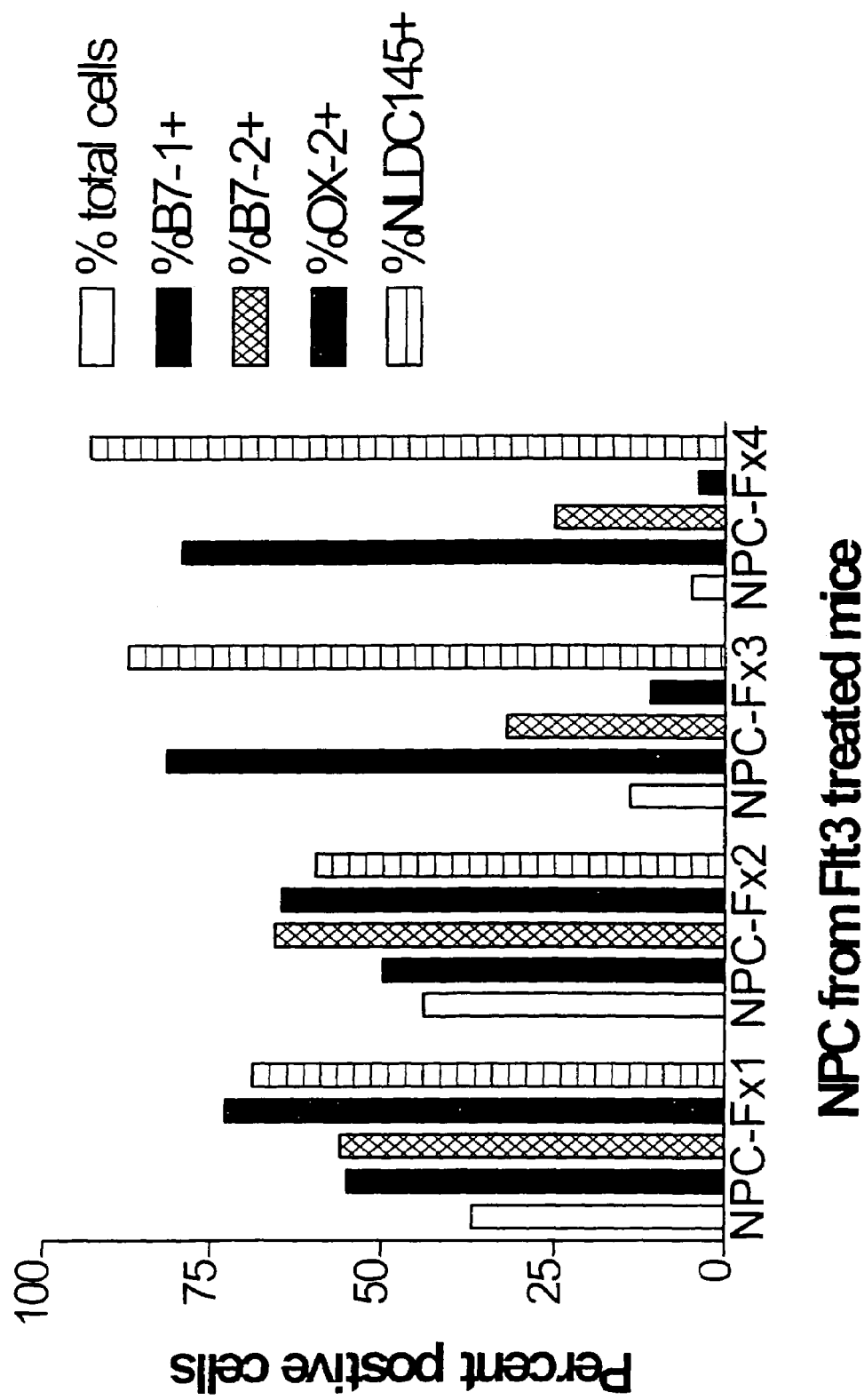
FIG. 11 is a bar graph analysis of FACS data showing OX-2 expression in a subpopulation of NPC.

FIG. 11 shows OX-2 expression in a subpopulation of NPC. It is a sedimentation analysis (cell profile) and FACS analysis of cells isolated at 10 days from Flt3L-treated C57BL/6 mice. Two C57BL/67 mice received 10 mg/mouse Flt3L iv daily for 10 days. Hepatic NPC were sedimented for 3 hrs at 4° C., and the fractions shown collected (Fxs 1-4 with sedimentation velocities 2.5-3.8, 3.8-5.1, 5.1-6.4 and 6.4-8.0 mm/hr respectively). Aliquots of the cells were stained in triplicate with the Mabs shown. The remainder of the cells were used as in FIGS. 12-14. Data are pooled from 3 studies.

In these same studies cells isolated from the various fractions shown in FIG. 11 were tested as follows. Firstly, cells were stained with FITC-labeled Mabs to B7-1, B7-2, NLDC145 and rat anti-mouse OX-2 (M3B5) with FITC anti-rat IgG as second antibody. In addition, mRNA extracted from the different cell samples were assayed by PCR for expression of GAPDH, B7-1, B7-2 and OX-2. Data are shown in FIG. 11 (pooled from 3 separate studies) and FIG. 12 (representative PCR data from one experiment).

FIG. 12 shows PCR detection of B7-1, B7-2 and OX-2 in hepatic NPMC. It is a PCR analysis for mRNA expression of OX-2, B7-1 and B7-2 in various hepatic NPC cell fractions isolated from Flt3L treated mice (see FIG. 11). Data are representative from 1 of 3 studies.

Further aliquots of the cells were used to stimulate fresh C3H spleen responder cells in culture. Proliferation and cytokine assays were performed as before (see FIG. 9), and in addition cells were taken from these primary cultures and added to fresh secondary cultures of C3H spleen responder cells and C57BL/6 bone marrow-derived DC. Again proliferation and cytokine production was assayed from these secondary cultures. Data pooled from 3 studies of this type are shown in FIG. 13 (panels A) and B).

Figure 13:
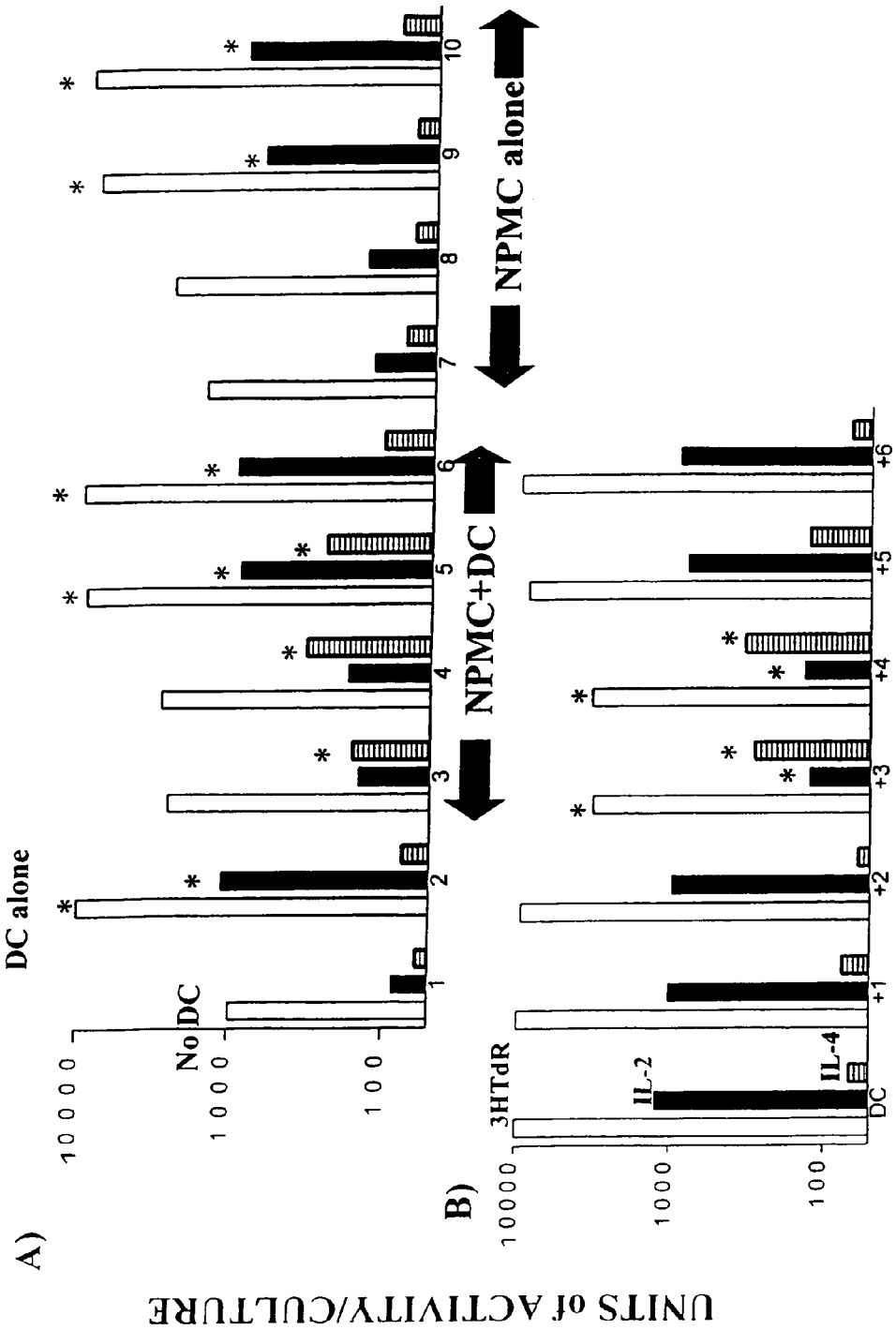
FIGS. 13A and 13B are bar graphs showing proliferation and cytokine production by NPMC from Flt3L treated mice.

FIG. 13 shows that hepatic NPMC from Flt3L treated mice results IL-2 and IL-4 production. Stimulation of proliferation/cytokine production by NPC from Flt3L treated mice, and inhibition of the same (where stimulation is induced by a separate population of DC) is a function of different cell populations. (See text and FIGS. 11-12 for more details.) Hepatic NPC fractions were derived from Flt3L treated C57BL/6 mice and were used to stimulate C3H spleen cells in triplicate cultures, alone or in the presence of bone-marrow derived C57BL/6 DC (see panel A). Data show arithmetic means for proliferation/cytokine production from 3 experiments. In addition, cells harvested from these primary cultures were added to fresh C3H spleen cells stimulated with C57BL/6 DC (panel B), and again proliferation/cytokine production assayed. * $p<0.05$ compared with control groups (far left of panel).

Finally, cells from the various fractions were infused iv into 2/group C3H mice which also received C57BL/6 renal allografts as antigen challenge. Spleen cells were harvested from these individual mice 10 days after transplantation and restimulated in culture with C57BL/6 or B10.D2 DC, again with cytokines measured at 40 hrs (see FIG. 14).

Figure 14:
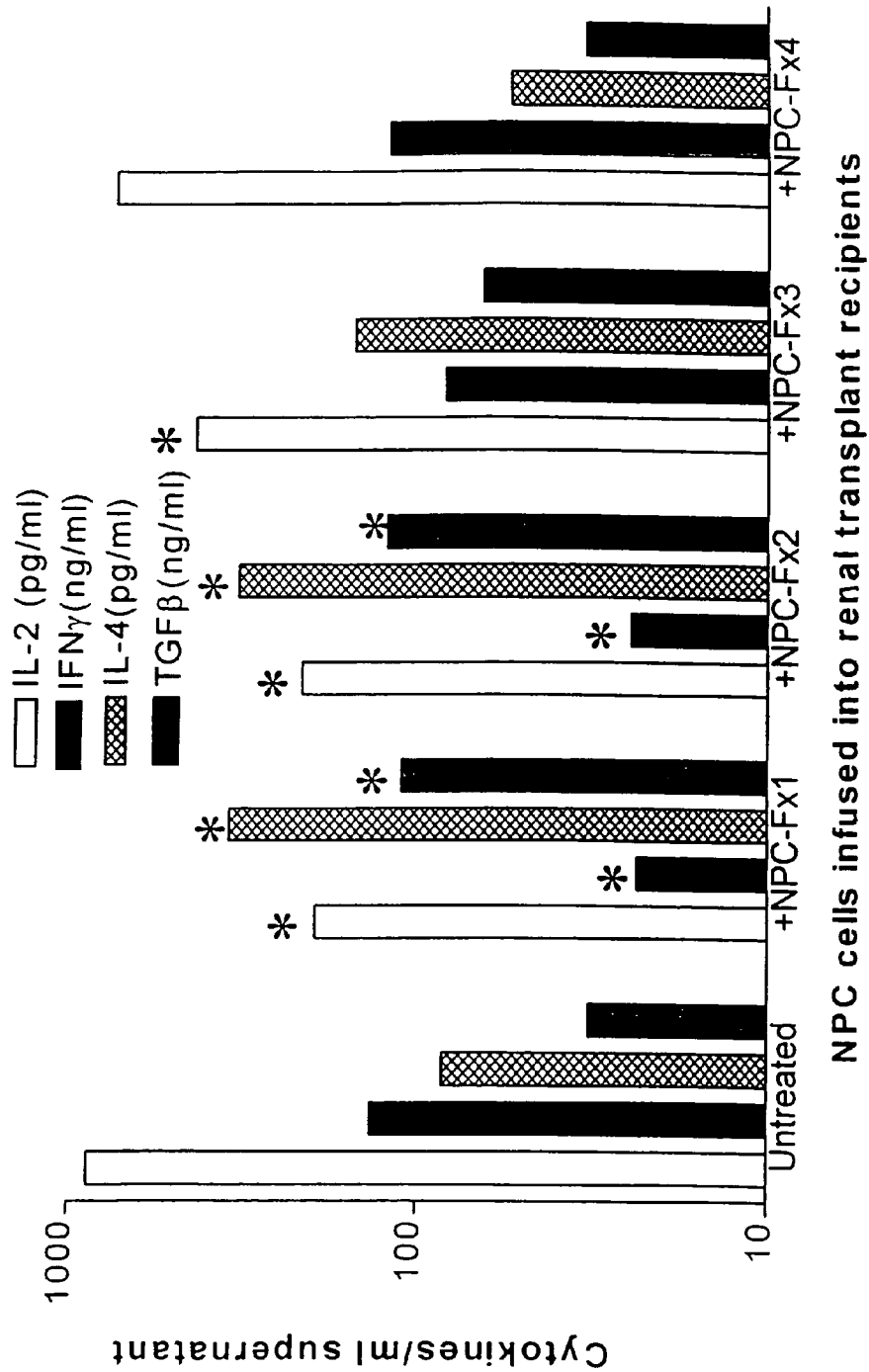
FIG. 14 is a bar graph showing cytokines produced from C3H mice with C57BL16 renal allografts and NPC from Flt3 treated C57BL16 donors.

FIG. 14 is a bar graph of cytokines produced from cells from C3H mice with C57BL/b renal allografts and NPC from Flt3 treated C57BL/6 donors. OX-2+ NPC infused iv into renal transplant allograft recipients leads to polarization of cytokine production (to IL-4, IL-10 and TGFβ) in spleen cells harvested from those mice and restimulated in vitro. Fractions of NPC from Flt3L treated C57BL/6 mice (from FIG. 11) were infused iv into 2/group C3H recipients, receiving C57BL/6 renal allografts (along with CsA) in standard fashion (see Materials and Methods). Mice were sacrificed 14 days after transplantation and spleen cells stimulated in vitro in triplicate with C57BL/6 DC stimulator cells. Cytokines were assayed in the supernatants of these cultures at 60 hrs. Data show arithmetic means pooled from cultures in 3 studies of this type. * p<0.05 compared with control groups (far left-no NPC infused).

Data in FIG. 11 show that distinct subpopulations of slow-sedimenting cells express OX-2 in the cells harvested from Flt3L treated mice, when compared with cells expressing B7-1 and/or B7-2. In general expression of OX-2 and B7-2 occured in equivalent subpopulations. Faster-sedimenting cells (Fx 3 and 4 in FIG. 11), while staining for NLDC145, were positive by fluorescence mainly for B7-1, not B7-2 or OX-2. Similar conclusions were reached both by FACS analysis of cell populations (FIG. 11), and by PCR analysis of mRNA (FIG. 12).

When the functional capacity of these different cell populations was investigated (FIGS. 13 and 14) it was found that optimal direct stimulation (or proliferation and IL-2 production) was seen from B7-1 expressing cells (Fxs 3 and 4 in panel A) of FIG. 13), while only OX-2 expressing cells (Fxs 1 and 2 in FIGS. 11 and 12) were capable of producing the inhibitory effects defined earlier (FIGS. 9 & 10) in the two-stage culture system (panel B) in FIG. 13). These same cells (Fxs 1 and 2) were in turn able, after iv infusion, to polarize cells from mice given renal allografts to produce predominantly IL-4, IL-10 and TGFβ production on restimulation in vitro (FIG. 14). These data are consistent with the notion that after FltL treatment of mice expansion of a population of immunostimulatory DC occurs within the liver, which also contains another distinct population of (facilitator) cells which promote immunoregulation.

Evidence that Cell Populations With "Facilitator" Activity from the Liver of Flt3L Treated Mice Prolong Graft Survival In Vivo:

Since it has been reported elsewhere that there is a good correlation between treatments (such as pv immunization) which decrease IL-2 production and increase IL-4 production from restimulated cells and prolongation of graft survival (Gorczynski, R. M., and D. Wojcik. 1994. *J. Immunol.* 152:2011-2019; Gorczynski, R. M. 1995a. *Cell. Immunol.* 160:224-231; Gorczynski, R. M. et al. *Transplantation* 62:1592-1600), and that increased expression of OX-2 is also independently associated with increased graft survival after pv immunization (Gorczynski, R. M. et al. 1998b. *Transplantation.* 65:1106-1114), the next question was whether cells isolated from Flt3L treated mice which induced inhibitory function in vitro (see FIGS. 9, 10 and 13), and expressed increased amounts of OX-2 (FIGS. 11, 12) were themselves capable of promoting increased graft survival in vivo.

Groups of 2 C57BL/6 mice received iv infusions of 10 mg/mouse Flt3L for 10 days as before. Cells were isolated from the liver by enzyme digestion, and fractionated by unit gravity sedimentation. 4 pools of cells were recovered, and an aliquot stained as before in FACS with anti-OX-2. Groups of 2 C3H mice received $10 \times 10^6$ cells iv from the 4 separate pools. A control group received saline injections only. Over the next 48 hrs all mice received C57BL/6 renal transplants. All mice received CsA (10 mg/Kg) on the day of renal transplantation. Data in FIG. 15 are pooled from 3 studies of this type (representing 6 mice/group), and show the animal survival in these 5 different groups.

Figure 15:
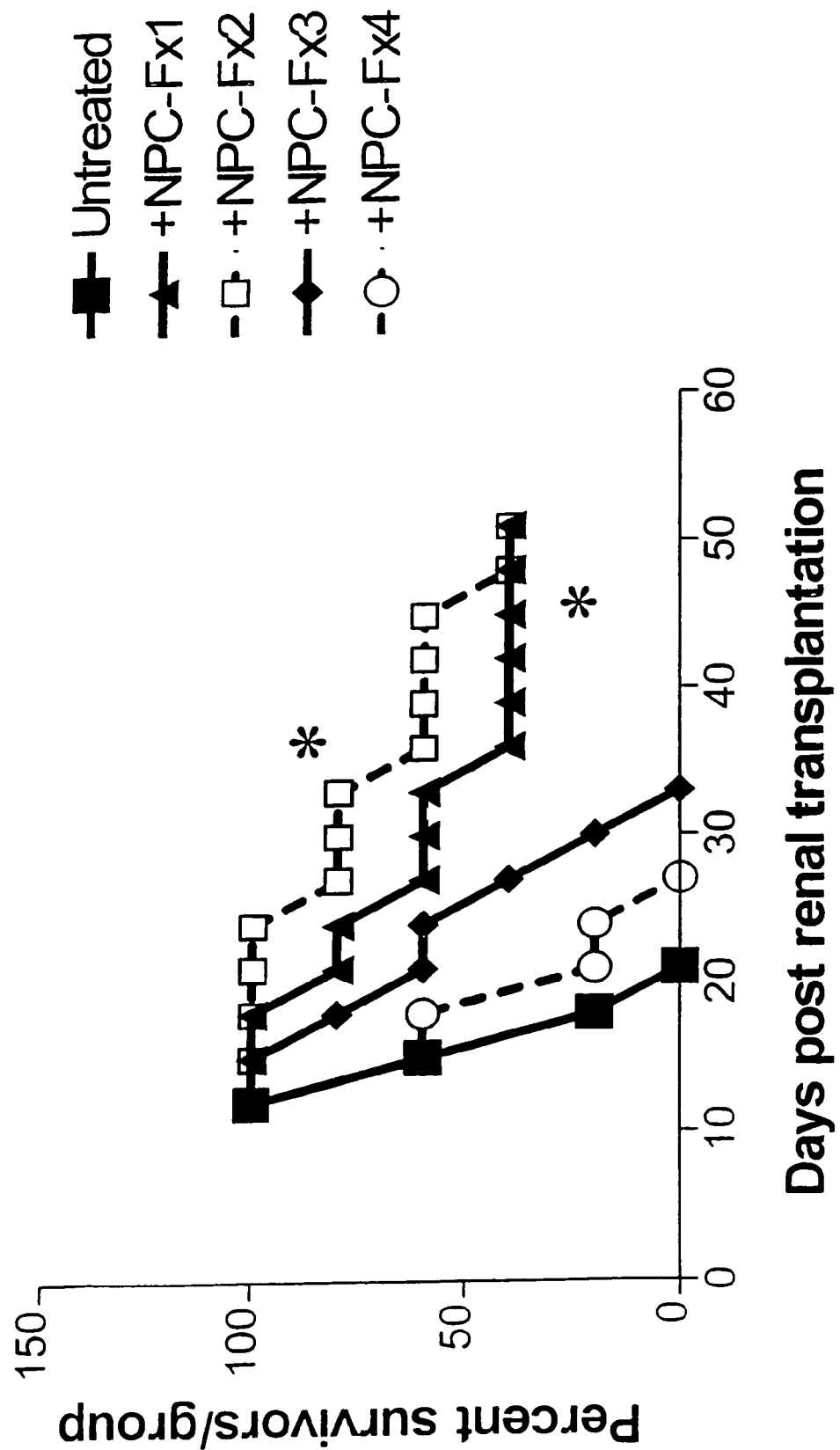
FIG. 15 is a graph showing inhibition of graft rejection with NPC from Flt3 treated mice.

FIG. 15 shows NPC from Flt3L treated C57BL/6 mice, infused iv into recipient C3H mice, inhibit C57BL/6 renal allograft rejection. Two mice groups received the different subpopulations of NPC derived from Flt3L treated mice shown in FIGS. 11 and 12. Fxs 1 and 2 were OX-2+. Mice received C57BL/6 renal allografts within 48 hrs along with CsA (see Materials and Methods). Animal survival was followed as an end point. Data shown are pooled from 3 studies (6 mice/group). *p<0.05 compared with mice receiving CsA only.

It is quite clear from this Figure that only hepatic cells expressing OX-2 (Fxs 1 and 2—see FIGS. 11 and 12) were capable of promoting increased graft survival after iv infusion. Comparison of these data with those in FIG. 13 confirm that these cell populations were also those identified, using a 2-stage culture assay system, as cells with functional "facilitator" activity (see also FIGS. 9 and 10). There was no significant difference in survival between groups receiving NPC-Fx1 or NPC-Fx2 in this experiment, in keeping with relatively equivalent levels of OX-2 expression in these fractions (FIG. 11).

Anti-OX-2 Monoclonal Antibody in Vitro Reverses Regulation Induced by Hepatic NPC:

A final study was directed to whether anti-OX-2 monoclonal antibody M3B5, added to cultures of C3H spleen responder cells, allogeneic (C57BL/6) DC and NPC from C57BL/6 mice, could prevent the inhibition of IL-2 production in primary cultures, and the development of cells able to inhibit such cytokine responses from freshly stimulated responder cells in secondary cultures (see FIGS. 9, 10 and 13). Data in FIGS. 16 and 17 are pooled from 3 studies of this type.

Figure 16:
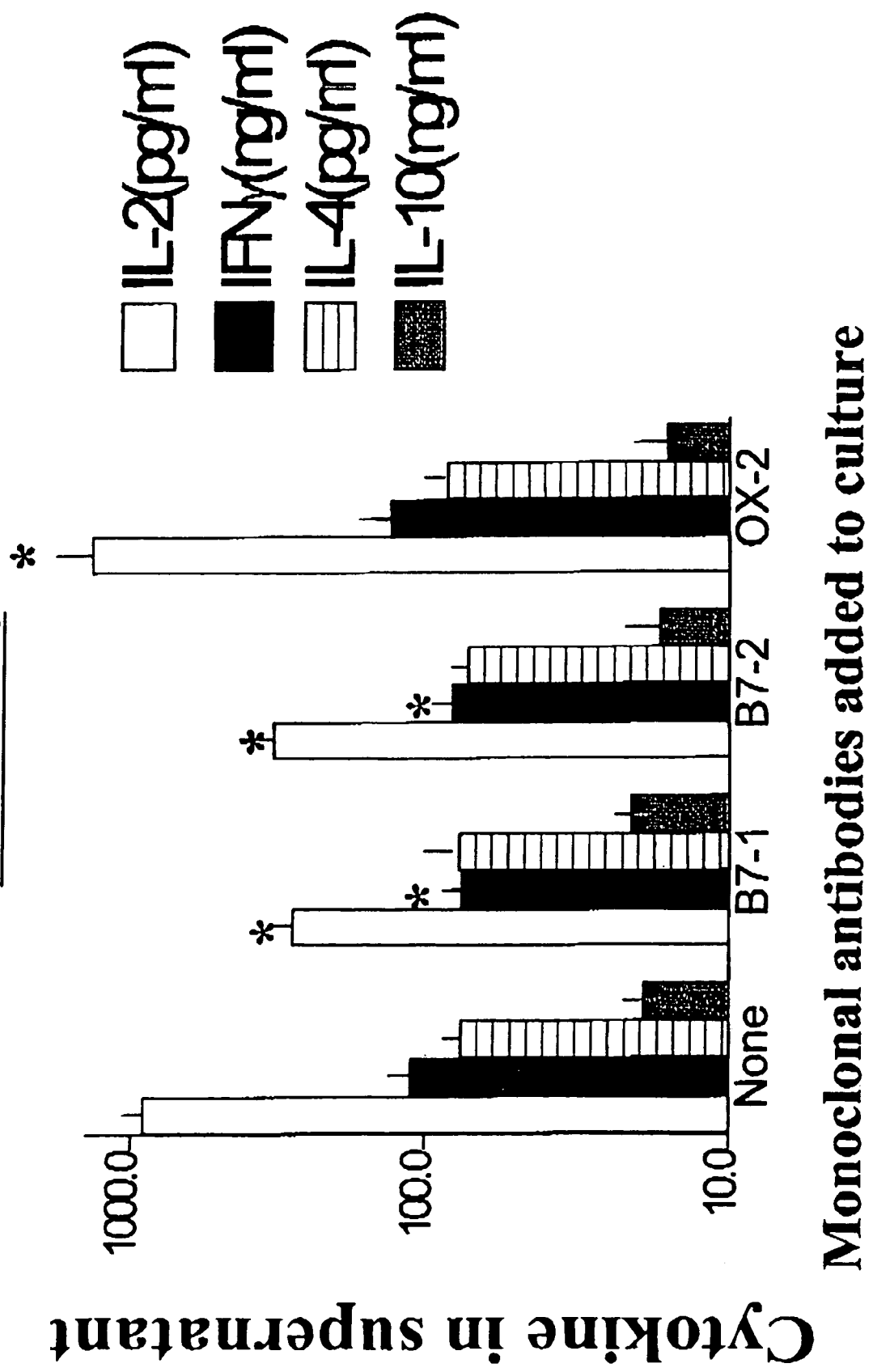
FIG. 16 is a graph showing that anti-OX-2 reverses inhibition by NPC. The effect of anti-B7-1, anti-B7-2 and anti-OX-2 on primary allostimulation is shown.

FIG. 16 is a bar graph showing the effect of anti B7-1; B7-2; or OX-2 on primary allostimulation. It shows that anti-OX-2 Mab increases IL-2 cytokine production in vitro after stimulation of C3H responder spleen cells with C57BL/6 DC. Subgroups of cultures contained the Mabs shown. Cytokines were assayed at 60 hrs. All data represent arithmetic means pooled from 3 repeat studies. *p<0.05 compared with control group (far left).

Figure 17:
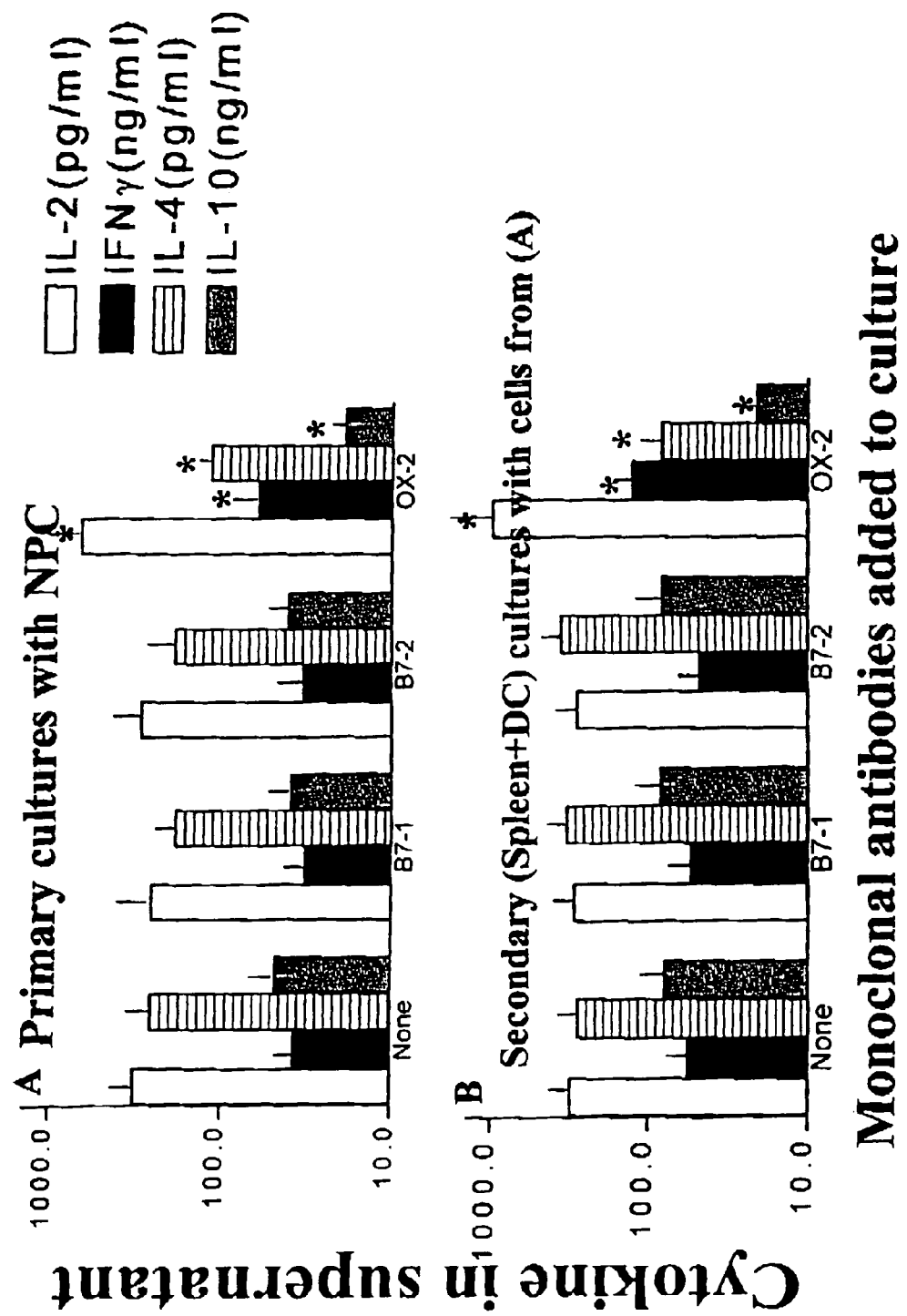
FIG. 17 is a graph showing that anti-OX-2 mAb reverses inhibition by NPC and inhibits the development of immunoregulatory cells.

FIG. 17 is a bar graph showing that anti-OX-2 reverses inhibition by NPC. It shows that anti-OX-2 Mab inhibits development of immunoregulatory cells in vitro following incubation with hepatic NPC. C3H responder spleen cells were incubated in triplicate with C57BL/6 DC along with NPC (see FIGS. 9 and 10). Subgoups of these cultures contained the Mabs shown. Cytokines were assayed in cultures at 60 hrs (panel A). In addition, cells were harvested from all groups, washed and added to fresh C3H responder spleen cells and C57BL/6 DC (panel B). Cytokines in these groups were assayed 60 hrs later. All data represent arithmetic means pooled from 3 repeat studies. *p<0.05 compared with control group from cultures of NPC with no monoclonal antibodies (far left in Figure)—see also FIG. 16.

Primary cultures were of two types, containing C3H responder spleen cells and C57BL/6 DC alone (FIG. 16), or the same mixture with added C57BL/6 NPC (FIG. 17). Subsets of these cultures contained in addition either 5 mg/ml of anti-B7-1, anti-B7-2 or anti-OX-2. Supernatants from responder cells stimulated in the presence of DC only were assayed after 60 hrs for cytokine production (FIG. 16).

For the primary cultures incubated with both DC and NPC, supernatants were harvested at 60 hrs and tested for cytokine production (FIG. 17A). In addition, cells were harvested after 5 days, washed, and added to secondary cultures of fresh C3H responder cells with fresh C57BL/6 DC. No monoclonal antibodies were added at this second culture stage. Data for cytokine production these secondary cultures are shown in FIG. 17B.

Addition of anti-B7-1 or anti-B7-2 to DC stimulated spleen cultures led to inhibition of cytokine production (FIG. 16), while in contrast anti-OX-2 monoclonal antibody led an increase in IL-2 production in these primary cultures (FIG. 16). We have reported similar findings elsewhere (Ragheb et al-submitted for publication). Interestingly, anti-OX-2 abolished the inhibition of cytokine production caused by NPC in these primary cultures (FIG. 17A—see also FIGS. 9, 10 and 13). In addition, anti-OX-2 prevented the functional development of a cell population capable of transferring inhibition of cytokine production to freshly stimulated spleen cells (FIG. 17B).

Discussion

There is considerable theoretical as well as practical interest in understanding the mechanism(s) by which a state of antigen specific tolerance can be induced in lymphoid populations. Limits to the effective induction of tolerance represent a major challenge to more successful allo (and xeno) transplantation, to name but one example (Akatsuka, Y., C. Cerveny, and J. A. Hansen. 1996. *Hum. Immunol.* 48:125-134). Significant efforts have been invested into exploring how pre-(or peri-) transplant donor-specific immunization might produce such a state (Qian, J. H. et al. 1985. *J. Immunol.* 134:3656-3663; Kenick, S., et al. 1987. *Transpl. Proc.* 19:478-480; Gorczynski, R. M. 1992. *Immunol. Lett.* 33:67-77; Thelen, M., and U. Wirthmueller. 1994. *Curr. Opin. Immunol.* 6:106-112; Akolkar, P. N. et al. 1993. *J. Immunol.* 150 (April 1):2761-2773; Ahvazi, B. C. et al. *J. Leu. Biol.* 58 (1):23-31; Albina, J. E. et al. 1991. *J. Immunol.* 147:144-152). There is good evidence that portal venous (pv) immunization somehow leads to tolerance induction, and this immunoregulation can apparently be monitored by following changes in cytokine production from host cells, with decreased production of IL-2, IL-12 and IFNγ, and increased IL-4, IL-10, IL-13 and TGFβ (Thelen, M., and U. Wirthmueller. 1994. *Curr. Opin. Immunol.* 6:106-112; Gorczynski, R. M. et al. 1998a. *Transplantation.* 66: 339-349). Which, if any, of these cytokine changes is directly and causally implicated nevertheless remains obscure.

Further analysis of the cell population able to induce tolerance after pv immunization led to the somewhat paradoxical observation that donor dendritic (DC) cells represented an excellent tolerizing population (Gorczynski, R. M. 1995a. *Cell. Immunol.* 160:224-231; Gorczynski, R. M. et al. 1996 *Transplantation* 62:1592-1600). Since antigen-pulsed DC are conventionally thought of as representing an optimal immunizing regime, the mechanism(s) activated following DC pv immmunization which led to tolerance (Banchereau, J., and R. M. Steinman. 1998. *Nature.* 392: 245-252) was of interest. It is already clear that DC themselves represent an extremely heterogeneous population, in terms of origin, cell surface phenotype, turnover in vivo and possibly function (Salomon, B. et al. 1998. *J. Immunol.* 160:708-717; Leenen, P. J. M. et al. 1998. *J. Immunol.* 160:2166-2173). In the mouse lymph node at least 3 discrete populations were identified, one of which comprised small $CD8a^+NLDC145^+$ cells, likely of lymphoid origin, with an immature phenotype, and whose numbers were profoundly increased (100×) following Flt3L treatment in vivo (Salomon, B. et al. 1998. *J. Immunol.* 160:708-717) (administration of the latter has been reported to lead to proliferation of dendritic cells and other cells of hematopoietic origin (Maraskovsky, E. et al. 1996. *J. Exptl. Med.* 184:1953-1962)). These cells resembled the interdigitating DC found in the T cell areas of the splenic white pulp, and have been implicated in regulation of immunity induced by other (myeloid derived) DC (Salomon, B. et al. 1998. *J. Immunol.* 160:708-717; Kronin, V. et al. 1996. *J. Immunol.* 157:3819-3827; Suss, G., and K. Shortman. 1996. *J. Exptl. Med.* 183:1789-1796).

A variety of other studies have indicated that the induction of immunity (vs tolerance) following antigen presentation was intrinsically dependent upon the co-existence of other signaling ligands at the surface of DC (interacting with appropriate counter-ligands on the surface of other cells (e.g. stimulated T cells)) (Larsen, C. P. et al. 1994. *J. Immunol.* 152:5208-5219; Lenschow, D. J. et al. 1996. *Annu. Rev. Immunol.* 14:233-258; Larsen, C. P., and T. C. Pearson. 1997. *Curr. Opin. Immunol.* 9:641-647). It was speculated that infusion of DC via the portal vein induced tolerance by co-opting another cell population, distinguishable by expression of unique cell surface ligands, whose biological function was to facilitate induction of tolerance, not immunity, when antigen was presented in association with otherwise immunogenic DC. Some preliminary evidence supporting this hypothesis was recently reported (Gorczynski, R. M. et al. 1999. *J. Immunol.* 162: 774-780). Herein, this is referred to as a facilitator cell. Moreover, because pv immunization has been shown to be associated with increased expression of a novel molecule, OX-2, previously reported to be expressed on DC (Barclay, A. N. 1981. *Immunology* 44:727; Barclay, A. N., and H. A. Ward. 1982. *Eur. J. Biochem.* 129:447; Chen, Z. et al. 1997. *BBA. Mol. Basis Dis.* 1362: 6-10; Gorczynski, R. M. et al. 1998b. *Transplantation.* 65:1106-1114), it was predicted that this molecule would in fact serve as a "marker" for the hypothetical facilitator cell described. Experiments reported herein are consistent with such a hypothesis.

It is here shown that within the hepatic NPC population there is a subset of cells able to inhibit stimulation by allogeneic DC in a non-MHC restricted fashion (see FIGS. 9 and 10), and able to induce the development of an antigen-specific immunoregulatory cell population in vitro (see FIGS. 9 and 10). The non-MHC-restricted nature of this "facilitator" cell interaction indicates that it functions by providing an accessory signal (a regulatory not a co-stimulatory signal) to the DC which stimulate T cells in the allogeneic mixed leukocyte reaction described, in a fashion analogous to the original description of costimulatory interactions (Jenkins, M. K. et al. 1988. *J. Immunol.* 140:3324-3329). As a result the stimulated lymphocytes alter their cytokine production profile (with decreased IL-2 production and proliferation), and become able to regulate the immune response seen from freshly stimulated lymphocytes (see panel B in FIGS. 9 and 10). Most interestingly, following expansion of DC in vivo by Flt3L treatment, it is shown that in fact the liver itself contains both an immunostimulating population (large cells by velocity sedimentation analysis), and this putative "facilitator" cell population (see FIGS. 11-15). Furthermore, the latter biological activity resides within a slow-sedimenting (small size) $NLDC145^+$ cell population expressing preferentially both cell surface B7-2 and OX-2 (see FIGS. 11 and 12). When it was investigated whether this same population of cells was active in vivo in regulating graft tolerance, it was found again that after prior Flt3L treatment, the liver contained a population of cells which transferred increased renal graft acceptance (FIG. 15) and in parallel altered the cytokine production profile of immunized mice towards increased IL-4 and TGFβ, and decreased IL-2 and IFNγ production (FIG. 14).

In a final attempt to explore the role for OX-2 expression itself in this regulatory function, fresh spleen cells were stimulated with DC alone or in the presence of anti-B7-1, anti-B7-2 or anti-OX-2. Note that other studies (data not shown) have confirmed that even the bone-marrow derived DC used contains small numbers of OX-2$^+$ cells (RMG-unpublished). Unlike anti-B7-1 and anti-B7-2 which decreased cytokine production, a result in keeping with the hypothesized role for these as costimulator molecules (Hancock, W. W. et al. 1996. *Proc. Natl. Acad. Sci. USA* 93:13967-13972; Freeman, G. J. et al. 1995. *Immunity.* 2:523-532; Kuchroo, V. K. et al. 1995. *Cell.* 80:707-718), anti-OX-2 produced a small but significant (1.7-2.5 fold in three studies) increase in IL-2 production in this system (FIG. 16). Most important, however, inclusion of anti-OX-2 Mab in a system where exogenous "facilitator" cells were added (from NPC), blocked completely the induction of inhibition normally seen in such cultures (FIGS. 9 and 10; compare with lower panel of FIG. 17). These data are consistent with the concept that OX-2 delivers a regulatory, not a costimulatory, signal in this situation.

How does the present data fit within the evolving framework of understanding in the heterogeneity of DC? As noted above, there has been speculation that a separate population of CD8a$^+$NLDC145$^+$ DC of lymphoid origin which proliferates in response to Flt3L, might be responsible for immunoregulation. Other data have implicated IL-10 as a cytokine which might modify development/maturation of DC into a population expressing increased amounts of B7-2 and capable of inducing tolerance (Steinbrink, K. et al. 1997. *J immunol.* 159:4772-4780). The role of regulation of expression of Fas as a controlling feature in this regard is unexplored (Suss, G., and K. Shortman. 1996. *J. Exptl. Med.* 183:1789-1796). The data disclosed herein is the first to implicate another molecule, OX-2, in the delivery of a tolerizing signal, perhaps in association with alterations in expression of B7-2, Fas etc. It is intriguing that while there is clearly a key role for intra-thymic DC in the regulation of self-tolerance (Banchereau, J., and R. M. Steinman. 1998. *Nature.* 392:245-252), natural expression of OX-2 was initially first described on thymic DC (as well as within the brain) (Barclay, A. N. 1981. *Immunology* 44:727)—there is as yet no evidence to suggest that this represents a functionally relevant expression for OX-2 in this location. However, other independent data have also implied an immunoregulatory role for OX-2 expression, again as assayed by altered cytokine production in vitro from cells stimulated in the presence/absence of expressed OX-2 (Borriello, F. et al. 1997. *J. Immuno.* 158:4548).

It has been reported that following pv immunization there is a measureable expansion in numbers of populations of γδTCR$^+$ cells capable of adoptive transfer of increased graft survival to naive recipients (Gorczynski, R. M. et al. 1996c. *Immunology.* 87 (3):381-389). Little is known concerning the nature of the antigen recognized by these cells, and why, as a population, their numbers are preferentially increased following pv immunization. It is speculated that this may be explainable ultimately in terms of a differential susceptibility of γδTCR$^+$ vs αβTC R$^+$ cells to immunoregulatory signals delivered following OX-2 expression. Indeed, FITC-OX-2:Fc bound to >80% of activated γδ T cells and <20% of activated αβ T cells.

In conclusion, the inventor has reported for the first time that functional heterogeneity in the DC pool may be understandable in terms of differential expression of OX-2 on the cell surface. Expression of this molecule seems to give cells the capability to induce immunoregulation, increased renal graft survival (and altered cytokine production both in vivo and in vitro). The present invention suggests that such OX-2 expressing cells are referred to as "facilitator" cells (for tolerance induction).

Example 4

Preparation of Murine Antibodies

Mouse and rat hybridomas to a 43 Kd molecule expressed in the thymus, on a subpopulation of dendritic cells, and in the brain, in mammalian tissue derived from mouse, rat and human were prepared. Using CHO cells transiently transfected with adenovirus vector(s) expressing a cDNA construct for the relevant OX-2 gene, the monoclonal antibodies (Mabs) detect a molecule encoded by this construct (rat OX-2 (rOX-2), mouse OX-2 (mOX-2) and human OX-2 (huOX-2) respectively). Furthermore, at least some of the anti-rat Mabs detect determinants expressed on the murine OX-2 molecule.

Materials and Methods

Antigen Preparation from Tissues and Western Blotting were Performed as Described in Gorczynski et al., Transplantation, 1998, 65:1106-1114:

Spleen cells (human samples were obtained from cadavers at the time of organ retrieval for transplantation) were used for preparation of dendritic cells/macrophages. Tissue was digested with a mixture of collagenase and dispase and centrifuged over lymphopaque. Cells were adhered for 2 hr at 37° C., washed vigorously, and incubated for 14 hr at 37° C. Dendritic cells were isolated as non-adherent cells (Gorczynski et al., Transplantation, 1996. 62:1592-1600). Routine staining of mouse splenocytes with NLDC-145 and FITC anti-rat IgG, or FITC-MAC-1 before and after overnight incubation produced the following staining pattern in these adherent cells: 8%±2%, 90%±11% and 92%±9%, 9%±3% respectively. The crude (non-adherent) dendritic cell preparation was extracted with lysis buffer, titred to a protein concentration of 10 mg/ml, and used for immunization. Some of the same material was used subsequently in screening ELISAs (below).

When brain tissue was used in Western gel analysis, whole tissue extract was electrophoresed in 12% SDS-PAGE and transferred to PVDF membranes (Novex Co., San Diego, Calif.). Putative anti-OX-2 Mabs were used as test reagent, with isotypic antibodies (negative in ELISA tests) used as controls. Membranes were developed using either anti-rat or anti-mouse horse radish peroxidase and appropriate substrate.

Immunization and Production of Mabs:

Four female BALB/c mice were initially immunized by intraperitoneal injections with 1 mg of human or rat dendritic antigen in Complete Freund's Adjuvant. Three subsequent boosts were administered as above, spaced at 3 week intervals, with Incomplete Freund's Adjuvant. When the serum titre had risen more than 10-fold from a pre-immune serum sample, as determined by ELISA, the 2 highest responders were boosted intravenously. Three days later the donor mice were sacrificed and the spleen cells were harvested and pooled. Fusion of the splenocytes with X63-

Ag8.6.5.3 BALB/c parental myeloma cells was performed as previously described (Kohler, G. and C. Milstein. 1975. *Nature*. 25: p. 256-259), except that one-step selection and cloning of the hybridomas was performed in 0.8% methylcellulose medium (Immuno-Precise Antibodies Ltd., Victoria, BC). This proprietary semi-solid medium allows HAT selection and cloning in a single step and eliminates the overgrowth of slower growing desirable clones by faster growing, perhaps undesirable, hybridomas. Clones were picked and resuspended in wells of 96-well tissue culture plates in 200 ml of D-MEM medium containing 1% hypoxanthine/thymidine, 20% Fetal Bovine serum, 1% OPI, and $1 \times 10^6$/ml BALB/c thymocytes. After 4 days, the supernatants were screened by ELISA for antibody activity on plates coated with the immunizing antigen. Putative positive hybridomas were re-cloned by limited dilution cloning to ensure monoclonality and screened in FACS on extracts prepared from brain tissue (below).

For the production of rat mAbs, 2 Fisher rats were immunized as above with mouse antigen. Essentially the same procedure was followed, except the parental cell line used for the fusion was YB2/0.

ELISA and FACS Analysis of Putative Mabs:

ELISA assays used polystyrene plates pre-coated with 100 ng/ml poly-L-lysine, followed by overnight incubation with the crude dendritic cell antigen (used for immunization) at 10 mg/ml. Wells were developed after binding of hybridoma supernatants using the anti-rat/anti-mouse horse radish peroxidase antibodies above and plates were analysed in an automatic ELISA plate reader (TiterTek Multiskan, MCC/340, FlowLabs, Mississauga, Ontario, Canada).

FACS analysis was performed using putative anti-OX-2 Mabs and the following cells. Fresh peripheral blood leucocytes (PBL), isolated over rat/mouse lymphopaque (Cedarlane laboratories) or Ficoll-Hypaque™ (human); fresh spleen dendritic cells (isolated after adherence and overnight incubation, as above); and CHO cells transduced with viral vectors engineered to contain a single copy of a cDNA inserted into the not1/bamH1 sites, encoding the relevant species-specific OX-2, as per published sequences (Chen, Z. et al. 1997. *BBA. Mol. Basis Dis*. 1362:6-10; McCaughan, G. W., et al. 1987. *Immunogenetics*. 25: p. 133-135), or with control vector alone. FITC anti-mouse (or anti-rat) IgG was used as secondary antibody.

Mixed Leucocyte Reactivity (MLR) and Cytokine Production:

Allogeneic MLR cultures, using 1:1 mixtures of $2.5 \times 10^6$ responder PBL and mitomycin C treated stimulator PBL, were set up in 24-well culture plates in 1 ml of aMEM medium supplemented with 10% FCS. Cells were obtained from C3H responder mice (with stimulator C57BL/6), Lewis (LEW) rats (with Brown Norway, BN, as stimulator), and individual human donors. Culture supernatants were harvested at 60 hrs and tested for different cytokines using previously described ELISA assays (mouse), or using CTLL-2 as bioassay for IL-2 production from all responder cell sources (Gorczynski, R. M., et al. 1998c. *Immunology*. 93: p. 221-229).

Results

Evaluation of a Number of Mabs for Staining of Cell Populations in Fresh PBL or Spleen:

All Mabs tested in the experiments herein described were previously screened as described in the Materials and Methods above, and detected a molecule in Western gel of brain extracts with Molecular Weight 42-45 Kd, and also stained CHO transduced by OX-2 encoding viral vectors. Data in Table 3 show FACS analysis for these Mabs using fresh cells. The data are summed over several independent analyses, using a number of Mabs directed to rat, mouse or human OX-2, for staining of cells harvested from fresh PBL or spleen (adherent cells only were tested for the latter: these represented some 5%-8% of the total cell population in all cases).

It is clear from Table 3 that PBL in all species tested contained some 1.3%-2.5% OX-2$^+$ cells by FACS analysis, and that spleen adherent cells similarly contained 4%-8% OX-2+cells. As confirmation of the inventor's previous work, spleen adherent cells taken from C3H mice or LEW rats treated 4 days earlier by portal venous immunization with $20 \times 10^6$ (or $50 \times 10^6$ respectively) of C57BL/6 (or BN) bone marrow cells showed some 3.5-5 fold elevation in OX-2$^+$ cells (see Table 3). Under these conditions specific increases in survival of subsequent allo-transplanted cells/tissue have been reported (Gorczynski, R. M. et al. 1996a. *Transplantation* 62:1592-1600).

Ability of Anti-OX-2 Mabs to Modulate Cytokine Production in MLR in Vitro:

In a final study the issue of whether these Mabs can modify the immune response (as-assayed by cytokine production) of cells stimulated in an allogeneic mixed leucocyte reaction (MLR) in vitro was addressed. The inventor has previously shown that cells taken from mice pretreated by portal allogeneic immunization produce predominantly type-2 cytokines, and that an anti-OX-2 Mab could apparently reverse this polarization in cytokine production (and indeed abolish the increased graft survival seen in such mice). Data in Table 4 confirm these results using 3 independent Mabs to mouse OX-2. Further, rat or human cells stimulated in the presence of anti-rat (or human) OX-2, similarly show more pronounced IL-2 production than cells stimulated in the presence of isotypic control Ig (or no Ig), without a generalized increase in cytokine production (as analysed here by no change in IL-6 production in any group).

Discussion

In the data in this example it is confirmed that using species specific Mabs, to human, rat or mouse OX-2, that Mabs to the molecule detected on the surface of host dendritic cells may play a role in regulating cytokine production after allostimulation in vitro, and more particularly that functionally blocking OX-2 expression leads to enhanced IL-2 production (a type-1 cytokine) after allostimulation (Table 4). Borriello et al also recently reported that OX-2 expression was not a costimulator for induction of IL-2 and IFNγ synthesis (Borriello, F. et al. 1997. *J. Immuno*. 158:4548)-our data imply it is in fact a negative signal for type-1 cytokine production. In mice preimmunized by the portal vein, as reported earlier, there is a 4-fold increase in OX-2 expressing cells in PBL and spleen, and a reversal of polarization in cytokine production (from type-2 cytokines to type-1 cytokines) after stimulation of cells in the presence of OX-2 (see Tables 3 and 4) (Gorczynski, R. M. et al. 1998b. *Transplantation*. 65:1106-1114).

Example 5

Preparation of Rat Antibodies

Five rats were immunized using GERBU adjuvant (GERBU Biotechnik, Gaiberg, Germany) with 500 mg of membrane protein purified from the mouse dendritic cell (DC) line DC2.4 (a gift from K. Rock, Harvard). Serum from these rats was tested 7 days after the third immunization, and compared with a pre-immunization sample in an ELISA using plate-bound material of Mol. Wt. 40 Kd-45 Kd eluted from Western blots, and Alk Pase anti-rat Ig. Two rats with high titre antibody were re-immunized and sacrificed 4 days later for fusion of spleen cells with HAT-sensitive Sp2/0 parent cells for preparation of hybridomas. Hybridomas were screened by ELISA (56/960+ve), subcloned, and frozen (−70° C). For further specificity testing of the anti-OX-2 Mabs will use CHO cells can be transfected with a pBK eukaryotic expression vector (Stratagene, Calif.) expressing OX-2. Full length OX-2 cDNA, including the leader sequence, was amplified from DC2.4 cells using sense and antisense primers constructed with Spe1 or Xba1 sites respectively at their 5' ends for directional cloning into the vector. A band of the expected size (849 bp) was obtained on agarose gel electrophoresis. The sequence of the cloned cDNA was confirmed by sequencing using an automated DNA sequencer (Chen, Z. and Gorczynski, R. M. 1997. *Biochem. Biophys. Acta.* 100, in press). CHO cells were transfected by electroporation (5×106 cells in 0.5 ml were pulsed at 960 MH$_2$ and 120V using a Bio-Rad Gene Pulser (Bio-Rad, Hercules, Calif.), using the full length OX-2 expression plasmid along with a plasmid encoding puromycin resistance (100:1 ratio), followed by selection in puromycin (12 mg/ml for 4 days). Puromycin resistant cells were cloned by limiting dilution. 5 CHO transfectant clones have been obtained expressing mRNA for OX-2 as confirmed by PCR. These clones can be used to screen the putative rat anti-mouse OX-2 Mabs.

(a) FACS Staining of Cells from Pv Immunized Mice with Anti-mouse OX-2

A 4-fold increase in staining of spleen and hepatic NLDC145+ (dendritic cell marker) cells from pv immunized mice with anti-rat OX-290 was observed. Spleen and liver tissue of mice at various times (12 hours; 2, 7 and 14 days) following pv immunization can be sectioned and stained by immunohistochemistry, using anti-NLDC145, anti-OX-2 Mabs. Single cell suspensions from the same tissues can be stained, using 3-colour FACS, with FITC-anti-mouse OX-2, rhodamine-anti-NLDC145, and phycoerythrin-anti-T200 (mouse lymphocyte marker). In all cases (both FACS and immunohistochemistry) the appropriate irrelevant isotype control antibodies are included. Tissue from control mice receiving renal grafts alone, or following additional iv immunization, can also be examined. Detection of NLDC145+(and/or MAC-1+) cells showing increased expression of OX-2 is predicted in pv immunized mice only (see Gorczynski, R. M. et al. 1998. *J. Immunol.* 160, in press). The inventor has shown DC-associated antigen persists only in animals with surviving grafts (Gorczynski, R. M., Chen, Z., Zeng, H. and Fu, X. M. 1998. *Transplantation* 66: 339-349). It was also assessed whether anti-OX-2, infused at different times post transplantation, causes rejection (b).

(b) Modulation of Graft Rejection and Cytokine Production by Anti-mouse OX-2

C3H mice receive pv immunization with cultured C57BL/6 bone-marrow derived dendritic cells (DC), CsA and renal allografts. Groups of mice receive intravenous infusion of various rat anti-mouse OX-2 Mabs (100-500 mg/mouse, ×5, at 2 day intervals), beginning at different times post transplantation (this will be guided by data from (a)). Serum creatinine and animal survival are followed. Serum from Mab-treated mice are tested in ELISA and by FACS with OX-2 expressing CHO transfectants (above) to ensure antibody excess. If OX-2 expression is important for pv induced increased graft survival, the anti-OX-2 treated pv immunized mice will reject grafts like untreated controls, with similar polarization of cytokine production to type-1 cytokines (assayed by PCR; ELISA with cultured, restimulated cells). As controls pv immunized, grafted mice receive anti-CD28 and anti-CTLA4 these Mabs do not modify the effects of pv immunization as assayed by graft survival or polarization in cytokine production. It is expected that OX-2 treatment but not other Mabs, will simultaneously abolish expansion of γδTCR+ cells after pv immunization.

Example 6

Preparation of a Fusion Protein Linking the Extracellular Domain of OX-2 to Mouse Fc Immunoadhesins, in which a hybrid molecule is created at the cDNA level by fusing the extracellular domain (ED) of an adhesion molecule with the carboxyl terminus of IgG heavy chain, the whole being expressed in mammalian cells or in a baculovirus system, have been powerful tools in the identification and isolation of the counter ligands for the adhesion molecule of interest. Ligands for a number of members of the TNFR family, were identified in this fashion (Goodwin, R. G. et al. 1993. *Eur. J. Immunol.* 23, 2631-2641; Gruss, H. and Dower, S. 1995. *Blood* 85, 3378-3404). Interest has developed in the potential application of immunoadhesins as therapeutic agents. A CTLA4 immunoadhesion, with the capacity to bind both B7-1 and B7-2, has been used to inhibit T cell costimulation and decrease rejection (Larsen, C. P. et al. 1996. *Nature* 381, 434-438). Note that CD28/CTLA4 are not counter ligands for OX-2. The fusion protein, is predicted to alter cytokine production (increased IL-4, IL-10; decreased IL-2, IFNγ) and increase renal graft survival like pv immunization. We expect that synergistic blockade of costimulation (e.g. by CTLA4-Fc) and triggering of a coregulatory pathway (by OX-2ED-Fc) will induce tolerance and produce indefinite graft survival.

a) Construction of an OX-2 Fusion Protein with Murine IgGFc2a

A cDNA encoding the extracellular region of OX-2 was amplified by PCR, using a 5' oligonucleotide primer which inserts a Sal1 site 5' immediately at the start of the V-region sequence and a 3' primer which creates a BamH1 site at the 3' end (the site of junction with Fc). Using cDNA prepared from mouse ConA activated spleen cells, with a 5' primer containing an Spe1 site, and a 3' primer containing a Sal1 site, the signal peptide for IL-6 (SP-IL-6) was amplified by PCR and ligated to the OX-2 amplicon. In frame ligation across the junction of SP-IL-6 and OX-2 was checked by manual sequencing-the final cDNA amplified by the 5'SP-IL-6 primer and the 3'OX-2 primer was, as expected, 695 bp. A plasmid expressing murine IgGFc2a (Fcg2a), modified to create a unique BamH1 site spanning the first codon of the hinge region, and with a unique Xba1 site 3' to the termination codon, has been obtained from Dr. Terry Strom (Zheng, X. X. et al. 1995. *Journal of Immunology.* 154, 5590-5600). The IgGFc2a in this insert has been further modified to replace the C1q binding motif (rendering it non-lytic) and inactivate the FcgR1 binding site (see Zheng, X. X. et al. 1995. *Journal of Immunology.* 154, 5590-5600). Ligation of OX-2 and IgGFc2a in the correct reading frame at the BamH1 site yields a 1446 bp long open reading frame encoding a single 478-amino acid polypeptide (including the 24-amino acid IL-6 signal peptide). The homodimer has a predicted 105 kDa Mol Wt, exclusive of glycosylation. The fusion gene is then cloned as an Spe1-Xba1 cassette into the eukaryotic expression plasmid pBK/CMV (Stratagene, Calif.). This plasmid has a CMV promoter/enhancer and a neomycin-resistance gene for selection using G418. The appropriate genetic construction of the OX-2-Fc can be confirmed by direct sequencing after cloning into the plasmid vector (Chen, Z. and Gorczynski, R. M. 1997. *Biochem. Biophys. Acta*. 100, in press)-see also above. The plasmid is transfected into CHO cells by electroporation (see above), and selected in medium with 1.5 mg/ml G418 (Geneticin: Life Technologies, Inc.). After subcloning, high producing clones are selected by screening culture supernatants in ELISA using anti-OX-2 Mabs as capture antibody, and Alk Pase coupled anti-IgGFc2a as detection antibody. OX-2-Fc fusion protein is purified from culture supernatants using protein A-Sepharose affinity chromatography, dialysed against PBS, filter-sterilized and stored in aliquots at $-20°$ C. The size, and OX-2 (+IgGFc2a) specificity of the secreted product can be confirmed using Western blot analysis under reducing (+DTT) and non-reducing (−DTT) conditions, with Mabs to OX-2 and rat monoclonal anti-mouse IgGFc2a (Pharmingen). The product can be titrated as an inhibitor for FACS staining of OX-2 expressing CHO cells (see above) using rat Mabs to OX-2 as probe. As a prelude to studies (below) using OX-2-Fc in vivo, the half-life (t1/2) in mouse serum following injection of groups of 6 8-week C3H mice will be studied. This is carried out by subjecting mice to iv injections of 50 mg or 10 mg of OX-2-Fc, and obtains serial 50 ml blood samples at 0.3, 1, 6, 24, 48, 72 and 96 hours. The serum is analyzed in ELISA using plates coated with anti-OX-2 as capture antibody, and Alk Pase coupled monoclonal anti-IgGFc2a for detection (thus ensuring the assay detects only OX-2-Fc, not OX-2 or IgGFc2a alone). Based on earlier data in which Fc fusion proteins were used to extend the in vivo half-life, a t1/2 in the range of 30-40 hrs (Zheng, X. et al. 1995. *Journal of Immunology*. 154, 5590-5600) is predicted.

b) OX-2: IqGFc Immunoadhesion Inhibits MLR

CHO cells were transduced with a vector carry the OX-2:Fc cDNA insert. Supernatant was harvested from the CHO cells at 7 days and was cultured with $5 \times 10^6$ LEW spleen and $2.5 \times 10^6$ irradiated LBNFI spleen cells. The supernatant contained 50ng/ml OX-2:Fc.

The results, shown in Table 5, demonstrate that the soluble OX-2:Fc immunoadhesion inhibits IL-2 production and generation of cytotoxic T cells and induces IL-4 production. These results support the use of OX-2 as an immunosuppressant.

c) Use of OX-2:Fc in Vivo for Prevention of Graft Rejection

It was shown in (b) that incubation in the presence of 50 ng/ml OX-2:Fc can inhibit an in vitro MLR reaction. To detect inhibition of in vivo graft rejection, C3H mice received C57BL/6 skin grafts along with iv injection of OX-2:Fc (50 mg/mouse) every 2 days ×4 injections. Grafts were inspected daily after 10 days for rejection. In a separate study 3 mice/group (receiving saline or OX-2:Fc) were sacrificed at 10 days and spleen cells restimulated in vitro (×48 hrs) for analysis of cytokine production. Data for these studies is shown in Tables 6 and 7. It is clear from these data that OX-2:Fc has the potential for use as an immunosuppressant to prolong graft acceptance. Furthermore, in association with increased graft survival in this model, OX-2:Fc alters polarization in cytokine production, as already described for portal vein donor-specific immunization.

Example 7

OX-2 Expression in Placenta

Using in situ hybridization, the inventor has shown that OX-2 is not expressed in the placenta of mice with increased potential for fetal loss. In contrast, OX-2 is expressed in the placenta of normal, non-aborting mice.

Figure 18A:
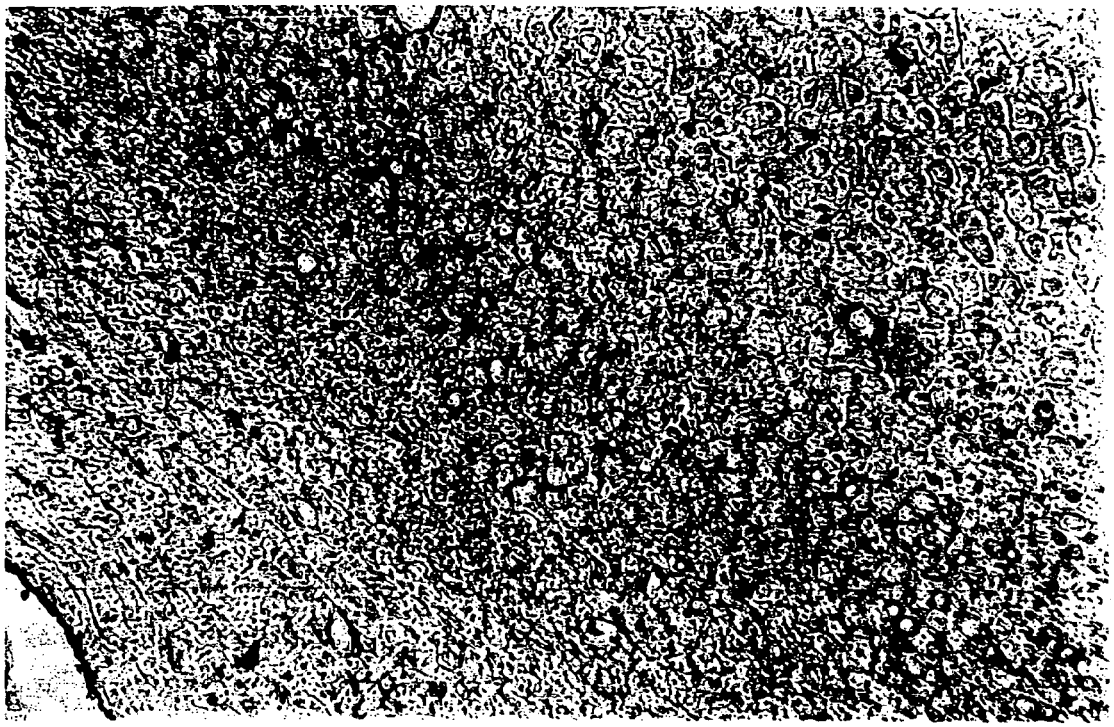
FIG. 18A is a photograph showing in situ hybridization with antisense OX-2 in a day 8.5 implantation site from a mouse CBA/JxDBA/2 that is susceptible to fetal loss.
Figure 18B:
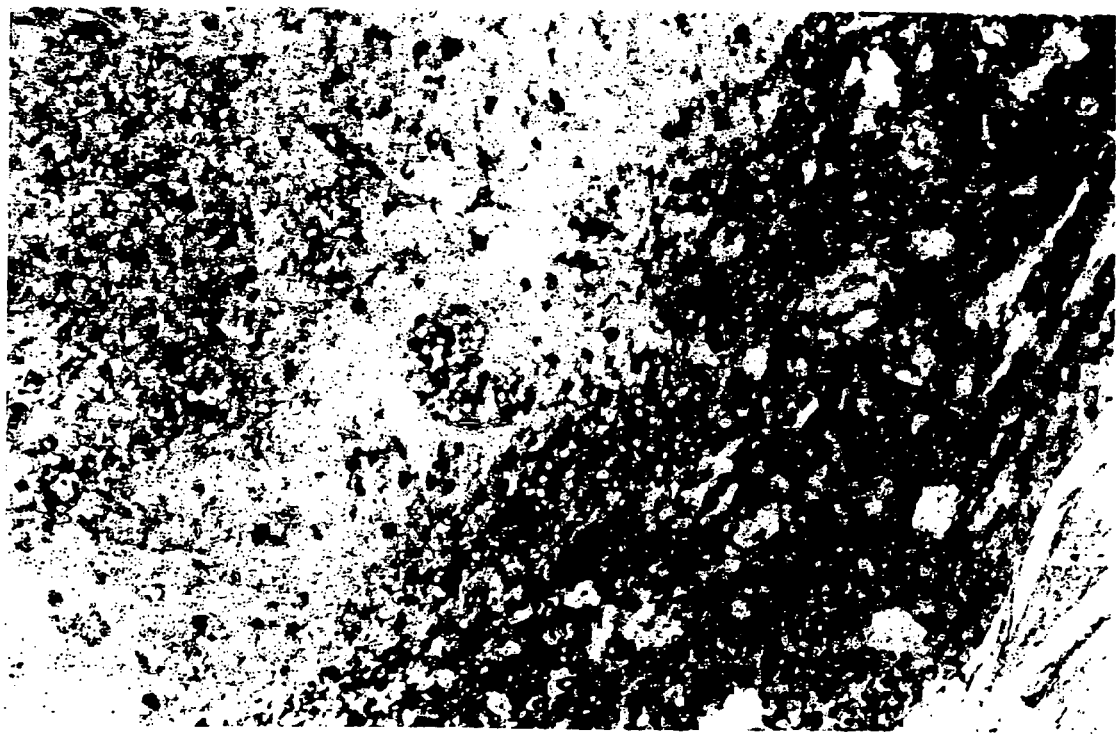
FIG. 18B is a photograph showing in situ hybridization with antisense OX-2 in a day 8.5 implantation site from a mouse DBA/2XCBA/J that is not susceptible to spontaneous fetal loss.

CBA/J and DBA/2J mice were used. Matings of CBA/J (females) with DBA/2J males show a high incidence of fetal loss (>80%), unlike the reverse scenario. Placental tissue was obtained from matings at 8-11 days of gestation. Uteri were snap frozen, 5 mm sections cut, and stained with a biotinylated anti-sense probe for murine OX-2. Data shown in FIGS. 18A and 18B indicate increased expression of OX-2 mRNA (in situ labeling) in the non-aborting strain combination, with essentially absent expression in the aborting combination. These data are consistent with the notion that OX-2 expression prevents spontaneous fetal loss syndrome.

The data show that there are fewer OX-2+ implantation sites on day 8.5 of pregnancy-in mice which are predisposed to fetal loss syndrome (CBA×DBA/2 matings) by contrast to CBA×BALB/c matings which are not so predisposed. Fgl2 is the trigger for low, and where OX-2 is also expressed, these potentially doomed implantations are "rescued". This follows from the finding that the abortion rate is lower than expected from % fgl2++ implantation sites, unless anti-OX-2 mAb is administered. In the latter instance, the abortion rate rises to equate with the estimated proportion of flg2++ implant sites.

Example 8

Treatment of Autoimmune Disease

Collagen-induced arthritis (CIA) is an animal model of rheumatoid arthritis which can be induced in susceptible mice (and rats) following immunization at the base of the tail with collagen in Freund's adjuvant. It is associated with activation of IFNγ (type-1 cytokine) producing T cells, though in humans production of TNFα has also been documented to be important in the pathophysiology of disease. Given our evidence that CD200Fc (OX-2:Fc) could inhibit type-1 cytokine production following allosensitization, we have now investigated the effect of CD200Fc on serum TNFα and IFNγ levels, and on cytokine production by lymphocytes taken from mice and stimulated in vitro with rat collagen. The experiments described below are from studies addressing the role of CD200Fc in suppressing the onset of arthritis, and show clearly that susceptible mice immunized with bovine type-II collagen develop a significant arthritis (~70% of mice by 30 days post injection), with increased IFNγ/TNFα production, both of which are abolished by treatment with CD200Fc from the time of collagen administration.

Materials and Methods

Animals:

8-week old DBA/1 mice ($H2^{q/q}$) were obtained from the Jackson Laboratories, Bar Harbour, Me., and kept 5/cage with food and water ad libitum. Mice were entered into experiments at 9 weeks of age.

Collagen Induced Arthritis Model:

Groups of 21 mice received 100 µg bovine collagen type-II (Sigma Chemical Co., St.Louis, Mo.) emulsified in Complete Freund's Adjuvant (CFA) in 100 µl 0.1M acetate, injected intradermally at the base of the tail. 18 days later animals received a further injection of 100 µg emulsified in Incomplete Freund's Adjuvant (ICFA) intradermally. Individual animals were monitored daily for signs of arthropathy, which was scored independently by 2 investigators for each limb on a 4-point scale as follows:
  0=No paw swelling
  1=Paw+a single joint
  2=Paw+multiple joints (of the same limb)
  3=Joint rigidity The total score/mouse was recorded (maximum=12). The correlation between total scores for investigators >0.93; scores recorded were thus arithmetic means of the 2 scores for each animal.

Where mice received CD200Fc, 15 µg/mouse was infused iv in 200 µl PBS at 3 day intervals into 7 mice/group, beginning on the first day of collagen immunization. Control (Hoek et al. (2000)) mice received 15 µg of normal mouse immunoglobulin (pooled from the serum of five 8-week normal DBA/1 mice). A further group (7 mice) received no additional treatment.

Antigen Stimulation in Vitro and Cytokine Assays:

Pooled peripheral lymph node (PLN) cells (axillary and inguinal nodes), as well as spleen cells, were harvested from individual mice at 36 days following the first immunization with collagen. Blood was also collected from individual animals by cardiac puncture, and serum obtained following centrifugation (14,000 rpm for 15 min) after overnight incubation at 4° C. Spleen and PLN cells were cultured in triplicate in microtitre plates ($1\times10^6$ cells/well in 300 µl of α-Minimal Essential Medium with 10% fetal calf serum, αF10) in the presence or absence of 500 ng/ml bovine collagen type-II. A further set of control cultures was stimulated with $5\times10^5$/well mitomycin-C treated (100 µg/ml, 45 min at 37° C.) BALB/c allogeneic spleen stimulator cells.

Culture supernatants (150 µl) were harvested at 40 hrs of culture and assessed for TNFα and IFNγ levels using an ELISA assay and commercial cytokine-specific mAbs obtained from Pharmingen (San Diego, Calif.). Plates pre-coated with 100 ng/ml R4-6A2 and developed with biotinylated XMG1.2 were used to assay IFNγ, and those precoated with G281-2626 and developed with biotinylated MP6-XT3 were used to assay TNFα. Streptavidin-coupled alkaline phosphatase with appropriate substrate was used to develop the assay, and recombinant mouse cytokines (Endogen, San Diego, Calif.) were used to quantitate the assay.

In addition to analyzing cytokines, proliferation of collagen (and allo)-stimulated cells was assessed by addition of 1 µCi $^3$HTdR at 72 hrs to each microtitre well (see above), and harvesting the wells for counting in a well-type β-counter at 14 hrs. All assays were performed in triplicate, with cultures containing unstimulated responder cells only serving as an appropriate control.

Measurement of Serum Anti-Collagen Type-II Antibody Isotypes:

Serum anti-collagen type-II levels were determined by ELISA, using plates precoated with 100 µl of 1 µg/ml collagen type-II and serial 3-fold dilutions of the sera (obtained at 36 days post immunization as described above) under test. Plates were developed with isotype-specific biotinylated rat mAbs to mouse IgM, IgG1, IgG2a/2b and IgG3, followed by streptavidin-alkaline phosphatase and use of appropriate substrate. All ELISA reagents were purchased from Cedarlane Labs, Hornby, Ontario, Canada. Purified mAb were used to standardize assays in order to calculate antibody levels. Total IgG levels were determined after adherence of serum to plates coated with poly-L-lysine (100 ng/ml), and developing with polyspecific biotinylated rat anti-mouse IgG.

Statistical Analysis:

Athritic scores in different groups were compared by Mann-Whitney U-tests. Proliferation in, and cytokine production from, cells of all groups were initially analysed for differences by ANOVA. Thereafter pair-wise comparison of different groups was performed by Student's t-test.

Results

Infusion of Murine CD200Fc Prevents Development of Collagen-induced Arthritis

Figure 19:
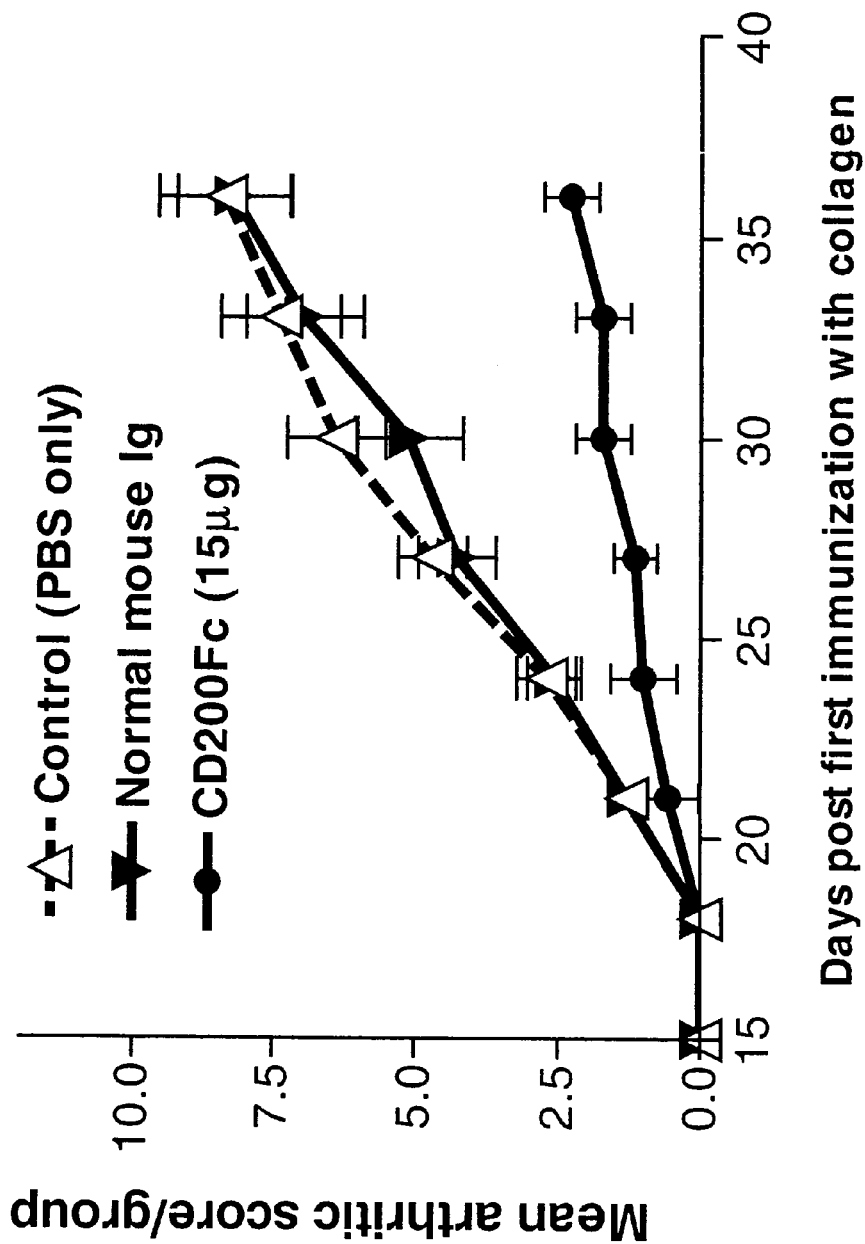
FIG. 19 is a graph showing CD200Fc inhibits induction of collagen-induced arthritis in mice. Groups of 7 DBA/1 mice were immunized with 100 μg bovine collagen type-II in CFA, followed by reimmunization at day 18 with 100 μg collagen in ICFA (see Materials and Methods in Example 8). Thereafter mice received 15 μg iv of normal mouse Ig or CD200Fc, at 3 day intervals until sacrifice. Scoring of disease in individual mice is described elsewhere (Gorczynski, Clin.Immunol; 2001, in press). Data are arithmetic means (±SEM) of the 7 scores/group at each time point.

In order to examine the effect of CD200Fc fusion protein on immunomodulation of collagen-induced arthritis in mice the following study was performed. Groups of 7 mice were immunized with collagen intradermally, followed by booster immunization 18 days later. Animals received iv injections of either PBS, or 15 µg/mouse of normal mouse Ig or CD200Fc, beginning on the day of initial immunization and at 3 day intervals thereafter. Arthritic scores were assessed for all limbs as described in the Materials and Methods. Data in FIG. 19 are taken from one of 2 studies of this type, and show the mean (+SEM) for each of the 3 groups. These data document that treatment with CD200Fc profoundly inhibits development of arthritis in this model (p<0.02, Mann Whitney U-test).

Inhibition of Sensitization to Collagen in CD200Fc-treated Mice

Figure 20:
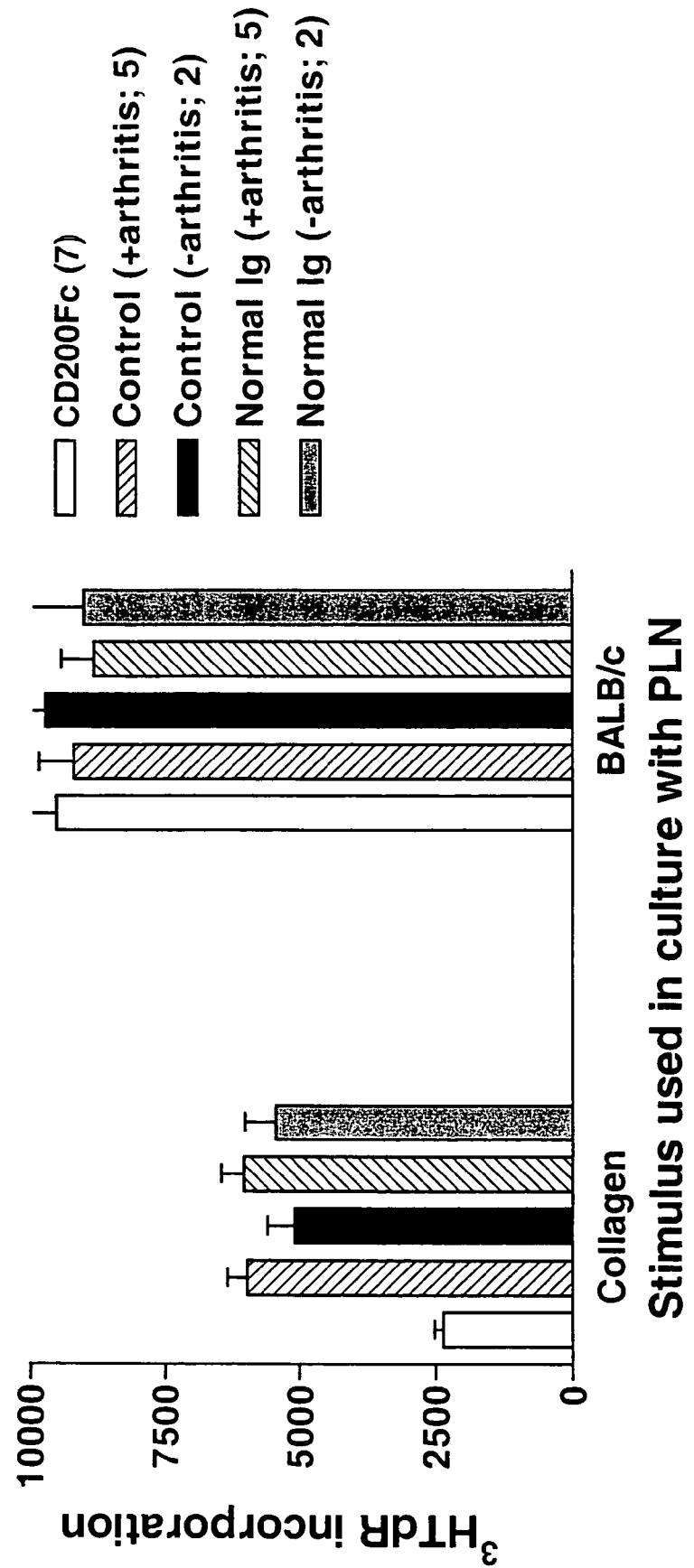
FIG. 20 is a bar graph showing $^3$HTdR incorporation in PLN cells harvested (at 36 days) from the groups of 7 mice treated in vivo with CD200Fc (or saline) following collagen immunization, as in FIG. 19, and restimulated in vitro with collagen or BALB/c spleen stimulator cells. No additional CD200Fc was included in vitro. For both sets of control mice (PBS injected and normal mouse Ig-treated groups), cells were further subdivided into those taken from mice with a mean arthritic score ≧6 (5/7 respectively) and ≦5 (2/7). All CD200Fc treated mice had arthritic scores <5. Background proliferation in cells from all groups without stimulation was in the same range (1250±450 cpm).

Data in FIG. 20 show the proliferation in PLN taken from the individual mice shown in FIG. 19, after restimulation of cells for 72 hrs in vitro with collagen or BALB/c spleen cells. Note that in each of the groups with high mean arthritic scores (see FIG. 19) 2/7 animals had scores $\leq 5$, within 2SD of the mean of the CD200Fc treated group. Accordingly data are shown separately for the group of mice with scores $\geq 6$ (5/7) and for those with scores $\leq 5$ (2/7).

It is clear from these data that treatment with CD200Fc inhibits sensitization to collagen as assessed by subsequent proliferation in response to collagen stimulation (p<0.05 with respect to all other groups). That this effect is limited to the response initiated at the time of CD200Fc infusion is clear from the lack of effect on proliferation in response to BALB/c cells. Interestingly, all animals immunized in the absence of CD200Fc, even those which did not develop overt arthritis (2/7 in each of the PBS injected or control 1g injected groups), showed equivalent proliferation in response to collagen restimulation (see Figure). Thus the expression of disease can be regulated at a stage beyond the sensitization of lymphocytes to autoantigen. Similar data to the above were seen using splenic lymphocytes from these donors (not shown), and for PLN in a separate repeat experiment.

Inhibition of Serum TNFα and IFNγ in Collagen Sensitized Mice by Injection of CD200Fc At the time of sacrifice of mice shown in FIG. 20 serum was collected for assay of the cytokines TNFα and IFNγ, which have been implicated in the inflammatory processes responsible for pathophysiology in arthritis. Data shown in FIG. 21 indicate that CD200Fc injection prevents the increase in serum TNFα and IFNγ levels which are seen in mice with overt arthritis (scores ≧6). Similar data were obtained in a repeat study. Interestingly, unlike the proliferation data in FIG. 20, mice sensitized in the absence of CD200Fc do not show increased serum cytokine levels if they do not simultaneously have arthritic disease. This is consistent with a causal role for these cytokines in at least some of these manifestations of arthritis in this model.

Figure 21:
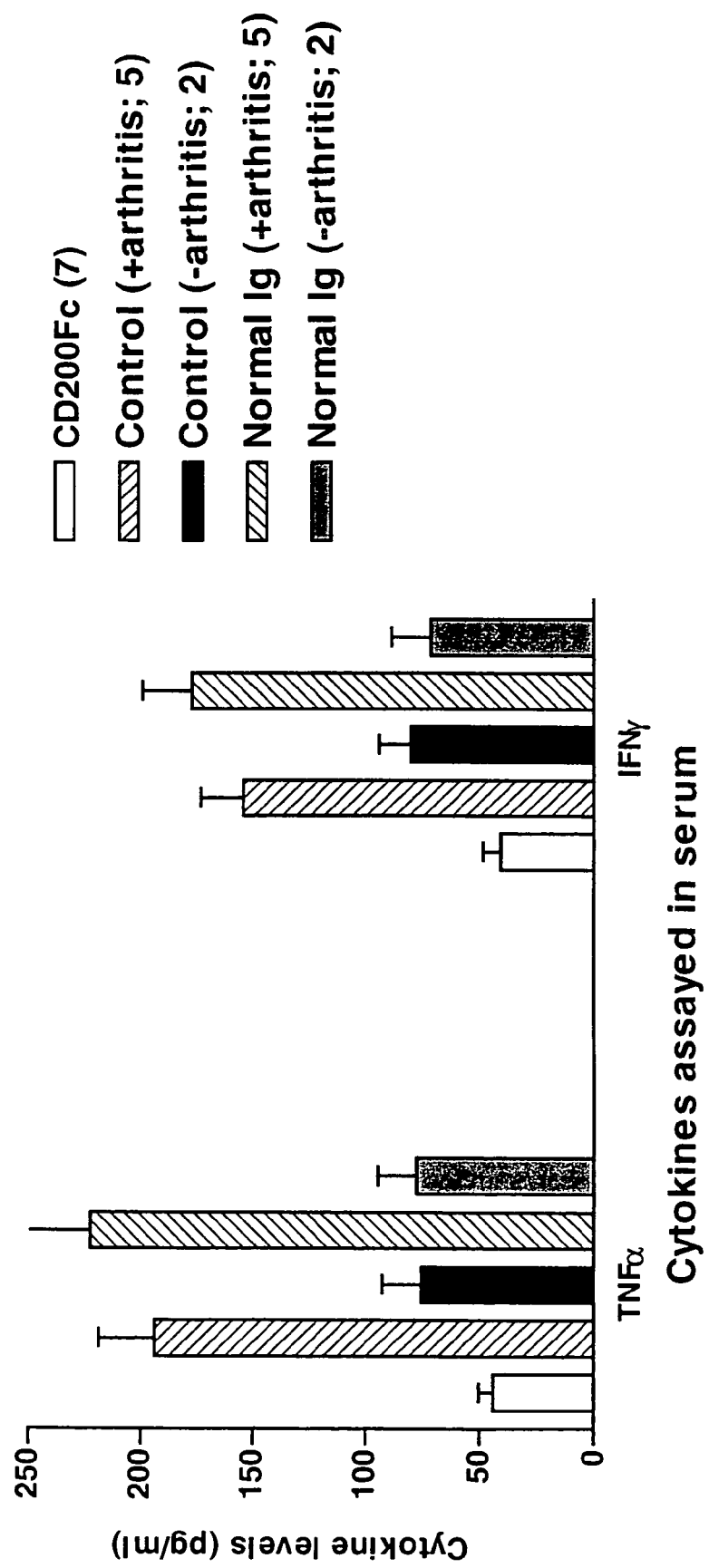
FIG. 21 is a bar graph showing CD200Fc given in vivo to mice immunized with bovine collagen (see FIGS. 19 and 20) blocks development of increased serum TNFα and IFNγ. Once again data for the two groups of control animals (untreated or control Ig treated) are subdivided into results from animals with arthritic score ≧6 or ≦5 respectively. Serum was assessed at 36 days post collagen immunization. Background serum TNFα and IFNγ cytokine levels (pg/ml) in a group of 5 normal DBA/1 mice (non-immunized) was 25±7.7 and 32±10 respectively.
Figure 22:
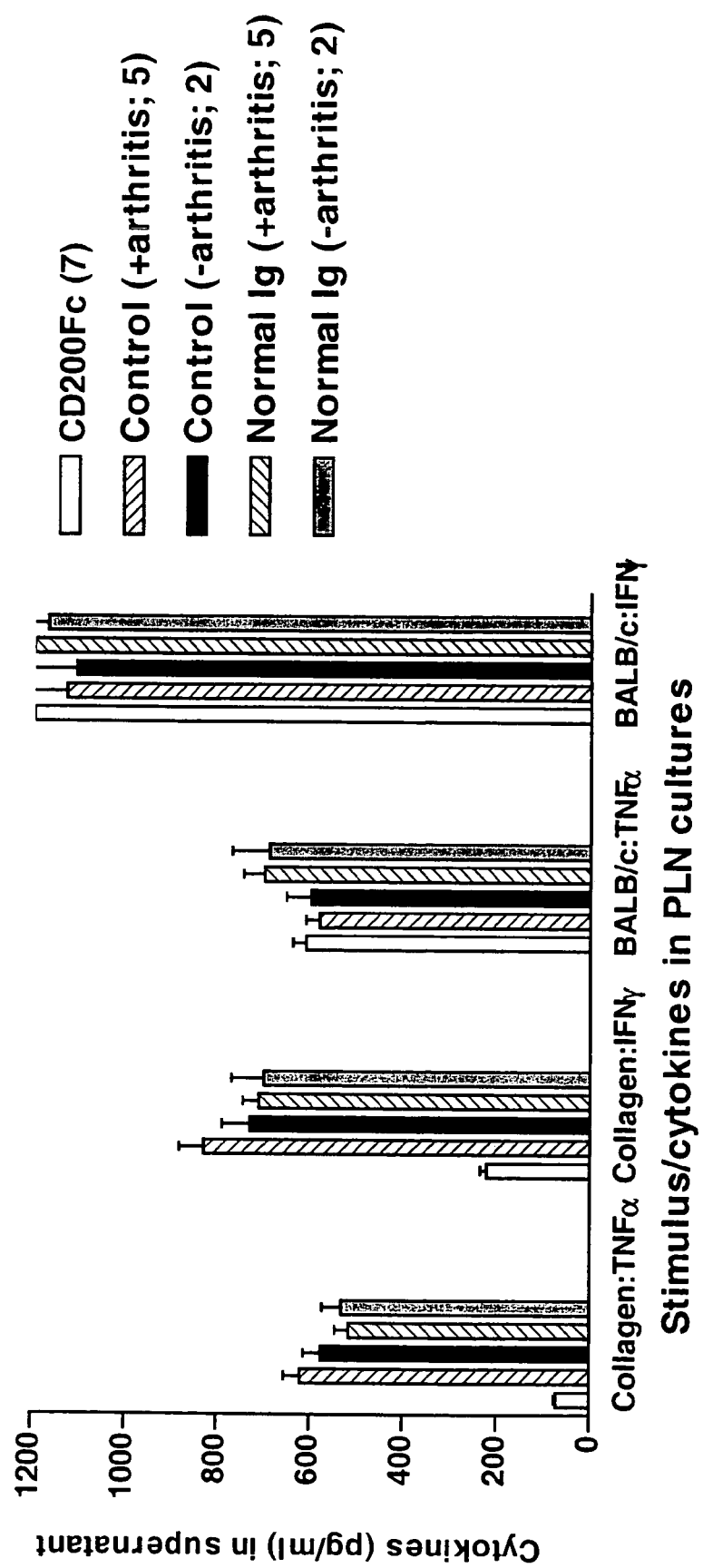
FIG. 22 is a bar graph showing inhibition of sensitization for further TNFα and IFNγ production in vitro using PLN cells of mice treated in vivo with CD200Fc and immunized with collagen as in FIGS. 19-21. Cells were taken from all groups at 36 days post collagen immunization, and were stimulated in vitro with either collagen or BALB/c cells. No further CD200Fc was included in the cultures. Cytokines were assayed in the culture supernatants by ELISA at 40 hrs. Control cytokine production, averaged over all groups in the absence of stimulation, for TNFα/IFNγ was 65±15 and 110±20 pg/ml respectively.

Inhibition of Production of TNFα and IFNγ in Cells of Collagen Sensitized Mice by Injection of CD200Fc Data shown in FIG. 22 are analogous to those of FIG. 21 except that in this case cytokine production was assayed in the supernatant of cultures from the individual mice (whose proliferative capacity was detailed in FIG. 20). Once again injection of CD200Fc clearly led to inhibition of TNFα and IFNγ production from restimulated cells, in a collagen-specific fashion (no inhibition if restimulation was with BALB/c cells). Interestingly, cytokine production by PLN from mice with/without overt joint inflammation was equivalent (in the absence of CD200Fc). Thus CD200Fc presumably inhibits sensitization to collagen antigen(s), while the presence of collagen-sensitized cells is not alone sufficient for development of arthritis. Similar data to the above were seen using supernatants from splenic lymphocytes from these donors (not shown), and for supernatants derived from PLN cells in a separate repeat experiment.

Inhibition of Anti-collagen Antibody Production Following Injection of CD200Fc

Figure 23:
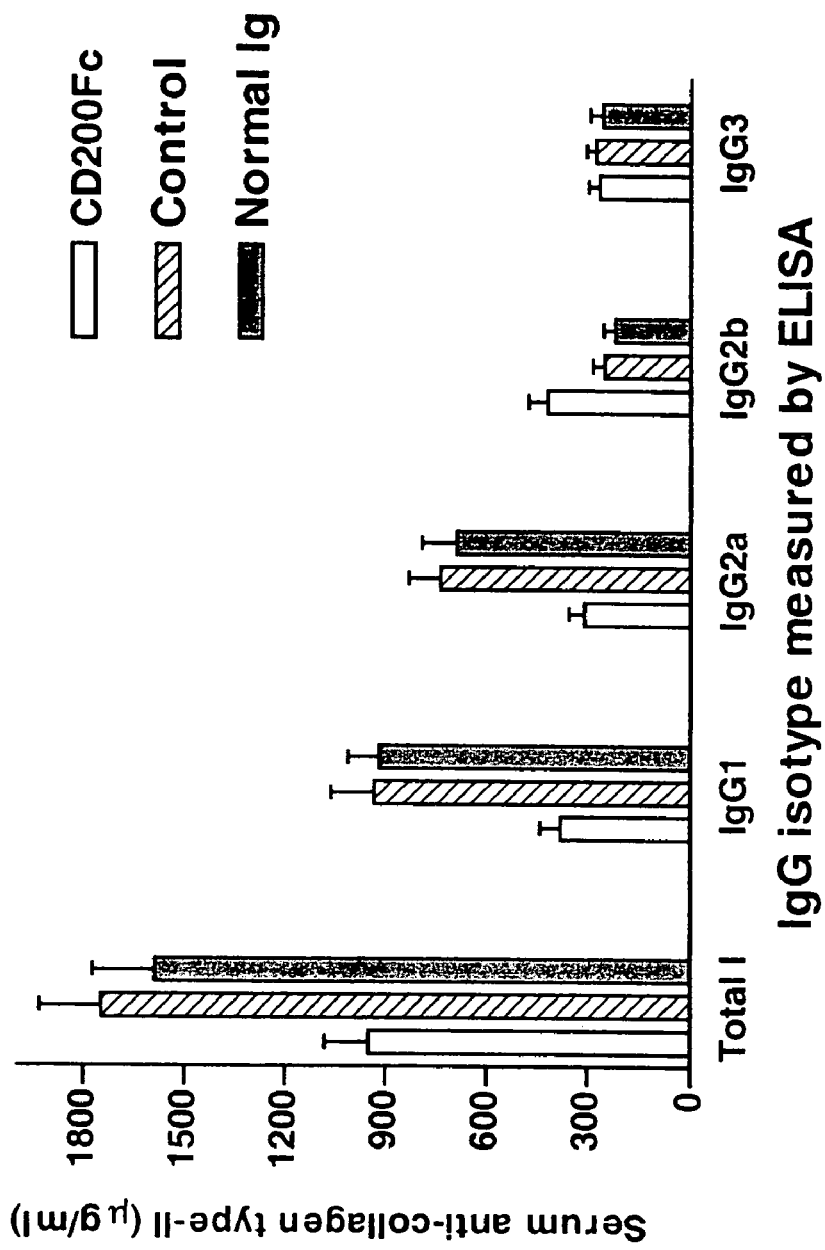
FIG. 23 is a bar graph showing CD200Fc alters quantitative and qualitative production of autoantibody to collagen type-II in collagen immunized mice. Data show total serum IgG and different IgG isotype levels at 36 days of sacrifice in the 3 groups of mice documented in FIGS. 19-22. All data points represent arithmetic means (±SD) of 7 mice/group. Similar data were obtained in a repeat study.

Data shown in FIG. 23 are derived from one of two studies analyzing the isotype profile of anti-collagen antibodies in day 36 sera from the 3 groups of mice (control, control-Ig treated and CD200Fc treated). There was no difference in total IgG levels in the different groups (data not shown: mean levels 11.2±3.2 mg/ml). It is clear that not only did treatment with CD200Fc decrease total anti-collagen IgG levels (by ~50%), but there was a clear shift in isotype profiles, with significantly more IgG2b relative to all other isotypes produced, and no significant inhibition of IgG3 isotype (relative to control mice), in mice treated with CD200Fc.

Discussion

Rheumatoid arthritis is a common chronic inflammatory arthropathy, with substantial human cost (Pincus et al. (1986)). Current drug therapy is relatively non-specific, and has limited efficacy (Scott et al. (1987)). Given the growing evidence that therapies aimed at controlling levels of inflammatory mediators, which ultimately are causally implicated in the destruction of cartilage and bone, can ameliorate disease, concerted efforts are directed at developing more of such novel reagents (Choy et al. (2001)). In humans, where TNFα is believed to be critical in the pathophysiology of disease, decoy TNFα receptor molecules, or mAbs to TNFα have both been used successfully for treatment (Moreland et al. (1999); Maini et al. (1999)). Interestingly, IL-10 and IL-4 (both type-2 cytokines) which would be expected to diminish inflammatory (predominantly type-1 cytokine driven) responses have not as yet produced dramatic effects in these clinical settings, perhaps due to their short half-lives (Choy et al. (2001)).

In mice, in which CIA following immunization with type-II collagen has long been used as a model of rheumatoid arthritis (Courtenay et al. (1980)), IFNγ has been documented to be crucial for development of disease (Boissier et al. (1995)). In keeping with these data, reduction in IL-12 production (believed to be crucial for production of IFNγ in vivo) is also associated with amelioration of CIA (McIntyre et al. (1996)). Disease outcome in both wild-type and IFNγ knockout mice immunized with collagen is more highly correlated with delayed-type hypersensitivity immune reactivity (type-1 cytokines) to autoantigen than with the presence of circulating autoantibody (Matthys et al. (2000)), data which has been interpreted in terms of a greater importance for DTH immunity than antibody in disease pathogenesis. Perhaps somewhat surprisingly, IFNγ-KO mice have a greater incidence of disease and more pronounced DTH responses than their wild-type counterparts, while serum autoantibody levels are suppressed some 5-6 fold. These studies and others have contributed to the hypothesis that in some situations IFNγ may play a protective role in CIA (Matthys et al. (2000); Nakajima et al. (1990); Ortmann et al. (2001)). Recently Ortmann and Shevach (Ortmann et al. (2001)) speculated that IFNγ might act in a protective manner early in disease development, while worsening pathology later in disease. They also reported a protective effect of IL-10 on disease severity, while IL-4, somewhat paradoxically, increased disease, perhaps by augmenting levels of anti-collagen Ig. Matthys et al. (2001) have concluded that IFNγ may exert its primary role in regulating disease severity by modulating development of Mac-1$^+$ cells whose proliferation is induced by mycobacterial products used in the Freund's Adjuvant commonly used in CIA models.

In the inventors' previously reported transplant models, the inventors had found that increased cellular expression of the molecule CD200 was associated with improved survival of allografts, in association with specific suppression of allo-specific CTL and type-1 cytokine production (IL-2, IFNγ) with sparing or augmentation of IL-10 and IL-4 (Gorczynski et al. (1998); Gorczynski et al. (1999)). The inventors speculated that CD200 might play a general immunosuppressive role which could be of value in autoimmune disorders (Chen et al. (1997); Gorczynski et al. (1998)). The same immunosuppressive effect was also achieved by infusion of the solubilized form of CD200, CD200Fc (Gorczynski et al. (1999)), and the inventors accordingly investigated in the studies described above whether CD200Fc was effective in decreasing induction of CIA in mice. Our data show unequivocally that this is indeed the case (see FIG. 19). Moreover, the cytokine changes observed, both in serum levels of IFNγ and TNFα (FIG. 21), and in production of the same cytokines after stimulation in vitro (FIG. 22), are in general accord with the previous reports in this murine model (Boissier et al. (1995); Mcintyre et al. (1996)). That the early infusion of CD200Fc actually blocked sensitization of collagen-reactive cells was inferred both from the cytokine data of FIG. 22 and the data of FIG. 20, showing that PLN of these mice even failed to proliferate in response to collagen stimulation. In keeping with earlier data studying the effect of CD200Fc on an anti-sheep erythrocyte antibody response, CD200Fc did indeed inhibit (by ~50%) the development of specific autoantibody to collagen in treated mice (see FIG. 23), along with causing a significant shift in the isotype profile of the Ig produced typical of that seen in more Th2 driven responses (relatively more IgG2b and IgG3 and less IgG2a). Whether the changes in autoantibody, and indeed of cytokine production, represent epiphenomena, or are causally linked with the reduction in arthritis in these mice, remains to be analysed in detail.

While no measures of IL-4 or IL-10 were performed, previous work with CD200Fc in allosensitized mice would lead us to predict that both cytokines would be elevated in CD200Fc and collagen-injected mice (Gorczynski et al. (1999); Gorczynski et al. (2000)). IL-10 might then produce the arthritis-protective effect suggested by others (Ortmann et al. (2001)). Interestingly, sensitization of T cells for increased IFNγ and TNFα production alone does not explain CIA in this model. The inventors observed uniform cytokine production from PLN in these mice (FIG. 22), but only ~70% of animals produced elevated serum cytokines and developed overt joint disease (FIGS. 19 and 21). It is interesting to note that while CD200 itself has a relatively ubiquitous expression pattern (Barclay (1981)), expression of CD200R is more limited. Both our own group (Gorczynski et al. (2000)) and others (Hoek et al. (2000)) have documented existence of CD200R+ cells in a macrophage/myeloid population, and the inventors have also suggested expression of CD200R exists on subpopulations of T cells (Gorczynski et al. (2000)). The important site(s) at which CD200R is expressed in the CIA model described, and where CD200Fc might thus be presumed to have its most important effect, has not yet been unequivocally identified.

In summary, the results are consistent with a crucial role for infused CD200Fc in regulation of induction of CIA in mice. Consequently CD200 may be useful in treating and preventing autoimmune disease.

Example 9

Cancer Therapy

Materials and Methods

Mice: Male C3H/HeJ, BALB/c and C57BL/6 mice were purchased from the Jackson laboratories, Bar Harbour, Me. Mice were housed 5/cage and allowed food and water ad libitum. All mice were used at 8-12 weeks of age.

Monoclonal antibodies: The following monoclonal antibodies (mAbs) were obtained from Pharmingen (San Diego, Calif., USA) unless stated otherwise: anti-IL-2 (S4B6, ATCC; biotinylated JES6-5H4); anti-IL-4 (11B11, ATCC; biotinylated BVD6-24G2); anti-IFNγ (R4-6A2, ATCC; biotinylated XMG1.2); anti-IL-10 (JES5-2A5; biotinylated, SXC-1); anti-IL-6 (MP5-20F3; biotinylated MP5-32C11); anti-TNFα (G281-2626; biotinylated MP6-XT3); FITC anti-CD80, FITC anti-CD86 and FITC anti-CD40 were obtained from Cedarlane Labs, Hornby, Ontario. The hybridoma producing DEC205 (anti-mouse dendritic cells) was a kind gift from Dr. R. Steinman, and was directly labeled with FITC. FITC anti-H2K$^b$, FITC anti-H2K$^k$, and anti-thy1.2 monoclonal antibodies (mAbs) were obtained from Cedarlane Labs, Hornby, Ontario. Unconjugated and PE-conjugated rat anti-mouse CD200 was obtained from Bio-Spark Inc., Mississauga, Ontario, Canada (Ragheb et al. 1999). CD200Fc was prepared in a Baculovirus expression system, using a cDNA encoding a murine IgG2aFc region (a kind gift from Dr. T Strom, Harvard, USA) which carried mutations to delete complement binding and FcR sites, as we described elsewhere (Gorczynski et al. 1999). Rat monoclonal antibody to CD200$^r$ was prepared from rats immunized with CHO cells transfected to express a cDNA encoding CD200$^r$ (Gorczynski 2001). Anti-CD4 (GK1.5, rat IgG2b) and anti-CD8 (2.43, rat IgG2b) were both obtained from ATCC, and used for in vivo depletion by iv infusion of 100 μg Ig/mouse weekly. A control IgG2b antibody (R35.38), as well as strepavidin horse radish peroxidase and recombinant mouse GM-CSF, was purchased from Pharmingen (San Diego, Calif.).

Preparation of cells: Single cell spleen suspensions were prepared aseptically and after centrifugation cells were resuspended in α-Minimal Essential Medium supplemented with 2-mercaptoethanol and 10% fetal calf serum (αF10). CD200$^{r+}$ LPS splenic Mph, stained (>20%) with FITC-CD200Fc, were obtained by velocity sedimentation of cells cultured for 48 hrs with 1 mg/ml LPS (Gorczynski et al. 2000). Bone marrow cells were flushed from the femurs of donor mice, washed and resuspended in αF10. Cells were depleted of mature T lymphocytes using anti-thy1.2 and rabbit complement.

C1498 (a spontaneous myeloid tumor) and EL4 (a radiation induced thymoma tumor) cells were obtained from The American Type Culture Collection (ATCC, Rockville, Md.). Cells used for transplantation into mice were passaged weekly ($5 \times 10^6$ cells/mouse) intraperitoneally in stock 8-week old C57BL/6 recipients. For experimental tumor challenge either $5 \times 10^6$ EL4 tumor cells, or $5 \times 10^5$ C1498 cells, were given intraperitoneally to groups of 6 mice (see results)-animals were sacrificed when they became moribund. EL4 cells stably transfected to express CD80 or CD86 were obtained from Dr. J. Allison, Cancer Research Labs, UC Berkeley, Calif., while C1498 transfected with CD80/CD86 (cloned into pBK vectors) were produced in the author's laboratory. Tumor cells (parent and transfected) were stored at −80° C. and thawed and cultured prior to use. Cells used for immunization, including the tumor cells transfected with CD80/CD86, were maintained in culture in aMEM medium supplemented with 10% FCS. Untransfected and transfected cells of each tumor line were used for immunization within 2 passages in culture. Over this time in culture transfected cells repeatedly showed stable expression (by FACS) of CD80/CD86 (>80% positive for each tumor assayed over a 6 month period with multiple vials thawed and cultured). Non-transfected tumor cells did not stain with these mAbs (<2%).

CD200$^{r+}$ cells were obtained from lymphocyte-depleted murine spleen cells. Cells were treated with rabbit anti-mouse lymphocyte serum and complement (both obtained from Cedarlane Labs. Hornby, Ontario), cultured with LPS (10 μg/ml) for 24 hours, and separated into populations of different size by velocity sedimentation (Gorczynski et al. 2000). Small CD200$^{r+}$ cells stained >65% by FACS with anti-CD200$^r$ antibody (Gorczynski 2001).

Bone marrow transplantation (BMT): C57BL/6 mice received 300 mg/Kg cyclophosphamide iv 24 hrs before intravenous infusion of $20 \times 10^6$ T-depleted C3H or C57BL/6 bone marrow cells. Immediately prior to use for tumor transplantation (28 days following bone marrow engrafting), a sample of PBL (50 μl/mouse) was obtained from the tail vein of individual mice and analysed by FACS with FITC-anti-H2K$^k$ or FITC-anti-H2K$^b$ mAb. Cells from normal C57BL/6 or C57BL/6 reconstituted C57BL/6 mice were 100% H2K$^b$ positive, as expected. In similar fashion, PBL from C3H mice were 100% H2K$^k$ positive. H2K$^k$ positive cells in the C3H-reconstituted C57BL/6 mice by FACS comprised 85%±8.5% of the total cell population (mean over ~100 mice used in the studies described below). Mice in all groups were gaining weight and healthy.

Cytotoxicity and Cytokine Assays:

In allogeneic mixed leukocyte cultures (MLC) used to assess cytokine production or CTL, responder spleen cells were stimulated with equal numbers of mitomycin-C treated (45 min at 37° C.) spleen stimulator cells in triplicate in αF10. Supernatants were pooled at 40 hr from replicate wells and assayed in triplicate in ELISA assays for lymphokine production as follows, using capture and biotinylated detection mAbs as described above. Varying volumes of supernatant were bound in triplicate at 4° C. to plates pre-coated with 100 ng/ml mAb, washed ×3, and biotinylated detection antibody added. After washing, plates were incubated with strepavidin-horse radish peroxidase (Cedarlane Labs), developed with appropriate substrate and $OD_{405}$ determined using an ELISA plate reader. Recombinant cytokines for standardization were obtained from Pharmingen (U.S.A.). All assays showed sensitivity in the range 40 to 4000 pg/ml. CTL assays were performed at 5 days using cells harvested from the same cultures (as used for cytokine assays). Various effector:target ratios were used in 4 hr $^{51}Cr$ release tests with 72 hr ConA activated spleen cell blasts of stimulator genotype.

Quantitation of CD200 mRNA by PCR:

RNA extraction from spleen tissue of tumor injected mice was performed using Trizol reagent. The OD280/260 of each sample was measured and reverse transcription performed using oligo (dT) primers (27-7858: Pharmacia, USA). cDNA was diluted to a total volume of 100 μl with water and frozen at −70° C. until use in PCR reactions with primers for mouse CD200 and GAPDH (Gorczynski et al. 1998). Different amounts of standard cDNA from 24 hr cultures of LPS stimulated peritoneal macrophages (known to express CD200 and GAPDH) were amplified in six serial 1:10 dilutions for 30 cycles by PCR, in the presence of a tracer amount of $^{32}P$. Samples were analysed in 12.5% polyacrylamide gels, the amplicons cut from the gel, and radioactivity measured in a β-counter. A standard curve was drawn for each set of primer pairs (amplicons). cDNAs from the various experimental groups were assayed in similar reactions using 0.1 μl cDNA, and all groups were normalized to equivalent amounts of GAPDH. CD200 cDNA levels in the different experimental groups were then expressed relative to the cDNA standard (giving a detectable $^{32}P$ signal over five logic dilutions). Thus a value of 5 (serial dilutions) indicates a test sample with approximately the same cDNA content as the standard, while a value of 0 indicates a test sample giving no detectable signal in an undiluted form ($<1/10^5$ the cDNA concentration of the standard).

Results

Growth of EL4 or C1498 Tumor Cells in C57BL/6 Mice, and in Allogeneic (C3H) BMT Mice:

Groups of 6 C57BL/6 mice received iv infusion of 300 mg/Kg cyclophosphamide (in 0.5 ml PBS). A control group received PBS only, as did a control group of 6 C3H mice. 24 hrs later cyclophosphamide treated C57BL/6 mice received iv injection of 20×10$^6$ T-depleted bone marrow cells pooled from C57BL/6 mice (syngeneic transplant), or C3H mice (allogeneic transplantation). All groups of animals received intraperitoneal injection (in 0.5 ml PBS) of 5×10$^6$ EL4 or 5×10$^5$ C1498 tumor cells (see FIG. 24) 28 days later. Animals were monitored daily post tumor inoculation.

Figure 24:
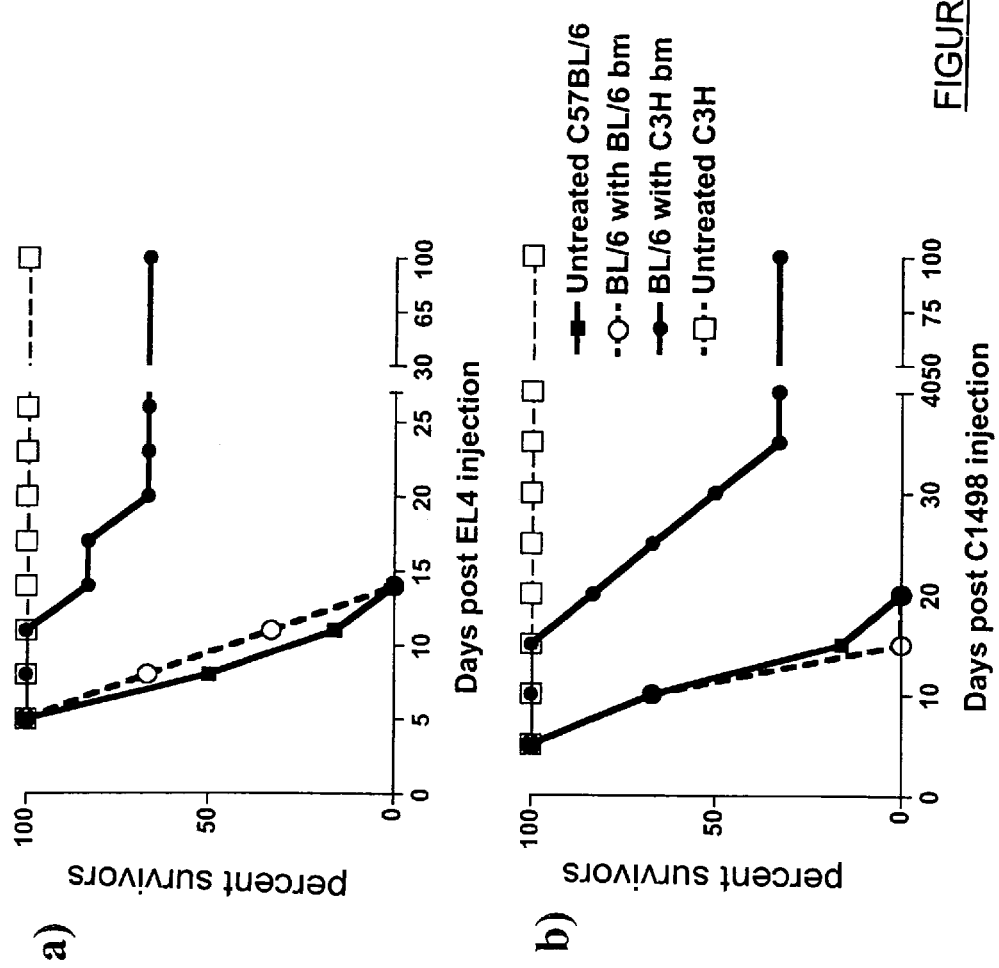
FIG. 24 is a graph showing inhibition of EL4 or C1498 tumor growth in C3H bone marrow reconstituted C57BL/6 mice. Groups of 6 BL/6 mice received $20 \times 10^6$ T-depleted BL/6 or C3H bone marrow cells 24 hrs following cyclophosphamide treatment. $5 \times 10^6$ EL4 or $5 \times 10^5$ C1498 tumor cells were injected 28 days later into these mice, and control BL/6 or C3H mice. >85% of PBL from C3H reconstituted BL/6 were stained by FITC anti-$H2K^k$ mAb at this time.

Data in FIG. 24 (one of 2 such studies) show clearly that while C3H mice rejected both EL4 and C1498 (allogeneic) leukemia cell growth, 100% mortality was seen within 9-12 days in normal C57BL/6 mice, or in syngeneic bone marrow reconstituted mice. Interestingly, despite the absence of overt GVHD (as defined by weight loss and overall health), two-thirds of C3H reconstituted C57BL/6 mice rejected EL4 tumor cells, reflecting the existence of a graft versus leukemia effect (GVL) (panel a of FIG. 24), and there was a marked delay of death for mice inoculated with C1498 leukemia cells (panel b of Figure). In separate studies similar findings were made using tumor inocula (for EL4/C1498 respectively) ranging from 2×10$^6$-10×10$^6$, or 1.5×10$^5$-10×10$^5$ (RMG-unpublished).

Figure 25:
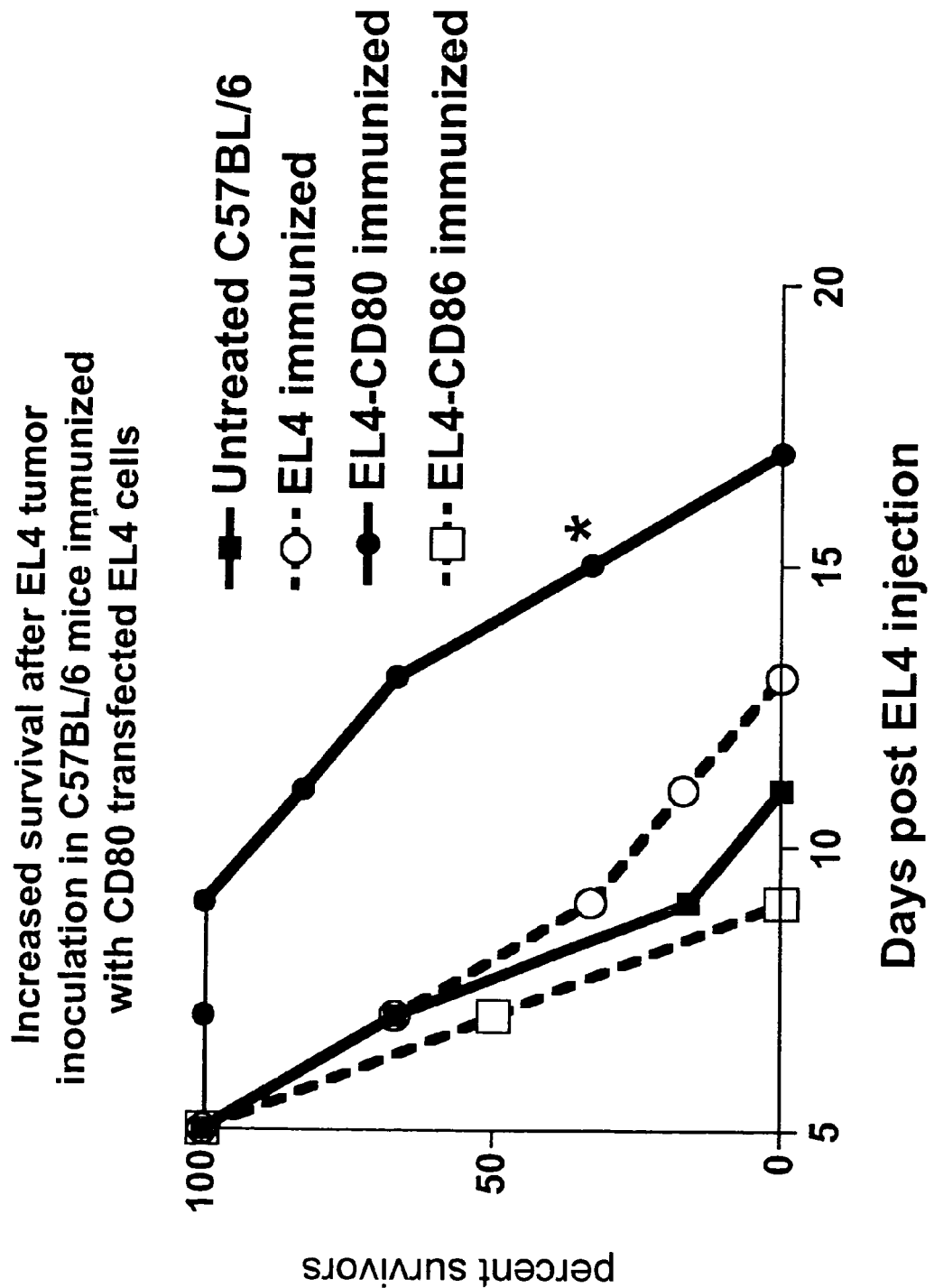
FIG. 25 is a graph showing EL4 tumor growth in BL/6 mice immunized twice, at 14 day intervals, with $5 \times 10^6$ EL4 cells transfected to express CD80 or CD86. $5 \times 10^6$ EL4 cells were injected as tumor challenge 10 days after the last immunization.

Immunization of Normal C57BL/6 Mice for Protection Against EL4 Tumor Growth:

Blazar and co-workers reported immunization for protection from tumor growth in C57BL/6 mice using tumor cells transfected to over-express mouse CD80 (Blazar et al. 1997). Using CD80 and CD86 transfected EL4 cells obtained from this same group, or C1498 cells transfected with CD80/CD86 in our laboratory, we immunized groups of 6 C57BL/6 mice ip with Complete Freund's adjuvant (CFA) alone, or with CFA mixed with 5×10$^6$ mitomycin-C treated tumor cells, or CD80/CD86 transfected tumor. Animals received 2 injections at 14 day intervals. 10 days after the last immunization all mice received 5×10$^6$ EL4 tumor cells, or 5×10$^5$ C1498 cells, and mortality followed. Data are shown in FIG. 25 (1 of 2 studies), for EL4 only.

Figure 28:
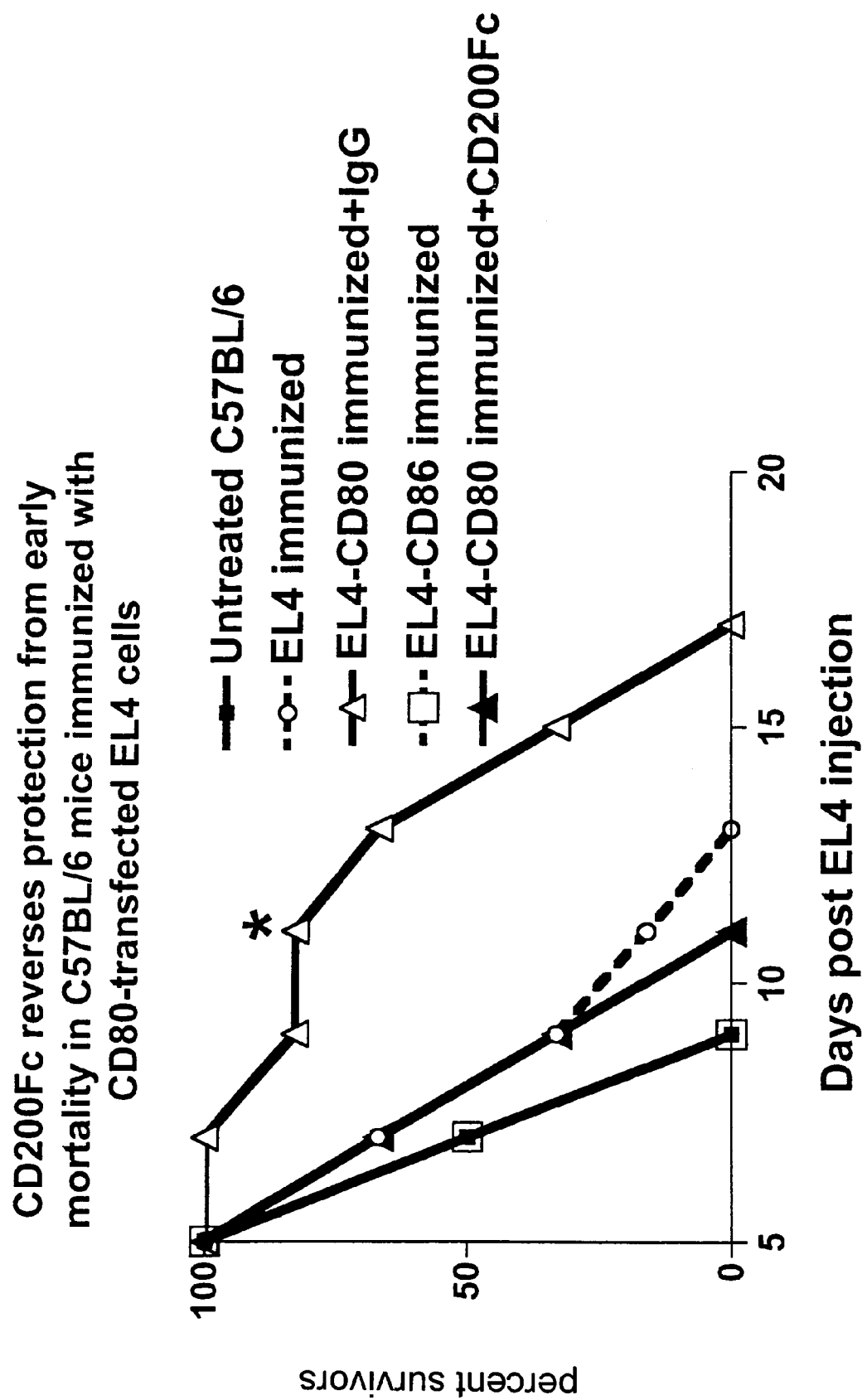
FIG. 28 is a graph showing inhibition of immunity to EL4 tumor cells in EL4-CD80 immunized BL/6 mice using CD200Fc-see FIG. 25 and text for details. Mice received iv infusion of control IgG or CD200Fc as described in FIG. 27.

In agreement with a number of other reports, mice pre-immunized with CD80-transfected EL4 survive significantly longer after challenge with viable EL4 tumor cells than non-immunized animals, or those immunized with non-transfected cells or CD86 transfected cells (p<0.05)—see also FIG. 28. Similar data were obtained using CD80-transfected C1498 cells (RMG-unpublished). In separate studies (not shown) mice immunized with tumor cells in the absence of Freund's Adjuvant failed to show any protection from tumor growth. However, equivalent protection (to that seen using Freund's Adjuvant) was also seen using concomitant immunization with poly(I:C) (100 μg/mouse) as adjuvant (data not shown).

Role of CD4$^+$ and/or CD8$^+$ Cells in Modulation of Tumor Growth After BMT:

In order to investigate the effector cells responsible for leukemia growth-inhibition in mice transplanted with allogeneic bone marrow (see FIG. 24), BMT recipients received weekly injections of 100 μg/mouse anti-CD4 (GK1.5) or anti-CD8 (2.43) mAb, followed at 28 days by leukemia cell injection as described for FIG. 24. Depletion of CD4 and CD8 cells in all mice with these treatments was >98% as defined by FACS analysis (not shown).

Figure 26:
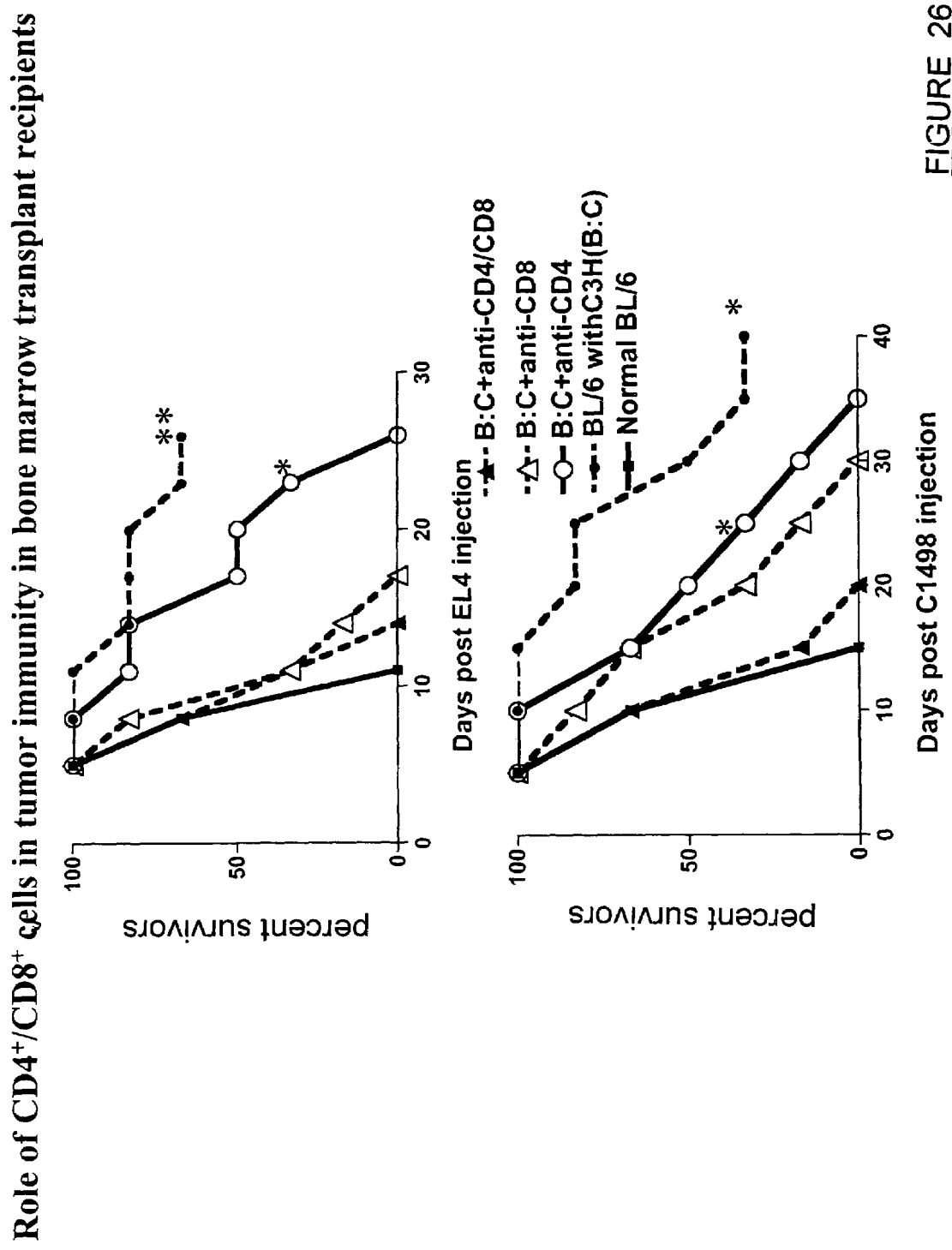
FIG. 26 is a graph showing suppression of growth inhibition in C57BL/6 BMT recipients of EL4 or C1498 tumor cells (see FIG. 19) following 4 weekly infusions of 100 μg/mouse anti-CD4 or anti-CD8 mAb, beginning on the day of BMT (tumor cells were injected at 28 days post BMT). Data are shown for 6 mice/group.

As shown in FIG. 26 (data from one of 3 studies), and in agreement with data reported elsewhere (Blazar et al. 1997), in this BMT model tumor growth inhibition for EL4 cells is predominantly a function of CD8 rather than CD4 cells, while for C1498 leukemia cells growth inhibition was equally, but not completely, inhibited by infusion of either anti-CD4 or anti-CD8 mAb (see pane b of Figure).

Evidence that Tumor Rejection in BMT Mice is Regulated by CD200:

Previous studies in rodent transplant models have implicated expression of a novel molecule, CD200, in the regulation of an immune rejection response. Specifically, blocking functional expression of CD200 by a monoclonal antibody to murine CD200 prevented the increased graft survival which followed donor-specific pretransplant immunization, while a soluble form of CD200 linked to murine IgG Fc (CD200Fc) was a potent immunosuppressant (Gorczynski et al. 1998; Gorczynski et al. 1999). In order to investigate whether expression of CD200 was involved in regulation of tumor immunity, we studied first the effect of infusion of CD200Fc on suppression of resistance to growth of EL4 or C1498 tumor in BMT mice as described in FIG. 24, and second the effect of CD200Fc infusion in mice immunized with CD80-transfected tumor cells as described in FIG. 25. Note this CD200FC lacks binding sites for mouse complement and FcR (see Materials and Methods, and Gorczynski et al. 1999). In all cases control groups of mice received infusion of equivalent amounts of pooled normal mouse IgG. Data for these studies is shown in FIGS. 27 and 28 respectively (data from one of 2 studies in each case).

Figure 27:
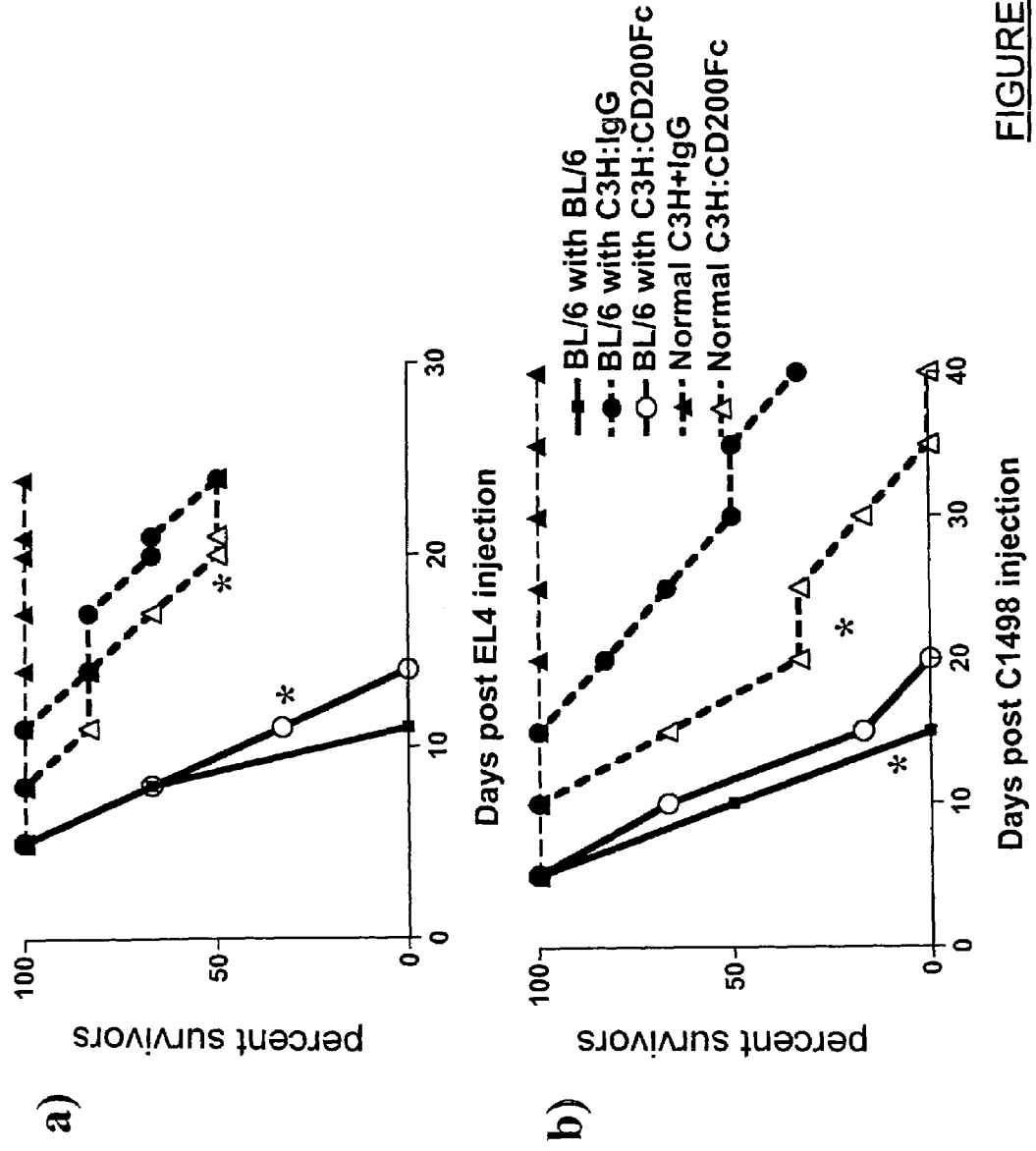
FIG. 27 is a graph showing inhibition of immunity to EL4 or C1498 tumor challenge following infusion of CD200Fc in C57BL/6 mice reconstituted with C3H bone marrow—see FIG. 24 and text for more details. Cyclophosphamide treated BL/6 mice received bone marrow rescue with T-depleted C3H or BL/6 cells. 28 days later all mice, and groups of control normal C3H mice, received ip injection with $5 \times 10^6$ EL4 or $5 \times 10^5$ C1498 tumor cells. Bone marrow reconstituted mice received further iv infusion of normal mouse IgG or CD200Fc (10 μg/mouse/injection) 5 times at 2 day intervals beginning on the day of tumor injection.

It is clear that suppression of growth of either EL4 or C1498 tumor cells in BMT mice is inhibited by infusion of CD200Fc, but not by pooled normal mouse IgG (FIG. 27). CD200Fc also caused increased mortality in EL4 or C1498 injected normal C3H mice. Data in FIG. 28 show that resistance to EL4 tumor growth in EL4-CD80 immunized mice (as documented in FIG. 25) is also inhibited by infusion of CD200Fc. In separate studies (not shown) a similar inhibition of immunity induced by CD80 transfected C1498 was demonstrated using CD200Fc.

Effect of Anti-CD200 mAb on Resistance to Tumor Growth in Mice Immunized with CD80/CD86 Transfected Tumor Cells:

As further evidence for a role for CD200 expression in tumor immunity in EL4-CD80/EL4-CD86, or C1498-CD80/ C1498-CD86 immunized mice, the inventors examined the effect of infusion of an anti-CD200 mAb on EL4 or C1498 tumor growth in this model. Infusion of anti-CD200 into mice preimmunized with EL4-CD86, or C1498-CD86 uncovered evidence for resistance to tumor growth. Separate studies (not shown) revealed that anti-CD200 produced no significant perturbation of EL4 growth in the EL4 or EL4-CD80 immunized mice, or of C1498 growth in C1498 or C1498-CD86 immunized mice. These data suggest that immunization with EL4-CD86 or C1498-CD86 elicited an antagonism of tumor immunity resulting from increased expression of CD200. Thus blocking the functional increase of CD200 expression with anti-CD200 reversed the inhibitory effect. Note that in studies not shown, these same effects of anti-CD200 have been reproduced (in mice immunized with CD86-transfected tumor cells) with F(ab')$_2$ anti-CD200 (RMG-unpublished).

Figure 29:
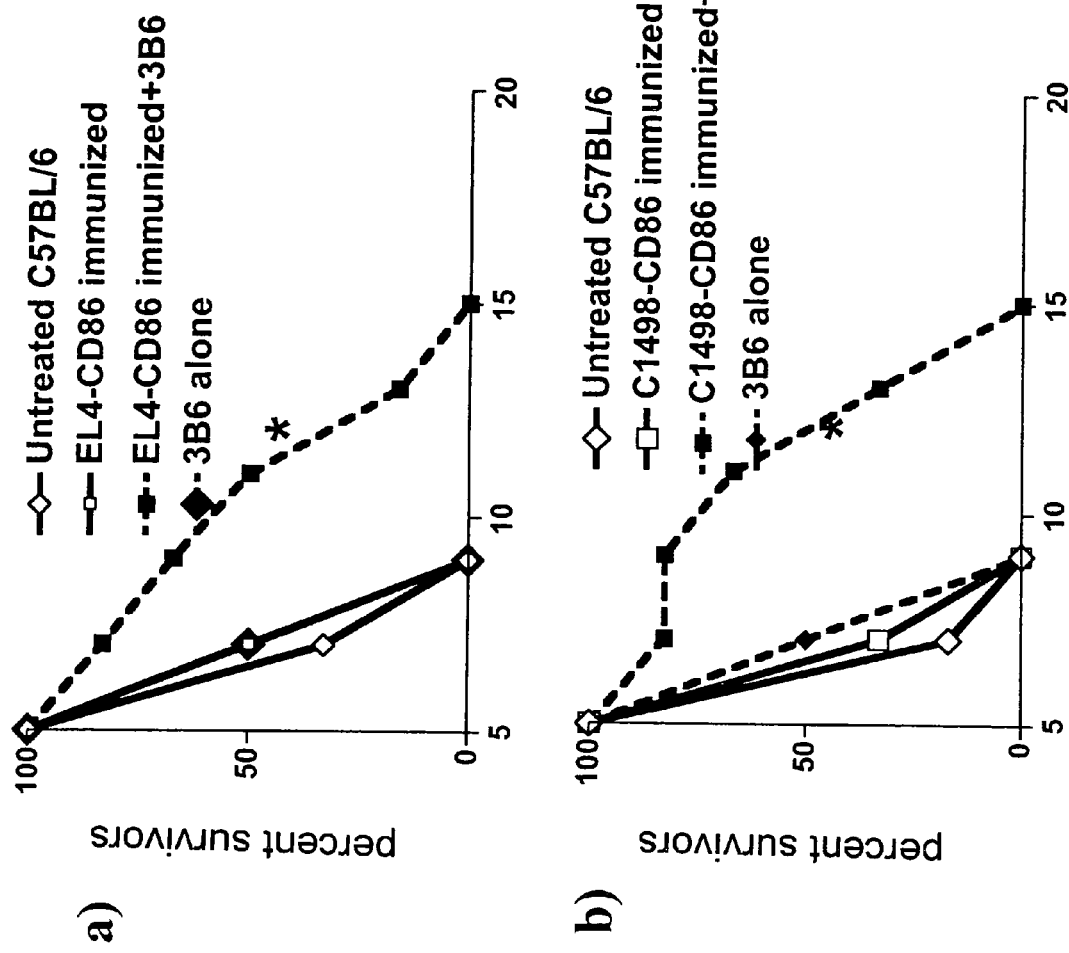
FIG. 29 is a graph showing improved tumor immunity in EL4-CD86 or C1498-CD86 immunized C57BL/6 mice following infusion of anti-CD200 mAb. See legend to FIG. 25 and text for more details. Where shown, groups of mice received iv infusion of anti-CD200, 100 mg/mouse, on 3 occasions at 3 day intervals beginning on the day of tumor injection.
Figure 30:
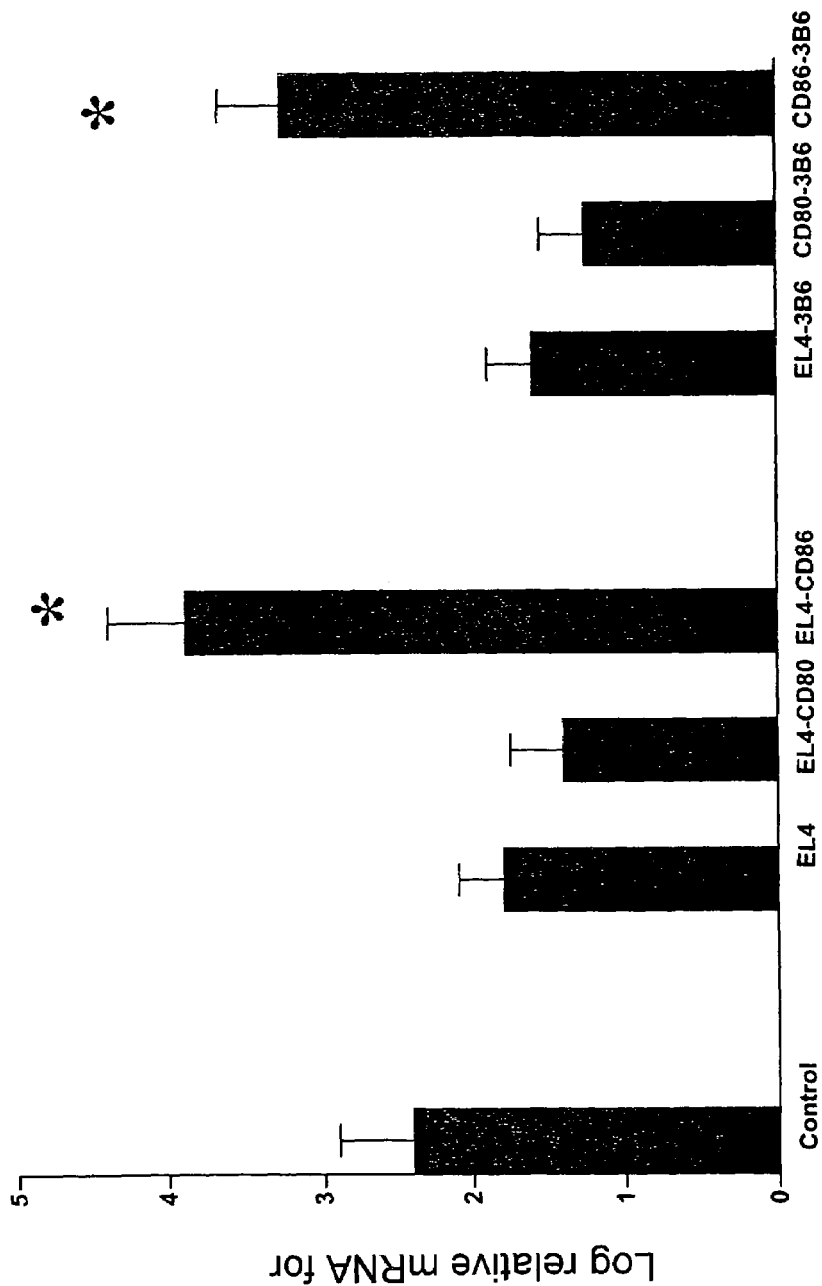
FIG. 30 is a graph showing log 10 relative concentrations of CD200 mRNAs compared with standardized control mRNA. All samples were first normalized for equivalent concentrations of GAPDH mRNA. Values shown represent arithmetic means±SD for 3 individual samples for each time point.Mice were preimmunized with CD80/CD86-transfected tumor cells as described in the text.

To confirm that indeed immunization with CD86-transfected tumor cells was associated with increased expression of CD200, the study shown in FIG. 29 was repeated, and sacrificed 3 mice/group at 4 days following EL4 tumor injection. RNA was isolated from the spleen of all mice, and assayed by quantitative PCR for expression of CD200 (using GAPDH as "housekeeping" mRNA control). Data for this study are shown in FIG. 30, and show convincingly that CD200 mRNA expression was >5-fold increased following preimmunization with EL4-CD86, a condition associated with increased tumor growth compared with EL4-immunized mice (FIGS. 25 and 29). In dual-staining FACS studies (not shown), with PE-anti-CD200 and FITC-DEC205, the predominant CD200$^+$ population seen in control and immunized mice were DEC205+(>80%)—see also Gorczynski et al. (1999). Similar results were obtained using C1498 tumor cells (data not shown).

Given this increase in CD200 expression following preimmunization with CD86-transfected cells, and the evidence that CD200 is associated with delivery of an immunosuppressive signal to antigen encountered at the same time, the inventors also examined the response of spleen cells taken from these C57BL/6 mice to allostimulation (with mitomycin-C treated BALB/c spleen cells), in the presence/absence of anti-CD200 mAb. Data from one of 3 studies are shown in Table 8. Interestingly, mice preimmunized with EL4-CD86 cells show a decreased ability to generate CTL on alloimmunization with third-party antigen (BALB/c), and decreased type-1 cytokine production (IL-2, IFNγ), with some trend to increased type-2 cytokines (IL-4 and IL-10). These effects were reversed by inclusion of anti-CD200 in culture, consistent with the hypothesis that they result from increased delivery of an immunosuppressive signal via CD200 in spleen cells obtained from these animals (Gorczynski et al. 1998).

Evidence for an Interaction Between CD200 and CD200$^{r+}$ Cells in Inhibition of EL4 Tumor Growth:

Inhibition resulting from infusion of CD200Fc into mice follows an interaction with immunosuppressive CD200$^{r+}$ cells (Gorczynski et al. 2000). At least one identifiable functionally active population of suppressive CD200$^{r+}$ cells was described as a small, F4/80$^+$ cell in a pool of splenic cells following LPS stimulation (Gorczynski et al. 2000)- F4/80 is a known cell surface marker for tissue macrophages. In a further study we investigated whether signaling induced by CD200:CD200$^r$ interaction (where CD200$^{r+}$ cells were from lymphocyte-depleted, LPS stimulated, spleen cells) was behind the suppression of tumor immunity seen following CD200Fc injection. All groups of 6 recipient mice received tumor cells ip. In addition to infusion of CD200Fc as immunosuppressant (in FIG. 31), one group of C3H reconstituted animals received CD200$^{r+}$ cells (in FIG. 31: >65% of these cells stained with an anti-CD200$^r$ mAb), while a final group received a mixture of both CD200Fc and CD200$^{r+}$ cells. It is clear from the Figure that it is this final group, in which interaction between CD200 and CD200$^r$ is possible, which showed maximum inhibition of tumor immunity compared with the C3H reconstituted control mice.

Role of CD4$^+$ and/or CD8$^+$ Cells in CD200 Regulated Modulation of Tumor Growth After BMT:

Data in FIG. 26 above, and elsewhere (Blazar et al. 1997) show that tumor growth inhibition for EL4 cells is predominantly a function of CD8 rather than CD4 cells, while for C1498 leukemia cells growth inhibition was equally, but not completely, inhibited by infusion of either anti-CD4 or anti-CD8 mAb. To investigate the role of CD200 in the protection mediated by different T cell subclasses, the following additional studies were performed. In the first, C57BL/6 recipients of C3H BMT received (at 28 days post BMT) inoculations of EL4 or C1498 tumor cells along with anti-CD4, anti-CD8 or CD200Fc alone, or combinations of (anti-CD4+CD200Fc) or (anti-CD8+CD200Fc). Survival was followed as before (see FIG. 32-*one* of 2 studies). In a second study (FIG. 33—data from one of 2 such experiments) a similar treatment regimen of mAbs or CD200Fc alone or in combination was used to modify growth of EL4 tumor cells in mice preimmunized with EL4-CD80 cells as described earlier in FIG. 25.

Figure 32:
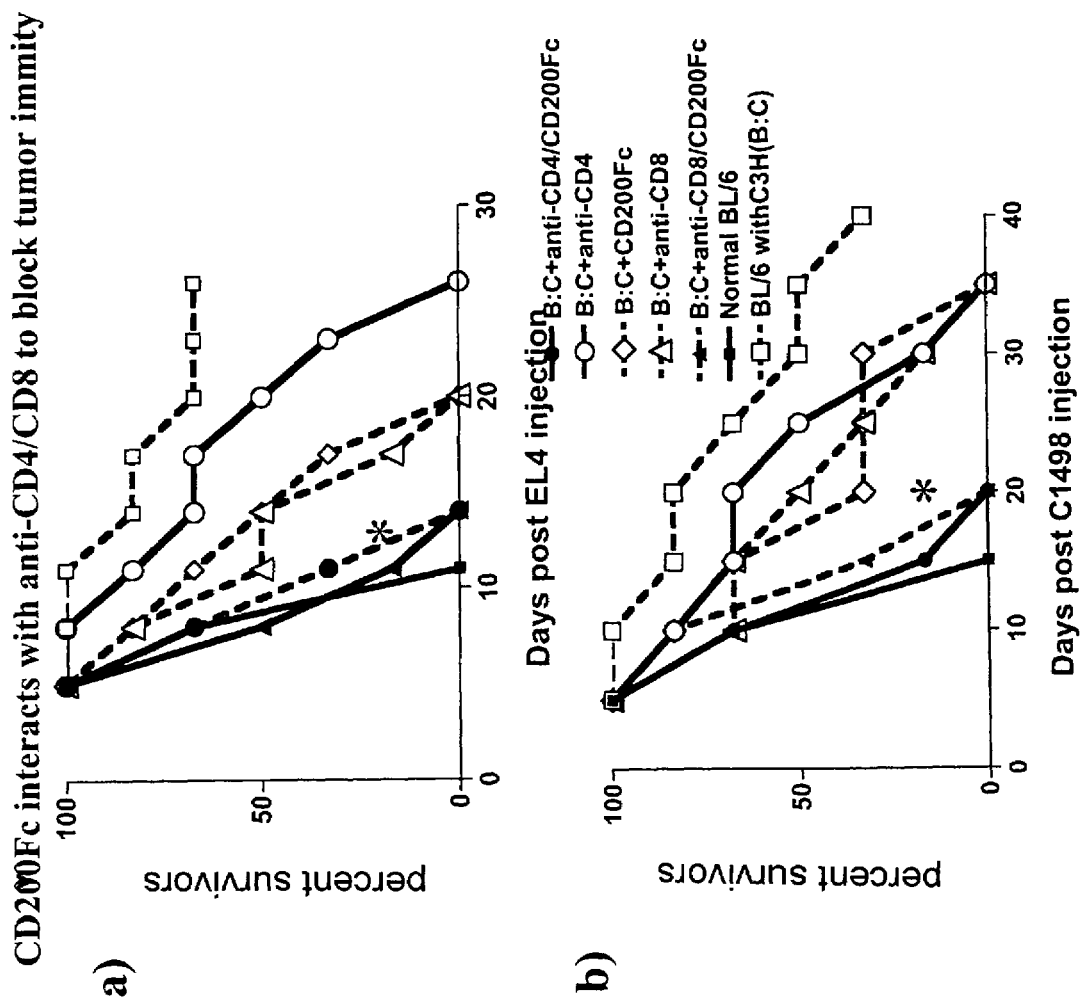
FIG. 32 is a graph showing combinations of CD200Fc and anti-CD4 or anti-CD8 mAb produce increased suppression of tumor growth inhibition in C57BL/6 recipients of C3H BMT. Groups of 6 mice received weekly iv infusions of 100 μg anti-T cell mab or 5 iv infusions of 10 μg/mouse CD200Fc, alone or in combination, beginning on the day of tumor injection (28 days post BMT).

Data in panel a of FIG. 32 confirm the effects previously documented in FIGS. 26 and 27, that CD200Fc and anti-CD8 each significantly impaired the growth inhibition in BMT recipients of EL4 cells, while anti-CD4 mAb was less effective. Combinations of CD200Fc and either anti-T cell mAb led to even more pronounced inhibition of tumor immunity in the BMT recipients, to levels seen with non-allogeneic transplanted mice. Data with C1498 tumor cells (panel b) were somewhat analogous, though as in FIG. 26, anti-CD4 alone produced equivalent suppression of growth inhibition to anti-CD8 with this tumor. As was the case for the EL4 tumor, combinations of CD200Fc and either anti-T cell mAb caused essentially complete suppression of C1498 tumor growth inhibition. Both sets of data, from panels a and b, are consistent with the notion that CD200Fc blocks (residual) growth-inhibitory functional activity in both CD4 and CD8 cells, thus further inhibiting tumor immunity remaining after depletion of T cell subsets.

Figure 33:
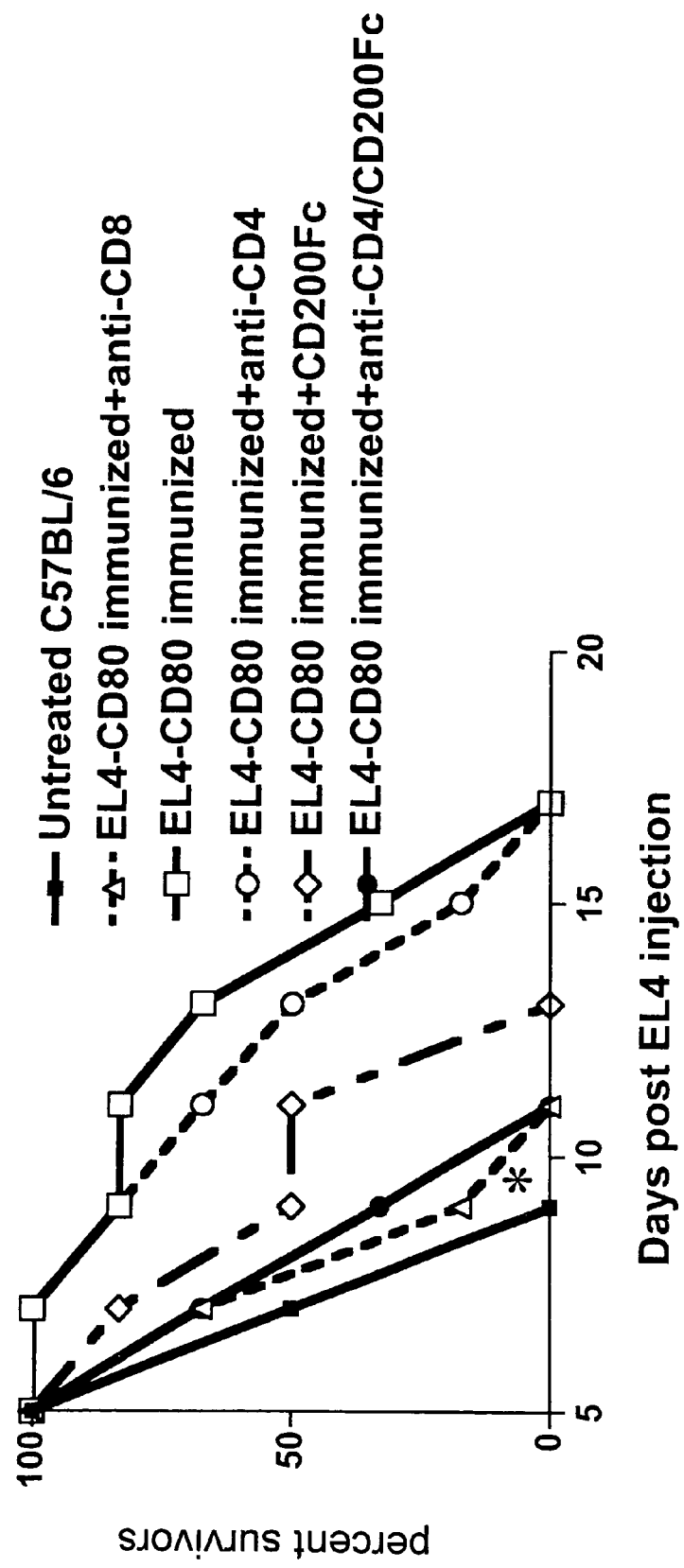
FIG. 33 is a graph showing effect of combined CD200Fc and anti-CD4 or anti-CD8 mAb on suppression of EL4 tumor growth inhibition in C57BL/6 recipients preimmunized with EL4-CD80 transfected cells (see FIG. 20). Data are shown for groups of 6 mice/group. Weekly iv infusions of 100 μg anti-T cell mab or 5 iv infusions of 10 μg/mouse CD200Fc, alone or in combination, were begun on the day of tumor injection (10 days after the final immunization with EL4-CD80 cells).

Data in FIG. 33, using EL4 immunized BL/6 mice, also showed combinations of CD200Fc and anti-CD4 treatment produced optimal suppression of tumor immunity to EL4 cells, consistent with an effect of CD200Fc on CD8+cells. Anti-CD8 alone abolished tumor immunity in these studies, so any potential additional effects of CD200Fc on CD4$^+$ cells could not be evaluated.

Discussion

In the studies described above, we have asked whether expression of the molecule CD200, previously reported to down-regulate rejection of tissue/organ allografts in rodents (see previous Examples), was implicated in immunity to tumor cells in syngeneic hosts. Two model systems were used. The one, in which tumor cells are injected into mice which had received an allogeneic bone marrow transplant following cyclophosphamide pre-conditioning, has been favoured as a model for studying potential innovative treatments of leukemia/lymphoma in man (Blazar et al. 1997; Imamura et al. 1996; Blazar et al. 1999; Champlin et al.1999). In the other EL4 or C1498 tumor cells were infused into BL/6 mice which had been preimmunized with tumor cells transfected to overexpress the costimulatory molecules CD80 or CD86. These studies were stimulated by the growing interest in such therapy for immunization of human tumor patients with autologous transfected tumor cells (Imro et al. 1998; Brady et al. 2000; Jung et al. 1999; Freund et al. 2000; MartinFontecha et al. 2000).

In both sets of models we found evidence for inhibition of tumor growth (FIGS. 24 and 25) which could be further modified by treatment designed to regulate expression of CD200. Infusion of CD200Fc suppressed tumor immunity (led to increased tumor growth, and faster mortality) in both models (FIGS. 27 and 28), while anti-CD200 improved tumor immunity in mice immunized with CD86-transfected EL4 or C1498 tumor cells (FIG. 29). This latter finding suggests that the failure to control tumor growth following immunization with EL4-CD86 or C1498-CD86 was associated with overexpression of endogenous CD200, a hypothesis which was confirmed by quantitative PCR analysis of tissue taken from such mice (FIG. 30). CD200 was predominantly expressed on DEC205$^+$ cells in the spleen of these mice (see text), which was associated with a decreased ability of these spleen cell populations to respond to allostimulation in vitro (see Table 8). Non antigen-specific inhibition following CD200 expression formed the basis of our previous reports that a soluble form of CD200 (CD200Fc) was a potent immunosuppressant (Gorczynski et al. 1998). Consistent with the hypothesis that increased expression of CD200 in mice immunized with CD86-transfected tumor cells was responsible for the inhibition of alloreactivity seen in Table 8, suppression was abolished by addition of anti-CD200 mAb (see lower half of Table 8). Earlier reports have already documented an immunosuppressive effect of CD200Fc on alloimmune responses (Gorczynski et al. 1999), and production of antibody in mice following immunization with sheep erythrocytes (Gorczynski et al. 1999).

Figure 31:
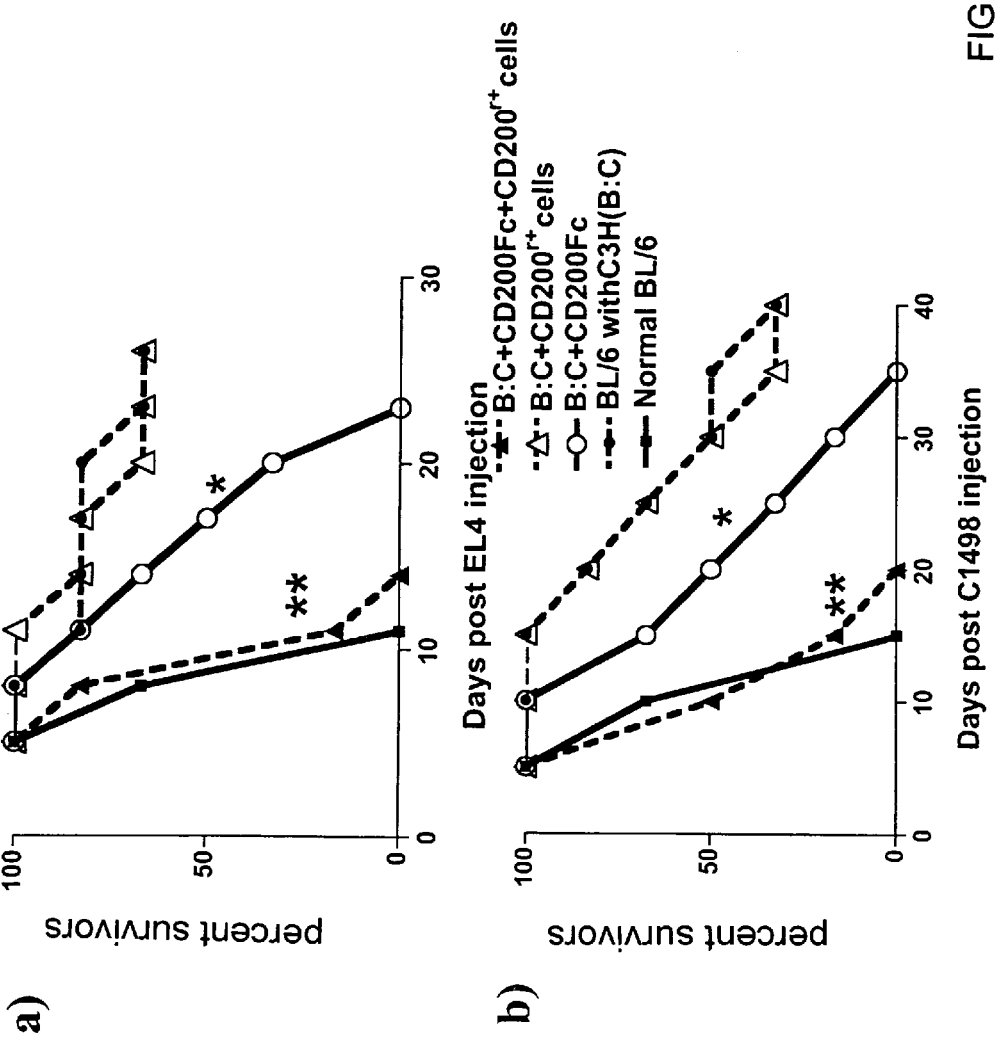
FIG. 31 is a graph showing increased inhibition of tumor immunity using infusion of CD200Fc with $CD200^{r+}$ cells in C57BL/6 recipients of C3H bone marrow. In this experiment some mice received not only CD200Fc with EL4 or C1498 tumor, but in addition a lymphocyte-depleted, LPS-stimulated, macrophage population stained (>65%) with anti-$CD200^r$ mAb (2F9).

Maximum inhibition of tumor immunity was achieved by concomitant infusion of CD200Fc and CD200$^{r+}$ cells (F4/80$^+$ macrophages—see FIG. 31). We next investigated the cell type responsible for tumor growth inhibition whose activity was regulated by CD200:CD200$^r$ interactions. The data confirmed previous reports that EL4 growth inhibition was predominantly associated with CD8 immune cells, while immunity to C1498 was a function of both CD4+ and CD8+ cells.(Bazar et al. 1997). For both tumors in BMT models suppression of tumor growth inhibition was maximal following combined treatment with CD200Fc and either anti-T cell mAb, consistent with the idea that CD200 suppression acts on both CD4$^+$ and CD8$^+$ T cells.

A number of studies have examined immunity to EL4 or C1498 tumor cells in similar models to those described above (Blazar et al. 1997; Boyer et al. 1995), concluding that CD8$^+$ cells are important in (syngeneic) immunity to each tumor, and CD4$^+$ T cells are also important in immunity to C1498 (Blazar et al. 1997). Evidence to date suggests that NK cell mediated killing is not relevant to tumor growth inhibition in BMT mice of the type used above (Blazar et al. 1997). Other reports have addressed the issue of the relative efficiency of induction of tumor immunity in a number of models following transfection with CD80 or CD86, and also concluded that CD80 may be superior in induction of anti-tumor immunity (Blazar et al. 1997; Chen et al. 1994), while CD86 may lead to preferential induction of type-2 cytokines (Freeman et al. 1995). This is of interest given the cytokine production profile seen in EL4-CD86 immunized mice (Table 8), which is similar to the profile seen following CD200Fc treatment of allografted mice (Gorczynski et al. 1998). EL4-CD86 immunized mice show increased expression of CD200 (FIG. 30), with no evidence for increased resistance to tumor growth (FIG. 25). Resistance is seen in these mice following treatment with anti-CD200 (FIG. 29A). Somewhat better protection from tumor growth is seen using viable tumor cells for immunization, rather than mitomycin-C treated cells as above (Blazar et al. 1997). Whether this would improve the degree of protection from tumor growth in our model, and/or significantly alter the role of CD200:CD200$^r$ interactions in its regulation, remains to be seen.

There are few studies exploring the manner in which suppression mediated by CD200:CD200$^r$ interactions occurs. In a recent study in CD200 KO mice Hoek et al observed a profound increase in the presence of activated macrophages and/or macrophage-like cells (Hoek et al. 2000), and we and others had previously found that CD200$^r$ was expressed on macrophages (Gorczynski et al. 2000; Wright et al. 2000). The inventors also reported that CD200$^r$ was present on a subpopulation of T cells, including the majority of activated γδTCR$^+$ cells (Gorczynski et al. 2000), a result we have recently confirmed by cloning a cDNA for CD200$^r$ from such cells (Kai et al-in preparation). γδTCR+ cells may mediate their suppressive function via cytokine production (Gorczynski et al. 1996), while unpublished data (RMG-in preparation) suggests that the CD200$^{r+}$ macrophage cell population may exert its activity via mechanisms involving the indoleamine 2,3-dioxygenase (IDO) tryptophan catabolism pathway (Mellor et al. 1999). We suggest that the mechanism by which CD200Fc leads to suppression of tumor growth inhibition in the models described is likely to be a function both of the tumor effector cell population involved (FIGS. 32, 33) as well as the CD200$^r$ cell population implicated in suppression.

In a limited series of studies (not shown) we have used other BMT combinations (B10 congenic mice repopulated with B10D2, B10.BR or B10.A bone marrow) to show a similar resistance to growth of EL4 or C1498 tumor cells, which is abolished by infusion of CD200Fc. Studies are in progress to examine whether DBA/2 or BALB/c mice can be immunized to resist growth of P815 syngeneic (H2$^d$) tumor cells by P815 cells tranfected with CD80/CD86, and whether this too can be abolished by CD200Fc. Taken together, however, our data are consistent with the hypothesis that the immunomodulation following CD200:CD200$^r$ interactions, described initially in a murine allograft model system, is important also in rodent models of tumor immunity. This has important implications clinically.

Example 10

Trim in the FSL Sarcoma Lung Metastasis Model:Cues from Pregnancy

Allogeneic leukocyte-induced transfusion-related immunomodulation (TRIM) has been shown to enhance tumor growth (Vamvakas et al. 1994; Bordin et al. 1994). OX-2 is expressed on a variety of cells in transfused blood (i.e. a subpopulation of dendritic cells and possibly B cells) (Wright et al. 2000; Hoek et al. 2000), thus the effect of anti-OX-2 on the TRIM enhancement of FSL10 lung nodules was examined.

Materials and Methods

Enhancement of Lung Nodules by TRIM

Figure 34:
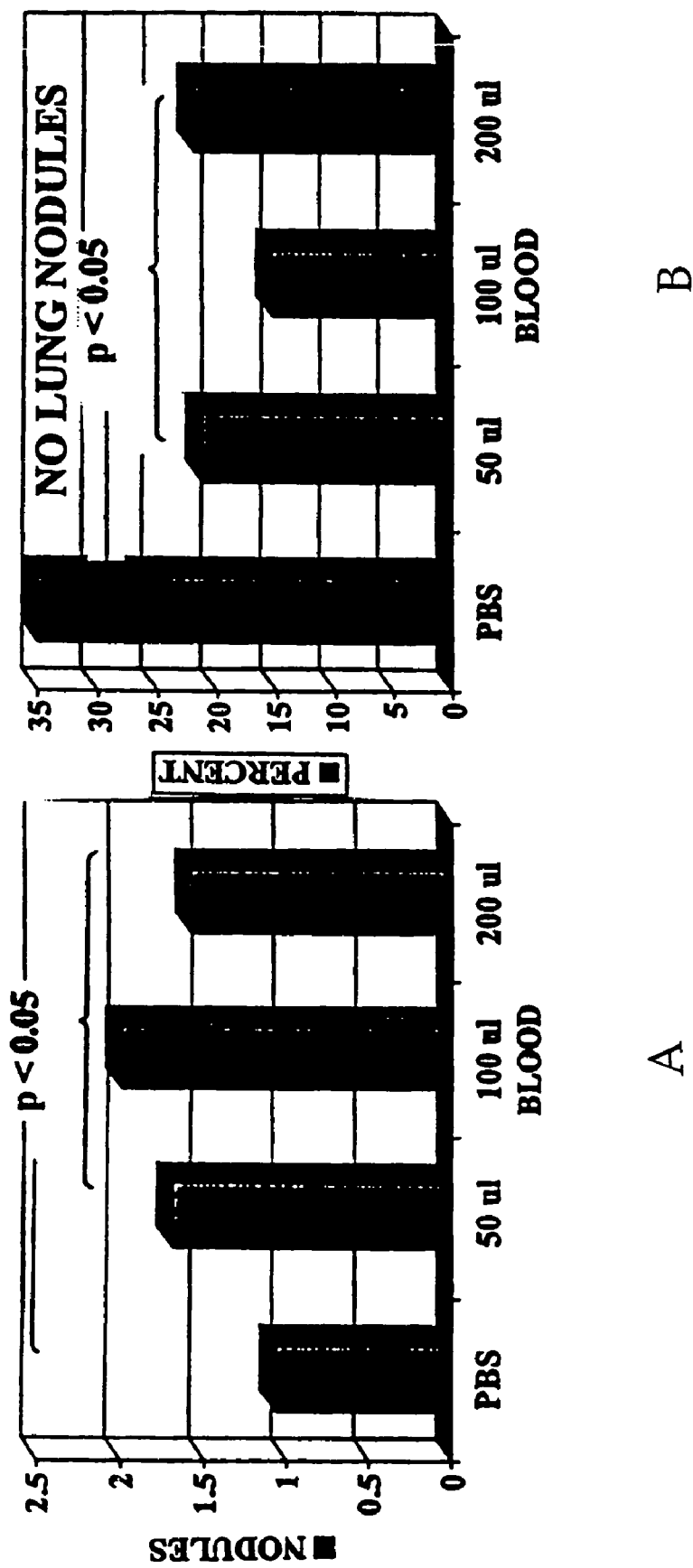
FIGS. 34A and B are bar graphs showing the median number of lung nodules in mice receiving allogeneic blood by tail vein.

A dose response curve demonstrated a plateau in the TRIM enhancement of lung metastases with 50, 100 or 200 µl of BALB/c heparinized blood given 4 days after tail vein injection of the cultured tumor cell by tail vein (see FIG. 34). A dose of 200 µl of BALB/c heparinized blood (about 15-20% of blood volume) was given 4 days after tail vein injection of the cultured tumor cells as a physiologically suitable model in which to screen for treatments that have a major abrogating effect on TRIM.

All animals were monitored for signs of illness daily, and 21 days after tumor inoculation, the mice were sacrificed, the lungs were removed and fixed in Bouin's solution, and the number of surface nodules was counted. To deal with variation in number of metastases between mice, 20-25 mice per group were used and medians were calculated (using log-transformed data, where 0 nodules was set at 0.1 for that animal). It was then possible to assess the significance of differences in log mean±sem with respect to our a prori hypotheses using Student's t test, and to construct 95% confidence intervals for the medians. Differences in the proportion of mice in different groups with no visible metastases was assessed by the $\chi^2$ statistic, or by Fisher's Exact test where appropriate.

FIG. 34A shows the median number of lung nodules in C57Bl/6J mice receiving the indicated dose of freshly-prepared allogeneic BALB/c strain blood by tail vein. The effect is seen if the blood is given 7 days prior to, or 4 days after a tail vein injection of 1×10 6 FSL sarcoma cells. FSL10 is a methlycholanthrene-induced fibrosarcoma generated in C57Bl/6 mice and maintained by standard tissue culture in vitro. Such cells are weakly antigenic. Group size is 20-25 per group, and P values showing increased numbers to lung nodules are on the figure. FIG. 34B shows the proportion of mice with no tumor nodules. P values were determined by Student's t test for A, and by Chi-square or Fisher's Exact test for B.

The Role of Dendritic Cells

MAb to a myeloid DC/APC surface marker (5 µg anti-CD11 c) or lymphoid dendritic cells (DC) (5 µg supernatant of DEC205 hybridoma, an amount shown to be sufficient using in vitro assays of DC function (Gorczynski et al. 2000)) was added to 200 µl of BALB/c blood or to PBS. The TRIM enhancement of tumor growth was analyzed using the same method as above.

Results

Enhancement of Lung Nodules by TRIM

FIG. 35A represents the effect of adding anti-OX-2 monoclonal antibody (3B6, 1 ug per million leukocytes) to the blood (or PBS control) before tumor cell transfer. A control is the same amount of 3B6 in PBS. The total dose was 3.3 ug per mouse. FIG. 35A shows this amount of anti-CD200 in PBS had no effect, whereas when added to blood, the stimulation of tumor nodule number was prevented,—indeed, it was reduced below control levels. FIG. 35B shows % with no lung nodules. In this and subsequent studies, 2×10 6 FSL cells were used, and the blood was always given 4 days after this.

Figure 35:
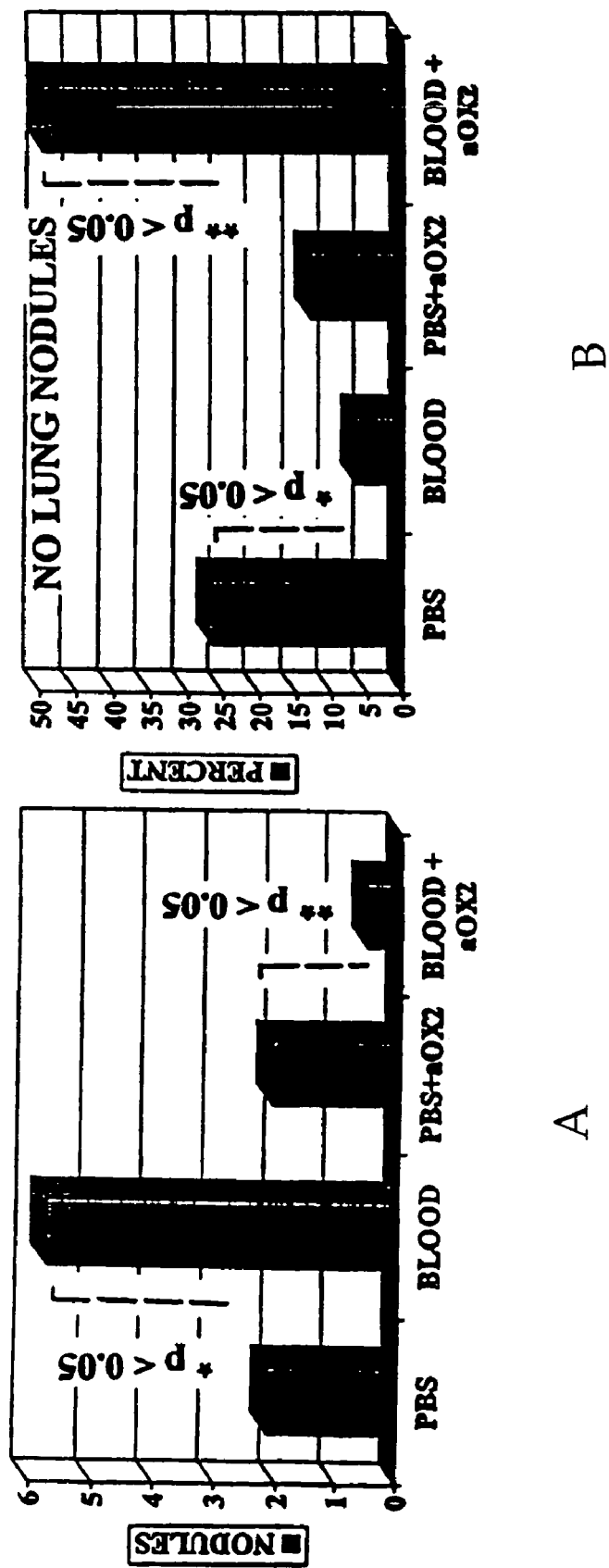
FIGS. 35A and B are bar graphs showing the number of lung nodules in the presence of anti-OX2 in mice receiving allogeneic blood by tail vein.

As illustrated in FIG. 35, the enhancement of lung nodules in mice given 2×10$^5$ sarcoma cells by 200 µl of BALB/c blood compared to phosphate buffered saline control (PBS) given 4 days after tumor injection, was completely blocked by adding 3.3 µg of anti-OX-2 (3B6 monoclonal antibody (mAb)) to the blood before the transfusion. The mAb in PBS had no effect. Interestingly, the proportion of mice with lung metastases was boosted by allogeneic blood compared to PBS but was reduced by blood to which anti-OX-2 had been added. The median number of nodules was greater in this study in part because we had doubled the tumor cell inoculum, but we do see experiment-to-experiment variation in the number of nodules in the control group which has been important in executing large experiments, as will be discussed.

The Role of Dendritic Cells

Figure 36:
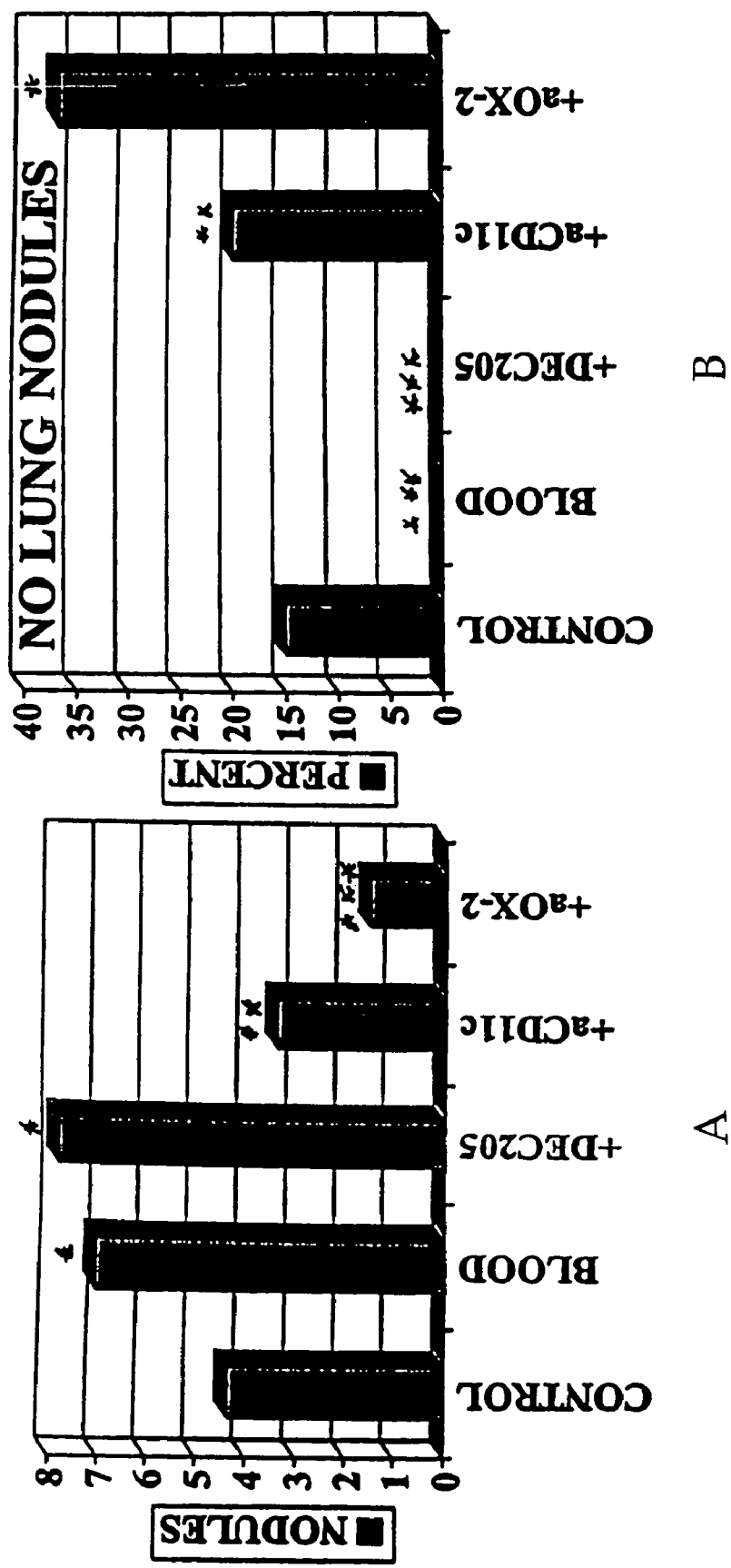
FIGS. 36A and B are bar graphs showing the number of lung nodules in the presence of anti-OX-2, DEC205 or anti-CD11c in mice receiving allogeneic blood by tail vein.

FIG. 36A is a repetition of FIG. 35A which confirms the effect of anti-OX-2, but with addition of antibodies to dentritic cells. Anti-CD11c was used for myeloid dendritic cells, and DEC205 for lymphoid dendritic cells. The latter are usually CD8-positive. It can be readily appreciated that monoclonal antibody to lymphoid dendritic cells had no effect on the stimulation of lung metastases, whereas anti-CD11c blocked the effect. The reason the number of nodules is not below control is thought to be due to the existence of OX-2-positive and OX-2-negative CD11c-type dendritic cells. The latter stimulate immunity, and this is seen when anti-OX-2 is used to block one of the subsets. Anti-CD11c leads to loss of both subsets.

The results show that anit-CD11c, but not DEC205, abrogated the TRIM effect (* indicates significant increase over control,  indicates significant abrogation of TRIM, * indicates significant decrease below control, P<0.05). There was no effect of anti-OX-2, DEC205 or anti-CD11c in PBS injected as a control (data not shown). Due to the large number of treatment groups in this experiment, it could not be done in a single day. Therefore, 5 mice in each group were treated in 4 experiments and the data was examined and pooled. The result therefore compensates for any effect of day-to-day variation in tumor cells, mice or blood used for transfusion.

Example 11

OX-2 Prevents Fetal Loss

Successful pregnancy in allopregnant mice can also be viewed as dependent upon control of graft rejection. Proinflammatory Th1 cytokines (TNF-α+IFN-γ+IL-1) can cause spontaneous abortion in mice by a mechanism which involves a novel prothrombinase, fgl2, which promotes fibrin deposition. However, the inventors found that spontaneous abortion rates in abortion-prone CBA×DBA/2 matings and in low abortion rate CBA×BALB/c matings were lower than the frequency of implantation sites showing fibrin$^{hi}$+fgl2 mRNA$^{hi}$. OX2 expression was present in the same sites as fgl2 mRNA, and neutralization of this OX2 expression by anti-OX-2 raised the abortion rate to predicted levels. Conversely, an OX2 immunoadhesin dramatically reduced the abortion rate. Therefore, in addition to its role in organ and tissue allograft rejection, OX2 expression is involved in the prevention of spontaneous abortion triggered by cytokine up-regulation of fgl2 at the feto-maternal interface.

In the Example detailed below, evidence is shown using anti-OX2 monoclonal antibody and a soluble form of OX2 in which the extracellular domains of the molecule are linked to an Ig Fc region (OX2:Fc) (described in Example 6), that OX2 is fundamentally important to achieving successful allopregnancy.

Methods

All of the techniques used, including mixed leukocyte cultures, cytokine analysis, and allografting, are detailed in previous publications (Gorczynski et al. 1996a; Arck et al. 1997a; and Clark 1999). The anti-OX2 mAb (3B6) was obtained from BioCan (Mississauga, Ontario) (Gorczynski et al. 1998b). 100 μg/mouse was used for each injection. A polyclonal, affinity-purified, rabbit antibody to fgl2 was described elsewhere, and used ip at a dose of 22 mg/mouse. OX2Fc immunoadhesin was given ip (35 μg/mouse).

Results

In Situ Expression of OX2 mRNA Following Renal Transplantation or Allopregnancy:

OX-2 has been reported at the fetomaternal interface using immunohistochemistry in rats (Example 7 and Bukovsky et al. 1984). To determine whether OX-2 was expressed in the uterus of allopregnant mice, the inventors carried out in situ hybridization for OX-2 mRNA in CBA×DBA/2 and CBA×BALB/c matings. Adjacent sections of the tissue samples were also used to stain for fgl2 mRNA (fgl2 is a prothrombinase molecule up-regulated by certain Th1 cytokines implicated triggering pregnancy loss). For comparison, we also examined OX2 expression in liver sections from C3H mice receiving C57BL/6 renal allografts following donor-specific portal vein preimmunization, a treatment which promotes tolerance and which is critically dependent upon up-regulation of expression of OX-2 on hepatic APC. Typical patterns for uterine staining (pregnant mice) are reported elsewhere (Clark et al. 2001), along with cumulative data for OX2 and fgl2 expression in the uteri of pregnant control mice and mice treated with TNFα +IFNγ to increase abortion rates (Clark et al. 2001).

In these studies the inventors found that OX2 mRNA expression was up-regulated following pv immunization and renal transplantation, and in allopregnant mice. In pregnant mice the inventors found a negative correlation between expression of the molecules fgl2 and OX-2 which did not reach statistical significance (Clark et al. 2001). With following cytokine treatment of pregnant animals, and prior to the onset of abortions, the proportion of fgl$_2^{hi}$ implantations increased, although this also did not achieve significance due to small numbers. However, with cytokine treatment, the proportion of OX-2$^{hi}$ implants decreased dramatically. These data support the hypothesis that in pregnancy, fgl2 and OX-2 expression are reciprocally regulated by cytokines, that their levels affect pregnancy outcome, and that a major determinant of success or failure of fgl$_2^{hi}$ 'at risk' implantations was the presence or absence of OX2. Most interestingly, the inventors also reported that continued expression of OX2, as occurs in pregnancy, was essential for successful survival of allografts following pv pretransplant immunization, and for the concomitant changes in cytokine production seen in those animals (previous Examples and Gorczynski et al. 2000).

Figure 37:
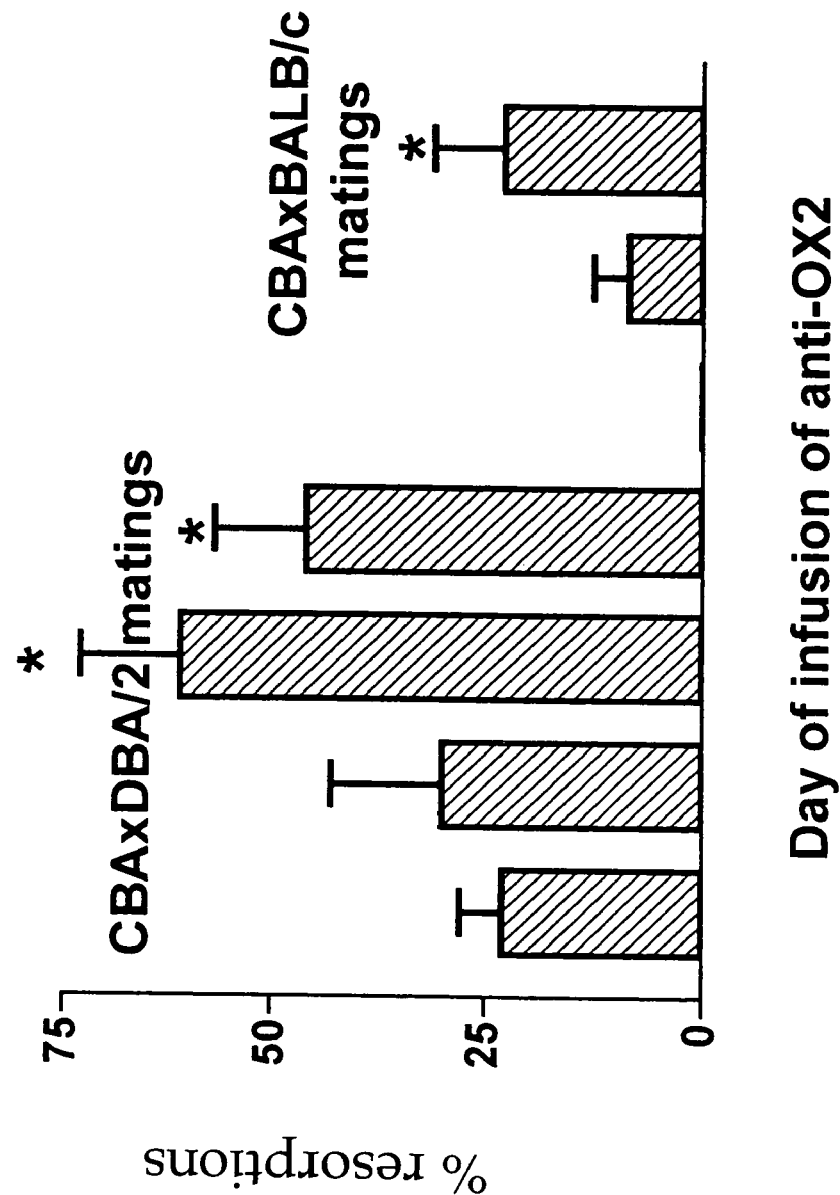
FIG. 37 is a graph showing the effect of anti-OX-2 monoclonal antibody 3B6 on spontaneous resorption (abortion) rates. Error bars show 1 standard deviation. A minimum of 20 implants was scored for each group. * significant increase in abortion rate, P<0.02.

Effect of Anti-OX2 mAb on Renal Transplant Survival and Pregnancy Outcome:

Fifty to 70% of implantations in control and cytokine-boosted CBA×DBA/2 pregnancies show the fgl$_2^{hi}$ phenotype (Clark et al. 2001). An injection of anti-Vg1.1 on day 8.5 of pregnancy, 1 day before abortions become evident, inactivates most of the trophoblast-recognizing γδ subset producing IL-10 and TGFβ and boosts abortion rates to approximately 48% (Arck et al. 1999). The inventors hypothesized that the "suppressor" γδT cells inactivated by this treatment might be dependent upon OX2 expression for their functional activity. The inventors have reported that following allotransplantation, the kinetics of expression of OX2 follows closely the development of immunoregulatory γδT cells. Functional blockade of OX2 expression (by anti-OX2 treatment) reverses increased graft survival (see FIG. 2) and prevents adoptive transfer of tolerance by γδT cells. To test whether OX-2 expression in pregnancy might similarly be activating anti-abortion mechanisms which 'rescued' fgl2$^{hi}$ implant sites from proceeding to embryo death where both OX-2 and fgl-2 were expressed, the inventors injected control CBA×DBA/2- and CBA×BALB/c-mated mice with the same anti-OX-2 monoclonal antibody that blocks induction of transplantation tolerance. FIG. 37 shows that injection on or after day 8.5 increased the spontaneous abortion rate to that expected if all fgl2$^{hi}$ sites in CBA×DBA/2 proceeded to resorb. The increase in abortion rate was not due to a toxic effect of anti-OX-2 on the embryo because co-administration of anti-fgl2 to neutralize prothrombinase activity abrogated the boost in abortion rates (data not shown). Injection of anti-OX-2 into CBA×BALB/c-mated mice also increased the abortion rate to 22%, consistent with the 21% fgl2 mRNA$^{hi}$ implantation site frequency.

Figure 38:
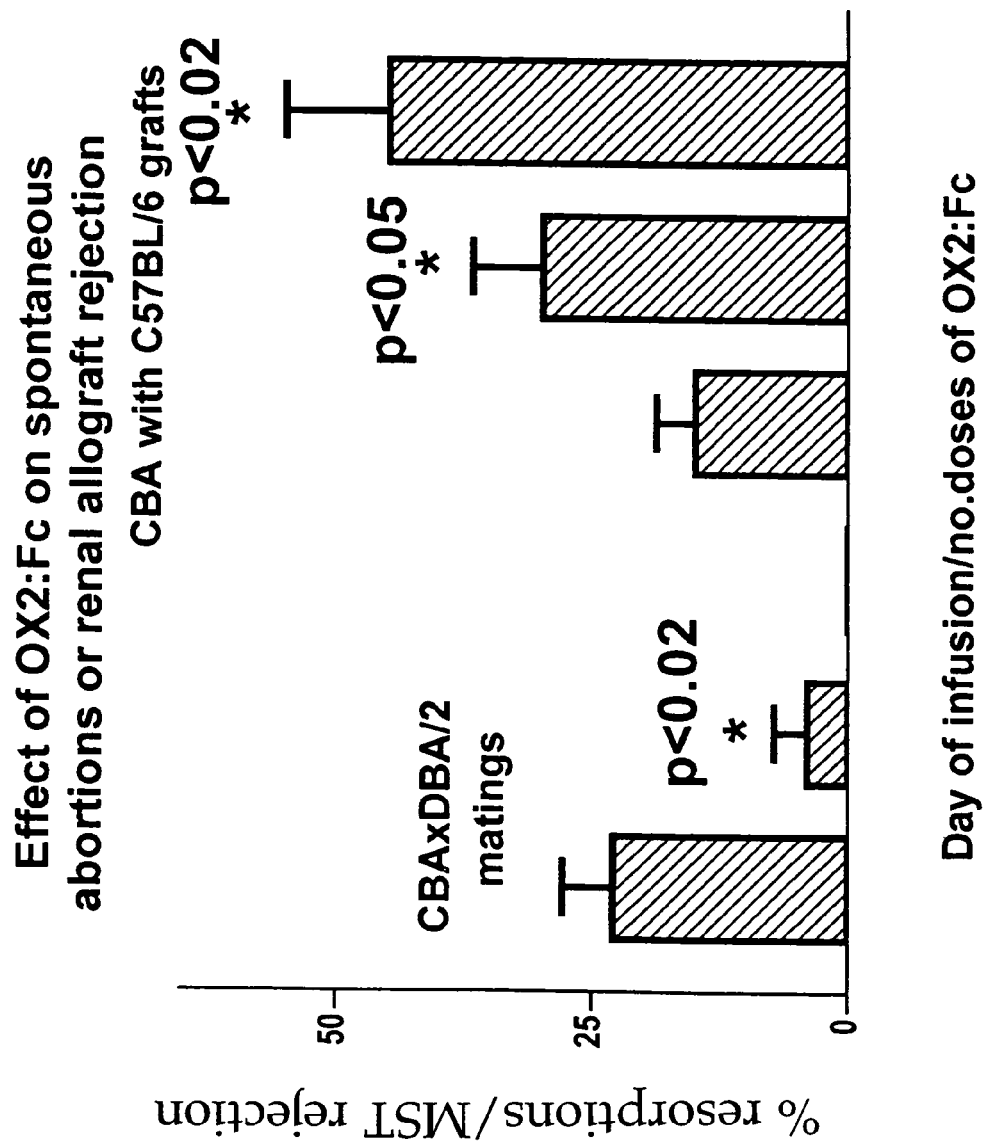
FIG. 38 is a graph showing effect of OX2 immunoadhesion (OX2:Fc) on spontaneous resorption (abortion) rates or renal allograft rejection. Error bars show 1 standard deviation. A minimum of 45 implants was scored for each group of pregnant mice (mice received a single dose of OX2:Fc at day 6.5; 10 mice/group were used for renal allografts, and mice received multiple iv injections of OX2:Fc, beginning on the day of transplant, and at 2 day intervals thereafter. * significant decrease in abortion rate, or increased graft survival, relative to controls.

Infusion of OX2 Immunoadhesin Modulates Renal Allograft Rejection and Spontaneous Abortion:

As further "proof of principle" that OX2 expression is functionally important for increased allograft survival the inventors used an immunoadhesin (OX2:Fc), in which the extracellular domains of OX2 were linked to a murine IgGFc region, to investigate modulation of allograft rejection and pregnancy. Data in the previous Examples has already indicated that this molecule has potent immunoregulatory properties in vivo, including the ability to decrease allograft rejection. Data in FIG. 38 represent a cumulative comparison of the effect of infusion of OX-2:Fc on renal allograft survival or rate of abortions in CBA×DBA/2 mated mice. Once again there was a clear parallel between the functional activity of OX2:Fc measured in these two assays.

Discussion

The notion that the rejection of organ allografts would be mimicked immunologically by immune recognition of the fetus in allopregnant mothers has been with us for decades. There has been intense interest in the role of altered cells and soluble factors (e.g.cytokines) in the phenomena seen in both situations. As an example, with decreased graft rejection (and successful pregnancy) there are numerous reports of the presence of unique γδT cells with "suppressor phenotypes", and altered cytokine patterns, with elevated levels of type-2 cytokines, in particular IL-10 and TGFβ (Chaouat et al. 1999; Tsuda et al. 2001; Clark et al. 2001b; Arck et al. 1999 and Arck et al. 1997a). In contrast, allograft rejection in rodents and man has been associated with elevated type-1 cytokines, and previous studies have also shown that both TNFα and IFNγ must be present for spontaneous abortions to be induced (Chaouat et al. 1999; Tsuda et al. 2001; Clark et al. 2001b; Arck et al. 1999 and Arck et al. 1997a). Since the fgl2 gene is activated by IFNγ but not by TNFA, the inventors have hypothesized that the obligatory role for the latter cytokine either involves activation of PMNL essential for abortions to be completed, or down-regulates OX-2 expression.

It is worthy of note that in the inventors' previous work, and in the studies described above, expression of fgl2, a thrombosis-inducing molecule, was up-regulated on the trophoblast in response to cytokines. Cytokine-treated IRF1$^{-/-}$ females mated to +/+ males do not abort, as there is no up-regulation of fgl2 in the maternal decidual tissues and the best explanation for lack of abortions is that fgl2$^+$ trophoblast and fgl2$^+$ maternal decidua must meet. In the regions where the two tissues meet, a zone of spontaneous cleavage, enough enzymatic activity presumably occurs to cause necrosis. The inventors have also documented a basal level of fgl2 expression in trophoblast tissue. Given the evidence that excessive anticoagulation with heparin or hirudin leads to retroplacental hemorrhage fatal to the embryo and sometimes mother, the inventors suggest that this low (basal) level of expression of the molecule fgl2 may reflect a normal homeostatic role for fgl2 in preventing spontaneous bleeding. However, cytokine-mediated (by TNFα and IFNγ) upregulation of fgl2 is associated with increased rates of abortion. These effects can in turn be counteracted by the combination of both TGF-β and IL-10, both perhaps produced by trophoblast cells, which are known to inhibit cell-mediated vascular injury and clotting. There is little data to date examining the role of fgl2 prothrombinase in allograft rejection. Interestingly xenograft rejection, a process in which acute and subacute vascular changes are believed crucial, is reportedly less pronounced in an fgl2 knockout mouse (Levy et al, personal communication). It thus becomes extremely interesting to know whether fgl2 has a more general role in immunomodulation in both allo and fetal grafts.

The present data shed further light on the mechanisms by which some of these changes occur in both the allopregnant mouse and in allo-transplant, by providing evidence for a crucial role for altered expression of another molecule OX2, in regulating both embryo execution triggered by cytokine up-regulation of fgl2 prothrombinase and the modulation of renal allograft rejection. The inventors have proposed that OX2 acts in transplantation as a co-stimulatory signal that deviates cytokine production away from Th1 (e.g. IL-2, IFN-γ) and towards Th2/3 (e.g. IL-4, IL-10, TGF-β) production. Associated with this is expansion of a γδ T cell subset that mediates tolerance via suppression. In support of such a hypothesis, the inventors have shown increased expression of OX2 is associated with decreased rejection and altered cytokine production; that the kinetics of expression of OX2 parallels altered cytokine production and γδT cell expansion; and that these effects are diminished by infusion of anti-OX2 mAbs, and enhanced by infusion of the immunoadhesin OX2:Fc. The inventors have now also documented that a similar correlation exists between OX2 expression and fetal loss in allopregnant mice, even when abortion rates are increased following infusion of cytokines (where our data suggests OX2 continues to act to counter the effects of fgl2).

It is now known that OX2 functions following interaction with its receptor (OX2$^r$) on target cells. At least 2 groups, ourselves (Gorczynski et al. 2000 and Wright et al. 2000) have documented the existence of OX2$^r$ on macrophages, and the inventors showed optimal inhibition of graft rejection in vivo occurred with infusion of both OX2:Fc and OX2r+ cells (Gorczynski et al. 2000). Unlike the Barclay group, the inventors have found that a large percentage (>80%) of ConA activated γδT cells also express an OX2$^r$, as defined by FACS with FITC-OX2:Fc. The inventors have recently confirmed this independently using our mAbs to OX2r, and following cDNA sequencing of the OX2r expressed in γδTCR+ hybridomas (Yu et al: manuscript in preparation). The inventors have not yet studied the functional activity of OX2r cells (whether macrophages or γδT cells) in allopregnant mice. However, extrapolating from the data shown above, it is suggested that increased expression of OX2$^r$ will correlate with successful allopregnancy, and that triggering intracellular signaling by cross-linking OX2r on cells by mAb (presumably in the same fashion as native cell-bound OX2 does when it interacts with OX2$^r$) rescues putatively doomed embryos mice from cytokine-induced spontaneous abortion (mediated by elevated fgl2 expression).

Example 12

OX-2 Expression Rescues Putatively Doomed Embryos

The importance of CD200 (OX-2) in rescuing potentially doomed mouse embryos is illustrated by the in situ hybridization result in FIG. 39. The pattern of hybridization with anti-sense probe for fgl2 (top panels) is compared with the pattern of hybridization using anti-sense probe for OX-2 for CBA×DBA/2 mated mice on day 8.5 of gestation. (Sense controls show no staining). Details of methods are provided in Molecular Human Reproduction 2001 (Clark et al. 2001). In section 1, left, fgl2 is ++ and OX-2 essentially negative. In section 2, fgl2 is still ++ but in this implantation, OX-2 hybridization can be seen in the same areas as fgl2. In section 3, fgl2 is only weakly expressed, and OX-2 is readily demonstrable. It has been shown that the observed rate of abortions is less than expected from the % of implantations showing fgl2$^{++}$. When anti-OX-2 neutralizing antibody is administered, all of the fgl2$^{++}$ implantation appear to be aborted. This is attributed to the demise of implantations showing pattern #2.

Example 13

OX-2 is Expressed in Successful Human Pregnancy

The importance of OX-2 (CD200) is rescue of potentially doomed fgl2$^{hi}$ mouse implantations has been shown above. Increased fgl2 expression is also seen in abortion of chromosomally normal human embryos in the first trimester, but not in chromosomally abnormal embryos. To determine if OX-2 is expressed in successful pregnancies (for which first trimester tissue is not available), term placentae were examined. The placentae were obtained after delivery, the decidua was scraped off, and the trophoblast cells were isolated by sequential enzymatic digestion, as described by Guilbert et al. To remove non-trophoblast cells, anti-CD9 antibody was added, and the suspension was passed over an anti-immunoglobulin column, according to the method of Guilbert et al. The adhered CD9$^+$ 'stroma' was obtained by physical agitation of the beads of the column. RNA was extracted in the usual manner from a similar number of CD9$^+$ and CD9$^-$ cells and RT-PCR was performed (30 cycles) using primers rto the full-length (3 exon) OX-2 gene, using primers to the 3rd exon that detects the truncated (exon 2-missing) mRNA. The PAGE gel in FIG. 40 shows the molecular size ladder (lane 1), trophoblast with full length primers (lane 2) and exon 3 primers (lane 3). The full length and shorter mRNA OX-2 transcripts are seen. Lane 4 (corresponding to lane 2) and lane 5 (corresponding to lane 3) represent negative result obtained with CD9$^+$ stromal cells.

Figure 41:
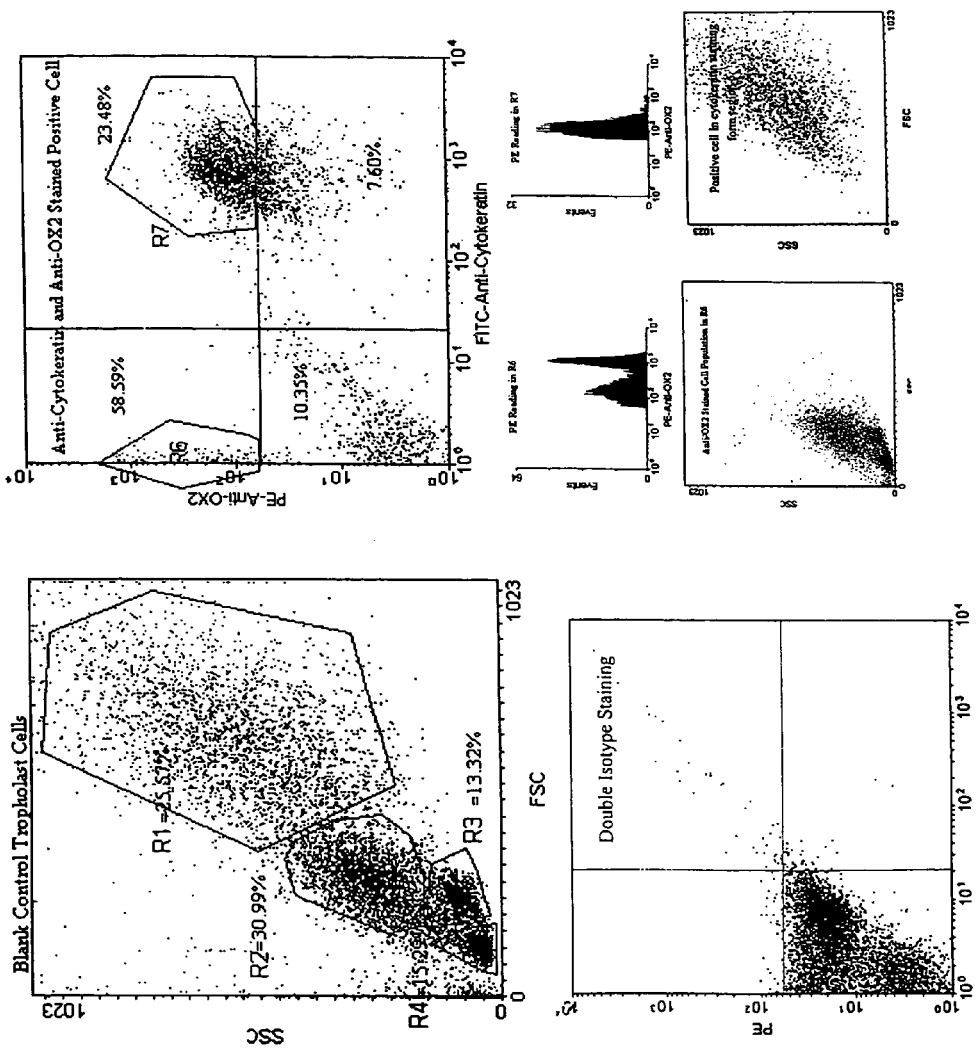
FIG. 41 shows result using antibody detecting CK5,6,8, 17; similar results have been obtained using FITC-anti-CK18. The upper left panel shows the forward and side scatter pattern. FITC and PE isotype controls used to set gates is shown below on left. Upper right panel shows cytokeratin-positive cells, the majority of which were also $OX-2^+$. A significant population of $CK-OX-2^{++}$ cells was also noted. The identity of this population has not been established. On the right, the middle panel shows staining profile for OX-2 for the CK− and $CK^+$ populations, and the lower panel shows the scatter. Clearly these populations have different properties. Velocity sedimentation separation indicates both populations may have OX-2-dependent immunoregulatory activity.

To test for OX-2 protein expression on trophoblast, the flow cytometry protocol (summarized at the end) was used with the CD9$^-$ fraction. Surface expression of OX-2 was detected using PE-tagged monoclonal antibody to human OX-2 (Cedarlane labs). Intracellular cytokeratin was stained using FITC-mAB from Dako. FIG. 41 shows result using antibody detecting CK5,6,8,17; similar results have been obtained using FITC-anti-CK18. The upper left panel shows the forward and side scatter pattern. FITC and PE isotype controls used to set gates is shown below on left. Upper right panel shows cytokeratin-positive cells, the majority of which were also OX-2$^+$. A significant population of CK-OX-2$^{++}$ cells was also noted. The identity of this population has not been established. On the right, the middle panel shows staining profile for OX-2 for the CK- and CK$^+$ populations, and the lower panel shows the scatter. Clearly these populations have different properties. Velocity sedimentation separation indicates both populations may have OX-2-dependent immunoregulatory activity.

Example 14

OX-2 Mab in the Prevention of Postcoital Pregnancy

The inventors have shown that infusion of an immunoadhesin, OX-2:Fc, reduces the rate of abortion in a mouse model system using animals with increased rates of spontaneous abortion. Antibodies to OX-2 on the other hand were shown to increase the rates of spontaneous abortion, and decrease litter size in this model. This allows the manipulation of fertility using non-hormonal methods.

This example confirms the ability of OX-2 Mab to reduce fertility in rodents.

The objection of this experiment is to determine if OX-2 Mab is capable of preventing or reducing the fertility in rodents after coitus.

Reduction in fertility is defined as:
a) the percent of treated impregnated females delivering pups is less than that observed in the control group.
b) the average litter size of treated impregnated females carrying a litter to term is less than that observed in the control group.

Materials and Methods

Rodents (rats/mice) were housed in individual cages with one female and one male/cage. Animals were inspected daily for vaginal plugs. Beginning on the day of fertilization (defined as the presence of a vaginal plug) females were kept one to a cage, and received ip injections of mAbs to OX2 rat anti-mouse (clone 3B6) for mice and mouse anti-rat (clone 6C2) for rats. The control group of the impregnated females received injections with control rat or mouse Ig.

Records were kept of the number of impregnated females producing litters in each group, as well as the litter size for each mother.

Animals
Mouse female, male—outbred Swiss-Webster.
Rat female, male—outbred Sprague-Dawley.

Statistical Considerations

Comparison of the percent of impregnated females carrying litters to term, and the mean litter size for successful pregnancies, were made independently for rats/mice using non parametric Chi-square or Fisher's Exact test where appropriate for pregnancy rates, and the Rank Sum test for litter sizes.

Methodology

Breeding
One animal of each sex is placed in a cage. The females are checked daily for vaginal plugs. Once a vaginal plug was observed the females were placed one to a cage.
Beginning on the day of impregnation (defined as the day a vaginal plug is observed), each female was moved to a new cage (housed alone) and begins treatment with mouse or rat OX2 antibodies by intraperitoneal injection.

Experiment No. 1
Mice: dose 100 micrograms per mouse every 3 days for 7 doses.
Rats: dose 300 micrograms per rat every 3 days for 7 doses Experiment No. 2
Mice: dose 250 micrograms per mouse every 36 hours for up to 18 days
Rats: dose 500 micrograms per rat every 3 days for 7 doses Methods of Assessment
Assessment of coitus: vaginal plug.
Assessment of pregnancy—number of pups delivered
In the second experiment the sex was also determined in each pup delivered.
The number of animals giving birth is counted as are the number of pups delivered.
Each female animal is housed in an individual cage until day 25 after breeding. Animals not delivering by day 25 were considered not to be pregnant and destroyed.

Study End Points
Number of animals in each group who delivered any pups.
Number of pups delivered to each animal achieving delivery at term.

Duration of the Study
Length of time the animal were held post impregnation . . . 25 days.
Methods of termination . . . pups were sacrificed after recording the total litter size per female. In the second study the sex of each pup was also recorded.
Tissue to be taken . . . none.

Schedule of Evaluations
Daily inspection of animals for impregnation (vaginal plugging)
Injection of pregnant animals every 3 days in the rat experiments and experiment 1 for the mice. The mice in experiment two were observed every 36 hours.
Daily inspection from day 19 for evidence of birthing.

Test Article and Concomitant Treatments

Test Article

Anti-OX2 mAbs were obtained from BioSpark, Canada.

Mouse anti-rat OX2: clone 6C2. Cat # SP 300X. Lot # 02 Stored at 1mg/ml (no azide) in PBS.

Rat anti-mouse OX2: clone 3B6. Cat # SP 200X Lot# 03 Stored at 1 mg/ml, no azide, in PBS.

Control Ig was also obtained from BioSpark, Canada. This represents a preparation from pooled normal ascites (from rats or mice).

Again storage is in PBS, with no azide, at 1 mg/ml.

Normal rat Ig: Lot #01. Cat. # SP89

Normal mouse Ig: Lot # 01; Cat # SP99

Inventory and accountability records are kept by the investigator a) The investigator kept study drugs in a locked freezer, a secure storage facility, in his laboratory at the TGH (MBRW-2-926).

Experiment 1:

Mice:

Control: 17/17 mice impregnated had successful pregnancies.

Mean litter size: 7

3B6 injected: 17/18 mice impregnated had successful pregnancies.

Mean litter size: 6

See Table 9

Statistics: Mice: 17 control and 18 treated

The proportion of mice pregnant was not significantly different by Fisher's Exact test; the litter size in each group, and the average number of pups per group were not significantly different by the Rank Sum test.

Rats:

Control: 11/12 rats impregnated had successful pregnancies.

Mean litter size: 9

6C2 injected: 5/8 rats impregnated had successful pregnancies.

Mean litter size for the group was 5 but for the 5 rats delivering pups the mean litter size was 8

See Table 11

$P<0.05$ for successful pregnancies.

Statistics: Rats 12 control and 8 treated

The proportion of animals pregnant in the treated group was not significantly reduced (P=0.153, Fisher's Exact test). Litter size in those delivering was reduced (P<0.018, Rank Sum test), and the total number of pups generated by the immune treated group was reduced (P<0.006, Rank Sum test)

Experiment 2:

Mice:

Control: 8/8 mice impregnated had successful pregnancies.

Mean litter size: 6

3B6 injected: 3/8 mice impregnated had successful pregnancies.

Mean litter size for the group was 2 but for the 3 rats delivering pups the mean litter size was 5

See Table 10

Statistics: Mice 8 control and 8 treated

The proportion of rats pregnant was significantly reduced by treatment (P=0.0128, Fisher's Exact test), and the number of pups overall was reduced (P<0.00021, Rank Sum test). The average litter size for animals successfully delivering was also reduced (P<0.024, Rank Sum test), but the number of litters was small.

Rats:

Control: 6/6 rats impregnated had successful pregnancies.

Mean litter size: 10

6C2 injected: 2/6 rats impregnated had successful pregnancies.

Mean litter size for the group was 2.5 but for the two rats delivering pups the mean litter size was 7.5

See Table 12

Statistics: Rats 6 control 6 treated

The proportion of animals that delivered litters was significantly reduced by treatment (P=0.03, Fisher's Exact test), as was the total number of pups produced by the treated group (P<0.002, Rank Sum test). Litter size was also slightly reduced in those delivering (P<0.03, Rank Sum test), but the number of litters was small.

Conclusions

The administration of OX-2 antibodies to rats and mice following impregnations has been shown to reduce the number of animals delivering pups. The average liter size of antibody treated animals that did deliver was not different from the control animals.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Summary of sequences and clones detected in cDNA library from pv immunized mice

| Match category | Number of clones represented (%) |
|---|---|
| Known mouse genes | 30 (45) |
| Non-mouse genes (rat/human) 10 | 14 (21) |
| No data base match | 22 (34) |

Footnotes:
Genes were considered a "match" with a BLAST score >250 with a minimum of 50 bp alignment.

TABLE 2

Cytokine production from cells of mice receiving pv immunization and anti-rat OX-2

| Mabs given to recipients[a] | Cytokine levels in culture supernatants[b] | | | |
|---|---|---|---|---|
| | IL-2 | IFNγ | IL-4 | IL-10 |
| No pv immunization (CsA only) | | | | |
| None | 750 ± 125 | 85 ± 18 | 29 ± 8 | 130 ± 40 |
| +anti-rat OX-2 | 890 ± 160 | 93 ± 19 | 30 ± 10 | 120 ± 35 |
| +anti-mouse CD28 | 415 ± 88* | 57 ± 9* | 105 ± 22* | 275 ± 55* |
| +anti-mouseCTLA4 | 505 ± 125* | 65 ± 8 | 95 ± 20* | 190 ± 45 |
| +anti-B7-1 | 340 ± 65* | 35 ± 7* | 120 ± 21* | 285 ± 60* |
| +anti-B7-2 | 495 ± 90* | 64 ± 7 | 90 ± 20* | 185 ± 45 |

TABLE 2-continued

Cytokine production from cells of mice receiving pv immunization and anti-rat OX-2

| Mabs given to recipients[a] | Cytokine levels in culture supernatants[b] | | | |
|---|---|---|---|---|
| | IL-2 | IFNγ | IL-4 | IL-10 |
| | PV Immunization + CsA | | | |
| None | 190 ± 55 | 25 ± 8 | 107 ± 21 | 780 ± 150 |
| +anti-rat OX-2 | 730 ± 140* | 60 ± 16* | 33 ± 10* | 220 ± 40* |
| +anti-mouse CD28 | 145 ± 38 | 20 ± 9 | 145 ± 34 | 1140 ± 245 |
| +anti-mouse CTLA4 | 85 ± 25 | 15 ± 6 | 125 ± 31 | 960 ± 220 |
| +anti-B7-1 | 110 ± 30 | 20 ± 6 | 144 ± 28 | 885 ± 180 |
| +anti-B7-2 | 75 ± 20 | 14 ± 5 | 150 ± 30 | 1230 ± 245 |

Footnotes:

[a]3 C3H mice/group were used in each experiment. All animals received CsA and C57BL/6 renal transplants as described in the Materials and Methods. Mice in the lower half of the Table also received pv infusions of 15 × 10^6 C57BL/6 bone marrow derived dendritic cells on the day of transplantation. Where monoclonal antibodies were given the dose used was 100 mg/mouse, x4 doses at 2 day intervals. All mice were sacrificed 14 days post transplantation. Spleen cells were cultured in triplicate from individual animals for 40 hrs in a 1:1 mixture with irradiated C57BL/6 spleen stimulator cells.

[b]Arithmetic mean (±SD) for triplicate determinations from individual samples of the animals described in the first column. All cytokines were assayed by ELISA. IL-2, IL-4 and IL-10 are shown as pg/ml, IFNγ as ng/ml. Data are pooled from 2 such studies (total of 6 individual mice tested/group).

*represents significantly different from control group with no Mab (p < 0.02)

TABLE 3

FACS staining of PBL and spleen adherent cells in different species, using anti-OX-2 Mabs

| Donor[b] | | | Percent stained cells[c] | |
|---|---|---|---|---|
| SPECIES[a] | Treatment | Mab | PBL | Spleen |
| Human | NONE | H4B4 | 1.5 ± 0.3 | 4.8 ± 1.7 |
| | | H4A9A2 | 1.5 ± 0.4 | 6.1 ± 2.0 |
| | | H4A9C7 | 1.3 ± 0.4 | 4.3 ± 1.7 |
| Mouse | NONE | M3B5 | 1.9 ± 0.4 | 6.7 ± 2.1 |
| | | M3B6 | 1.7 ± 0.4 | 5.2 ± 1.6 |
| | | M2C8 | 1.4 ± 0.4 | 4.2 ± 1.4 |
| Mouse | PV immune | M3B5 | 5.9 ± 1.5 | 20 ± 4.1 |
| | | M3B6 | 5.2 ± 1.4 | 17 ± 3.6 |
| | | M2C8 | 4.7 ± 1.4 | 15 ± 3.3 |
| Rat | NONE | RC6A3 | 1.3 ± 0.3 | 5.3 ± 1.6 |
| | | RC6C2 | 1.5 ± 0.4 | 6.5 ± 1.7 |
| | | RC6D1 | 1.9 ± 0.6 | 6.8 ± 1.5 |
| Rat | PV immune | RC6A3 | 4.8 ± 1.3 | 16 ± 4.2 |
| | | RC6C2 | 4.9 ± 1.6 | 18 ± 3.9 |
| | | RC6D1 | 5.3 ± 1.7 | 20 ± 4.5 |

Footnotes:

[a]Fresh cells were obtained from normal human donors (PBL), cadaveric transplant donors (human spleen), or from adult (8–10 week) mouse or rat donors. The same 3 separate tissue donors were used for each Mab tested.

[b]Donor pretreatment refers to infusion of allogeneic bone marrow cells into the portal vein (C57BL/6 for C3H mouse donors; BN for LEW rat donors) 4 days before harvest of PBL or spleen (see text and (6)).

[c]Arithmetic mean (+SD) for percent cells stained in 3 independent assays. Control antibodies (FITC anti-mouse IgG (for anti-human or anti-rat Mabs, or FITC anti-rat IgG for anti-mouse Mabs) gave no significant staining above background (<0.2%).

TABLE 4

Type-1 cytokine production in MLR cultures is increased by anti-OX-2 Mabs

| | Cytokine levels in culture supernatants[b] | | | | | |
|---|---|---|---|---|---|---|
| | ELISA assays (murine only) | | | | Bioassay (CTTL-2) | |
| Mabs in culture[a] | IL-2 | IFNγ | IL-4 | IL-10 | IL-2 | IL-6 |
| MOUSE MLR | | | | | | |
| None | 350 ± 55 | 35 ± 18 | 345 ± 63 | 340 ± 50 | 480 ± 160 | 365 ± 74 |
| M3B5 | 890 ± 160* | 115 ± 29* | 130 ± 10* | 168 ± 42* | 820 ± 200* | 265 ± 46 |
| M3B6 | 915 ± 155* | 117 ± 25* | 135 ± 32* | 135 ± 38* | 850 ± 175* | 303 ± 55 |
| M2C8 | 855 ± 155* | 105 ± 28* | 120 ± 32* | 140 ± 37* | 830 ± 165* | 279 ± 61 |
| control Ig | 370 ± 75 | 36 ± 11 | 330 ± 55 | 310 ± 45 | 335 ± 60 | 349 ± 59 |
| None** | 710 ± 145 | 108 ± 23 | 110 ± 21 | 105 ± 23 | 690 ± 155 | 285 ± 54 |
| RAT MLR | | | | | | |
| None | | | | | 490 ± 145 | 360 ± 57 |
| RC6A3 | | | | | 690 ± 155* | 295 ± 55 |
| RC6C2 | | | | | 845 ± 180* | 345 ± 68 |
| RC6D1 | | | | | 830 ± 160* | 370 ± 57 |
| Control Ig | | | | | 475 ± 160 | 356 ± 58 |
| HUMAN MLR | | | | | | |
| None | | | | | 395 ± 85 | 295 ± 45 |
| H4B4 | | | | | 570 ± 125* | 315 ± 50 |
| H4A9A2 | | | | | 630 ± 145* | 320 ± 48 |

TABLE 4-continued

Type-1 cytokine production in MLR cultures is increased by anti-OX-2 Mabs

| | Cytokine levels in culture supernatants[b] | | | | | |
|---|---|---|---|---|---|---|
| | ELISA assays (murine only) | | | | Bioassay (CTTL-2) | |
| Mabs in culture[a] | IL-2 | IFNγ | IL-4 | IL-10 | IL-2 | IL-6 |
| H4A9C7 | | | | | 625 ± 140* | 345 ± 56 |
| Control Ig | | | | | 360 ± 120 | 320 ± 50 |

Footnotes:
[a]MLR cultures were set up as described in the Materials and Methods. For human MLR cultures the same 3 different responder preparations were used for each Mab, and stimulated with a pool of mitomycin C treated spleen stimulator cells (from a random mixture of 6 spleen donors). For mouse (C3H anti-C57BL/6) and rat (LEW anti-BN) MLR cultures all assays were set up in triplicate for each Mab. Mouse responder spleen cells were from mice treated 4days earlier by portal vein infusion of C57BL/6 bone marrow cells, except for data shown as (None**) where responder cells were from non-injected C3H mice. Mab was added as a 30% superntatant concentration. Supernatants were harvested for cytokine assays at 60 hrs.
[b]Data show arithmetic means (+SD) for each Mab. For mouse assays all supernatants were assayed for a number of cytokines (ELISA), and for IL-2/IL-6 using bioassays (proliferation of CTLL-2, B9 respectively). Supernatants from rat/human cultures were assayed in bioassays only. Note that cells incubated with isotype control Igs (non-reactive by ELISA or FACS) gave cytokine data indistinguishable from cultures incubated in the absence of Mab.
p < 0.05, compared with cultures without Mabs.

TABLE 5

OX-2:FC Immunoadhesin Inhibits Mixed Leukocyte Reaction in vitro

| Added supernatant[a] | Percent lysis $^{51}$Cr targets[b] | Cytokines in culture | |
|---|---|---|---|
| (pg/ml)[c] | (50:1, effector:target) | IL-2 | IL-4 |
| NONE (control) | 31 ± 4.0 | 1005 ± 185 | 60 ± 20 |
| Control CHO (vector transduced) | 33 ± 4.3 | 810 ± 190 | 45 ± 20 |
| CHO transduced with OX-2:Fc | 4.2 ± 2.1 | 175 ± 45 | 245 ± 55 |

Footnotes:
[a]Supernatant was harvested at 7 days from CHO cells transduced with control pbK vector, or vector carrying a cDNA insert encoding OX-2 linked to murine Fc. A 1:1 mixture of supernatant was used in cultures containing 5 × 10⁶ LEW spleen and 2.5 × 10⁶ irradiatedLBNF1 spleen cells; this corresponded to 50 ng/ml OX-2:Fc
[b]and[c]Percent lysis with cells at 5 days, using 1 × 10⁴ $^{51}$Cr BN spleen ConA targets; cytokines in culture supernatants at 60 hrs.

TABLE 6

Inhibition of skin graft rejection by OX-2:Fc

| Treatment of mice | Rejection of skin grafts (mean + SD) in days |
|---|---|
| NIL | 12 + 3.8 |
| OX-2:Fc | 19 + 4.2 |

Footnotes:
6 mice/group were treated as shown.
NIL indicates infusion of normal mouse IgG only.
Arithmetic mean (+SD) graft survival for group.

TABLE 7

OX-2:Fc infused into mice receiving skin allografts reverses polarization in cytokine production

| Treatment of mice | Cytokines in culture supernatant at 48 hrs | |
|---|---|---|
| (pg/ml) | IL-2 | IL-4 |
| NIL | 1250 + 160 | 80 + 20 |
| OX-2:Fc | 350 + 85 | 245 + 50 |

Footnotes:
3 mice/group received iv infusions of saline or OX-2:Fc (50 mg/mouse) every 2 days x4 from the time of grafting with C57BL/6 skin. Mice were sacrificed at 10 days and spleen cells stimulated in vitro with irradiated C57BL/6 spleen stimulator cells.
Arithmetic mean (+SD) for IL-2/IL-4 in supernatant at 48 hrs. Data are pooled from triplicate cultures for each mouse spleen.

TABLE 8

Preimmunization of mice with EL4-CD86 causes increased CD200 expression which leads to generalized suppression to newly encountered alloantigen

| | | Cytokines in Supernatant[c] | | | |
|---|---|---|---|---|---|
| Tumor used for Immunization[a] | % Lysis[b] | IL-2 | IL-4 | IFNγ | IL-10 |
| NONE (control) | 43 ± 5.5 | 980 ± 125 | 50 ± 10 | 455 ± 65 | 35 ± 10 |
| EL4 | 41 ± 6.2 | 890 ± 135 | 60 ± 15 | 515 ± 70 | 30 ± 10 |

TABLE 8-continued

Preimmunization of mice with EL4-CD86 causes increased CD200 expression which leads to generalized suppression to newly encountered alloantigen

|  |  | Cytokines in Supernatant[c] | | | |
|---|---|---|---|---|---|
| Tumor used for Immunization[a] | % Lysis[b] | IL-2 | IL-4 | IFNγ | IL-10 |
| EL4-CD80 | 46 ± 6.3 | 955 ± 140 | 45 ± 15 | 525 ± 55 | 30 ± 10 |
| EL4-CD86 | 16 ± 4.2* | 420 ± 75* | 125 ± 20* | 240 ± 40* | 120 ± 20* |
| NONE (control) + | 46 ± 5.8 | 950 ± 105 | 55 ± 15 | 490 ± 60 | 40 ± 10 |
| EL4 + | 44 ± 4.9 | 940 ± 115 | 50 ± 20 | 530 ± 60 | 35 ± 10 |
| EL4-CD80 + | 44 ± 6.0 | 905 ± 120 | 60 ± 15 | 555 ± 75 | 35 ± 10 |
| EL4-CD86 + | 39 ± 4.29 | 870 ± 125 | 75 ± 20 | 540 ± 65 | 40 ± 15 |

Footnotes:
[a]Spleen cells were pooled from 3 C57BL/6 mice/group, pretreated as described in the text, by immunization with $5 \times 10^6$ mitomycin-C treated EL4 tumor cells, or CD80/CD86-transfected tumor cells, in Complete Freund's Adjuvant 4 days earlier. $5 \times 10^6$ spleen cells were incubated in triplicate with equal numbers of mitomycin-C treated BALB/c spleen stimulator cells. + indicates anti-CD200 (anti-OX2) added to cultures (5 μg/ml)
[b]% specific lysis in 4-hr $^{51}$Cr release assays with 72-hr cultured BALB/c spleen Con A blast cells (effector:target ratio shown is 100:1).
[c]Cytokines in culture supernatants assayed in triplicate by ELISA at 40 hrs (see Materials and Methods). Data represent pg/ml except for IL-10 (ng/ml). *p < 0.05 compared with all groups.

TABLE 9

Mice Experiment
Mouse type: Swiss-Webster-Outbred
Test Article: Clone 3B6rat - anti-mouse OX-2
Dose 100 pg IP Q 3 days
Placebo: Mouse Igg

| Mouse Number | Date Plugged | Delivery Date | Litter size |  |
|---|---|---|---|---|
| Controls | | | | |
| 1 | 28-Feb-01 | Mar-21 | 8 | Controls % Pregnant 100 |
| 2 | Feb-29 | Mar-21 | 6 | |
| 3 | Feb-29 | Mar-21 | 8 | |
| 4 | Mar-01 | Mar-22 | 6 | |
| 5 | Mar-01 | Mar-22 | 6 | |
| 6 | Mar-03 | Mar-24 | 8 | |
| 7 | Mar-03 | Mar-24 | 4 | |
| 8 | Mar-05 | Mar-26 | 5 | |
| 9 | Mar-05 | Mar-26 | 8 | |
| 10 | Mar-06 | Mar-27 | 8 | |
| 11 | Mar-06 | Mar-27 | 6 | |
| 12 | Mar-06 | Mar-28 | 8 | |
| 13 | Mar-08 | Mar-29 | 8 | |
| 14 | Mar-08 | Mar-29 | 6 | |
| 15 | Mar-08 | Mar-30 | 4 | |
| 16 | Mar-08 | Mar-30 | 8 | |
| 17 | Mar-11 | Mar-31 | 6 | |
| Treated | | | | |
| 1 | Feb-28 | Mar-20 | 7 | |
| 2 | Feb-29 | Mar-21 | 8 | |
| 3 | Feb-29 | Mar-21 | 8 | Treated: % Pregnant 94 |
| 4 | Feb-29 | Mar-21 | 4 | |
| 5 | Mar-01 | Mar-22 | 5 | |
| 6 | Mar-03 | Mar-22 | 8 | |
| 7 | Mar-03 | Mar-23 | 8 | |
| 8 | Mar-05 | Mar-25 | 6 | |
| 9 | Mar-05 | Mar-25 | 6 | |
| 10 | Mar-06 | Mar-25 | 5 | |
| 11 | Mar-06 | Mar-26 | 4 | |
| 12 | Mar-06 | Mar-27 | 4 | |
| 13 | Mar-06 | Mar-27 | 8 | |
| 14 | Mar-08 | Nil | 0 | |
| 15 | Mar-08 | Mar-29 | 6 | |
| 16 | Mar-08 | Mar-29 | 7 | |
| 17 | Mar-08 | Mar-29 | 8 | |
| 18 | Mar-11 | Mar-31 | 7 | |

TABLE 10

Mice Experiment
Mouse type: Swiss-Webster-Outbred
Test Article: Clone 3B6rat - anti-mouse OX-2
Dose 250 micrograms IP every 36 hours
Placebo: Mouse Igg

| Mouse Number | Date Plugged | Delivery Date | Litter Size Males | Litter Size Females | Litter Size Total |
|---|---|---|---|---|---|
| Controls | | | | | |
| 1 | Apr-01 | Apr-21 | 4 | 2 | 6 |
| 2 | Apr-01 | Apr-22 | 4 | 3 | 7 |
| 3 | Apr-03 | Apr-25 | 3 | 3 | 6 |
| 4 | Apr-05 | Apr-26 | 2 | 4 | 6 |
| 5 | Apr-05 | Apr-27 | 5 | 3 | 8 |
| 6 | Apr-08 | Apr-29 | 4 | 4 | 8 |
| 7 | Apr-09 | Apr-30 | 3 | 3 | 6 |
| 8 | Apr-10 | Apr-30 | 2 | 4 | 6 |
| Treated | | | | | |
| 1 | Apr-01 | Nil | 0 | 0 | 0 |
| 2 | Apr-02 | Nil | 0 | 0 | 0 |
| 3 | Apr-04 | Apr-25 | 4 | 2 | 6 |
| 4 | Apr-05 | Nil | 0 | 0 | 0 |
| 5 | Apr-07 | Apr-29 | 1 | 3 | 4 |
| 6 | Apr-09 | Apr-30 | 4 | 2 | 6 |
| 7 | Apr-10 | Nil | 0 | 0 | 0 |
| 8 | Apr-13 | Nil | 0 | 0 | 0 |

Controls % Pregnant 100
Treated % Pregnant 38

TABLE 11

Rat Experiment
Rat type: Sprague-Dawley-Outbred
Test Article: Clone 6C2 Mouse - anti-rat OX-2
Dose 300 micrograms IP Q 3 days
Placebo: Rat Igg

| Rat Number | Date Plugged | Delivery Date | Litter size | |
|---|---|---|---|---|
| | | Controls | | |
| 1 | Feb-29 | Mar-21 | 11 | |
| 2 | Feb-29 | Mar-22 | 13 | Controls % Pregnant 92 |
| 3 | Mar-01 | Mar-24 | 10 | |
| 4 | Mar-01 | Mar-24 | 11 | |
| 5 | Mar-03 | Mar-25 | 12 | |
| 6 | Mar-03 | Mar-25 | 9 | |
| 7 | Mar-05 | Nil | 0 | |
| 8 | Mar-05 | Mar-27 | 9 | |
| 9 | Mar-06 | Mar-28 | 8 | |
| 10 | Mar-07 | Mar-28 | 9 | |
| 11 | Mar-07 | Mar-29 | 10 | |
| 12 | Mar-09 | Mar-31 | 8 | |
| | | Treated | | |
| 1 | Feb-29 | Mar-21 | 8 | Treated: % Pregnant 63 |
| 2 | Mar-01 | Mar-23 | 9 | |
| 3 | Mar-01 | Nil | 0 | |
| 4 | Mar-01 | Mar-24 | 9 | |
| 5 | Mar-03 | Nil | 0 | |
| 6 | Mar-05 | Nil | 0 | |
| 7 | Mar-06 | Mar-28 | 8 | |
| 8 | Mar-07 | Mar-29 | 6 | |

TABLE 12

Rat Experiment
Rat type: Sprague-Dawley-Outbred
Test Article: Clone 6C2 Mouse - anti-rat OX-2
Dose 500 micrograms IP Q 3 days
Placebo: Rat Igg

| Rat Number | Date Plugged | Delivery Date | Litter Size Males | Litter Size Females | Litter Size Total |
|---|---|---|---|---|---|
| | | Controls | | | |
| 1 | Apr-04 | Apr-25 | 6 | 4 | 10 |
| 2 | Apr-04 | Apr-27 | 6 | 5 | 11 |
| 3 | Apr-08 | Apr-29 | 4 | 6 | 10 |
| 4 | Apr-09 | Apr-30 | 3 | 7 | 10 |
| 5 | Apr-13 | May-02 | 4 | 5 | 9 |
| 6 | Apr-14 | May-03 | 6 | 5 | 11 |

Controls % Pregnant 100

| Rat Number | | Treated | | | |
|---|---|---|---|---|---|
| 1 | Apr-05 | Nil | 0 | 0 | 0 |
| 2 | Apr-06 | Nil | 0 | 0 | 0 |
| 3 | Apr-09 | Apr-30 | 3 | 4 | 7 |
| 4 | Apr-12 | Nil | 0 | 0 | 0 |
| 5 | Apr-14 | Nil | 0 | 0 | 0 |
| 6 | Apr-16 | May-06 | 4 | 4 | 8 |

Treated: % Pregnant 33

Full CITATIONS FOR REFERENCES REFERRED TO IN THE SPECIFICATION

Ahvazi, B. C., P. Jacobs, and M. M. Stevenson. 1995. Role of macrophage-derived nitric oxide in suppression of lymphocyte proliferation during blood-stage malaria. J. Leu. Biol. 58 (1):23-31.

Akatsuka, Y., C. Cerveny, and J. A. Hansen. 1996. T cell receptor clonal diversity following allogeneic marrow grafting. Hum. Immunol. 48:125-134.

Akolkar, P. N., B. Gulwani-Akolkar, R. Pergolizzi, R. D. Bigler, and J. Silver. 1993. Influence of HLA genes on T cell receptor V segment frequencies and expression levels in peripheral blood lymphocytes. J. Immunol. 150 (April 1):2761-2773.

Albina, J. E., J. A. Abate, and W. L. Henry. 1991. Nitric oxide production is required for murine resident peritoneal macrophages to suppress mitogen-stimulated T cell proliferation. J. Immunol. 147:144-152.

Banchereau, J., and R. M. Steinman. 1998. Dendritic cells and the control of immunity. Nature. 392:245-252.

Barclay, A. N. 1981. Different reticular elements in rat lymphoid tissue identified by localization of Ia, Thy-1 and MRC OX-2 antigens. *Immunology* 44:727.

Barclay, A. N., and H. A. Ward. 1982. Purification and chemical characterization of membrane glycoproteins from rat thymocytes and brain, recognized by monoclonal antibody MRC OX-2. *Eur. J. Biochem.* 129:447.

Boissier, M. C., Chiocchia, G., Bessis, N., Hajnal, J., Garotta, G., Nocoletti, F., and Fournier, C. Biphasic effect of interferon-gamma in murine collagen-induced arthritis. *Eur. J. Immunol.* 25:1184-1190, 1995

Borriello, F., J. Lederer, S. Scott, and A. H. Sharpe. 1997. MRC OX-2 defines a novel T cell costimulatory pathway. *J. Immuno.* 158:4548.

Brasel, K., H. J. McKenna, K. Charrier, P. J. Morrissey, D. E. Williams, and S. D. Lyman. 1997. Flt3 ligand synergizes with granulocyte-macrophage colony-stimulating factor or granulocyte colony-stimulating factor to mobilize hematopoietic progenitor cells into the peripheral blood of mice. Blood. 90:3781-3788.

Bronstein, I., J. C. Voyta, O. J. Murphy, L. Bresnick, and L. J. Kricka. 1992. Improved chemiluminescence Western blotting procedure. *Biotechniques* 12:748.

Castle, B. E., K. Kishimoto, C. Stearns, M. L. Brown, and M. R. Kehry. 1993. Regulation of the expression of the ligand for CD40 on T helper lymphocytes. *J. Immunol.* 151:1777.

Chen, Z., H. Zeng, and R. M. Gorczynski. 1997. Cloning and characterization of the murine homologue of the rat/human MRC OX-2 gene. BBA. Mol. Basis Dis. 1362: 6-10.

Choy, E. H., and Panayi, G. S. Cytokine pathways and joint inflammation in rheumatoid arthritis. *New Engl. J. Med.* 344:907-916, 2001

Clark, D. A., J.-W. Ding, G. Yu, G. A. Levy and R. Gorczynski. 2001. Fgl2 prothrombinase expression in mouse trophoblast and decidua triggers abortion but may be counted by OX-2. Mol. Human Reproduction, Vol. 7, No. 2, pp. 185-194.

Courtenay, J. S., Dallman, M. J., Dayan, A. D., Martin, A., and Mosedale, B. Immunization against heterologous type 11 collagen induces arthritis in mice. Nature 283: 666-668, 1980

Freeman, G. J., V. A. Boussiotis, A. Anumanthan, G. M. Bernstein, X. Y. Ke, P. D. Rennert, G. S. Gray, J. G. Gribben, and L. M. Nadler. 1995. B7-1 and B7-2 do not deliver identical costimulatory signals, since B7-2 but not B7-1 preferentially costimulates the initial production of IL-4. Immunity. 2:523-532.

Garside, P., and A. M. Mowat. 1997. Mechanisms of oral tolerance. Crit. Rev. Immunol. 17:119-137.

Goodwin, R. G., Din, W. S., Davis-Smith, T. et al. 1993. Eur. J. Immunol. 23, 2631-2641

Gorczynski, R. M. 1992. Immunosuppression induced by hepatic Dortal venous immunization spares reactivity in IL-4 producing T lymphocytes. Immunol. Lett. 33:67-77.

Gorczynski, R. M., and D. Wojcik. 1992. Antigen presentation by murine splenic, but not hepatic, antigen-presenting cells to induce IL-2/IL-4 production from immune T cells is regulated by interactions between LFA-1/ICAM-1. Immunol. Lett. 34:177-182.

Gorczynski, R. M., and D. Wojcik. 1994. A role for non-specific (cyclosporin A) or specific (monoclonal antibodies to ICAM-1, LFA-1 and interleukin-10) immunomodulation in the prolongation of skin allografts after antigen-specific pre-transplant immunization or transfusion. J. Immunol. 152:2011-2019.

Gorczynski, R. M., Z. Chen, S. Chung, Z. Cohen, G. Levy, B. Sullivan, and X.-M. Fu. 1994a. Prolongation of rat small bowel or renal allograft survival by pretransplant transfusion and/or by varying the route of allograft venous drainage. Transplantation 58:816-820.

Gorczynski, R. M. 1994b. Adoptive transfer of unresponsiveness to allogenic skin grafts with hepatic γδ+ T cells. Immunology 81:27-35.

Gorczynski, R. M. 1995a. Regulation of IFNγ and IL-10 synthesis in vivo, as well as continuous antigen exposure, is associated with tolerance to murine skin allografts. Cell. Immunol. 160:224-231.

Gorczynski, R. M., N. Hozumi, S. W. Wolfe, and Z. Chen. 1995b. Interleukin-12, in combination with anti-interleukin-10, reverses graft prolongation after portal venous immunization. Transplantation. 60:1337-1341.

Gorczynski, R. M., Z. Cohen, X. M. Fu, Z. Hua, Y. L. Sun, and Z. Q. Chen. 1996a. lnterleukin-13, in combination with anti interleukin-12, increases graft prolongation after portal venous immunization with cultured allogenic bone marrow-derived dendritic cells. Transplantation 62:1592-1600.

Gorczynski, R. M., Z. Cohen, G. Levy, and X. M. Fu. 1996b. A role for gamma delta TCR(+) cells in regulation of rejection of small intestinal allografts in rats. Transplantation. 62:844-851.

Gorczynski, R. M., Z. Chen, Y. Hoang, and B. RossiBergman. 1996c. A subset of gamma delta T-cell receptor-positive cells produce T-helper type-2 cytokines and regulate mouse skin graft rejection following portal venous pretransplant preimmunization. Immunology. 87 (3):381-389.

Gorczynski, R. M., Z. Chen, H. Zeng, and X. M. Fu. 1998a. A role for persisting antigen, antigen presentation and ICAM-1 in the increased renal graft survival following oral or portal vein donor-specific immunization. Transplantation. 66: 339-349.

Gorczynski, R. M., Z. Chen, X. M. Fu, and H. Zeng. 1998b. Increased expression of the novel molecule Ox-2 is involved in prolongation of murine renal allograft survival. Transplantation. 65:1106-1114.

Gorczynski, R. M., et al. 1998c. Analysis of cytokine production and V beta T-cell receptor subsets in irradiated recipients receiving portal or peripheral venous reconstitution with allogeneic bone marrow cells, with or without additional anti-cytokine monoclonal antibodies. Immunology. 93: p. 221-229.

Gorczynski, R. M., Chen, Z., Zeng, H. and Fu, X. M. 1998 Increased expression of the novel molecule OX-2 is involved in prolongation of murine renal allograft survival. Transplantation: 65:1106-1114

Gorczynski, L., Chen, Z., Hu, J., Kai, G., Ramakrishna, V., and Gorczynski, R. M. Evidence that an OX-2 positive cell can inhibit the stimulation of type-1 cytokine production by bone-marrow-derived B7-1 (and B7-2) positive dendritic cells. J. Immunol. 162:774-781, 1999.

Gorczynski, R. M., Cattral, M. S., Chen, Z. G., Hu, J. A., Lei, J., Min, W. P., Yu, G., and Ni, J. An immunoadhesin incorporating the molecule OX-2 is a potent immunosuppressant that prolongs allo- and xenograft survival. J. Immunol. 163:1654-1660, 1999.

Gorczynski, R. M., Yu, K., and Clark, D. Receptor engagement on cells expressing a ligand for the tolerance-inducing molecule OX2 induces an immunoregulatory population that inhibits alloreactivity in vitro and in vivo. J. Immunol. 165:4854-4860, 2000.

Gruss, H. and Dower, S. 1995. Blood 85, 3378-3404.

Hancock, W. W., M. H. Sayegh, X. G. Zheng, R. Peach, P. S. Linsley, and L. A. Turka. 1996. Costimulatory function and expression of CD40 ligand, CD80, and CD86 in vascularized murine cardiac allograft rejection. Proc. NatI. Acad. Sci. USA. 93:13967-13972.

Hoek, R. M., Ruuls, S. R., Murphy, C. A., Wright, G. J., Goddard, R., Zurawski, S. M., Blom, B., Homola, M. E., Streit, W. J., Brown, M. H., Barclay, A. N., and Sedgwick, J. D. Down-regulation of the macrophage lineage through interaction with OX2 (CD200). Science 290:1768-1771, 2000.

Jenkins, M. K., J. D. Ashwell, and R. H. Schwartz. 1988. Allogeneic non-T spleen cells restore the responsiveness of normal T cell clones stimulated with antigen and chemically modified antigen-presenting cells. J. Immunol. 140:3324-3329.

Kenick, S., R. P. Lowry, R. D. S. Forbes, and R. Lisbona. 1987. Prolonged cardiac allograft survival following portal venous inoculation of allogeneic cells: What is "hepatic tolerance?". Transpl. Proc. 19:478-480.

Kohler, G. and C. Milstein. 1975. Preparation of monoclonal antibodies. Nature. 25: p. 256-259.

Kronin, V., K. Winkel, G. Suss, A. Kelso, W. Heath, J. Kirberg, H. vonBoehmer, and K. Shortman. 1996. Subclass of dendritic cells regulates the response of naive CD8 T cells by limiting their IL-2 production. J. Immunol. 157:3819-3827.

Kuchroo, V. K., M. P. Das, J. A. Brown, A. M. Ranger, S. S. Zamvil, A. Sobel, H. L. Weiner, N. Nabavi, and L. H. Glimcher. 1995. B7-1 and B7-2 costimulatory molecules activate differentially the Th1/Th2 developmental pathways: application to autoimmune disease therapy. Cell. 80:707-718.

Larsen, C. P., S. C. Ritchie, R. Hendrix, P. S. Linsley, K. S. Hathcock, R. J. Hodes, R. P. Lowry, and T. C. Pearson. 1994. Regulation of immunostimulatory function and costimulatory molecule (B7-1 and B7-2) expression on murine dendritic cells. J. Immunol. 152:5208-5219.

Larsen, C. P., Elwood, E. T., Alexander, D. Z. et al. 1996. Nature 381, 434-438

Larsen, C. P., and T. C. Pearson. 1997. The CD40 pathway in allograft rejection, acceptance, and tolerance. Curr. Opin. Immunol. 9:641-647.

Leenen, P. J. M., K. Radosevic, J. S. A. Voerman, B. Salomon, N. vanRooijen, D. Klatzmann, and W. vanEwijk. 1998. Heterogeneity of mouse spleen dendritic cells: In vivo phagocytic activity, expression of macrophage markers, and subpopulation turnover. J. Immunol. 160:2166-2173.

Lenschow, D. J., T. L. Walunas, and J. A. Bluestone. 1996. CD28/B7 system of T cell costimulation. Annu. Rev. Immunol. 14:233-258.

Maini, R., St. Clair, E. W., and Breedveld, F. INfliximab (chimeric tumor necrosis factor a monoclonal antibody) versus placebo in rheumatoid arthritis patients receiving concomitant methotrexate: a randomized phase III trial. *Lancet* 354:1932-1939, 1999.

Maraskovsky, E., K. Brasel, M. Teepe, E. R. Roux, S. D. Lyman, K. Shortman, and H. J. McKenna. 1996. Dramatic increase in the numbers of functionally mature dendritic cells in Flt 3 Ligand-treated mice: multiple dendritic cell subpopulations identified. J. Exptl. Med. 184:1953-1962.

Matthys, P., Vermeire, K., Heremans, H., and Billiau, A. The protective effect of IFN-gamma in experimental autoimmune diseases: a central role of mycobacterial adjuvant-induced myelopoiesis. *J. Leuk. Biol.* 68:447-454, 2000.

Mattys, P., Vermeire, K., and Billiau, A. Mac-1+ myelopoiesis induced by CFA: a clue to the paradoxical effects of IFNA in autoimmune disease models. *TRENDS in Immunol.* 22:367-371, 2001

Mayer, L. 1996. Yin and Yang of mucosal immunology. Transpl. Proc. 28:2435-2437.

McCaughan, G. W., et al. 1987. The gene for MRC OX-2 membrane glycoprotein is localized on human chromosome 3. Immunogenetics. 25: p. 133-135.

McIntyre, K. W., Shuster, D. J., Gillooly, K. M., Warrier, R. R., Connaughton, S. E., Hall, L. B., Arp, L. H., Gately, M. K., and Magram, J. Reduced incidence of collagen-induced arthritis in interleukin-12-deficient mice. *Eur. J. Immunol.* 26:2933-2938, 1996

Miller, R. G., and R. A. Phillips. 1969. The separation of cells by velocity sedimentation. J. Cell. Comp. Physiol. 73:191-198.

Moreland, L. W., Schiff, M. H., and Baumgartner, S. W. Etanercept therapy in rheumatoid arthritis: a randomized control trial. *Ann. Intern. Med.* 130:478-486, 1999.

Nakajima, H., Takamori, H., Hiyama, Y., and Tsukada, W. The effect of treatment with interferon-gamma on type 11 collagen-induced arthritis. *Clin. Exp. Immunol.* 81:441-445, 1990

Ortmann, R. A., and Shevach, E. M. Susceptibility to collagen-induced arthritis:cytokine-mediated regulation. *Clin. Immunol.* 98:109-118, 2001

Pincus, T., and Callahan, L. F. Taking mortality in rheumatoid arthritis seriously-predictive markers, socioeconomic status and comorbidity. *J. Rheumatol.* 13:841-845, 1986.

Preston, S., et al. 1997. The leukocyte/neuron cell surface antigen OX2 binds to a ligand on macrophages. Eur J Immunol. 27(8): p. 1911-8.

Qian, J. H., T. Hashimoto, H. Fujiwara, and T. Hamaoka. 1985. Studies on the induction of tolerance to alloantigens. I. The abrogation of potentials for delayed-type hypersensitivity responses to alloantigens by portal venous inoculation with allogeneic cells. J. Immunol. 134:3656-3663.

Rosenzwajg, M., S. Camus, M. Guigon, and J. C. Gluckman. 1998. The influence of interleukin (IL) 4, IL-13, and Flt3 ligand on human dendritic cell differentiation from cord blood CD34(+) progenitor cells. Exp. Hematol. 26:63-72.

Salomon, B., J. L. Cohen, C. Masurier, and D. Klatzmann. 1998. Three populations of mouse lymph node dendritic cells with different origins and dynamics. J. Immunol. 160:708-717.

Sandhu, G. S., B. W. Eckloff, and B. C. Kline. 1991. Chemiluminescent substrates increase sensitivity of antigen detection in Western blots. *Biotechniques* 11:14.

Schwartz, R. H. 1996. Models of T cell anergy: Is there a common molecular mechanism? J Exp Med. 184: p. 1-8.

Scott, D. L., Symmons, D. P., Coulton, B. L., and Popert, A. J. Long-term outcome of treating rheumatoid arthritis: results after 20 years. *Lancet* 1:1108-1111, 1987.

Steinbrink, K., M. Wolfl, H. Jonuleit, J. Knop, and A. H. Enk. 1997. Induction of tolerance by IL-10-treated dendritic cells. J Immunol. 159:4772-4780.

Steptoe, R. J., F. M. Fu, W. Li, M. L. Drakes, L. A. Lu, A. J. Demetris, S. G. Qian, H. J. McKenna, and A. W. Thomson. 1997. Augmentation of dendritic cells in murine organ donors by Flt3 ligand alters the balance between transplant tolerance and immunity. J Immunol. 159:5483-5491.

Suss, G., and K. Shortman. 1996. A subclass of dendritic cells kills CD4+ T cells via Fas/Fas-ligand-induced aoptosis. J. Exptl. Med. 183:1789-1796.

Swain, S. L. 1995. Who does the polarizing? Curr. Biol. 5:849-851.

Thelen, M., and U. Wirthmueller. 1994. Phospholipases and protein kinases during phagocytic activation. Curr. Opin. Immunol. 6:106-112.

Zheng, X. X., Steele, A. W., Nickerson, P. W. et al. 1995. Journal of Immunology 154, 5590-5600.

I claim:

1. A method of treating an allergy by suppressing an immune response comprising administering an effective amount of a CD200 protein or fragment thereof, to an animal in need thereof, wherein said CD200 protein or fragment thereof is capable of suppressing an immune response selected from the group consisting of: inhibiting a mixed leukocyte reaction; inhibiting a cytotoxic T lymphocyte response; inhibiting interleukin-2 production; and inhibiting interferon-γ production.

2. The method according to claim 1 wherein the CD200 protein is a human CD200 protein or a fragment thereof.

3. The method according to claim 1 wherein the CD200 protein is a soluble fusion protein.

4. The method according to claim 3 wherein the soluble fusion protein comprises a CD200 protein or fragment thereof linked to an immunoglobulin Fc region.

5. The method according to claim 4 wherein the CD200 fragment comprises an extracellular domain of a CD200 protein.

6. The method according to claim 1, wherein the CD200 fragment comprises the extracellular domain of a CD200 protein.

7. A method of treating an allergy by suppressing an immune response comprising administering an effective amount of a CD200 protein, to an animal in need thereof, wherein said CD200 protein is capable of suppressing an immune response.

* * * * *

SEQUENCE LISTING

```
<160> NUMBER OF SEQ ID NOS: 22

<210> SEQ ID NO 1
<211> LENGTH: 2791
<212> TYPE: DNA
<213> ORGANISM: Mus musculus

<400> SEQUENCE: 1
actatagggc acgcgtggtc gacggcccgg gctggtactg agaaggaata ggatgcagtc      60
agagggaagg gacttgagga agacctttgg tttagactct ctccacatgt ctgtctgtgg     120
```

-continued

```
gtctctgaac cagattttat ctgttgctgc ctctctgatg acagctggtc aaggccccaa      180
tctattagta tagcagaatg tcattaagaa tcattctttt cttccttcca tttttcttc       240 ttcttctact ccctccccct ttctctctct ctctttcttt ctttctttct ttcttttct       300 ttctttcttt ctctctctcc ctctttctct ctctccctct ctctcttcct ttctttcttt     360
ctttctcttt ttctttctgt ctttctctct ctttccttct ttccttcccc agctgtgttt     420
ggttctaccc taggactctg gcctttccat tatctggttc ttgaccatcc aggcaatata     480
ggtacaagct ctctcttata gggtgggcct caagttaaac taaacattgg ttggtcactc     540
cctcacgttt tctactaaaa tctcataggc aggacatatt gtgggtagag gatttagagg     600
caggtttagt gtccaggttt gtcttttcat ggtctgtaga ataccttctc acaccagaga     660
gactagagtc tagagtccaa acctcagctc tagcctctct atgttcagtg agctgaatga     720
aagttgacct cagcaatggg tcccactgtc aggttttaga gggtgacctt cagttgtagg     780
tcccaagtct ctctctcctc tctctccctt tctcgatctc tctctctctc tctctctctc     840
tctctctctc tctctctctc tctctctctc tctctctgct ttatacttgt gattgaagat     900
gtgatctctc tggcagcctg gtaccatgcc tcctggtcac ttagagactc tcctcctgta     960
gctataagcc caacaaatct tttccacag gtttctactc tagtacagaa acagaaatgt     1020
caccaatata gtcaatcgtt tctgtaaagc tttcatcaag gaaaacctca gttccagggc     1080
ttcctgtgac tcatttgatc tgtcccttga ttctcatctg ttttaaggaa tactgcggga     1140
caatctgatt agcagaaaga aagtgctttt gggttttcag gaagtgtgtt cacaggtagc     1200
tctgagccct taggacttct aaagctctag atgaggtacc tggtaaccac acacacacac     1260
acacacacac acacacacac acgcactg gcctttaata taacaaatca taaaataaag      1320 ttttctttt tttttcccca gggtgtctgt atgaatctcc ttaccttctt cccctacac      1380 acacacacac acacacacac acacacacac acactattgt tctgttctcc gagtttacct     1440
tttgctgtac agaaccacag gatgcaccgg gtttctgact caaattactg tccactcaag     1500
ttagttccca ctccgatttt tctgtatgga ctacgtcacc ctatactgcc atttggcacg     1560
ggagagaggc cagtgatggg aatgcagacg aaacatgcat acacatgtaa aataagataa     1620
ataaatctaa aatgaaaaaa aatatagagt gattctttca catttttgct atattactct     1680
aaaaggcgag aacctggcgg gggcggggc aggggctagg gacgaggttg tagagggcgt      1740
ggttggttgg tcgtctcttc ctccacacta gaggagctgt agagtctgcc tgtgcggtgg     1800 aggggctct ctctacggcg aatagtagtg tccctgctca caggtgttgc ggagatatcc      1860
tccatcgtgg aagagctcag accccgagaa gctggtgtct agctgcggcc ccgagcaagg     1920
atgggcagtc tggtgagtgg aatctgagat gcgaaggagg gcggaatggg cgatctggag     1980
ccgcggctct cagaagccag tggagcctgc gagaaaagca aggaagctgt ctttggaga     2040 agtggtatcc ggggctcgga gctctgtaag gaggcaccgg ccggagaaag cccggggaac     2100
gcgtgtatct agggtgggcg gctttgctcc ttgctgcgat tccattgcga aaacacggcc     2160
tgagctccat ggctcccaga aggggaggag tagctctttg cgtcccctat gttggtcctt     2220
aacctgcagc agggtgtag cctagtaatc tcgcttgctc tctttctcac cccctctctt      2280
gctgcatttc tgctccttgc ctagaaaacc atgaagcatc tagcagtact gcagcgagca    2340
agccacagct tagtggtctt gttaaatgca aggtattta gaggagaggc cgacattttg      2400
agtctttggt actgtttaca aggcagaaaa ttttaaaagg aagggtggtc atacgcctta     2460
```

```
ttctttatac acacggaatt ggtagaattg aatgcgaatc taaacgcaat taaaccccag    2520
gtaccacttt tcatcaggct gacaaagacc gacttgtgtt acctttccta acaaagagga    2580
atgtggatct gtcagctaga tgctcttagt gttcaaacaa ggaattgctt tctgttttac    2640
aaagaatcgg agagagaggt tctttttttt ctctccaagt ctctgtggct gcaatgaaat    2700
aaggtacaaa atcagaccta gaaagaatag gggaatgggg ctatgcacct agcagaccag    2760
cccgggccgt cgaccacgcg tgccctatag t                                   2791
```

<210> SEQ ID NO 2
<211> LENGTH: 278
<212> TYPE: PRT
<213> ORGANISM: Mus musculus

<400> SEQUENCE: 2

```
Met Gly Ser Leu Val Phe Arg Arg Pro Phe Cys His Leu Ser Thr Tyr
1               5                   10                  15

Ser Leu Ile Trp Gly Met Ala Ala Val Ala Leu Ser Thr Ala Gln Val
            20                  25                  30

Glu Val Val Thr Gln Asp Glu Arg Lys Ala Leu His Thr Thr Ala Ser
        35                  40                  45

Leu Arg Cys Ser Leu Lys Thr Ser Gln Glu Pro Leu Ile Val Thr Trp
    50                  55                  60

Gln Lys Lys Lys Ala Val Ser Pro Glu Asn Met Val Thr Tyr Ser Lys
65                  70                  75                  80

Thr His Gly Val Val Ile Gln Pro Ala Tyr Lys Asp Arg Ile Asn Val
                85                  90                  95

Thr Glu Leu Gly Leu Trp Asn Ser Ser Ile Thr Phe Trp Asn Thr Thr
            100                 105                 110

Leu Glu Asp Glu Gly Cys Tyr Met Cys Leu Phe Asn Thr Phe Gly Ser
        115                 120                 125

Gln Lys Val Ser Gly Thr Ala Cys Leu Thr Leu Tyr Val Gln Pro Ile
    130                 135                 140

Val His Leu His Tyr Asn Tyr Phe Glu Asp His Leu Asn Ile Thr Cys
145                 150                 155                 160

Ser Ala Thr Ala Arg Pro Ala Pro Ala Ile Ser Trp Lys Gly Thr Gly
                165                 170                 175

Thr Gly Ile Glu Asn Ser Thr Glu Ser His Phe His Ser Asn Gly Thr
            180                 185                 190

Thr Ser Val Thr Ser Ile Leu Arg Val Lys Asp Pro Lys Thr Gln Val
        195                 200                 205

Gly Lys Glu Val Ile Cys Gln Val Leu Tyr Leu Gly Asn Val Ile Asp
    210                 215                 220

Tyr Lys Gln Ser Leu Asp Lys Gly Phe Trp Phe Ser Val Pro Leu Leu
225                 230                 235                 240

Leu Ser Ile Val Ser Leu Val Ile Leu Leu Val Leu Ile Ser Ile Leu
                245                 250                 255

Leu Tyr Trp Lys Arg His Arg Asn Gln Glu Arg Gly Glu Ser Ser Gln
            260                 265                 270

Gly Met Gln Arg Met Lys
        275
```

<210> SEQ ID NO 3
<211> LENGTH: 14
<212> TYPE: DNA
<213> ORGANISM: Artificial Sequence

```
<220> FEATURE:
<223> OTHER INFORMATION: Primer

<400> SEQUENCE: 3
ttttgtacaa gctt                                                14

<210> SEQ ID NO 4
<211> LENGTH: 44
<212> TYPE: DNA
<213> ORGANISM: Artificial Sequence
<220> FEATURE:
<223> OTHER INFORMATION: Adapter 1

<400> SEQUENCE: 4
ctaatacgac tcactatagg gctcgagcgg ccgcccgggc aggt                44

<210> SEQ ID NO 5
<211> LENGTH: 43
<212> TYPE: DNA
<213> ORGANISM: Artificial Sequence
<220> FEATURE:
<223> OTHER INFORMATION: Adapter 2

<400> SEQUENCE: 5
tgtagcgtga agacgacaga aagggcgtgg tgcggagggc ggt                 43

<210> SEQ ID NO 6
<211> LENGTH: 22
<212> TYPE: DNA
<213> ORGANISM: Artificial Sequence
<220> FEATURE:
<223> OTHER INFORMATION: Primer 1

<400> SEQUENCE: 6
ctaatacgac tcactatagg gc                                       22

<210> SEQ ID NO 7
<211> LENGTH: 22
<212> TYPE: DNA
<213> ORGANISM: Artificial Sequence
<220> FEATURE:
<223> OTHER INFORMATION: Nested Primer 1

<400> SEQUENCE: 7
tcgagcggcc gcccgggcag gt                                       22

<210> SEQ ID NO 8
<211> LENGTH: 21
<212> TYPE: DNA
<213> ORGANISM: Artificial Sequence
<220> FEATURE:
<223> OTHER INFORMATION: Primer 2

<400> SEQUENCE: 8
tgtagcgtga agacgacaga a                                        21

<210> SEQ ID NO 9
<211> LENGTH: 22
<212> TYPE: DNA
<213> ORGANISM: Artificial Sequence
<220> FEATURE:
<223> OTHER INFORMATION: Nested Primer 2

<400> SEQUENCE: 9
agggcgtggt gcggagggcg gt                                       22
```

<210> SEQ ID NO 10
<211> LENGTH: 25
<212> TYPE: DNA
<213> ORGANISM: Artificial Sequence
<220> FEATURE:
<223> OTHER INFORMATION: GADPH Sense

<400> SEQUENCE: 10
tgatgacatc aagaaggtgg tgaag                                   25

<210> SEQ ID NO 11
<211> LENGTH: 23
<212> TYPE: DNA
<213> ORGANISM: Artificial Sequence
<220> FEATURE:
<223> OTHER INFORMATION: GADPH Antisense

<400> SEQUENCE: 11
tccttggagg ccatgtaggc cat                                     23

<210> SEQ ID NO 12
<211> LENGTH: 20
<212> TYPE: DNA
<213> ORGANISM: Artificial Sequence
<220> FEATURE:
<223> OTHER INFORMATION: B7-1 Sense

<400> SEQUENCE: 12
ccttgccgtt acaactctcc                                         20

<210> SEQ ID NO 13
<211> LENGTH: 20
<212> TYPE: DNA
<213> ORGANISM: Artificial Sequence
<220> FEATURE:
<223> OTHER INFORMATION: B7-1 Antisense

<400> SEQUENCE: 13
cggaagcaaa gcaggtaatc                                         20

<210> SEQ ID NO 14
<211> LENGTH: 20
<212> TYPE: DNA
<213> ORGANISM: Artificial Sequence
<220> FEATURE:
<223> OTHER INFORMATION: B7-2 Sense

<400> SEQUENCE: 14
tctcagatgc tgtttccgtg                                         20

<210> SEQ ID NO 15
<211> LENGTH: 20
<212> TYPE: DNA
<213> ORGANISM: Artificial Sequence
<220> FEATURE:
<223> OTHER INFORMATION: B7-2 Antisense

<400> SEQUENCE: 15
ggttcactga agttggcgat                                         20

<210> SEQ ID NO 16
<211> LENGTH: 20
<212> TYPE: DNA
<213> ORGANISM: Artificial Sequence
<220> FEATURE:
<223> OTHER INFORMATION: OX-2 Sense

<400> SEQUENCE: 16
gtggaagtgg tgacccagga                                                    20

<210> SEQ ID NO 17
<211> LENGTH: 20
<212> TYPE: DNA
<213> ORGANISM: Artificial Sequence
<220> FEATURE:
<223> OTHER INFORMATION: OX-2 Antisense

<400> SEQUENCE: 17
atagagagta aggcaagctg                                                    20

<210> SEQ ID NO 18
<211> LENGTH: 825
<212> TYPE: DNA
<213> ORGANISM: Homo sapiens

<400> SEQUENCE: 18
gtgatcagga tgcccttctc tcatctctcc tcctacagcc tggtttgggt catggcagca        60
gtggtgctgt gcacagcaca agtgcaagtg gtgacccagg atgaaagaga gcagctgtac       120
acacctgctt ccttaaaatg ctctctgcaa aatgcccagg aagccctcat tgtgacatgg       180
cagaaaaaga aagctgtaag cccagaaaac atggtcacct tcagcgagaa ccatgggtg        240
gtgatccagc ctgcctataa ggacaagata acattaccc agctgggact ccaaaactca        300
accatcacct tctggaatat caccctggag gatgaagggt gttacatgtg tctcttcaat       360
acctttggtt tgggaagat ctcaggaacg gcctgcctca ccgtctatgt acagcccata       420
gtatcccttc actacaaatt ctctgaagac cacctaaata tcacttgctc tgccactgcc       480
cgcccagccc ccatggtctt ctggaaggtc cctcggtcag ggattgaaaa tagtacagtg       540
actctgtctc acccaaatgg gaccacgtct gttaccagca tcctccatat caaagaccct       600
aagaatcagg tggggaagga ggtgatctgc caggtgctgc acctggggac tgtgaccgac       660
tttaagcaaa ccgtcaacaa aggatattgg ttttcagttc cgctattgct aagcattgtt       720
tccctggtaa ttcttctcat cctaatctca atcttactgt actggaaacg tcaccggaat       780
caggaccgag gtgaattgtc acagggagtt caaaaaatga cataa                       825

<210> SEQ ID NO 19
<211> LENGTH: 274
<212> TYPE: PRT
<213> ORGANISM: Homo sapiens

<400> SEQUENCE: 19

Val Ile Arg Met Pro Phe Ser His Leu Ser Thr Tyr Ser Leu Val Trp
1               5                   10                  15

Val Met Ala Ala Val Val Leu Cys Thr Ala Gln Val Gln Val Val Thr
                20                  25                  30

Gln Asp Glu Arg Glu Gln Leu Tyr Thr Thr Ala Ser Leu Lys Cys Ser
            35                  40                  45

Leu Gln Asn Ala Gln Glu Ala Leu Ile Val Thr Trp Gln Lys Lys Lys
        50                  55                  60

Ala Val Ser Pro Glu Asn Met Val Thr Phe Ser Glu Asn His Gly Val
65                  70                  75                  80

Val Ile Gln Pro Ala Tyr Lys Asp Lys Ile Asn Ile Thr Gln Leu Gly
                85                  90                  95

```
Leu Gln Asn Ser Thr Ile Thr Phe Trp Asn Ile Thr Leu Glu Asp Glu
                100                 105                 110

Gly Cys Tyr Met Cys Leu Phe Asn Thr Phe Gly Phe Lys Ile Ser
            115                 120                 125

Gly Thr Ala Cys Leu Thr Val Tyr Val Gln Pro Ile Val Ser Leu His
        130                 135                 140

Tyr Lys Phe Ser Glu Asp His Leu Asn Ile Thr Cys Ser Ala Thr Ala
145                 150                 155                 160

Arg Pro Ala Pro Met Val Phe Trp Lys Val Pro Arg Ser Gly Ile Glu
                165                 170                 175

Asn Ser Thr Val Thr Leu Ser His Pro Asn Gly Thr Thr Ser Val Thr
            180                 185                 190

Ser Ile Leu His Ile Lys Asp Pro Lys Asn Gln Val Gly Lys Glu Val
        195                 200                 205

Ile Cys Gln Val Leu His Leu Gly Thr Val Thr Asp Phe Lys Gln Thr
210                 215                 220

Val Asn Lys Gly Tyr Trp Phe Ser Val Pro Leu Leu Leu Ser Ile Val
225                 230                 235                 240

Ser Leu Val Ile Leu Leu Val Leu Ile Ser Ile Leu Leu Tyr Trp Lys
                245                 250                 255

Arg His Arg Asn Gln Asp Arg Gly Glu Leu Ser Gln Gly Val Gln Lys
            260                 265                 270

Met Thr
```

<210> SEQ ID NO 20
<211> LENGTH: 837
<212> TYPE: DNA
<213> ORGANISM: Rattus norvegicus

<400> SEQUENCE: 20

| | |
|---|---:|
| atgggcagtc cggtattcag gagaccttc tgccatctgt ccacctacag cctgctctgg | 60 |
| gccatagcag cagtagcgct gagcacagct caagtggaag tggtgaccca ggatgaaaga | 120 |
| aagctgctgc acacaactgc atccttacgc tgttctctaa aaacaaccca ggaacccttg | 180 |
| attgtgacat ggcagaaaaa gaaagccgta ggcccagaaa acatggtcac ttacagcaaa | 240 |
| gcccatgggg ttgtcattca gcccacctac aaagacagga taaacatcac tgagctggga | 300 |
| ctcttgaaca caagcatcac cttctggaac acaaccctgg atgatgaggg ttgctacatg | 360 |
| tgtctcttca acatgtttgg atctgggaag gtctctggga cagcttgcct tactctctat | 420 |
| gtacagccca tagtacacct tcactacaac tattttgaag accacctaaa catcacgtgc | 480 |
| tctgcaactg cccgcccagc ccctgccatc tcctggaagg gcactgggtc aggaattgag | 540 |
| aatagtactg agagtcactc ccattcaaat ggactacat ctgtcaccag catcctccgg | 600 |
| gtcaaagacc ccaaaactca ggttggaaag gaagtgatct gccaggtttt atacttgggg | 660 |
| aatgtgattg actacaagca gagtctggac aaaggatttt ggttttcagt cccactgctg | 720 |
| ctgagcattg tttctctggt aattcttctg gtcttgatct ccatcttatt atactggaaa | 780 |
| cggcaccgaa atcaggagcg gggtgagtca tcacagggga tgcaaagaat gaaataa | 837 |

<210> SEQ ID NO 21
<211> LENGTH: 278
<212> TYPE: PRT
<213> ORGANISM: Rattus norvegicus

<400> SEQUENCE: 21

```
Met Gly Ser Pro Val Phe Arg Arg Pro Phe Cys His Leu Ser Thr Tyr
1               5                   10                  15

Ser Leu Leu Trp Ala Ile Ala Ala Val Ala Leu Ser Thr Ala Gln Val
            20                  25                  30

Glu Val Val Thr Gln Asp Glu Arg Lys Leu Leu His Thr Thr Ala Ser
                35                  40                  45

Leu Arg Cys Ser Leu Lys Thr Thr Gln Glu Pro Leu Ile Val Thr Trp
50                      55                  60

Gln Lys Lys Lys Ala Val Gly Pro Glu Asn Met Val Thr Tyr Ser Lys
65                  70                  75                  80

Ala His Gly Val Val Ile Gln Pro Thr Tyr Lys Asp Arg Ile Asn Ile
                85                  90                  95

Thr Glu Leu Gly Leu Leu Asn Thr Ser Ile Thr Phe Trp Asn Thr Thr
                100                 105                 110

Leu Asp Asp Gly Gly Cys Tyr Met Cys Leu Phe Asn Met Phe Gly Ser
            115                 120                 125

Gly Lys Val Ser Gly Thr Ala Cys Leu Thr Leu Tyr Val Gln Pro Ile
130                 135                 140

Val His Leu His Tyr Asn Tyr Phe Glu His His Leu Asn Ile Thr Cys
145                 150                 155                 160

Ser Ala Thr Ala Arg Pro Ala Pro Ala Ile Ser Trp Lys Gly Thr Gly
                165                 170                 175

Ser Gly Ile Glu Asn Ser Thr Glu Ser His Ser His Ser Asn Gly Thr
            180                 185                 190

Thr Ser Val Thr Ser Ile Leu Arg Val Lys Asp Pro Lys Thr Gln Val
        195                 200                 205

Gly Lys Glu Val Ile Cys Gln Val Leu Tyr Leu Gly Asn Val Ile Asp
210                 215                 220

Tyr Lys Gln Ser Leu Asp Lys Gly Phe Trp Phe Ser Val Pro Leu Leu
225                 230                 235                 240

Leu Ser Ile Val Ser Leu Val Ile Leu Leu Val Leu Ile Ser Ile Leu
                245                 250                 255

Leu Tyr Trp Lys Arg His Arg Asn Gln Glu Arg Gly Glu Ser Ser Gln
            260                 265                 270

Gly Met Gln Arg Met Lys
        275

<210> SEQ ID NO 22
<211> LENGTH: 837
<212> TYPE: DNA
<213> ORGANISM: Mus musculus

<400> SEQUENCE: 22
atgggcagtc tggtattcag gagacctttc tgccatctct ccacctacag cctgatttgg      60
ggcatagcag cagtagcgct gagcacagct caagtggaag tggtgaccca ggatgaaaga     120
aaggcgctgc acacaactgc atccttacga tgttctctaa aacatcccag gaacccttg     180 attgtgacat ggcagaaaaa gaaagccgtg agcccagaaa acatggtcac ctacagcaaa     240
acccatgggg ttgtaatcca gcctgcctac aaagacagga taaatgtcac agagctggga     300
ctctggaact caagcatcac cttctggaac acacacattg agatggaggc tgctacatg     360 tgtctcttca acacgtttgg ttctcagaag gtctcaggaa cagcttgcct tactctctat     420
gtacagccca gtacacacct tcactacaac tattttgaac accacctaaa catcacttgc     480
tctgcgactg cccgtccagc ccctgccatc acctggaagg gtactgggac aggaattgag     540
```

```
aatagtaccg agagtcactt ccattcaaat gggactacat ctgtcaccag catcctccgg    600
gtcaaagacc ccaaaactca agttgggaag gaagtgatct gccaggtttt atacctgggg    660
aatgtgattg actacaagca gagtctggac aaaggatttt ggttttcagt tccactgttg    720
ctaagcattg tttctctggt aattcttctg atcttgatct ccatcttact atactggaaa    780
cgtcaccgaa atcaggagcg gggtgaatca tcacagggga tgcaaagaat gaaataa      837
```